(12) United States Patent
Dennis et al.

(10) Patent No.: US 12,240,902 B2
(45) Date of Patent: Mar. 4, 2025

(54) ANTI-TREM2 ANTIBODIES AND METHODS OF USE THEREOF

(71) Applicant: Denali Therapeutics Inc., South San Francisco, CA (US)

(72) Inventors: Mark S. Dennis, South San Francisco, CA (US); Sherie Duncan, South San Francisco, CA (US); Kathleen Lisaingo, South San Francisco, CA (US); Kathryn M. Monroe, South San Francisco, CA (US); Joshua I. Park, South San Francisco, CA (US); Rachel Prorok, South San Francisco, CA (US); Ju Shi, South San Francisco, CA (US); Ankita Srivastava, South San Francisco, CA (US); Bettina Van Lengerich, South San Francisco, CA (US); Riley Walsh, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 654 days.

(21) Appl. No.: 17/402,986

(22) Filed: Aug. 16, 2021

(65) Prior Publication Data
US 2022/0119522 A1   Apr. 21, 2022

Related U.S. Application Data

(63) Continuation of application No. PCT/US2020/019104, filed on Feb. 20, 2020.

(60) Provisional application No. 62/808,141, filed on Feb. 20, 2019.

(51) Int. Cl.
*A61K 39/00* (2006.01)
*C07K 16/28* (2006.01)

(52) U.S. Cl.
CPC .... *C07K 16/2803* (2013.01); *A61K 2039/505* (2013.01); *C07K 2317/24* (2013.01); *C07K 2317/565* (2013.01); *C07K 2317/75* (2013.01); *C07K 2317/92* (2013.01)

(58) Field of Classification Search
CPC ............ C07K 16/2803; C07K 2317/24; C07K 2317/565; C07K 2317/75; C07K 2317/92; C07K 2317/33; C07K 2317/34; A61K 2039/505; A61P 25/28
See application file for complete search history.

(56) References Cited

U.S. PATENT DOCUMENTS

| 8,231,878 | B2 | 7/2012 | Colonna et al. |
| 8,981,061 | B2 | 3/2015 | Colonna et al. |
| 9,663,587 | B2 | 5/2017 | Hsieh et al. |
| 10,457,717 | B2 | 10/2019 | Chen et al. |
| 10,870,837 | B2 | 12/2020 | Henry et al. |
| 11,124,567 | B2 | 9/2021 | Dennis et al. |
| 2017/0240631 | A1 | 8/2017 | Monroe et al. |
| 2020/0216522 | A1 | 7/2020 | Chen et al. |
| 2020/0223935 | A1 | 7/2020 | Chen et al. |
| 2020/0262890 | A1 | 8/2020 | Chen et al. |
| 2020/0277373 | A1 | 9/2020 | Chen et al. |
| 2020/0289627 | A1 | 9/2020 | Dennis et al. |
| 2020/0369746 | A1 | 11/2020 | Chen et al. |
| 2021/0070881 | A1 | 3/2021 | Dennis et al. |
| 2021/0130485 | A1 | 5/2021 | Dennis et al. |
| 2021/0198640 | A1 | 7/2021 | Astarita et al. |
| 2021/0284702 | A1 | 9/2021 | Di Paolo et al. |
| 2022/0002436 | A1 | 1/2022 | Dennis et al. |
| 2022/0017634 | A1 | 1/2022 | Kannan et al. |
| 2022/0025039 | A1 | 1/2022 | Astarita et al. |
| 2022/0025065 | A1 | 1/2022 | Arguello et al. |
| 2022/0073609 | A1 | 3/2022 | Dennis et al. |
| 2022/0177576 | A1 | 6/2022 | Dennis et al. |
| 2022/0184186 | A1 | 6/2022 | Andersen et al. |
| 2022/0213155 | A1 | 7/2022 | Cherf et al. |

FOREIGN PATENT DOCUMENTS

| CN | 105218669 A | 1/2016 |
| KR | 10-2156165 B1 | 9/2020 |
| WO | 2010/079039 A1 | 7/2010 |
| WO | 2014/178820 A1 | 11/2014 |
| WO | 2015/033223 A2 | 3/2015 |
| WO | 2016/023019 A2 | 2/2016 |
| WO | 2016/049641 A1 | 3/2016 |
| WO | 2016/156291 A1 | 10/2016 |
| WO | 2017/058866 A1 | 4/2017 |
| WO | 2017/062672 A2 | 4/2017 |
| WO | 2017/147509 A1 | 8/2017 |
| WO | 2017/189959 A1 | 11/2017 |
| WO | 2018/015573 A2 | 1/2018 |

(Continued)

OTHER PUBLICATIONS

Cheng et al., "TREM2-activating antibodies abrogate the negative pleiotropic effects of the Alzheimer's disease variant Trem2R47H on murine myeloid cell function," J. Biol. Chem., 2018, vol. 293, Issue 32, pp. 12620-12633.

(Continued)

*Primary Examiner* — Kimberly Ballard
*Assistant Examiner* — Stacey N MacFarlane
(74) *Attorney, Agent, or Firm* — Kilpatrick Townsend & Stockton LLP

(57) ABSTRACT

In one aspect, antibodies that specifically bind to a human triggering receptor expressed on myeloid cells 2 (TREM2) protein are provided. In some embodiments, the antibody decreases levels of soluble TREM2 (sTREM2). In some embodiments, the antibody enhances TREM2 activity.

20 Claims, 25 Drawing Sheets
Specification includes a Sequence Listing.

(56) References Cited

FOREIGN PATENT DOCUMENTS

| | | | |
|---|---|---|---|
| WO | 2018/119351 | A1 | 6/2018 |
| WO | 2018/134815 | A2 | 7/2018 |
| WO | 2018/195506 | A1 | 10/2018 |
| WO | 2019/021233 | A1 | 1/2019 |
| WO | 2019/028292 | A1 | 2/2019 |
| WO | 2019/055841 | A1 | 3/2019 |
| WO | 2019/079529 | A1 | 4/2019 |
| WO | 2019/118513 | A1 | 6/2019 |
| WO | 2020/011968 | A1 | 1/2020 |
| WO | 2020/055975 | A1 | 3/2020 |
| WO | 2020/079580 | A1 | 4/2020 |
| WO | 2020/121195 | A1 | 6/2020 |
| WO | 2020/123664 | A1 | 6/2020 |
| WO | 2020/172450 | A1 | 8/2020 |
| WO | 2020/194317 | A1 | 10/2020 |
| WO | 2021/146256 | A1 | 7/2021 |
| WO | 2021/158986 | A1 | 8/2021 |
| WO | 2021/168194 | A1 | 8/2021 |
| WO | 2022/081765 | A1 | 4/2022 |

OTHER PUBLICATIONS

Database NCBI [Online] Jul. 23, 2016, "immunoglobulin heavy chain variable region, partial [Mus musculus]," GenBank: CAM98769. 1, 3 pages.
GenBank Accession No. AWK57454.1, mailed May 2018, 2 pages.
GenBank Accession No. P01834.2, mailed Mar. 2017, 6 pages.
Hsieh et al., "A Role for TREM2 Ligands in the Phagocytosis of Apoptotic Neuronal Cells by Microglia," J. Neurochem, 2009, 109(4), pp. 1144-1156.
Hu et al., "Triggering Receptor Expressed On Myeloid Cells 2 (Trem2) Dependent Microglial Activation Promotes Cisplatin-Induced Peripheral Neuropathy In Mice," Brain, Behavior and Immunity, vol. 68, 2018, pp. 132-145.
International Search Report and Written Opinion received for International Appl. No. PCT/US2020/019093, mailed on Jul. 15, 2020, 28 pages.
International Search Report and Written Opinion received for International Appl. No. PCT/US2020/019104, mailed on Jun. 11, 2020, 10 pages.
Invitation to Pay Additional Fees, Partial Search Report, and Provisional Opinion for International Appl. No. PCT/US2021/013200, mailed May 7, 2021, 18 pages.
Jay et al., "TREM2 in Neurodegenerative Diseases," Molecular Neurodegeneration, vol. 12, Aug. 2, 2017, pp. 1-33. Available online at https://molecularneurodegeneration.biomedcentral.com/track/pdf/10.1186/s13024-017-0197-5.pdf.
Jiang et al., "Upregulation of TREM2 Ameliorates Neuropathology and Rescues Spatial Cognitive Impairment in a Transgenic Mouse Model of Alzheimer's Disease," Neuropsychopharmacology, 2014, 39, pp. 2949-2962.
Kariolis et al., "Brain delivery of therapeutic proteins using an Fc fragment blood-brain barrier transport vehicle in mice and monkeys," Sci. Transl. Med., 2020, vol. 12, Issue 545, eaay1359, pp. 1-13.
Kobayashi et al., "TREM2/DAP12 Signal Elicits Proinflammatory Response in Microglia and Exacerbates Neuropathic Pain," The Journal of Neuroscience, vol. 36, No. 43, Oct. 26, 2016, pp. 11138-11150.
Kussie et al., "A single engineered amino acid substitution changes antibody fine specificity," Journal of Immunology, 152(1): 146-152, 1994.
Lewcock et al., "Emerging Microglia Biology Defines Novel Therapeutic Approaches for Alzheimer's Disease," Neuron, Dec. 9, 2020, 108(5), pp. 801-821.
Nugent et al., "TREM2 Regulates Microglial Cholesterol Metabolism upon Chronic Phagocytic Challenge," Neuron, Mar. 4, 2020, 105(5), pp. 1-18. e1-e9.
Panka et al., "Variable region framework differences result in decreased or increased affinity of variant anti-digoxin antibodies," Proc Natl Acad Sci USA, 85(9):3080-4, May 1988.
Piccio et al., "Blockade of TREM-2 exacerbates experimental autoimmune encephalomyelitis," Eur. J. Immunol., 2007, 37, pp. 1290-1301.
Rudikoff et al., "Single amino acid substitution altering antigen-binding specificity," Proc. Nat. Acad. Sci. USA, vol. 79, pp. 1979-1983, Mar. 1982.
Satoh et al., "A survey of TREM2 antibodies reveals neuronal but not microglial staining in formalin-fixed paraffin-embedded post-mortem Alzheimer's brain tissues," Alzheimer's Research & Therapy, vol. 5, No. 4, Article 30, pp. 1-3, Jul. 8, 2013.
Schlepckow et al., "Enhancing Protective Microglial Activities with a Dual Function TREM2 Antibody to the Stalk Region," EMBO Mol Med., Apr. 7, 2020, 12(4):e11227, pp. 1-22.
Sudom et al., "Molecular basis for the loss-of-function effects of the Alzheimer's disease-associated R47H variant of the immune receptor TREM2," J. Biol. Chem., 2018, vol. 293, Issue 32, pp. 12634-12646.
Sun et al., "TREM-2 Promotes Host Resistance Against Pseudomonas aeruginosa Infection by Suppressing Corneal Inflammation via a PI3K/Akt Signaling Pathway," Immunology and Microbiology, Invest Ophthalmol Vis Sci, vol. 54, No. 5, May 2013, pp. 3451-3462.
Zhao et al., "A tetravalent TREM2 agonistic antibody reduced amyloid pathology in a mouse model of Alzheimer's disease," Sci. Transl. Med., 14:eabq0095, Sep. 7, 2022, 15 pages.
Almagro, J. et al., "Progress and Challenges in the Design and Clinical Development of Antibodies for Cancer Therapy," Frontiers in Immunology, 8(1751): 1-19, 2018.
Dondelinger, M. et al., "Understanding the Significance and Implications of Antibody Numbering and Antigen-Binding Surface/Residue Definition," Front. Immunol., 9(2278): 1-15, 2018.
Frenzel, A. et al., "Chapter 6: Antibody Affinity," Handbook of Therapeutic Antibodies, Eds S. Dubel and J.M. Reichert, Wiley-VCH Verlag Gmbh & Co., Weinheim, Germany, pp. 115-139, 2014.
Gonzales, N. et al., "Minimizing the Immunogenicity of Antibodies for Clinical Application," Tumor Biology, 26(1):31-43, 2005.
Kunik, V. et al., "Structural consensus among antibodies defines the antigen binding site," PLOS Comput. Biol., 8(2):e1002388, 2012, 12 pages.
Liu, L., "Pharmacokinetics of monoclonal antibodies and FC-fusion proteins," Protein Cell, 9(1): 15-32, 2018.
Lucchese, G. et al., "How a single amino acid change may alter the immunological information of a peptide," Frontiers in Bioscience, 4(5):1843-52, 2012.
Mix, E. et al., "Immunoglobulins-basic considerations," J. Neurol., 253(Suppl 5): V9-17, 2006.
Sela-Culang, I. et al., "The structural basis of antibody-antigen recognition," Frontiers in Immunology, 4(302):1- 13, 2013.
Wark, K. and P. Hudson, "Latest technologies for the enhancement of antibody affinity," Adv. Drug Deliv. Rev., 58(5-6):657-70, 2006.
Wu, H. et al., "Humanization of a murine monoclonal antibody by simultaneous optimization of framework and CDR residues," J. Mol. Biol., 294(1): 151-62, 1999.

CL0020188

CL0020123

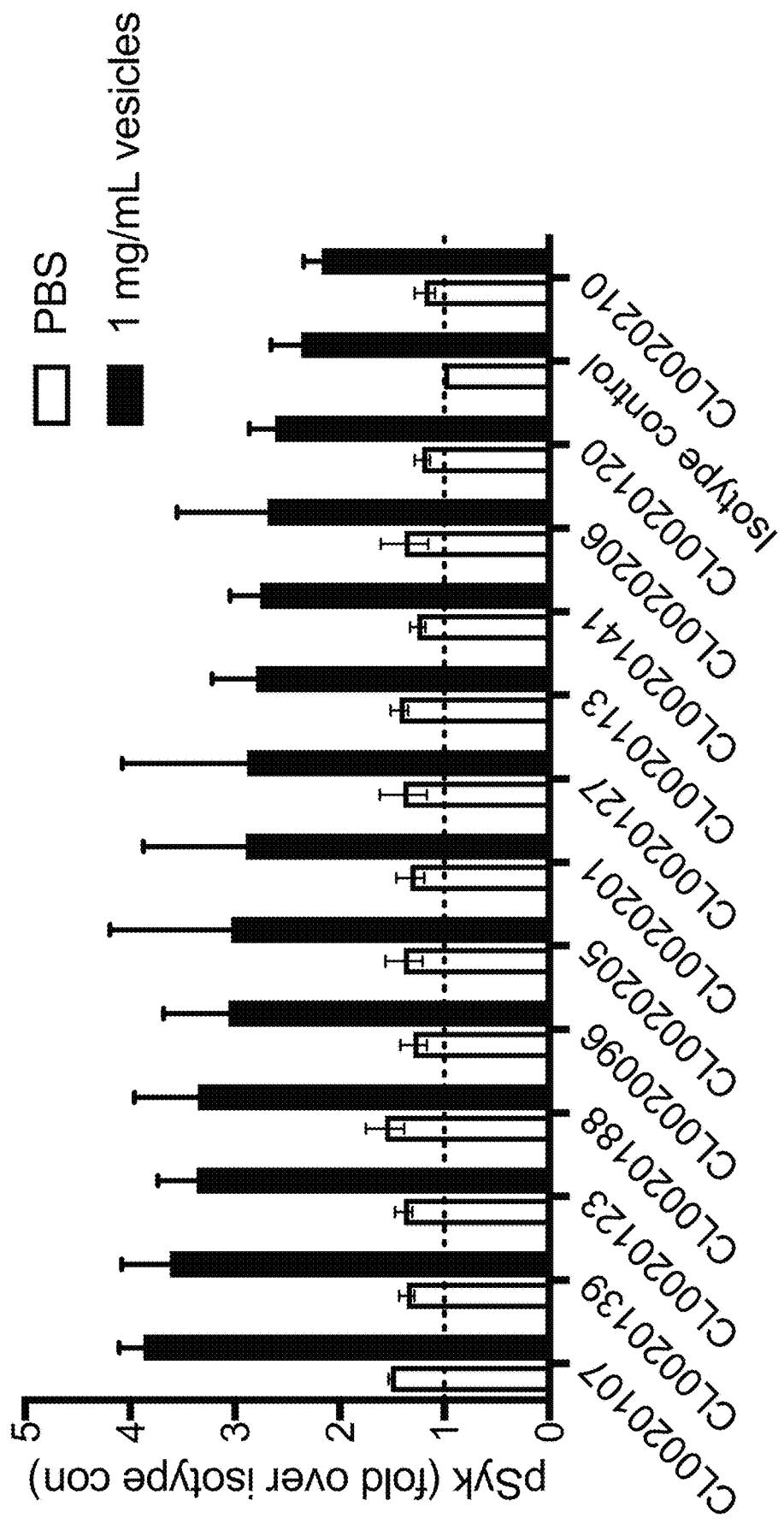

CL0020141

CL0020188

CL0020139

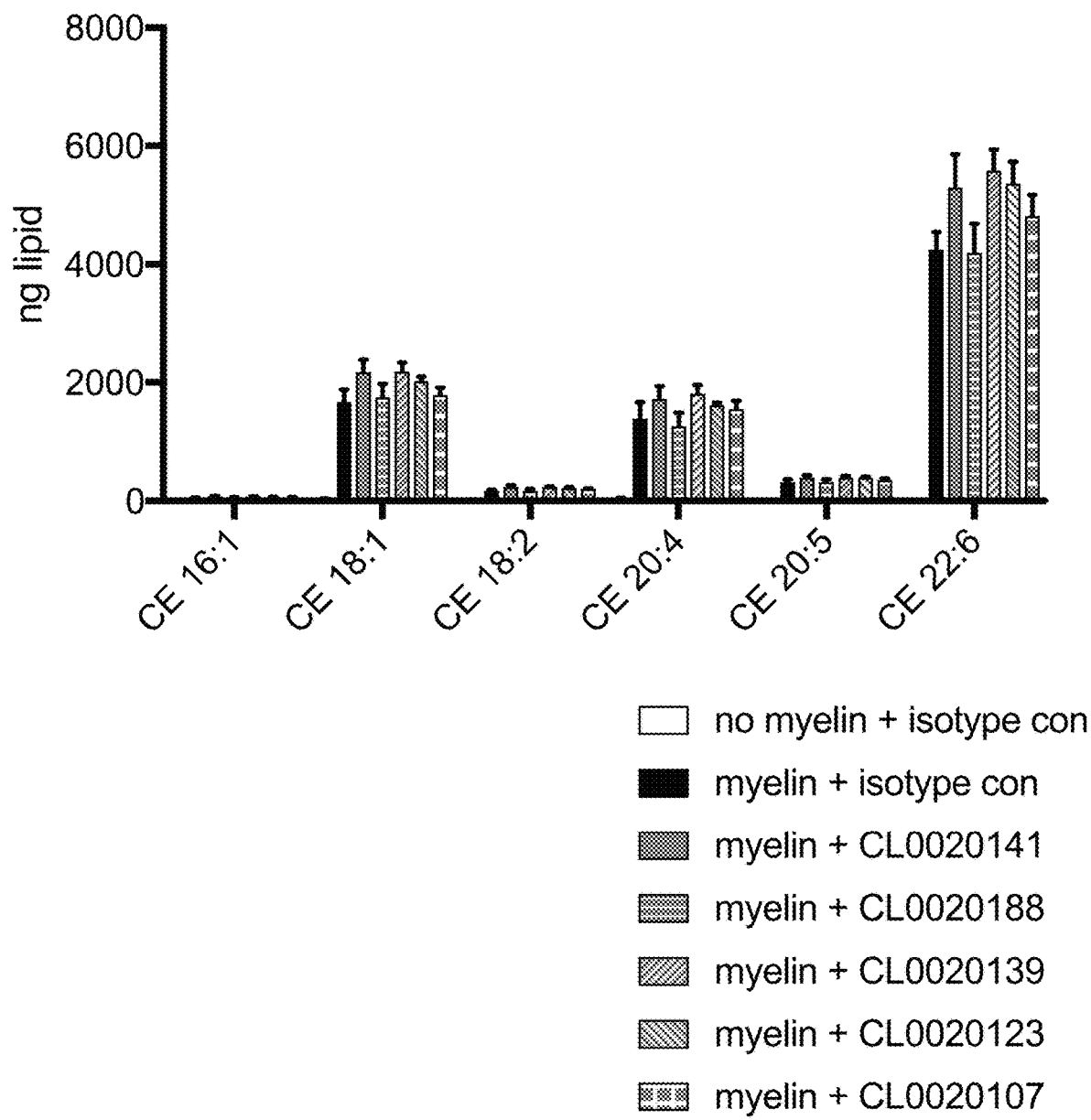

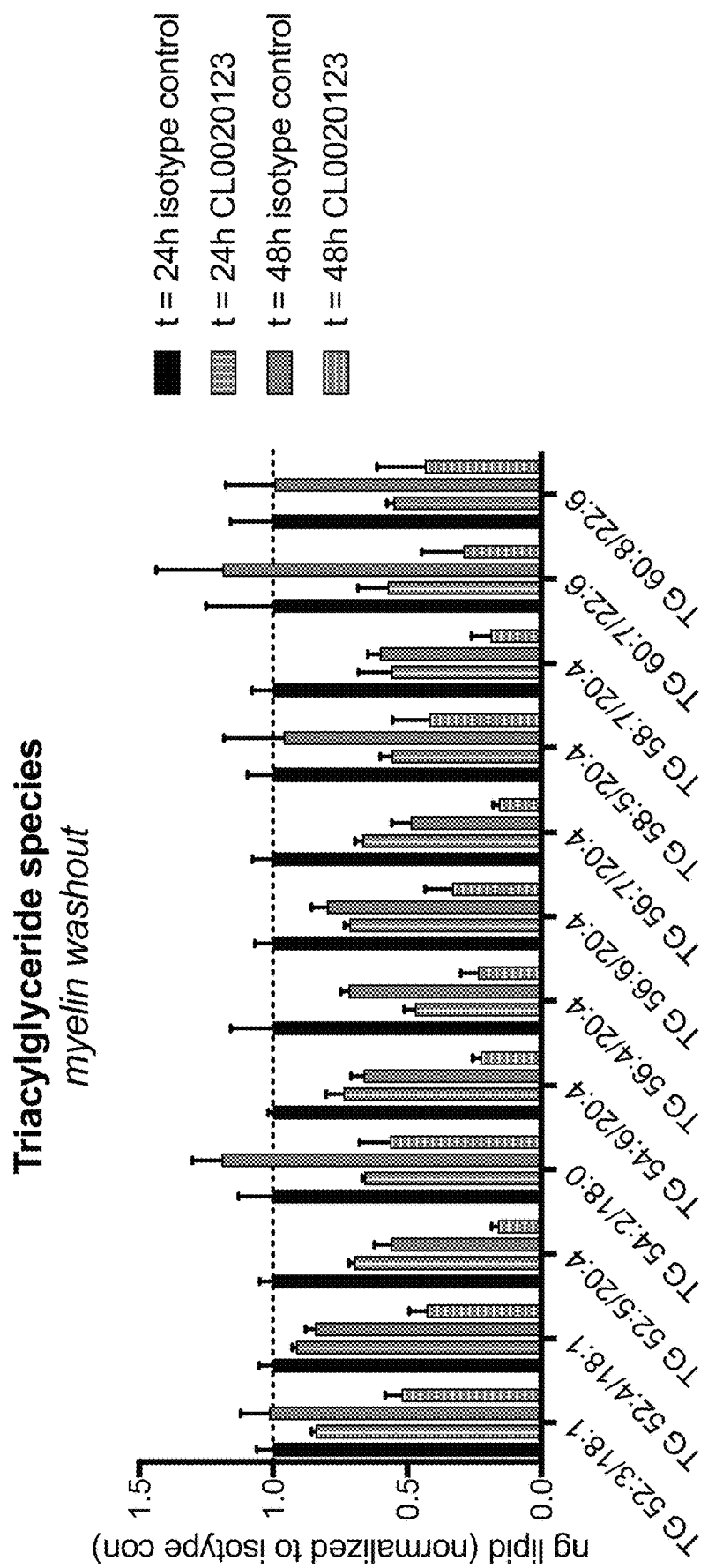

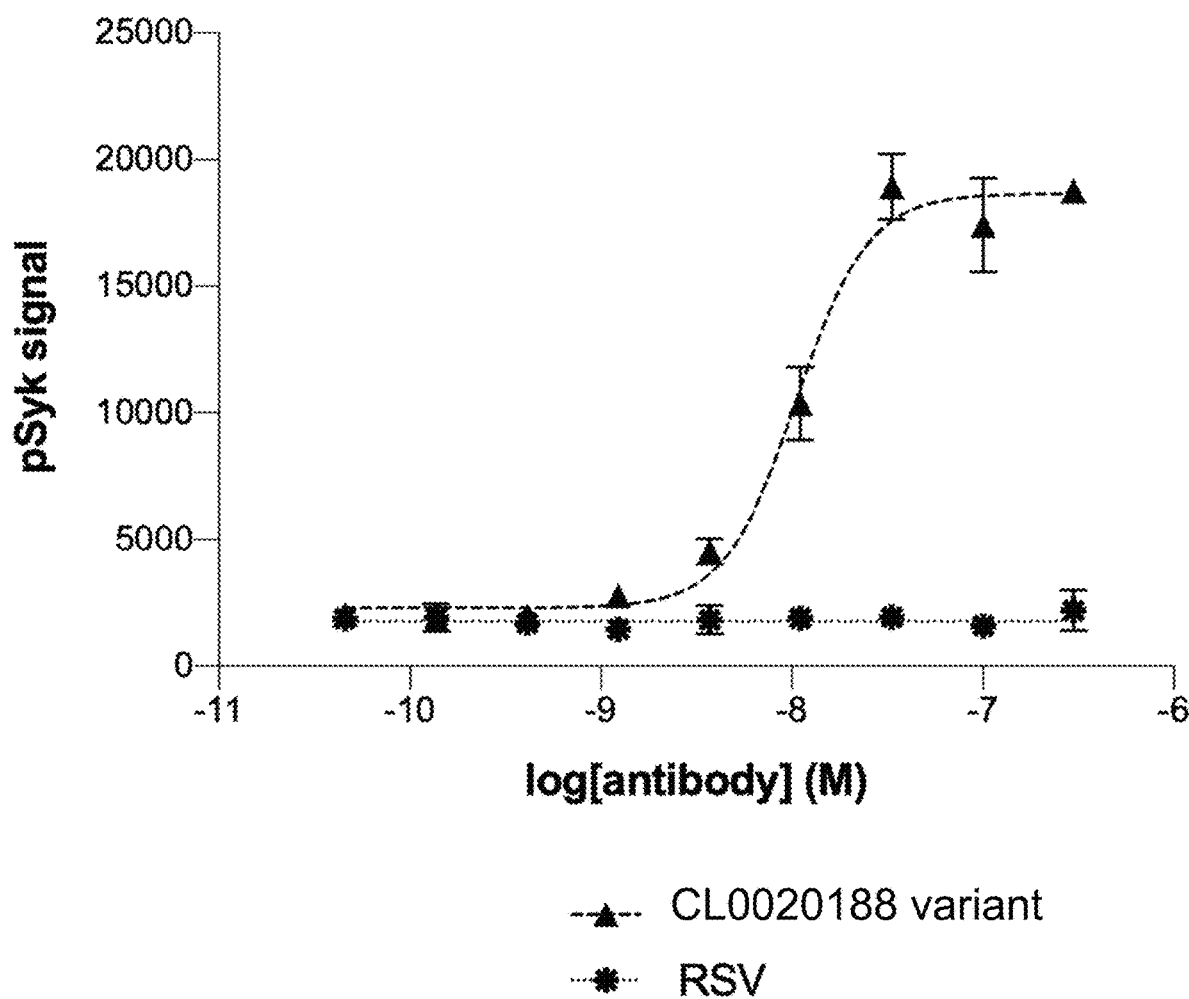

CL0020188 Variant

CL0020123 Variant

ANTI-TREM2 ANTIBODIES AND METHODS OF USE THEREOF

CROSS-REFERENCE TO RELATED APPLICATIONS

This application is a continuation of International Application No. PCT/US2020/019104, filed Feb. 20, 2020, which claims priority to U.S. Provisional Application No. 62/808,141, filed Feb. 20, 2019, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Aug. 17, 2021, is named 102342-003320US-1263123_SL.txt and is 194,047 bytes in size.

BACKGROUND

Triggering receptor expressed on myeloid cells-2 (TREM2) is a transmembrane receptor that is expressed on microglia and is believed to function in regulating phagocytosis, cell survival, and the production of pro-inflammatory cytokines. Mutations in TREM2 have been identified in neurodegenerative diseases including Alzheimer's disease, Nasu-Hakola disease, Parkinson's disease, amyotrophic lateral sclerosis, and frontotemporal dementia. Additionally, altered levels of soluble TREM2 (sTREM2) have been reported in the cerebrospinal fluid of patients having Alzheimer's disease or frontotemporal dementia who have a mutation in TREM2.

There remains a need for therapeutic agents that modulate TREM2 activity or levels of sTREM2.

BRIEF SUMMARY

In one aspect, isolated antibodies or antigen-binding fragments thereof that specifically binds to a human triggering receptor expressed on myeloid cells 2 (TREM2) are provided. In some embodiments, the antibody or antigen-binding fragment thereof comprises:

(a) a CDR-H1 sequence comprising the sequence of G-Y-T-F-T-$\alpha_6$-Y-$\alpha_8$-$\alpha_9$-$\alpha_{10}$ (SEQ ID NO:293), wherein $\alpha_6$ is N, S, or D; as is W or N; $\alpha 9$ is I or M; and am is S, T, M, or H;

(b) a CDR-H2 sequence comprising the sequence of $\beta_1$-I-$\beta_3$-P-$\beta_5$-$\beta_6$-$\beta_7$-$\beta_8$-$\beta_9$-$\beta_{10}$-Y-N-$\beta_{13}$-$\beta_{14}$-F-$\beta_{16}$-$\beta_{17}$ (SEQ ID NO:294), wherein $\beta_1$ is D or Y; $\beta_3$ is Y or F; $\beta_5$ is H, G, S, N, or Y; $\beta_6$ is S or N; $\beta_7$ is T or G; $\beta_8$ is S, N, or G; $\beta_9$ is T or N; $\beta_{10}$ is N or G; $\beta_{13}$ is E or Q; $\beta_{14}$ is R or K; $\beta_{16}$ is R or K; and $\beta_{17}$ is S, G, or N;

(c) a CDR-H3 sequence comprising the sequence of $\gamma_1$-R-$\gamma_3$-G-$\gamma_5$-G-$\gamma_7$-$\gamma_8$-$\gamma_9$ (SEQ ID NO:295), wherein $\gamma_1$ is A or S; $\gamma_3$ is E or S; $\gamma_5$ is F, Y, R, or T; $\gamma_7$ is I or F; $\gamma_8$ is S or A; and $\gamma_9$ is A or Y;

(d) a CDR-L1 sequence comprising:
(i) the sequence of $\delta_1$-A-$\delta_3$-$\delta_4$-$\delta_5$-V-$\delta_7$-$\delta_8$-Y-$\delta_{10}$-$\delta_{11}$ (SEQ ID NO:296), wherein $\delta_1$ is S or K; $\delta_3$ is T or S; $\delta_4$ is S or E; $\delta_5$ is S or N; $\delta_7$ is absent or G; $\delta_8$ is S or T; $\delta_{10}$ is M or V; and $\delta_{11}$ is H or S; or
(ii) the sequence of $\delta_1$-S-S-$\delta_4$-S-L-L-$\delta_8$-S-$\delta_{10}$-N-$\delta_{12}$-$\delta_{13}$-$\delta_{14}$-Y-L-$\delta_{17}$ (SEQ ID NO:297), wherein $\delta_1$ is K or R; $\delta_4$ is Q or K; $\delta_8$ is N or H; $\delta_{10}$ is G or absent; $\delta_{12}$ is Q or G; $\delta_{13}$ is K or N; $\delta_{14}$ is N or T; and $\delta_{17}$ is T or Y;

(e) a CDR-L2 sequence comprising the sequence of $\varepsilon_1$-$\varepsilon_2$-S-$\varepsilon_4$-$\varepsilon_5$-$\varepsilon_6$-$\varepsilon_7$ (SEQ ID NO:298), wherein $\varepsilon_1$ is S, G, W or Q; $\varepsilon_2$ is T, A, or M; $\varepsilon_4$ is N or T; $\varepsilon_5$ is L or R; $\varepsilon_6$ is A, Y, or E; and $\varepsilon_7$ is S or T; and (f) a CDR-L3 sequence comprising the sequence of $\phi_1$-$\phi_2$-$\phi_3$-$\phi_4$-$\phi_5$-$\phi_6$-P-$\phi_8$-T (SEQ ID NO:299), wherein $\phi_1$ is Q, G, or M; $\phi_2$ is Q or N; $\phi_3$ is R, S, D, or H; $\phi_4$ is S, Y, or L; $\phi_5$ is S or Q; $\phi_6$ is Y or F; and $\phi_8$ is L, F, or Y.

In some embodiments, the CDR-H1 sequence is selected from SEQ ID NOS:4, 12, 20, 28, and 36. In some embodiments, the CDR-H2 sequence is selected from SEQ ID NOS:5, 13, 21, 29, and 37. In some embodiments, the CDR-H3 sequence is selected from SEQ ID NOS:6, 14, 22, 30, and 38. In some embodiments, the CDR-L1 sequence is selected from SEQ ID NOS:7, 15, 23, 31, and 39. In some embodiments, the CDR-L2 sequence is selected from SEQ ID NOS:8, 16, 24, 32, and 40. In some embodiments, the CDR-L3 sequence is selected from SEQ ID NOS:9, 17, 25, 33, and 41.

In some embodiments, the antibody or antigen-binding fragment comprises:
(a) a CDR-H1 comprising the amino acid sequence of SEQ ID NO:28, a CDR-H2 comprising the amino acid sequence of SEQ ID NO:29, a CDR-H3 comprising the amino acid sequence of SEQ ID NO:30, a CDR-L1 comprising the amino acid sequence of SEQ ID NO:31, a CDR-L2 comprising the amino acid sequence of SEQ ID NO:32, and a CDR-L3 comprising the amino acid sequence of SEQ ID NO:33; or
(b) a CDR-H1 comprising the amino acid sequence of SEQ ID NO:36, a CDR-H2 comprising the amino acid sequence of SEQ ID NO:37, a CDR-H3 comprising the amino acid sequence of SEQ ID NO:38, a CDR-L1 comprising the amino acid sequence of SEQ ID NO:39, a CDR-L2 comprising the amino acid sequence of SEQ ID NO:40, and a CDR-L3 comprising the amino acid sequence of SEQ ID NO:41.

In some embodiments, the antibody or antigen-binding fragment comprises a heavy chain variable region ($V_H$) sequence that has at least 85% sequence identity to any one of SEQ ID NOS:2, 10, 18, 26, or 34. In some embodiments, the $V_H$ sequence has at least 90% sequence identity to SEQ ID NO:2. In some embodiments, the $V_H$ sequence has at least 95% sequence identity to SEQ ID NO:2. In some embodiments, the $V_H$ sequence comprises SEQ ID NO:2.

In some embodiments, the antibody or antigen-binding fragment comprises a light chain variable region ($V_L$) sequence that has at least 85% sequence identity to any one of SEQ ID NOS:3, 11, 19, 27, or 35. In some embodiments, the $V_L$ sequence has at least 90% sequence identity to SEQ ID NO:3. In some embodiments, the $V_L$ sequence has at least 95% sequence identity to SEQ ID NO:3. In some embodiments, the $V_L$ sequence comprises SEQ ID NO:3.

In some embodiments, the antibody or antigen-binding fragment comprises:
(a) a $V_H$ sequence comprising SEQ ID NO:26 and a $V_L$ sequence comprising SEQ ID NO:27; or
(b) a $V_H$ sequence comprising SEQ ID NO:34 and a $V_L$ sequence comprising SEQ ID NO:35.

In some embodiments, the antibody or antigen-binding fragment comprises:

(a) a CDR-H1 sequence comprising the sequence of G-Y-T-F-T-$\alpha_6$-Y-W-I-$\alpha_{10}$ (SEQ ID NO:300), wherein $\alpha_6$ is N or S; and am is S, T or M;

(b) a CDR-H2 sequence comprising the sequence of D-I-Y-P-$\beta_5$-S-$\beta_7$-$\beta_8$-T-N-Y-N-E-$\beta_{14}$-F-$\beta_{16}$-$\beta_{17}$ (SEQ ID NO:301), wherein $\beta_5$ is H, G, or S; $\beta_7$ is T or G; $\beta_8$ is S or N; $\beta_{14}$ is R or K; $\beta_{16}$ is R or K; and $\beta_{17}$ is S or N;

(c) a CDR-H3 sequence comprising the sequence of $\gamma_1$-R-E-G-$\gamma_5$-G-I-S-A (SEQ ID NO:302), wherein $\gamma_1$ is A or S; and $\gamma_5$ is F or Y;

(d) a CDR-L1 sequence comprising the sequence of $\delta_1$-A-$\delta_3$-$\delta_4$-$\delta_5$-V-$\delta_7$-$\delta_8$-Y-$\delta_{10}$-$\delta_{11}$ (SEQ ID NO:303), wherein $\delta_1$ is S or K; $\delta_3$ is T or S; $\delta_4$ is S or E; $\delta_5$ is S or N; $\delta_7$ is absent or G; $\delta_8$ is absent or T; $\delta_{10}$ is M or V; and $\delta_{11}$ is H or S;

(e) a CDR-L2 sequence comprising the sequence of $\epsilon_1$-$\epsilon_2$-S-N-$\epsilon_5$-$\epsilon_6$-$\epsilon_7$ (SEQ ID NO:304), wherein $\epsilon_1$ is S or G; $\epsilon_2$ is T or A; $\epsilon_5$ is L or R; $\epsilon_6$ is A or Y; and $\epsilon_7$ is S or T; and (f) a CDR-L3 sequence comprising the sequence of $\phi_1$-Q-$\phi_3$-$\phi_4$-S-$\phi_6$-P-$\phi_8$-T (SEQ ID NO:305), wherein $\phi_1$ is Q or G; $\phi_3$ is R or S; $\phi_4$ is S or Y; $\phi_6$ is Y or F; and $\phi_8$ is L or F.

In some embodiments, the CDR-H1 sequence is selected from SEQ ID NOS:4, 12, and 20. In some embodiments, the CDR-H2 sequence is selected from SEQ ID NOS:5, 13, and 21. In some embodiments, the CDR-H3 sequence is selected from SEQ ID NOS:6, 14, and 22. In some embodiments, the CDR-L1 sequence is selected from SEQ ID NOS:7, 15, and 23. In some embodiments, the CDR-L2 sequence is selected from SEQ ID NOS:8, 16, and 24. In some embodiments, the CDR-L3 sequence is selected from SEQ ID NOS:9, 17, and 25.

In some embodiments, the antibody or antigen-binding fragment comprises:
  (a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO:6, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO:9; or
  (b) a CDR-H1 comprising the amino acid sequence of SEQ ID NO:12, a CDR-H2 comprising the amino acid sequence of SEQ ID NO:13, a CDR-H3 comprising the amino acid sequence of SEQ ID NO:14, a CDR-L1 comprising the amino acid sequence of SEQ ID NO:15, a CDR-L2 comprising the amino acid sequence of SEQ ID NO:16, and a CDR-L3 comprising the amino acid sequence of SEQ ID NO:17; or
  (c) a CDR-H1 comprising the amino acid sequence of SEQ ID NO:20, a CDR-H2 comprising the amino acid sequence of SEQ ID NO:21, a CDR-H3 comprising the amino acid sequence of SEQ ID NO:22, a CDR-L1 comprising the amino acid sequence of SEQ ID NO:23, a CDR-L2 comprising the amino acid sequence of SEQ ID NO:24, and a CDR-L3 comprising the amino acid sequence of SEQ ID NO:25.

In some embodiments, the antibody or antigen-binding fragment comprises:
  (a) a $V_H$ sequence comprising SEQ ID NO:2 and a $V_L$ sequence comprising SEQ ID NO:3; or
  (b) a $V_H$ sequence comprising SEQ ID NO:10 and a $V_L$ sequence comprising SEQ ID NO:11; or
  (c) a $V_H$ sequence comprising SEQ ID NO:18 and a $V_L$ sequence comprising SEQ ID NO:19.

In some embodiments, an antibody or antigen-binding fragment thereof that specifically binds to TREM2 comprises:
  (a) a CDR-H1 sequence comprising the sequence of G-Y-$\alpha_3$-F-$\alpha_5$-S-$\alpha_7$-as-$\alpha_9$-$\alpha_{10}$ (SEQ ID NO:306), wherein $\alpha_3$ is S or K; $\alpha_5$ is T or P; $\alpha_7$ is Y or F; $\alpha_8$ is L or I; $\alpha_9$ is M or I; and $\alpha_{10}$ is N or H;
  (b) a CDR-H2 sequence comprising the sequence of Y-I-N-P-Y-S-$\beta_7$-G-$\beta_9$-N-Y-N-E-K-F-K-$\beta_{17}$ (SEQ ID NO:307), wherein $\beta_7$ is A or D; $\beta_9$ is S or T; and $\beta_{17}$ is D or G;
  (c) a CDR-H3 sequence comprising the sequence of comprising the sequence of ARSSYRYGFDY (SEQ ID NO:46);
  (d) a CDR-L1 sequence comprising the sequence of comprising the sequence of KASEDIYNRLA (SEQ ID NO:47);
  (e) a CDR-L2 sequence comprising the sequence of comprising the sequence of GATSLET (SEQ ID NO:48); and
  (f) a CDR-L3 sequence comprising the sequence of comprising the sequence Q-Q-$\phi_3$-W-S-$\phi_6$-P-W-T (SEQ ID NO:308), wherein $\phi_3$ is Y or S; and $\phi_6$ is T or I.

In some embodiments, the CDR-H1 sequence is selected from SEQ ID NOS:44, 52, and 56. In some embodiments, the CDR-H2 sequence is selected from SEQ ID NOS:45, 53, and 57. In some embodiments, the CDR-L4 sequence is selected from SEQ ID NOS:49 and 292.

In some embodiments, the antibody or antigen-binding fragment comprises:
  (a) a CDR-H1 comprising the amino acid sequence of SEQ ID NO:44, a CDR-H2 comprising the amino acid sequence of SEQ ID NO:45, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49; or
  (b) a CDR-H1 comprising the amino acid sequence of SEQ ID NO:52, a CDR-H2 comprising the amino acid sequence of SEQ ID NO:53, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:292; or
  (c) a CDR-H1 comprising the amino acid sequence of SEQ ID NO:56, a CDR-H2 comprising the amino acid sequence of SEQ ID NO:57, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49.

In some embodiments, the antibody or antigen-binding fragment comprises a $V_H$ sequence that has at least 85% sequence identity to any one of SEQ ID NOS:42, 50, or 54. In some embodiments, the $V_H$ sequence has at least 90% sequence identity to SEQ ID NO:42. In some embodiments, the $V_H$ sequence has at least 95% sequence identity to SEQ ID NO:42. In some embodiments, the $V_H$ sequence comprises SEQ ID NO:42.

In some embodiments, the antibody or antigen-binding fragment comprises a $V_L$ sequence that has at least 85% sequence identity to any one of SEQ ID NOS:43, 51, or 55.

In some embodiments, the $V_L$ sequence has at least 90% sequence identity to SEQ ID NO:43. In some embodiments, the $V_L$ sequence has at least 95% sequence identity to SEQ ID NO:43. In some embodiments, the $V_L$ sequence comprises SEQ ID NO:43.

In some embodiments, the antibody or antigen-binding fragment comprises:
(a) a $V_H$ sequence comprising SEQ ID NO:42 and a $V_L$ sequence comprising SEQ ID NO:43; or
(b) a $V_H$ sequence comprising SEQ ID NO:50 and a $V_L$ sequence comprising SEQ ID NO:51; or
(c) a $V_H$ sequence comprising SEQ ID NO:54 and a $V_L$ sequence comprising SEQ ID NO:55.

In some embodiments, an antibody or antigen-binding fragment thereof that specifically binds to TREM2 comprises:
(a) a CDR-H1 sequence comprising the sequence of GFSIEDFYIH (SEQ ID NO:105);
(b) a CDR-H2 sequence comprising the sequence of W-I-D-P-E-$\beta_6$-G-$\beta_8$-S-K-Y-A-P-K-F-Q-G (SEQ ID NO:309), wherein $\beta_6$ is N or Q and $\beta_8$ is D or E;
(c) a CDR-H3 sequence comprising the sequence of HADHGNYGSTMDY (SEQ ID NO:107);
(d) a CDR-L1 sequence comprising the sequence of HASQHINVWLS (SEQ ID NO:108);
(e) a CDR-L2 sequence comprising the sequence of KASNLHT (SEQ ID NO:109); and
(f) a CDR-L3 sequence comprising the sequence of QQGQTYPRT (SEQ ID NO:110).

In some embodiments, the CDR-H2 sequence is selected from SEQ ID NOS:106, 115, 117, and 119.

In some embodiments, the antibody or antigen-binding fragment comprises:
(a) a CDR-H1 comprising the amino acid sequence of SEQ ID NO:105, a CDR-H2 comprising the amino acid sequence of SEQ ID NO:106, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(b) a CDR-H1 comprising the amino acid sequence of SEQ ID NO:105, a CDR-H2 comprising the amino acid sequence of SEQ ID NO:115, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(c) a CDR-H1 comprising the amino acid sequence of SEQ ID NO:105, a CDR-H2 comprising the amino acid sequence of SEQ ID NO:117, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(d) a CDR-H1 comprising the amino acid sequence of SEQ ID NO:105, a CDR-H2 comprising the amino acid sequence of SEQ ID NO:119, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110.

In some embodiments, the antibody or antigen-binding fragment comprises a $V_H$ sequence that has at least 85% sequence identity to any one of SEQ ID NOS:103, 111, 113, 114, 116, 118, 120, 121, and 122. In some embodiments, the $V_H$ sequence has at least 90% sequence identity to SEQ ID NO:103. In some embodiments, the $V_H$ sequence has at least 95% sequence identity to SEQ ID NO:103. In some embodiments, the $V_H$ sequence comprises SEQ ID NO:103. In some embodiments, the $V_H$ sequence has at least 90% sequence identity to SEQ ID NO:118. In some embodiments, the $V_H$ sequence has at least 95% sequence identity to SEQ ID NO:118. In some embodiments, the $V_H$ sequence comprises SEQ ID NO:118. In some embodiments, the $V_H$ sequence has at least 90% sequence identity to SEQ ID NO:121. In some embodiments, the $V_H$ sequence has at least 95% sequence identity to SEQ ID NO:121. In some embodiments, the $V_H$ sequence comprises SEQ ID NO:121.

In some embodiments, the antibody or antigen-binding fragment comprises a $V_L$ sequence that has at least 85% sequence identity to SEQ ID NO:104 or SEQ ID NO:112. In some embodiments, the $V_L$ sequence has at least 90% sequence identity to SEQ ID NO:104. In some embodiments, the $V_L$ sequence has at least 95% sequence identity to SEQ ID NO:104. In some embodiments, the $V_L$ sequence comprises SEQ ID NO:104. In some embodiments, the $V_L$ sequence has at least 90% sequence identity to SEQ ID NO:112. In some embodiments, the $V_L$ sequence has at least 95% sequence identity to SEQ ID NO:112. In some embodiments, the $V_L$ sequence comprises SEQ ID NO:112.

In some embodiments, the antibody or antigen-binding fragment comprises:
(a) a $V_H$ sequence comprising SEQ ID NO:103 and a $V_L$ sequence comprising SEQ ID NO:104; or
(b) a $V_H$ sequence comprising SEQ ID NO:111 and a $V_L$ sequence comprising SEQ ID NO:112; or
(c) a $V_H$ sequence comprising SEQ ID NO:113 and a $V_L$ sequence comprising SEQ ID NO:112; or
(d) a $V_H$ sequence comprising SEQ ID NO:114 and a $V_L$ sequence comprising SEQ ID NO:112; or
(e) a $V_H$ sequence comprising SEQ ID NO:116 and a $V_L$ sequence comprising SEQ ID NO:112; or
(f) a $V_H$ sequence comprising SEQ ID NO:118 and a $V_L$ sequence comprising SEQ ID NO:112; or
(g) a $V_H$ sequence comprising SEQ ID NO:120 and a $V_L$ sequence comprising SEQ ID NO:112; or
(h) a $V_H$ sequence comprising SEQ ID NO:121 and a $V_L$ sequence comprising SEQ ID NO:112; or
(i) a $V_H$ sequence comprising SEQ ID NO:122 and a $V_L$ sequence comprising SEQ ID NO:112.

In some embodiments, an antibody or antigen-binding fragment thereof that specifically binds to TREM2 comprises:
(a) a CDR-H1 sequence comprising the sequence of G-F-S-L-T-$\alpha_6$-Y-G-$\alpha_9$-$\alpha_{10}$ (SEQ ID NO:310), wherein $\alpha_6$ is T or S; $\alpha_9$ is I or V; and $\alpha_{10}$ is H or Q;
(b) a CDR-H2 sequence comprising the sequence of V-I-W-T-G-G-$\beta_7$-T-$\beta_9$-$\beta_{10}$-N-A-A-F-M-S (SEQ ID NO:311), wherein $\beta_7$ is S or T; $\beta_9$ is A or D; and $\beta_{10}$ is F or Y;
(c) a CDR-H3 sequence comprising the sequence of A-K-$\gamma_3$-G-F-H-S-A-$\gamma_9$-D-Y (SEQ ID NO:312), wherein $\gamma_3$ is V or I; and $\gamma_9$ is T, M, or V;
(d) a CDR-L1 sequence comprising the sequence of R-S-S-Q-N-$\delta_6$-V-H-S-N-G-N-T-Y-L-E (SEQ ID NO:313), wherein $\delta_6$ is L or I;
(e) a CDR-L2 sequence comprising the sequence of KVSNRFS (SEQ ID NO:89); and (f) a CDR-L3 sequence comprising the sequence of F-Q-G-S-H-$\phi_6$-P-F-T (SEQ ID NO:314), wherein $\phi_6$ is V or I.

In some embodiments, the CDR-H1 sequence is selected from SEQ ID NOS:85, 93, or 100, In some embodiments, the CDR-H2 sequence is selected from SEQ ID NOS:86, 94, or 101. In some embodiments, the CDR-H3 sequence is selected from SEQ ID NOS:87, 95, or 102. In some embodiments, the CDR-L1 sequence is selected from SEQ ID NOS:88 or 96. In some embodiments, the CDR-L3 sequence is selected from SEQ ID NOS:90 or 97.

In some embodiments, the antibody or antigen-binding fragment comprises:
(a) a CDR-H1 comprising the amino acid sequence of SEQ ID NO:85, a CDR-H2 comprising the amino acid sequence of SEQ ID NO:86, a CDR-H3 comprising the amino acid sequence of SEQ ID NO:87, a CDR-L1 comprising the amino acid sequence of SEQ ID NO:88, a CDR-L2 comprising the amino acid sequence of SEQ ID NO:89, and a CDR-L3 comprising the amino acid sequence of SEQ ID NO:90; or
(b) a CDR-H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:97; or
(c) a CDR-H1 comprising the amino acid sequence of SEQ ID NO:100, a CDR-H2 comprising the amino acid sequence of SEQ ID NO:101 a CDR-H3 comprising the amino acid sequence of SEQ ID NO:102, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:90.

In some embodiments, the antibody or antigen-binding fragment comprises a $V_H$ sequence that has at least 85% sequence identity to any one of SEQ ID NOS:83, 91, or 98. In some embodiments, the $V_H$ sequence has at least 90% sequence identity to SEQ ID NO:83. In some embodiments, the $V_H$ sequence has at least 95% sequence identity to SEQ ID NO:83. In some embodiments, the $V_H$ sequence comprises SEQ ID NO:83.

In some embodiments, the antibody or antigen-binding fragment comprises a $V_L$ sequence that has at least 85% sequence identity to any one of SEQ ID NOS:84, 92, or 99. In some embodiments, the $V_L$ sequence has at least 90% sequence identity to SEQ ID NO:84. In some embodiments, the $V_L$ sequence has at least 95% sequence identity to SEQ ID NO:84. In some embodiments, the $V_L$ sequence comprises SEQ ID NO:84.

In some embodiments, the antibody or antigen-binding fragment comprises:
(a) a $V_H$ sequence comprising SEQ ID NO:83 and a $V_L$ sequence comprising SEQ ID NO:84; or
(b) a $V_H$ sequence comprising SEQ ID NO:91 and a $V_L$ sequence comprising SEQ ID NO:92; or
(c) a $V_H$ sequence comprising SEQ ID NO:98 and a $V_L$ sequence comprising SEQ ID NO:99.

In some embodiments, an antibody or antigen-binding fragment thereof that specifically binds to TREM2 comprises:
(a) a CDR-H1 sequence comprising the sequence of G-F-T-F-T-$\alpha_6$-F-Y-M-S (SEQ ID NO:315), wherein $\alpha_6$ is D or N;
(b) a CDR-H2 sequence comprising the sequence of V-I-R-N-$\beta_5$-$\beta_6$-N-$\beta_8$-Y-T-$\beta_{11}$-$\beta_{12}$-Y-N-P-S-V-K-G (SEQ ID NO:316), wherein $\beta_5$ is K or R; $\beta_6$ is A or P; $\beta_8$ is G or A; $\beta_{11}$ is A or T; and $\beta_{12}$ is G or D;
(c) a CDR-H3 sequence comprising the sequence of $\gamma_1$-R-L-$\gamma_4$-Y-G-F-D-Y (SEQ ID NO:317), wherein $\gamma_1$ is A or T; and $\gamma_4$ is T or S;
(d) a CDR-L1 sequence comprising the sequence of Q-S-S-K-S-L-L-H-S-$\delta_{10}$-G-K-T-Y-L-N (SEQ ID NO:318), wherein $\delta_{10}$ is N or T;
(e) a CDR-L2 sequence comprising the sequence of WMSTRAS (SEQ ID NO:64); and
(f) a CDR-L3 sequence comprising the sequence of Q-Q-F-L-E-$\phi_6$-P-F-T (SEQ ID NO:319), wherein $\phi_6$ is Y or F.

In some embodiments, the CDR-H1 sequence is selected from SEQ ID NOS:60 or 68. In some embodiments, the CDR-H2 sequence is selected from SEQ ID NOS:61, 69, or 81. In some embodiments, the CDR-H3 sequence is selected from SEQ ID NOS:62, 70, or 73. In some embodiments, the CDR-L1 sequence is selected from SEQ ID NOS:63 or 79. In some embodiments, the CDR-L3 sequence is selected from SEQ ID NOS:65 or 74.

In some embodiments, the antibody or antigen-binding fragment comprises:
(a) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or
(b) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or
(c) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or
(d) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or
(e) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:62, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or
(f) a CDR-H1 comprising the amino acid sequence of SEQ ID NO:68, a CDR-H2 comprising the amino acid sequence of SEQ ID NO:69, a CDR-H3 comprising the amino acid sequence of SEQ ID NO:70, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65.

In some embodiments, the antibody or antigen-binding fragment comprises a $V_H$ sequence that has at least 85% sequence identity to any one of SEQ ID NOS:58, 66, 71, 75, 77, 80, 82, and 350. In some embodiments, the $V_H$ sequence has at least 90% sequence identity to SEQ ID NO:71. In some embodiments, the $V_H$ sequence has at least 95% sequence identity to SEQ ID NO:71. In some embodiments, the $V_H$ sequence comprises SEQ ID NO:71. In some embodiments, the $V_H$ sequence has at least 90% sequence identity to SEQ ID NO:80. In some embodiments, the $V_H$ sequence has at least 95% sequence identity to SEQ ID NO:80. In some embodiments, the $V_H$ sequence comprises SEQ ID NO:80. In some embodiments, the $V_H$ sequence has at least 90% sequence identity to SEQ ID NO:350. In some embodiments, the $V_H$ sequence has at least 95% sequence identity to SEQ ID NO:350. In some embodiments, the $V_H$ sequence comprises SEQ ID NO:350.

In some embodiments, the antibody or antigen-binding fragment comprises a $V_L$ sequence that has at least 85% sequence identity to any one of SEQ ID NOS:59, 67, 72, 76, 78, and 339. In some embodiments, the $V_L$ sequence has at least 90% sequence identity to SEQ ID NO:72. In some embodiments, the $V_L$ sequence has at least 95% sequence identity to SEQ ID NO:72. In some embodiments, the $V_L$ sequence comprises SEQ ID NO:72. In some embodiments, the $V_L$ sequence has at least 90% sequence identity to SEQ ID NO:78. In some embodiments, the $V_L$ sequence has at least 95% sequence identity to SEQ ID NO:78. In some embodiments, the $V_L$ sequence comprises SEQ ID NO:78. In some embodiments, the $V_L$ sequence has at least 90% sequence identity to SEQ ID NO:339. In some embodiments, the $V_L$ sequence has at least 95% sequence identity to SEQ ID NO:339. In some embodiments, the $V_L$ sequence comprises SEQ ID NO:339.

In some embodiments, the antibody or antigen-binding fragment comprises:
 (a) a $V_H$ sequence comprising SEQ ID NO:71 and a $V_L$ sequence comprising SEQ ID NO:72; or
 (b) a $V_H$ sequence comprising SEQ ID NO:75 and a $V_L$ sequence comprising SEQ ID NO:76; or
 (c) a $V_H$ sequence comprising SEQ ID NO:77 and a $V_L$ sequence comprising SEQ ID NO:76; or
 (d) a $V_H$ sequence comprising SEQ ID NO:75 and a $V_L$ sequence comprising SEQ ID NO:78; or
 (e) a $V_H$ sequence comprising SEQ ID NO:350 and a $V_L$ sequence comprising SEQ ID NO:78; or
 (f) a $V_H$ sequence comprising SEQ ID NO:80 and a $V_L$ sequence comprising SEQ ID NO:76; or
 (g) a $V_H$ sequence comprising SEQ ID NO:82 and a $V_L$ sequence comprising SEQ ID NO:76; or
 (h) a $V_H$ sequence comprising SEQ ID NO:80 and a $V_L$ sequence comprising SEQ ID NO:78; or
 (i) a $V_H$ sequence comprising SEQ ID NO:82 and a $V_L$ sequence comprising SEQ ID NO:78; or
 (j) a $V_H$ sequence comprising SEQ ID NO:58 and a $V_L$ sequence comprising SEQ ID NO:59; or
 (k) a $V_H$ sequence comprising SEQ ID NO:66 and a $V_L$ sequence comprising SEQ ID NO:67; or
 (l) a $V_H$ sequence comprising SEQ ID NO:80 and a $V_L$ sequence comprising SEQ ID NO:339.

In some embodiments, an antibody or antigen-binding fragment thereof that specifically binds to TREM2 comprises:
 (a) a CDR-H1 sequence comprising the sequence of GFTFTDYYMS (SEQ ID NO:125);
 (b) a CDR-H2 sequence comprising the sequence of F-I-R-$\beta_4$-K-A-N-G-Y-T-T-$\beta_{12}$-Y-S-A-S-V-K-G (SEQ ID NO:320), wherein $\beta_4$ is N or D; and $\beta_{12}$ is E or D;
 (c) a CDR-H3 sequence comprising the sequence of $\gamma_1$-R-$\gamma_3$-L-R-A-Q-G-F-A-Y (SEQ ID NO:321), wherein $\gamma_1$ is A or S; $\gamma_3$ is V or L;
 (d) a CDR-L1 sequence comprising the sequence of $\delta_1$-S-$\delta_3$-Q-S-L-L-Y-S-$\delta_{10}$-N-Q-K-N-Y-L-A (SEQ ID NO:322), wherein $\delta_1$ is T or K; $\delta_3$ is G or S; and $\delta_{10}$ is N or S;
 (e) a CDR-L2 sequence comprising the sequence of WASTRES (SEQ ID NO:32); and
 (f) a CDR-L3 sequence comprising the sequence of Q-Q-Y-Y-$\phi_5$-N-P-F-T (SEQ ID NO:323), wherein $\phi_5$ is R or G.

In some embodiments, the CDR-H2 sequence is selected from SEQ ID NOS:126, 132, and 136. In some embodiments, the CDR-H3 sequence is selected from SEQ ID NOS:127 and 137. In some embodiments, the CDR-L1 sequence is selected from SEQ ID NOS:128 and 138. In some embodiments, the CDR-L3 sequence is selected from SEQ ID NOS:129, 133, and 139.

In some embodiments, the antibody or antigen-binding fragment comprises:
 (a) a CDR-H1 comprising the amino acid sequence of SEQ ID NO:125, a CDR-H2 comprising the amino acid sequence of SEQ ID NO:136, a CDR-H3 comprising the amino acid sequence of SEQ ID NO:137, a CDR-L1 comprising the amino acid sequence of SEQ ID NO:138, a CDR-L2 comprising the amino acid sequence of SEQ ID NO:32, and a CDR-L3 comprising the amino acid sequence of SEQ ID NO:139; or
 (b) a CDR-H1 comprising the amino acid sequence of SEQ ID NO:125, a CDR-H2 comprising the amino acid sequence of SEQ ID NO:126, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:129; or
 (c) a CDR-H1 comprising the amino acid sequence of SEQ ID NO:125, a CDR-H2 comprising the amino acid sequence of SEQ ID NO:132, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:133.

In some embodiments, the antibody or antigen-binding fragment comprises a $V_H$ sequence that has at least 85% sequence identity to any one of SEQ ID NOS:123, 130, or 134. In some embodiments, the $V_H$ sequence has at least 90% sequence identity to SEQ ID NO:134. In some embodiments, the $V_H$ sequence has at least 95% sequence identity to SEQ ID NO:134. In some embodiments, the $V_H$ sequence comprises SEQ ID NO:134.

In some embodiments, the antibody or antigen-binding fragment comprises a $V_L$ sequence that has at least 85% sequence identity to any one of SEQ ID NOS:124, 131, or 135. In some embodiments, the $V_L$ sequence has at least 90% sequence identity to SEQ ID NO:135. In some embodiments, the $V_L$ sequence has at least 95% sequence identity to SEQ ID NO:135. In some embodiments, the $V_L$ sequence comprises SEQ ID NO:135.

In some embodiments, the antibody or antigen-binding fragment comprises:
- (a) a $V_H$ sequence comprising SEQ ID NO:134 and a $V_L$ sequence comprising SEQ ID NO:135; or
- (b) a $V_H$ sequence comprising SEQ ID NO:123 and a $V_L$ sequence comprising SEQ ID NO:124; or
- (c) a $V_H$ sequence comprising SEQ ID NO:130 and a $V_L$ sequence comprising SEQ ID NO:131.

In some embodiments, an antibody or antigen-binding fragment thereof that specifically binds to TREM2 comprises:
- (a) a CDR-H1 sequence comprising the amino acid sequence of any one of SEQ ID NOS:4, 12, 20, 28, 36, 44, 52, 56, 60, 68, 85, 93, 100, 105, 125, 142, 149, 157, 165, 172, 180, 188, 196, 202, 222, 228, 239, 253, 266, 274, and 282;
- (b) a CDR-H2 sequence comprising the amino acid sequence of any one of SEQ ID NOS:5, 13, 21, 29, 37, 45, 53, 57, 61, 69, 81, 86, 94, 101, 106, 115, 117, 119, 126, 132, 136, 143, 150, 158, 166, 173, 181, 189, 197, 203, 209, 214, 217, 223, 229, 236, 240, 254, 267, 275, 283, and 289;
- (c) a CDR-H3 sequence comprising the amino acid sequence of any one of SEQ ID NOS:6, 14, 22, 30, 38, 46, 62, 70, 73, 87, 95, 102, 107, 127, 137, 144, 151, 159, 167, 174, 182, 190, 198, 204, 210, 230, 241, 245, 249, 255, 260, 268, 276, and 284;
- (d) a CDR-L1 sequence comprising the amino acid sequence of any one of SEQ ID NOS:7, 15, 23, 31, 39, 47, 63, 79, 88, 96, 108, 128, 138, 145, 152, 160, 168, 175, 183, 191, 199, 205, 218, 224, 231, 242, 246, 256, 261, 269, 277, and 285;
- (e) a CDR-L2 sequence comprising the amino acid sequence of any one of SEQ ID NOS:8, 16, 24, 32, 40, 48, 64, 89, 109, 153, 161, 176, 184, 211, 219, 232, 250, 262, 270, 278, and 286; and
- (f) a CDR-L3 sequence comprising the amino acid sequence of any one of SEQ ID NOS:9, 17, 25, 33, 41, 49, 65, 74, 90, 97, 110, 129, 133, 139, 146, 154, 162, 169, 177, 185, 193, 206, 212, 225, 233, 257, 263, 271, 279, 287, and 290.

In some embodiments, the antibody or antigen-binding fragment comprises:
- (a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO:6, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO:9; or
- (b) a CDR-H1 comprising the amino acid sequence of SEQ ID NO:12, a CDR-H2 comprising the amino acid sequence of SEQ ID NO:13, a CDR-H3 comprising the amino acid sequence of SEQ ID NO:14, a CDR-L1 comprising the amino acid sequence of SEQ ID NO:15, a CDR-L2 comprising the amino acid sequence of SEQ ID NO:16, and a CDR-L3 comprising the amino acid sequence of SEQ ID NO:17; or
- (c) a CDR-H1 comprising the amino acid sequence of SEQ ID NO:20, a CDR-H2 comprising the amino acid sequence of SEQ ID NO:21, a CDR-H3 comprising the amino acid sequence of SEQ ID NO:22, a CDR-L1 comprising the amino acid sequence of SEQ ID NO:23, a CDR-L2 comprising the amino acid sequence of SEQ ID NO:24, and a CDR-L3 comprising the amino acid sequence of SEQ ID NO:25; or
- (d) a CDR-H1 comprising the amino acid sequence of SEQ ID NO:28, a CDR-H2 comprising the amino acid sequence of SEQ ID NO:29, a CDR-H3 comprising the amino acid sequence of SEQ ID NO:30, a CDR-L1 comprising the amino acid sequence of SEQ ID NO:31, a CDR-L2 comprising the amino acid sequence of SEQ ID NO:32, and a CDR-L3 comprising the amino acid sequence of SEQ ID NO:33; or
- (e) a CDR-H1 comprising the amino acid sequence of SEQ ID NO:36, a CDR-H2 comprising the amino acid sequence of SEQ ID NO:37, a CDR-H3 comprising the amino acid sequence of SEQ ID NO:38, a CDR-L1 comprising the amino acid sequence of SEQ ID NO:39, a CDR-L2 comprising the amino acid sequence of SEQ ID NO:40, and a CDR-L3 comprising the amino acid sequence of SEQ ID NO:41; or
- (f) a CDR-H1 comprising the amino acid sequence of SEQ ID NO:44, a CDR-H2 comprising the amino acid sequence of SEQ ID NO:45, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49; or
- (g) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:62, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or
- (h) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or
- (i) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or
- (j) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or
- (k) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or (l) a CDR-H1 comprising the amino acid sequence of SEQ ID NO:68, a CDR-H2 comprising the amino acid sequence of SEQ ID NO:69, a CDR-H3 comprising the amino acid sequence of SEQ ID NO:70, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or (m) a CDR-H1 comprising the amino acid sequence of SEQ ID NO:85, a CDR-H2 comprising the amino acid sequence of SEQ ID NO:86, a CDR-H3 comprising the amino acid sequence of SEQ ID NO:87, a CDR-L1 comprising the amino acid sequence of SEQ ID NO:88, a CDR-L2 comprising the amino acid sequence of SEQ ID NO:89, and a CDR-L3 comprising the amino acid sequence of SEQ ID NO:90; or (n) a CDR-H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:97; or (o) a CDR-H1 comprising the amino acid sequence of SEQ ID NO:100, a CDR-H2 comprising the amino acid sequence of SEQ ID NO:101, a CDR-H3 comprising the amino acid sequence of SEQ ID NO:102, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:90; or (p) a CDR-H1 comprising the amino acid sequence of SEQ ID NO:105, a CDR-H2 comprising the amino acid sequence of SEQ ID NO:106, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (q) a CDR-H1 comprising the amino acid sequence of SEQ ID NO:105, a CDR-H2 comprising the amino acid sequence of SEQ ID NO:115, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (r) a CDR-H1 comprising the amino acid sequence of SEQ ID NO:105, a CDR-H2 comprising the amino acid sequence of SEQ ID NO:117, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (s) a CDR-H1 comprising the amino acid sequence of SEQ ID NO:105, a CDR-H2 comprising the amino acid sequence of SEQ ID NO:119, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (t) a CDR-H1 comprising the amino acid sequence of SEQ ID NO:125, a CDR-H2 comprising the amino acid sequence of SEQ ID NO:126, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:129; or (u) a CDR-H1 comprising the amino acid sequence of SEQ ID NO:125, a CDR-H2 comprising the amino acid sequence of SEQ ID NO:132, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:133; or (v) a CDR-H1 comprising the amino acid sequence of SEQ ID NO:125, a CDR-H2 comprising the amino acid sequence of SEQ ID NO:136, a CDR-H3 comprising the amino acid sequence of SEQ ID NO:137, a CDR-L1 comprising the amino acid sequence of SEQ ID NO:138, a CDR-L2 comprising the amino acid sequence of SEQ ID NO:32, and a CDR-L3 comprising the amino acid sequence of SEQ ID NO:139; or (w) a CDR-H1 comprising the amino acid sequence of SEQ ID NO:142, a CDR-H2 comprising the amino acid sequence of SEQ ID NO:143, a CDR-H3 comprising the amino acid sequence of SEQ ID NO:144, a CDR-L1 comprising the amino acid sequence of SEQ ID NO:145, a CDR-L2 comprising the amino acid sequence of SEQ ID NO:32, and a CDR-L3 comprising the amino acid sequence of SEQ ID NO:146; or (x) a CDR-H1 comprising the amino acid sequence of SEQ ID NO:149, a CDR-H2 comprising the amino acid sequence of SEQ ID NO:150, a CDR-H3 comprising the amino acid sequence of SEQ ID NO:151, a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; or (y) a CDR-H1 comprising the amino acid sequence of SEQ ID NO:157, a CDR-H2 comprising the amino acid sequence of SEQ ID NO:158, a CDR-H3 comprising the amino acid sequence of SEQ ID NO:159, a CDR-L1 comprising the amino acid sequence of SEQ ID NO:160, a CDR-L2 comprising the amino acid sequence of SEQ ID NO:161, and a CDR-L3 comprising the amino acid sequence of SEQ ID NO:162; or (z) a CDR-H1 comprising the amino acid sequence of SEQ ID NO:165, a CDR-H2 comprising the amino acid sequence of SEQ ID NO:166, a CDR-H3 comprising the amino acid sequence of SEQ ID NO:167, a CDR-L1 comprising the amino acid sequence of SEQ ID NO:168, a CDR-L2 comprising the amino acid sequence of SEQ ID NO:161, and a CDR-L3 comprising the amino acid sequence of SEQ ID NO:169; or (aa) a CDR-H1 comprising the amino acid sequence of SEQ ID NO:172, a CDR-H2 comprising the amino acid sequence of SEQ ID NO:173, a CDR-H3 comprising the amino acid sequence of SEQ ID NO:174, a CDR-L1 comprising the amino acid sequence of SEQ ID NO:175, a CDR-L2 comprising the amino acid sequence of SEQ ID NO:176, and a CDR-L3 comprising the amino acid sequence of SEQ ID NO:177; or (bb) a CDR-H1 comprising the amino acid sequence of SEQ ID NO:180, a CDR-H2 comprising the amino acid sequence of SEQ ID NO:181, a CDR-H3 comprising the amino acid sequence of SEQ ID NO:182, a CDR-L1 comprising the amino acid sequence of SEQ ID NO:183, a CDR-L2 comprising the amino acid sequence of SEQ ID NO:184, and a CDR-L3 comprising the amino acid sequence of SEQ ID NO:185; or (cc) a CDR-H1 comprising the amino acid sequence of SEQ ID NO:188, a CDR-H2 comprising the amino acid sequence of SEQ ID NO:189, a CDR-H3 comprising the amino acid sequence of SEQ ID NO:190, a CDR-L1 comprising the amino acid sequence of SEQ ID NO:191, a CDR-L2 comprising the amino acid sequence of SEQ ID NO:32, and a CDR-L3 comprising the amino acid sequence of SEQ ID NO:146; or (dd) a CDR-H1 comprising the amino acid sequence of SEQ ID NO:188, a CDR-H2 comprising the amino acid sequence of SEQ ID NO:189, a CDR-H3 comprising the amino acid sequence of SEQ ID NO:190, a CDR-L1 comprising the amino acid sequence of SEQ ID NO:191, a CDR-L2 comprising the amino acid sequence of SEQ ID NO:32, and a CDR-L3 comprising the amino acid sequence of SEQ ID NO:193; or (ee) a CDR-H1 comprising the amino acid sequence of SEQ ID NO:196, a CDR-H2 comprising the amino acid sequence of SEQ ID NO:197, a CDR-H3 comprising the amino acid sequence of SEQ ID NO:198, a CDR-L1 comprising the amino acid sequence of SEQ ID NO:199, a CDR-L2 comprising the amino acid sequence of SEQ ID NO:89, and a CDR-L3 comprising the amino acid sequence of SEQ ID NO:90; or (ff) a CDR-H1 comprising the amino acid sequence of SEQ ID NO:202, a CDR-H2 comprising the amino acid sequence of SEQ ID NO:203, a CDR-H3 comprising the amino acid sequence of SEQ ID NO:204, a CDR-L1 comprising the amino acid sequence of SEQ ID NO:205, a CDR-L2 comprising the amino acid sequence of SEQ ID NO:89, and a CDR-L3 comprising the amino acid sequence of SEQ ID NO:206; or (gg) a CDR-H1 comprising the amino acid sequence of SEQ ID NO:28, a CDR-H2 comprising the amino acid sequence of SEQ ID NO:209, a CDR-H3 comprising the amino acid sequence of SEQ ID NO:210, a CDR-L1 comprising the amino acid sequence of SEQ ID NO:205, a CDR-L2 comprising the amino acid sequence of SEQ ID NO:211, and a CDR-L3 comprising the amino acid sequence of SEQ ID NO:212; or (hh) a CDR-H1 comprising the amino acid sequence of SEQ ID NO:172, a CDR-H2 comprising the amino acid sequence of SEQ ID NO:214, a CDR-H3 comprising the amino acid sequence of SEQ ID NO:174, a CDR-L1 comprising the amino acid sequence of SEQ ID NO:175, a CDR-L2 comprising the amino acid sequence of SEQ ID NO:176, and a CDR-L3 comprising the amino acid sequence of SEQ ID NO:177; or (ii) a CDR-H1 comprising the amino acid sequence of SEQ ID NO:149, a CDR-H2 comprising the amino acid sequence of SEQ ID NO:217, a CDR-H3 comprising the amino acid sequence of SEQ ID NO:167, a CDR-L1 comprising the amino acid sequence of SEQ ID NO:218, a CDR-L2 comprising the amino acid sequence of SEQ ID NO:219, and a CDR-L3 comprising the amino acid sequence of SEQ ID NO:169; or (jj) a CDR-H1 comprising the amino acid sequence of SEQ ID NO:222, a CDR-H2 comprising the amino acid sequence of SEQ ID NO:223, a CDR-H3 comprising the amino acid sequence of SEQ ID NO:22, a CDR-L1 comprising the amino acid sequence of SEQ ID NO:224, a CDR-L2 comprising the amino acid sequence of SEQ ID NO:8, and a CDR-L3 comprising the amino acid sequence of SEQ ID NO:225; or (kk) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:230, a CDR-L1 comprising the amino acid sequence of SEQ ID NO:231, a CDR-L2 comprising the amino acid sequence of SEQ ID NO:232, and a CDR-L3 comprising the amino acid sequence of SEQ ID NO:233; or (ll) a CDR-H1 comprising the amino acid sequence of SEQ ID NO:149, a CDR-H2 comprising the amino acid sequence of SEQ ID NO:236, a CDR-H3 comprising the amino acid sequence of SEQ ID NO:151, a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; or (mm) a CDR-H1 comprising the amino acid sequence of SEQ ID NO:239, a CDR-H2 comprising the amino acid sequence of SEQ ID NO:240, a CDR-H3 comprising the amino acid sequence of SEQ ID NO:241, a CDR-L1 comprising the amino acid sequence of SEQ ID NO:242, a CDR-L2 comprising the amino acid sequence of SEQ ID NO:89, and a CDR-L3 comprising the amino acid sequence of SEQ ID NO:212; or (nn) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:245, a CDR-L1 comprising the amino acid sequence of SEQ ID NO:246, a CDR-L2 comprising the amino acid sequence of SEQ ID NO:232, and a CDR-L3 comprising the amino acid sequence of SEQ ID NO:233; or (oo) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:249, a CDR-L1 comprising the amino acid sequence of SEQ ID NO:246, a CDR-L2 comprising the amino acid sequence of SEQ ID NO:250, and a CDR-L3 comprising the amino acid sequence of SEQ ID NO:233; or (pp) a CDR-H1 comprising the amino acid sequence of SEQ ID NO:253, a CDR-H2 comprising the amino acid sequence of SEQ ID NO:254, a CDR-H3 comprising the amino acid sequence of SEQ ID NO:255, a CDR-L1 comprising the amino acid sequence of SEQ ID NO:256, a CDR-L2 comprising the amino acid sequence of SEQ ID NO:32, and a CDR-L3 comprising the amino acid sequence of SEQ ID NO:257; or (qq) a CDR-H1 comprising the amino acid sequence of SEQ ID NO:253, a CDR-H2 comprising the amino acid sequence of SEQ ID NO:254, a CDR-H3 comprising the amino acid sequence of SEQ ID NO:260, a CDR-L1 comprising the amino acid sequence of SEQ ID NO:261, a CDR-L2 comprising the amino acid sequence of SEQ ID NO:262, and a CDR-L3 comprising the amino acid sequence of SEQ ID NO:263; or (rr) a CDR-H1 comprising the amino acid sequence of SEQ ID NO:266, a CDR-H2 comprising the amino acid sequence of SEQ ID NO:267, a CDR-H3 comprising the amino acid sequence of SEQ ID NO:268, a CDR-L1 comprising the amino acid sequence of SEQ ID NO:269, a CDR-L2 comprising the amino acid sequence of SEQ ID NO:270, and a CDR-L3 comprising the amino acid sequence of SEQ ID NO:271; or (ss) a CDR-H1 comprising the amino acid sequence of SEQ ID NO:274, a CDR-H2 comprising the amino acid sequence of SEQ ID NO:275, a CDR-H3 comprising the amino acid sequence of SEQ ID NO:276, a CDR-L1 comprising the amino acid sequence of SEQ ID NO:277, a CDR-L2 comprising the amino acid sequence of SEQ ID NO:278, and a CDR-L3 comprising the amino acid sequence of SEQ ID NO:279; or (tt) a CDR-H1 comprising the amino acid sequence of SEQ ID NO:282, a CDR-H2 comprising the amino acid sequence of SEQ ID NO:283, a CDR-H3 comprising the amino acid sequence of SEQ ID NO:284, a CDR-L1 comprising the amino acid sequence of SEQ ID NO:285, a CDR-L2 comprising the amino acid sequence of SEQ ID NO:286, and a CDR-L3 comprising the amino acid sequence of SEQ ID NO:287; or (uu) a CDR-H1 comprising the amino acid sequence of SEQ ID NO:60, a CDR-H2 comprising the amino acid sequence of SEQ ID NO:289, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:290; or (vv) a CDR-H1 comprising the amino acid sequence of SEQ ID NO:52, a CDR-H2 comprising the amino acid sequence of SEQ ID NO:53, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:292; or (ww) a CDR-H1 comprising the amino acid sequence of SEQ ID NO:56, a CDR-H2 comprising the amino acid sequence of SEQ ID NO:57, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49.

In some embodiments, the antibody or antigen-binding fragment comprises a heavy chain variable region that has at least 85% sequence identity to any one of SEQ ID NOS:2, 10, 18, 26, 34, 42, 50, 54, 58, 66, 71, 75, 77, 80, 82, 83, 91, 98, 103, 111, 113, 114, 116, 118, 120, 121, 122, 123, 130, 134, 140, 147, 155, 163, 170, 178, 186, 194, 200, 207, 213, 215, 220, 226, 234, 237, 243, 247, 251, 258, 264, 272, 280, 288, and 350. In some embodiments, the antibody or antigen-binding fragment comprises a light chain variable region that has at least 85% sequence identity to any one of SEQ ID NOS:3, 11, 19, 27, 35, 43, 51, 55, 59, 67, 72, 76, 78, 84, 92, 99, 104, 112, 124, 131, 135, 141, 148, 156, 164, 171, 179, 187, 192, 195, 201, 208, 216, 221, 227, 235, 238, 244, 248, 252, 259, 265, 273, 281, and 339.

In some embodiments, the antibody or antigen-binding fragment comprises:

(a) a $V_H$ sequence that has at least 85% sequence identity to SEQ ID NO:2 and a $V_L$ sequence that has at least 85% sequence identity to SEQ ID NO:3; or (b) a $V_H$ sequence that has at least 85% sequence identity to SEQ ID NO:10 and a $V_L$ sequence that has at least 85% sequence identity to SEQ ID NO:11; or (c) a $V_H$ sequence that has at least 85% sequence identity to SEQ ID NO:18 and a $V_L$ sequence that has at least 85% sequence identity to SEQ ID NO:19; or (d) a $V_H$ sequence that has at least 85% sequence identity to SEQ ID NO:26 and a $V_L$ sequence that has at least 85% sequence identity to SEQ ID NO:27; or (e) a $V_H$ sequence that has at least 85% sequence identity to SEQ ID NO:34 and a $V_L$ sequence that has at least 85% sequence identity to SEQ ID NO:35; or (f) a $V_H$ sequence that has at least 85% sequence identity to SEQ ID NO:42 and a $V_L$ sequence that has at least 85% sequence identity to SEQ ID NO:43; or (g) a $V_H$ sequence that has at least 85% sequence identity to SEQ ID NO:50 and a $V_L$ sequence that has at least 85% sequence identity to SEQ ID NO:51; or (h) a $V_H$ sequence that has at least 85% sequence identity to SEQ ID NO:54 and a $V_L$ sequence that has at least 85% sequence identity to SEQ ID NO:55; or (i) a $V_H$ sequence that has at least 85% sequence identity to SEQ ID NO:58 and a $V_L$ sequence that has at least 85% sequence identity to SEQ ID NO:59; or (j) a $V_H$ sequence that has at least 85% sequence identity to SEQ ID NO:66 and a $V_L$ sequence that has at least 85% sequence identity to SEQ ID NO:67; or (k) a $V_H$ sequence that has at least 85% sequence identity to SEQ ID NO:71 and a $V_L$ sequence that has at least 85% sequence identity to SEQ ID NO:72; or (l) a $V_H$ sequence that has at least 85% sequence identity to SEQ ID NO:75 and a $V_L$ sequence that has at least 85% sequence identity to SEQ ID NO:76; or (m) a $V_H$ sequence that has at least 85% sequence identity to SEQ ID NO:77 and a $V_L$ sequence that has at least 85% sequence identity to SEQ ID NO:76; or (n) a $V_H$ sequence that has at least 85% sequence identity to SEQ ID NO:75 and a $V_L$ sequence that has at least 85% sequence identity to SEQ ID NO:78; or (o) a $V_H$ sequence that has at least 85% sequence identity to SEQ ID NO:350 and a $V_L$ sequence that has at least 85% sequence identity to SEQ ID NO:78; or (p) a $V_H$ sequence that has at least 85% sequence identity to SEQ ID NO:80 and a $V_L$ sequence that has at least 85% sequence identity to SEQ ID NO:76; or (q) a $V_H$ sequence that has at least 85% sequence identity to SEQ ID NO:82 and a $V_L$ sequence that has at least 85% sequence identity to SEQ ID NO:76; or (r) a $V_H$ sequence that has at least 85% sequence identity to SEQ ID NO:80 and a $V_L$ sequence that has at least 85% sequence identity to SEQ ID NO:78; or (s) a $V_H$ sequence that has at least 85% sequence identity to SEQ ID NO:82 and a $V_L$ sequence that has at least 85% sequence identity to SEQ ID NO:78; or (t) a $V_H$ sequence that has at least 85% sequence identity to SEQ ID NO:83 and a $V_L$ sequence that has at least 85% sequence identity to SEQ ID NO:84; or (u) a $V_H$ sequence that has at least 85% sequence identity to SEQ ID NO:91 and a $V_L$ sequence that has at least 85% sequence identity to SEQ ID NO:92; or (v) a $V_H$ sequence that has at least 85% sequence identity to SEQ ID NO:98 and a $V_L$ sequence that has at least 85% sequence identity to SEQ ID NO:99; or (w) a $V_H$ sequence that has at least 85% sequence identity to SEQ ID NO:103 and a $V_L$ sequence that has at least 85% sequence identity to SEQ ID NO:104; or (x) a $V_H$ sequence that has at least 85% sequence identity to SEQ ID NO:111 and a $V_L$ sequence that has at least 85% sequence identity to SEQ ID NO:112; or (y) a $V_H$ sequence that has at least 85% sequence identity to SEQ ID NO:113 and a $V_L$ sequence that has at least 85% sequence identity to SEQ ID NO:112; or (z) a $V_H$ sequence that has at least 85% sequence identity to SEQ ID NO:114 and a $V_L$ sequence that has at least 85% sequence identity to SEQ ID NO:112; or (aa) a V_H sequence that has at least 85% sequence identity to SEQ ID NO:116 and a V_L sequence that has at least 85% sequence identity to SEQ ID NO:112; or
(bb) a V_H sequence that has at least 85% sequence identity to SEQ ID NO:118 and a V_L sequence that has at least 85% sequence identity to SEQ ID NO:112; or
(cc) a V_H sequence that has at least 85% sequence identity to SEQ ID NO:120 and a V_L sequence that has at least 85% sequence identity to SEQ ID NO:112; or
(dd) a V_H sequence that has at least 85% sequence identity to SEQ ID NO:121 and a V_L sequence that has at least 85% sequence identity to SEQ ID NO:112; or
(ee) a V_H sequence that has at least 85% sequence identity to SEQ ID NO:122 and a V_L sequence that has at least 85% sequence identity to SEQ ID NO:112; or
(ff) a V_H sequence that has at least 85% sequence identity to SEQ ID NO:123 and a V_L sequence that has at least 85% sequence identity to SEQ ID NO:124; or
(gg) a V_H sequence that has at least 85% sequence identity to SEQ ID NO:130 and a V_L sequence that has at least 85% sequence identity to SEQ ID NO:131; or
(hh) a V_H sequence that has at least 85% sequence identity to SEQ ID NO:134 and a V_L sequence that has at least 85% sequence identity to SEQ ID NO:135; or
(ii) a V_H sequence that has at least 85% sequence identity to SEQ ID NO:140 and a V_L sequence that has at least 85% sequence identity to SEQ ID NO:141; or
(jj) a V_H sequence that has at least 85% sequence identity to SEQ ID NO:147 and a V_L sequence that has at least 85% sequence identity to SEQ ID NO:148; or
(kk) a V_H sequence that has at least 85% sequence identity to SEQ ID NO:155 and a V_L sequence that has at least 85% sequence identity to SEQ ID NO:156; or
(ll) a V_H sequence that has at least 85% sequence identity to SEQ ID NO:163 and a V_L sequence that has at least 85% sequence identity to SEQ ID NO:164; or
(mm) a V_H sequence that has at least 85% sequence identity to SEQ ID NO:170 and a V_L sequence that has at least 85% sequence identity to SEQ ID NO:171; or
(nn) a V_H sequence that has at least 85% sequence identity to SEQ ID NO:178 and a V_L sequence that has at least 85% sequence identity to SEQ ID NO:179; or
(oo) a V_H sequence that has at least 85% sequence identity to SEQ ID NO:186 and a V_L sequence that has at least 85% sequence identity to SEQ ID NO:187; or
(pp) a V_H sequence that has at least 85% sequence identity to SEQ ID NO:186 and a V_L sequence that has at least 85% sequence identity to SEQ ID NO:192; or
(qq) a V_H sequence that has at least 85% sequence identity to SEQ ID NO:194 and a V_L sequence that has at least 85% sequence identity to SEQ ID NO:195; or
(rr) a V_H sequence that has at least 85% sequence identity to SEQ ID NO:200 and a V_L sequence that has at least 85% sequence identity to SEQ ID NO:201; or
(ss) a V_H sequence that has at least 85% sequence identity to SEQ ID NO:207 and a V_L sequence that has at least 85% sequence identity to SEQ ID NO:208; or
(tt) a V_H sequence that has at least 85% sequence identity to SEQ ID NO:213 and a V_L sequence that has at least 85% sequence identity to SEQ ID NO:171; or
(uu) a V_H sequence that has at least 85% sequence identity to SEQ ID NO:215 and a V_L sequence that has at least 85% sequence identity to SEQ ID NO:216; or
(vv) a V_H sequence that has at least 85% sequence identity to SEQ ID NO:220 and a V_L sequence that has at least 85% sequence identity to SEQ ID NO:221; or
(ww) a V_H sequence that has at least 85% sequence identity to SEQ ID NO:226 and a V_L sequence that has at least 85% sequence identity to SEQ ID NO:227; or
(xx) a V_H sequence that has at least 85% sequence identity to SEQ ID NO:234 and a V_L sequence that has at least 85% sequence identity to SEQ ID NO:235; or
(yy) a V_H sequence that has at least 85% sequence identity to SEQ ID NO:237 and a V_L sequence that has at least 85% sequence identity to SEQ ID NO:238; or
(zz) a V_H sequence that has at least 85% sequence identity to SEQ ID NO:243 and a V_L sequence that has at least 85% sequence identity to SEQ ID NO:244; or
(aaa) a V_H sequence that has at least 85% sequence identity to SEQ ID NO:247 and a V_L sequence that has at least 85% sequence identity to SEQ ID NO:248; or
(bbb) a V_H sequence that has at least 85% sequence identity to SEQ ID NO:251 and a V_L sequence that has at least 85% sequence identity to SEQ ID NO:252; or
(ccc) a V_H sequence that has at least 85% sequence identity to SEQ ID NO:258 and a V_L sequence that has at least 85% sequence identity to SEQ ID NO:259; or
(ddd) a V_H sequence that has at least 85% sequence identity to SEQ ID NO:264 and a V_L sequence that has at least 85% sequence identity to SEQ ID NO:265; or
(eee) a V_H sequence that has at least 85% sequence identity to SEQ ID NO:272 and a V_L sequence that has at least 85% sequence identity to SEQ ID NO:273; or
(fff) a V_H sequence that has at least 85% sequence identity to SEQ ID NO:280 and a V_L sequence that has at least 85% sequence identity to SEQ ID NO:281; or
(ggg) a V_H sequence that has at least 85% sequence identity to SEQ ID NO:288 and a V_L sequence that has at least 85% sequence identity to SEQ ID NO:291; or
(hhh) a V_H sequence that has at least 85% sequence identity to SEQ ID NO:80 and a V_L sequence that has at least 85% sequence identity to SEQ ID NO:339.

In some embodiments, an antibody or antigen-binding fragment thereof that specifically binds to TREM2 recognizes an epitope that is the same or substantially the same as the epitope recognized by antibody clone selected from the group consisting of: Clone CL0020107, Clone CL0020300, Clone CL0020215, Clone CL0020301, Clone CL0020302, Clone CL0020139, Clone CL0020304, Clone CL0020305, Clone CL0020306, Clone CL0020188, Clone CL0020188-1, Clone CL0020188-2, Clone CL0020188-3, Clone CL0020188-4, Clone CL0020188-5, Clone CL0020188-6, Clone CL0020188-7, Clone CL0020188-8, Clone CL0020307, Clone CL0020308, Clone CL0020309, Clone CL0020310, Clone CL0020123, Clone CL0020123-1, Clone CL0020123-2, Clone CL0020123-3, Clone CL0020123-4, Clone CL0020123-5, Clone CL0020123-6, Clone CL0020123-7, Clone CL0020123-8, Clone CL0020311, Clone CL0020312, Clone CL0020141, Clone CL0020103, Clone CL0020201, Clone CL0020120, Clone CL0020127, Clone CL0020109, Clone CL0020214, Clone CL0020096, Clone CL0020210, Clone CL0020313, Clone CL0020314, Clone CL0020315, Clone CL0020205, Clone CL0020206, Clone CL0020111, Clone CL0020112, Clone CL0020124, Clone CL0020125, Clone CL00220183, Clone CL0020186, Clone CL0020113, Clone CL0020162, Clone CL0020195, Clone CL0020161, Clone CL0020173, and Clone CL0020164.

In some embodiments, the antibody or antigen-binding fragment recognizes an epitope that is the same or substantially the same as the epitope recognized by an antibody clone selected from the group consisting of: Clone CL0020107, Clone CL0020300, Clone CL0020215, Clone CL0020301, and Clone CL0020302. In some embodiments, the antibody or antigen-binding fragment recognizes an epitope that is the same or substantially the same as the epitope recognized by an antibody clone selected from the group consisting of: Clone CL0020139, Clone CL0020304, and CL0020305. In some embodiments, the antibody or antigen-binding fragment recognizes an epitope that is the same or substantially the same as the epitope recognized by an antibody clone selected from the group consisting of: Clone CL0020123, Clone CL0020123-1, Clone CL0020123-2, Clone CL0020123-3, Clone CL0020123-4, Clone CL0020123-5, Clone CL0020123-6, Clone CL0020123-7, and Clone CL0020123-8. In particular embodiments, the antibody or antigen-binding fragment recognizes one or more of the following epitopes in SEQ ID NO:1: (i) amino acid residues 55-63 (GEKGPCQRV (SEQ ID NO:341)), (ii) amino acids 96-107 (TLRNLQPHDAGL (SEQ ID NO:342)), and (iii) amino acid residues 126-129 (VEVL (SEQ ID NO:343)). In another aspect, the disclosure features an isolated antibody or antigen-binding fragment thereof that specifically binds to a human TREM2, wherein the antibody or antigen-binding fragment thereof recognizes an epitope comprising or consisting of one or more of the following epitopes in SEQ ID NO:1: (i) amino acid residues 55-63 (GEKGPCQRV (SEQ ID NO:341)), (ii) amino acids 96-107 (TLRNLQPHDAGL (SEQ ID NO:342)), and (iii) amino acid residues 126-129 (VEVL (SEQ ID NO:343)). In some embodiments, the antibody or antigen-binding fragment recognizes an epitope that is the same or substantially the same as the epitope recognized by an antibody clone selected from the group consisting of: Clone CL0020308, Clone CL0020309, and Clone CL0020310. In some embodiments, the antibody or antigen-binding fragment recognizes an epitope that is the same or substantially the same as the epitope recognized by an antibody clone selected from the group consisting of: Clone CL0020188, Clone CL0020188-1, Clone CL0020188-2, Clone CL0020188-3, Clone CL0020188-4, Clone CL0020188-5, Clone CL0020188-6, Clone CL0020188-7, Clone CL0020188-8, Clone CL0020307, and Clone CL0020306. In particular embodiments, the antibody or antigen-binding fragment recognizes amino acid residues 143-149 (FPGESES (SEQ ID NO:340)) in SEQ ID NO:1. In another aspect, the disclosure features an isolated antibody or antigen-binding fragment thereof that specifically binds to a human TREM2, wherein the antibody or antigen-binding fragment thereof recognizes an epitope comprising or consisting of amino acid residues 143-149 (FPGESES (SEQ ID NO:340)) in SEQ ID NO:1. In some embodiments, the antibody or antigen-binding fragment recognizes an epitope that is the same or substantially the same as the epitope recognized by an antibody clone selected from the group consisting of: Clone CL0020141, Clone CL0020311, and Clone CL0020312.

In some embodiments, an antibody or antigen-binding fragment as disclosed herein decreases levels of soluble TREM2 protein (sTREM2). In some embodiments, an antibody or antigen-binding fragment as disclosed herein binds soluble TREM2 protein (sTREM2) in healthy human CSF or cynomolgus CSF with better potency compared to a reference antibody. In some embodiments, the reference antibody is represented by a combination of sequences selected from the group consisting of: SEQ ID NOS:344 and 345; SEQ ID NOS:346 and 347; and SEQ ID NOS:348 and 349. In some embodiments, the potency assay is carried out substantially as described in Example 11. In some embodiments, an antibody or antigen-binding fragment as disclosed herein enhances TREM2 activity. In some embodiments, the antibody or antigen-binding fragment thereof enhances phagocytosis or enhances the migration, differentiation, function, or survival of myeloid cells, microglia, or macrophages. In some embodiments, the antibody or antigen-binding fragment thereof enhances microglia function without increasing neuroinflammation. In some embodiments, the antibody or antigen-binding fragment thereof enhances Syk phosphorylation. In some embodiments, the antibody or antigen-binding fragment thereof enhances Syk phosphorylation in the presence of a TREM2 ligand. In some embodiments, the antibody or antigen-binding fragment thereof exhibits cross-reactivity with a cynomolgus TREM2 protein.

In some embodiments, an antibody or antigen-binding fragment as disclosed herein is a monoclonal antibody. In some embodiments, an antibody or antigen-binding fragment as disclosed herein is a chimeric antibody. In some embodiments, an antibody or antigen-binding fragment as disclosed herein is a humanized antibody. In some embodiments, an antibody or antigen-binding fragment as disclosed herein is a fully human antibody. In some embodiments, an antibody or antigen-binding fragment as disclosed herein is a Fab, a F(ab')$_2$, a scFv, or a bivalent scFv.

In another aspect, the disclosure provides antibodies or antigen-binding fragments thereof that competes with an isolated anti-TREM2 antibody as disclosed herein for binding to the human TREM2 protein.

In another aspect, the disclosure provides pharmaceutical compositions comprising an antibody or antigen-binding fragment as disclosed herein that specifically binds to TREM2 and a pharmaceutically acceptable carrier.

In yet another aspect, the disclosure provides kits comprising: an antibody or antigen-binding fragment as disclosed herein that specifically binds to TREM2 or a pharmaceutical composition comprising the anti-TREM2 antibody or antigen-binding fragment; and instructions for use thereof.

In still another aspect, the disclosure provides methods of treating a neurodegenerative disease in a subject. In some embodiments, the method comprises administering to the subject an anti-TREM2 antibody or antigen-binding fragment as disclosed herein or a pharmaceutical composition comprising an anti-TREM2 antibody or antigen-binding fragment as disclosed herein.

In some embodiments, the neurodegenerative disease is selected from the group consisting of: Alzheimer's disease, primary age-related tauopathy, progressive supranuclear palsy (PSP), frontotemporal dementia, frontotemporal dementia with parkinsonism linked to chromosome 17, argyrophilic grain dementia, amyotrophic lateral sclerosis, amyotrophic lateral sclerosis/parkinsonism-dementia complex of Guam (ALS-PDC), corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, Gerstmann-Straussler-Scheinker disease, globular glial tauopathy, Guadeloupean parkinsonism with dementia, Guadelopean PSP, Hallevorden-Spatz disease, hereditary diffuse leukoencephalopathy with spheroids (HDLS), Huntington's disease, inclusion-body myositis, multiple system atrophy, myotonic dystrophy, Nasu-Hakola disease, neurofibrillary tangle-predominant dementia, Niemann-Pick disease type C, pallido-ponto-nigral degeneration, Parkinson's disease, Pick's disease, postencephalitic parkinsonism, prion protein cerebral amyloid angiopathy, progressive subcortical gliosis, subacute sclerosing panencephalitis, and tangle only dementia.

In yet another aspect, the disclosure provides methods of decreasing levels of sTREM2 in a subject having a neurodegenerative disease. In some embodiments, the method comprises administering to the subject an anti-TREM2 antibody or antigen-binding fragment as disclosed herein or a pharmaceutical composition comprising an anti-TREM2 antibody or antigen-binding fragment as disclosed herein.

In still another aspect, the disclosure provides methods of enhancing TREM2 activity in a subject having a neurodegenerative disease. In some embodiments, the method comprises administering to the subject an anti-TREM2 antibody or antigen-binding fragment as disclosed herein or a pharmaceutical composition comprising an anti-TREM2 antibody or antigen-binding fragment as disclosed herein.

BRIEF DESCRIPTION OF THE DRAWINGS

FIGS. 3A and 3B include representative dose-response curves of pSyk signal activation in human iPSC microglia cells after pre-treatment with exemplary anti-TREM2 antibodies for 5 minutes (FIG. 3A) or for 24 hours (FIG. 3B), followed by dosing with lipid vesicles and assessment of liposome response in the cells.

FIGS. 8C-8F include bar charts illustrating quantified levels of cholesteryl ester species (FIGS. 8C and 8E) and triacylglyceride lipid species (FIGS. 8D and 8F) in iPSC microglia treated with myelin, followed by incubation with exemplary anti-TREM2 antibodies. FIGS. 8E and 8F represents data for iPSC microglia for which a myelin washout step was included prior to incubation with the exemplary anti-TREM2 antibodies.

FIGS. 12A and 12B include dose-response curves of pSyk signal activation by exemplary humanized and sequence-optimized anti-TREM2 antibodies in HEK293-H6 cells.

DETAILED DESCRIPTION

I. Introduction

Figure 1:
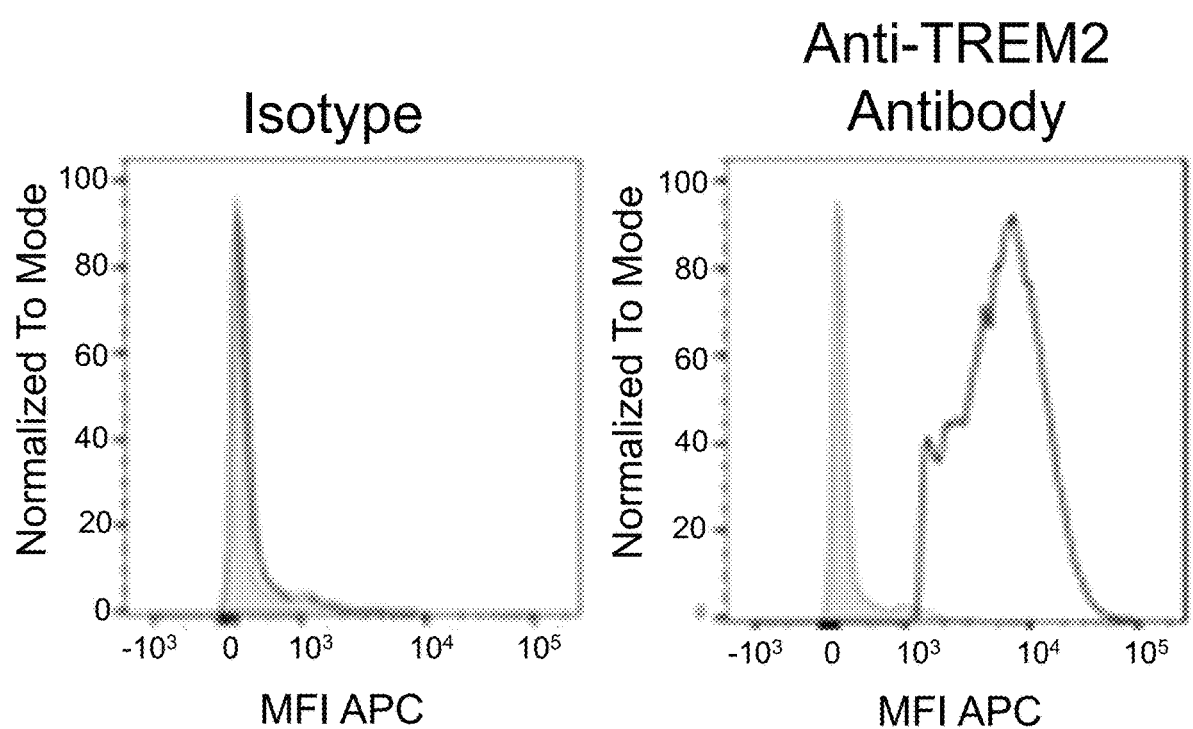
FIG. 1 includes representative flow cytometry histograms representing binding of an exemplary anti-TREM2 antibody to surface TREM2 on HEK cells expressing TREM2 (FIG. 1A) or wild-type (WT) iPSC microglia cells (FIG. 1B), or lack of binding to Trem2 knockout (KO) iPSC microglia cells (FIG. 1C).

TREM2 is a transmembrane receptor that is expressed on the cell surface of microglia, dendritic cells, macrophages, and osteoclasts. Without being bound to a particular theory, it is believed that upon ligand binding, TREM2 forms a signaling complex with a transmembrane adapter protein, DNAX-activating protein 12 (DAP12), which in turn is tyrosine phosphorylated by the protein kinase SRC. It is believed that the activated TREM2/DAP12 signaling complex mediates intracellular signaling by recruiting and phosphorylating kinases such as Syk kinase. TREM2/DAP12 signaling modulates activities such as phagocytosis, cell growth and survival, pro-inflammatory cytokine secretion, and the migration of cells such as microglia and macrophages. TREM2 undergoes regulated intramembrane proteolysis, in which the membrane-associated full-length TREM2 is cleaved by the metalloprotease ADAM10 into a sTREM2 portion that is shed from the cell and a membrane-retained C-terminal fragment that is further degraded by a gamma-secretase. Altered levels of sTREM2 have been reported in patients having Alzheimer's disease or frontotemporal dementia and having a mutation in TREM2. Additionally, mutations in TREM2 are associated with altered functions such as impaired phagocytosis and reduced microglial function.

As detailed in the Examples section below, antibodies have been generated that specifically bind to human TREM2 and that modulate one or more downstream functions of the TREM2/DAP12 signaling complex. Accordingly, in one aspect, the present disclosure provides anti-TREM2 antibodies and antigen-binding fragments thereof. Accordingly, in one aspect, the present disclosure provides anti-TREM2 antibodies and antigen-binding portions thereof.

In some embodiments, the anti-TREM2 antibodies enhance TREM2 activity, e.g., enhance phagocytosis or enhance the differentiation, function, migration, or survival of myeloid cells, microglia, or macrophages. Thus, in another aspect, methods of enhancing TREM2 activity, e.g., in a subject having a neurodegenerative disease, are provided.

In some embodiments, the anti-TREM2 antibodies reduce shedding of sTREM2. Thus, in another aspect, methods of decreasing levels of sTREM2, e.g., in a subject having a neurodegenerative disease, are provided.

II. Definitions

As used herein, the singular forms "a," "an" and "the" include plural referents unless the content clearly dictates otherwise. Thus, for example, reference to "an antibody" optionally includes a combination of two or more such molecules, and the like.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

As used herein, the term "TREM2 protein" refers to a triggering receptor expressed on myeloid cells 2 protein that is encoded by the gene TREM2. As used herein, a "TREM2 protein" refers to a native (i.e., wild-type) TREM2 protein of any vertebrate, such as but not limited to human, non-human primates (e.g., cynomolgus monkey), rodents (e.g., mice, rat), and other mammals. In some embodiments, a TREM2 protein is a human TREM2 protein having the sequence identified in UniprotKB accession number Q9NZC2 (SEQ ID NO:1).

As used herein, the term "anti-TREM2 antibody" refers to an antibody that specifically binds to a TREM2 protein (e.g., human TREM2).

As used herein, the term "antibody" refers to a protein with an immunoglobulin fold that specifically binds to an antigen via its variable regions. The term encompasses intact polyclonal antibodies, intact monoclonal antibodies, single chain antibodies, multi specific antibodies such as bispecific antibodies, monospecific antibodies, monovalent antibodies, chimeric antibodies, humanized antibodies, and human antibodies. The term "antibody," as used herein, also includes antibody fragments that retain binding specificity via its variable regions, including but not limited to Fab, F(ab')$_2$, Fv, scFv, and bivalent scFv. Antibodies can contain light chains that are classified as either kappa or lambda. Antibodies can contain heavy chains that are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

The term "variable region" or "variable domain" refers to a domain in an antibody heavy chain or light chain that is derived from a germline Variable (V) gene, Diversity (D) gene, or Joining (J) gene (and not derived from a Constant (Cμ and Cδ) gene segment), and that gives an antibody its specificity for binding to an antigen. Typically, an antibody variable region comprises four conserved "framework" regions interspersed with three hypervariable "complementarity determining regions."

The term "complementarity determining region" or "CDR" refers to the three hypervariable regions in each chain that interrupt the four framework regions established by the light and heavy chain variable regions. The CDRs are primarily responsible for antibody binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 or CDR-H3 is located in the variable region of the heavy chain of the antibody in which it is found, whereas a VL CDR1 or CDR-L1 is the CDR1 from the variable region of the light chain of the antibody in which it is found.

The "framework regions" or "FRs" of different light or heavy chains are relatively conserved within a species. The framework region of an antibody, that is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The amino acid sequences of the CDRs and framework regions can be determined using various well-known definitions in the art, e.g., Kabat, Chothia, international ImMunoGeneTics database (IMGT), AbM, and observed antigen contacts ("Contact"). In some embodiments, CDRs are determined according to the Contact definition. See, MacCallum et al., *J. Mol. Biol.*, 262:732-745 (1996). In some embodiments, CDRs are determined by a combination of Kabat, Chothia, and/or Contact CDR definitions.

The terms "antigen-binding portion" and "antigen-binding fragment" are used interchangeably herein and refer to one or more fragments of an antibody that retains the ability to specifically bind to an antigen (e.g., a TREM2 protein) via its variable region. Examples of antigen-binding fragments include, but are not limited to, a Fab fragment (a monovalent fragment consisting of the VL, VH, CL and CH1 domains), F(ab')2 fragment (a bivalent fragment comprising two Fab fragments linked by a disulfide bridge at the hinge region), single chain Fv (scFv), disulfide-linked Fv (dsFv), complementarity determining regions (CDRs), a VL (light chain variable region), and a VH (heavy chain variable region).

The term "epitope" refers to the area or region of an antigen to which the CDRs of an antibody specifically binds and can include a few amino acids or portions of a few amino acids, e.g., 5 or 6, or more, e.g., 20 or more amino acids, or portions of those amino acids. For example, where the target is a protein, the epitope can be comprised of consecutive amino acids (e.g., a linear epitope), or amino acids from different parts of the protein that are brought into proximity by protein folding (e.g., a discontinuous or conformational epitope). In some embodiments, the epitope is phosphorylated at one amino acid (e.g., at a serine or threonine residue).

As used herein, the phrase "recognizes an epitope," as used with reference to an anti-TREM2 antibody, means that the antibody CDRs interact with or specifically bind to the antigen (i.e., the TREM2 protein) at that epitope or a portion of the antigen containing that epitope.

As used herein, the term "multispecific antibody" refers to an antibody that comprises two or more different antigen-binding portions, in which each antigen-binding portion comprises a different variable region that recognizes a different antigen, or a fragment or portion of the antibody that binds to the two or more different antigens via its variable regions. As used herein, the term "bispecific antibody" refers to an antibody that comprises two different antigen-binding portions, in which each antigen-binding portion comprises a different variable region that recognizes a different antigen, or a fragment or portion of the antibody that binds to the two different antigens via its variable regions.

A "monoclonal antibody" refers to antibodies produced by a single clone of cells or a single cell line and consisting of or consisting essentially of antibody molecules that are identical in their primary amino acid sequence.

A "polyclonal antibody" refers to an antibody obtained from a heterogeneous population of antibodies in which different antibodies in the population bind to different epitopes of an antigen.

A "chimeric antibody" refers to an antibody molecule in which the constant region, or a portion thereof, is altered, replaced or exchanged so that the antigen-binding site (i.e., variable region, CDR, or portion thereof) is linked to a constant region of a different or altered class, effector function and/or species, or in which the variable region, or a portion thereof, is altered, replaced or exchanged with a variable region having a different or altered antigen specificity (e.g., CDR and framework regions from different species). In some embodiments, a chimeric antibody is a monoclonal antibody comprising a variable region from one source or species (e.g., mouse) and a constant region derived from a second source or species (e.g., human). Methods for producing chimeric antibodies are described in the art.

A "humanized antibody" is a chimeric immunoglobulin derived from a non-human source (e.g., murine) that contains minimal sequences derived from the non-human immunoglobulin outside the CDRs. In general, a humanized antibody will comprise at least one (e.g., two) antigen-binding variable domain(s), in which the CDR regions substantially correspond to those of the non-human immunoglobulin and the framework regions substantially correspond to those of a human immunoglobulin sequence. The humanized antibody can also comprise at least a portion of an immunoglobulin constant region (Fc), typically that of a human immunoglobulin sequence. Methods of antibody humanization are known in the art.

A "human antibody" or a "fully human antibody" is an antibody having human heavy chain and light chain sequences, typically derived from human germline genes. In some embodiments, the antibody is produced by a human cell, by a non-human animal that utilizes human antibody repertoires (e.g., transgenic mice that are genetically engineered to express human antibody sequences), or by phage display platforms.

The term "specifically binds" refers to a molecule (e.g., an antibody or an antigen-binding portion thereof) that binds to an epitope or target with greater affinity, greater avidity, and/or greater duration to that epitope or target in a sample than it binds to another epitope or non-target compound (e.g., a structurally different antigen). In some embodiments, an antibody (or an antigen-binding portion thereof) that specifically binds to an epitope or target is an antibody (or an antigen-binding portion thereof) that binds to the epitope or target with at least 5-fold greater affinity than other epitopes or non-target compounds, e.g., at least 6-fold, 7-fold, 8-fold, 9-fold, 10-fold, 20-fold, 25-fold, 50-fold, 100-fold, 1,000-fold, 10,000-fold, or greater affinity. The term "specific binding," "specifically binds to," or "is specific for" a particular epitope or target, as used herein, can be exhibited, for example, by a molecule having an equilibrium dissociation constant $K_D$ for the epitope or target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. It will be recognized by one of skill that an antibody that specifically binds to a target (e.g., a TREM2 protein) from one species may also specifically bind to orthologs of that target (e.g., the TREM2 protein).

The term "binding affinity" is used herein to refer to the strength of a non-covalent interaction between two molecules, e.g., between an antibody (or an antigen-binding portion thereof) and an antigen. Thus, for example, the term may refer to 1:1 interactions between an antibody (or an antigen-binding portion thereof) and an antigen, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet platform). As used herein, "binding affinity" includes not only formal binding affinities, such as those reflecting 1:1 interactions between an antibody (or an antigen-binding portion thereof) and an antigen, but also apparent affinities for which $K_D$ values are calculated that may reflect avid binding.

The term "cross-reacts," as used herein, refers to the ability of an antibody to bind to an antigen other than the antigen against which the antibody was raised. In some embodiments, cross-reactivity refers to the ability of an antibody to bind to an antigen from another species than the antigen against which the antibody was raised. As a non-limiting example, an anti-TREM2 antibody as described herein that is raised against a human TREM2 peptide can exhibit cross-reactivity with a TREM2 peptide or protein from a different species (e.g., monkey or mouse).

The term "isolated," as used with reference to a nucleic acid or protein (e.g., antibody), denotes that the nucleic acid or protein is essentially free of other cellular components with which it is associated in the natural state. Purity and homogeneity are typically determined using analytical chemistry techniques such as electrophoresis (e.g., polyacrylamide gel electrophoresis) or chromatography (e.g., high performance liquid chromatography). In some embodiments, an isolated nucleic acid or protein (e.g., antibody) is at least 85% pure, at least 90% pure, at least 95% pure, or at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof "Amino acid analogs" refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e., two) or multimer (i.e., three or more) of single chain polypeptides. The single chain polypeptides of a protein may be joined by a covalent bond, e.g., a disulfide bond, or non-covalent interactions.

The terms "polynucleotide" and "nucleic acid" interchangeably refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. Examples of polynucleotides contemplated herein include single- and double-stranded DNA, single- and double-stranded RNA, and hybrid molecules having mixtures of single- and double-stranded DNA and RNA.

The terms "conservative substitution" and "conservative mutation" refer to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60%, at least 65%, at least 70%, at least 75%, at least 80%, at least 85%, at least 90%, or at least 95% or greater, that are identical over a specified region when compared and aligned for maximum correspondence over a comparison window, or designated region as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the subject, individual, or patient is a human.

The terms "treating," "treatment," and the like are used herein to generally mean obtaining a desired pharmacologic and/or physiologic effect. "Treating" or "treatment" may refer to any indicia of success in the treatment or amelioration of a neurodegenerative disease (e.g., Alzheimer's disease or another neurodegenerative disease described herein), including any objective or subjective parameter such as abatement, remission, improvement in patient survival, increase in survival time or rate, diminishing of symptoms or making the disease more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "pharmaceutically acceptable excipient" refers to a non-active pharmaceutical ingredient that is biologically or pharmacologically compatible for use in humans or animals, such as, but not limited to a buffer, carrier, or preservative.

As used herein, a "therapeutic amount" or "therapeutically effective amount" of an agent (e.g., an antibody as described herein) is an amount of the agent that treats, alleviates, abates, or reduces the severity of symptoms of a disease in a subject. A "therapeutic amount" of an agent (e.g., an antibody as described herein) may improve patient survival, increase survival time or rate, diminish symptoms, make an injury, disease, or condition (e.g., a neurodegenerative disease) more tolerable, slow the rate of degeneration or decline, or improve a patient's physical or mental wellbeing.

The term "administer" refers to a method of delivering agents, compounds, or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, an antibody as described herein is administered intravenously.

The term "control" or "control value" refers to a reference value or baseline value. Appropriate controls can be determined by one skilled in the art. In some instances, control values can be determined relative to a baseline within the same subject or experiment, e.g., a measurement of sTREM2 taken prior to treatment with an anti-TREM2 antibody can be a control value for a post-treatment measurement of sTREM2 levels in the same subject. In other instances, the control value can be determined relative to a control subject (e.g., a healthy control or a disease control) or an average value in a population of control subjects (e.g., healthy controls or disease controls, e.g., a population of 10, 20, 50, 100, 200, 500, 1000 control subjects or more), e.g., a measurement of a subject's level of sTREM2 either at baseline or after treatment can be compared to a healthy control value.

III. Anti-TREM2 Antibodies

In one aspect, antibodies and antigen-binding fragments thereof that specifically bind to a TREM2 protein are provided. In some embodiments, the antibody specifically binds to a human TREM2 protein. In some embodiments, an anti-TREM2 antibody is selective for TREM2 over other TREM-like receptors (e.g., TREM1).

In some embodiments, an anti-TREM2 antibody is an antibody that comprises one or more complementarity determining region (CDR), heavy chain variable region, and/or light chain variable region sequences as disclosed herein. In some embodiments, an anti-TREM2 antibody comprises one or more CDR, heavy chain variable region, and/or light chain variable region sequences as disclosed herein and further comprises one or more functional characteristics as disclosed herein, e.g., an antibody that enhances TREM2 activity (e.g., enhances phagocytosis, or enhances the migration, differentiation, function, or survival of a cell such as a myeloid cell, microglia, or macrophage) or an antibody that decreases levels of sTREM2.

Anti-TREM2 Antibody Sequences

In some embodiments, an anti-TREM2 or antigen-binding fragment thereof comprises a heavy chain sequence, or a portion thereof, and/or a light chain sequence, or a portion thereof, derived from any of the following anti-TREM2 antibodies described herein: Clone CL0020107, Clone CL0020300, Clone CL0020215, Clone CL0020301, Clone CL0020302, Clone CL0020139, Clone CL0020304, Clone CL0020305, Clone CL0020306, Clone CL0020188, Clone CL0020307, Clone CL0020308, Clone CL0020309, Clone CL0020310, Clone CL0020123, Clone CL0020311, Clone CL0020312, Clone CL0020141, Clone CL0020103, Clone CL0020201, Clone CL0020120, Clone CL0020127, Clone CL0020109, Clone CL0020214, Clone CL0020096, Clone CL0020210, Clone CL0020313, Clone CL0020314, Clone CL0020315, Clone CL0020205, Clone CL0020206, Clone CL0020111, Clone CL0020112, Clone CL0020124, Clone CL0020125, Clone CL00220183, Clone CL0020186, Clone CL0020113, Clone CL0020162, Clone CL0020195, Clone CL0020161, Clone CL0020173, and Clone CL0020164. The CDR, heavy chain variable region, and light chain variable region amino acid sequences of these clones is set forth in the Informal Sequence Listing. In some embodiments, the anti-TREM2 antibody is a chimeric antibody. In some embodiments, the anti-TREM2 antibody is a humanized and/or affinity matured antibody.

In some embodiments, an anti-TREM2 antibody comprises one or more CDRs selected from the group consisting of:

(a) a heavy chain CDR1 (CDR-H1) sequence having at least 90% sequence identity to the amino acid sequence of any one of SEQ ID NOS:4, 12, 20, 28, 36, 44, 52, 56, 60, 68, 85, 93, 100, 105, 125, 142, 149, 157, 165, 172, 180, 188, 196, 202, 222, 228, 239, 253, 266, 274, and 282 or having up to two amino acid substitutions relative to the amino acid sequence of any one of SEQ ID NOS:4, 12, 20, 28, 36, 44, 52, 56, 60, 68, 85, 93, 100, 105, 125, 142, 149, 157, 165, 172, 180, 188, 196, 202, 222, 228, 239, 253, 266, 274, and 282;

(b) a heavy chain CDR2 (CDR-H2) sequence having at least 90% sequence identity to the amino acid sequence of any one of SEQ ID NOS:5, 13, 21, 29, 37, 45, 53, 57, 61, 69, 81, 86, 94, 101, 106, 115, 117, 119, 126, 132, 136, 143, 150, 158, 166, 173, 181, 189, 197, 203, 209, 214, 217, 223, 229, 236, 240, 254, 267, 275, 283, and 289 or having up to two amino acid substitutions relative to the amino acid sequence of any one of SEQ ID NOS:5, 13, 21, 29, 37, 45, 53, 57, 61, 69, 81, 86, 94, 101, 106, 115, 117, 119, 126, 132, 136, 143, 150, 158, 166, 173, 181, 189, 197, 203, 209, 214, 217, 223, 229, 236, 240, 254, 267, 275, 283, and 289;

(c) a heavy chain CDR3 (CDR-H3) sequence having at least 90% sequence identity to the amino acid sequence of any one of SEQ ID NOS:6, 14, 22, 30, 38, 46, 62, 70, 73, 87, 95, 102, 107, 127, 137, 144, 151, 159, 167, 174, 182, 190, 198, 204, 210, 230, 241, 245, 249, 255, 260, 268, 276, and 284 or having up to two amino acid substitutions relative to the amino acid sequence of any one of SEQ ID NOS:6, 14, 22, 30, 38, 46, 62, 70, 73, 87, 95, 102, 107, 127, 137, 144, 151, 159, 167, 174, 182, 190, 198, 204, 210, 230, 241, 245, 249, 255, 260, 268, 276, and 284;

(d) a light chain CDR1 (CDR-L1) sequence having at least 90% sequence identity to the amino acid sequence of any one of SEQ ID NOS:7, 15, 23, 31, 39, 47, 63, 79, 88, 96, 108, 128, 138, 145, 152, 160, 168, 175, 183, 191, 199, 205, 218, 224, 231, 242, 246, 256, 261, 269, 277, and 285 or having up to two amino acid substitutions relative to the amino acid sequence of any one of SEQ ID NOS:7, 15, 23, 31, 39, 47, 63, 79, 88, 96, 108, 128, 138, 145, 152, 160, 168, 175, 183, 191, 199, 205, 218, 224, 231, 242, 246, 256, 261, 269, 277, and 285;

(e) a light chain CDR2 (CDR-L2) sequence having at least 90% sequence identity to the amino acid sequence of any one of SEQ ID NOS:8, 16, 24, 32, 40, 48, 64, 89, 109, 153, 161, 176, 184, 211, 219, 232, 250, 262, 270, 278, and 286 or having up to two amino acid substitutions relative to the amino acid sequence of any one of SEQ ID NOS:8, 16, 24, 32, 40, 48, 64, 89, 109, 153, 161, 176, 184, 211, 219, 232, 250, 262, 270, 278, and 286; and (f) a light chain CDR3 (CDR-L3) sequence having at least 90% sequence identity to the amino acid sequence of any one of SEQ ID NOS:9, 17, 25, 33, 41, 49, 65, 74, 90, 97, 110, 129, 133, 139, 146, 154, 162, 169, 177, 185, 193, 206, 212, 225, 233, 257, 263, 271, 279, 287, and 290 or having up to two amino acid substitutions relative to the amino acid sequence of any one of SEQ ID NOS:9, 17, 25, 33, 41, 49, 65, 74, 90, 97, 110, 129, 133, 139, 146, 154, 162, 169, 177, 185, 193, 206, 212, 225, 233, 257, 263, 271, 279, 287, and 290.

In some embodiments, an anti-TREM2 antibody comprises two, three, four, five, or all six of (a)-(f). In some embodiments, an anti-TREM2 antibody comprises the CDR-H1 of (a), the CDR-H2 of (b), and the CDR-H3 of (c). In some embodiments, an anti-TREM2 antibody comprises the CDR-L1 of (d), the CDR-L2 of (e), and the CDR-L3 of (f). In some embodiments, a CDR having up to two amino acid substitutions has one amino acid substitution relative to the reference sequence. In some embodiments, a CDR having up to two amino acid substitutions has two amino acid substitutions relative to the reference sequence. In some embodiments, the up to two amino acid substitutions are conservative substitutions.

In some embodiments, an anti-TREM2 antibody comprises one or more CDRs selected from the group consisting of:

(a) a CDR-H1 sequence comprising the amino acid sequence of any one of SEQ ID NOS:4, 12, 20, 28, 36, 44, 52, 56, 60, 68, 85, 93, 100, 105, 125, 142, 149, 157, 165, 172, 180, 188, 196, 202, 222, 228, 239, 253, 266, 274, and 282;

(b) a CDR-H2 sequence comprising the amino acid sequence of any one of SEQ ID NOS:5, 13, 21, 29, 37, 45, 53, 57, 61, 69, 81, 86, 94, 101, 106, 115, 117, 119, 126, 132, 136, 143, 150, 158, 166, 173, 181, 189, 197, 203, 209, 214, 217, 223, 229, 236, 240, 254, 267, 275, 283, and 289;

(c) a CDR-H3 sequence comprising the amino acid sequence of any one of SEQ ID NOS:6, 14, 22, 30, 38, 46, 62, 70, 73, 87, 95, 102, 107, 127, 137, 144, 151, 159, 167, 174, 182, 190, 198, 204, 210, 230, 241, 245, 249, 255, 260, 268, 276, and 284;

(d) a CDR-L1 sequence comprising the amino acid sequence of any one of SEQ ID NOS:7, 15, 23, 31, 39, 47, 63, 79, 88, 96, 108, 128, 138, 145, 152, 160, 168, 175, 183, 191, 199, 205, 218, 224, 231, 242, 246, 256, 261, 269, 277, and 285;

(e) a CDR-L2 sequence comprising the amino acid sequence of any one of SEQ ID NOS:8, 16, 24, 32, 40, 48, 64, 89, 109, 153, 161, 176, 184, 211, 219, 232, 250, 262, 270, 278, and 286; and (f) a CDR-L3 sequence comprising the amino acid sequence of any one of SEQ ID NOS:9, 17, 25, 33, 41, 49, 65, 74, 90, 97, 110, 129, 133, 139, 146, 154, 162, 169, 177, 185, 193, 206, 212, 225, 233, 257, 263, 271, 279, 287, and 290.

In some embodiments, an anti-TREM2 antibody comprises two, three, four, five, or all six of (a)-(f). In some embodiments, an anti-TREM2 antibody comprises the CDR-H1 of (a), the CDR-H2 of (b), and the CDR-H3 of (c). In some embodiments, an anti-TREM2 antibody comprises the CDR-L1 of (d), the CDR-L2 of (e), and the CDR-L3 of (f).

In some embodiments, an anti-TREM2 antibody comprises:

(a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO:6, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO:9; or (b) a CDR-H1 comprising the amino acid sequence of SEQ ID NO:12, a CDR-H2 comprising the amino acid sequence of SEQ ID NO:13, a CDR-H3 comprising the amino acid sequence of SEQ ID NO:14, a CDR-L1 comprising the amino acid sequence of SEQ ID NO:15, a CDR-L2 comprising the amino acid sequence of SEQ ID NO:16, and a CDR-L3 comprising the amino acid sequence of SEQ ID NO:17; or (c) a CDR-H1 comprising the amino acid sequence of SEQ ID NO:20, a CDR-H2 comprising the amino acid sequence of SEQ ID NO:21, a CDR-H3 comprising the amino acid sequence of SEQ ID NO:22, a CDR-L1 comprising the amino acid sequence of SEQ ID NO:23, a CDR-L2 comprising the amino acid sequence of SEQ ID NO:24, and a CDR-L3 comprising the amino acid sequence of SEQ ID NO:25; or (d) a CDR-H1 comprising the amino acid sequence of SEQ ID NO:28, a CDR-H2 comprising the amino acid sequence of SEQ ID NO:29, a CDR-H3 comprising the amino acid sequence of SEQ ID NO:30, a CDR-L1 comprising the amino acid sequence of SEQ ID NO:31, a CDR-L2 comprising the amino acid sequence of SEQ ID NO:32, and a CDR-L3 comprising the amino acid sequence of SEQ ID NO:33; or (e) a CDR-H1 comprising the amino acid sequence of SEQ ID NO:36, a CDR-H2 comprising the amino acid sequence of SEQ ID NO:37, a CDR-H3 comprising the amino acid sequence of SEQ ID NO:38, a CDR-L1 comprising the amino acid sequence of SEQ ID NO:39, a CDR-L2 comprising the amino acid sequence of SEQ ID NO:40, and a CDR-L3 comprising the amino acid sequence of SEQ ID NO:41; or (f) a CDR-H1 comprising the amino acid sequence of SEQ ID NO:44, a CDR-H2 comprising the amino acid sequence of SEQ ID NO:45, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49; or (g) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:62, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or (h) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or (i) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or (j) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or (k) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or (l) a CDR-H1 comprising the amino acid sequence of SEQ ID NO:68, a CDR-H2 comprising the amino acid sequence of SEQ ID NO:69, a CDR-H3 comprising the amino acid sequence of SEQ ID NO:70, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or (m) a CDR-H1 comprising the amino acid sequence of SEQ ID NO:85, a CDR-H2 comprising the amino acid sequence of SEQ ID NO:86, a CDR-H3 comprising the amino acid sequence of SEQ ID NO:87, a CDR-L1 comprising the amino acid sequence of SEQ ID NO:88, a CDR-L2 comprising the amino acid sequence of SEQ ID NO:89, and a CDR-L3 comprising the amino acid sequence of SEQ ID NO:90; or (n) a CDR-H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:97; or (o) a CDR-H1 comprising the amino acid sequence of SEQ ID NO:100, a CDR-H2 comprising the amino acid sequence of SEQ ID NO:101, a CDR-H3 comprising the amino acid sequence of SEQ ID NO:102, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:90; or (p) a CDR-H1 comprising the amino acid sequence of SEQ ID NO:105, a CDR-H2 comprising the amino acid sequence of SEQ ID NO:106, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (q) a CDR-H1 comprising the amino acid sequence of SEQ ID NO:105, a CDR-H2 comprising the amino acid sequence of SEQ ID NO:115, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (r) a CDR-H1 comprising the amino acid sequence of SEQ ID NO:105, a CDR-H2 comprising the amino acid sequence of SEQ ID NO:117, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (s) a CDR-H1 comprising the amino acid sequence of SEQ ID NO:105, a CDR-H2 comprising the amino acid sequence of SEQ ID NO:119, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or (t) a CDR-H1 comprising the amino acid sequence of SEQ ID NO:125, a CDR-H2 comprising the amino acid sequence of SEQ ID NO:126, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:129; or (u) a CDR-H1 comprising the amino acid sequence of SEQ ID NO:125, a CDR-H2 comprising the amino acid sequence of SEQ ID NO:132, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:133; or (v) a CDR-H1 comprising the amino acid sequence of SEQ ID NO:125, a CDR-H2 comprising the amino acid sequence of SEQ ID NO:136, a CDR-H3 comprising the amino acid sequence of SEQ ID NO:137, a CDR-L1 comprising the amino acid sequence of SEQ ID NO:138, a CDR-L2 comprising the amino acid sequence of SEQ ID NO:32, and a CDR-L3 comprising the amino acid sequence of SEQ ID NO:139; or (w) a CDR-H1 comprising the amino acid sequence of SEQ ID NO:142, a CDR-H2 comprising the amino acid sequence of SEQ ID NO:143, a CDR-H3 comprising the amino acid sequence of SEQ ID NO:144, a CDR-L1 comprising the amino acid sequence of SEQ ID NO:145, a CDR-L2 comprising the amino acid sequence of SEQ ID NO:32, and a CDR-L3 comprising the amino acid sequence of SEQ ID NO:146; or (x) a CDR-H1 comprising the amino acid sequence of SEQ ID NO:149, a CDR-H2 comprising the amino acid sequence of SEQ ID NO:150, a CDR-H3 comprising the amino acid sequence of SEQ ID NO:151, a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; or
(y) a CDR-H1 comprising the amino acid sequence of SEQ ID NO:157, a CDR-H2 comprising the amino acid sequence of SEQ ID NO:158, a CDR-H3 comprising the amino acid sequence of SEQ ID NO:159, a CDR-L1 comprising the amino acid sequence of SEQ ID NO:160, a CDR-L2 comprising the amino acid sequence of SEQ ID NO:161, and a CDR-L3 comprising the amino acid sequence of SEQ ID NO:162; or
(z) a CDR-H1 comprising the amino acid sequence of SEQ ID NO:165, a CDR-H2 comprising the amino acid sequence of SEQ ID NO:166, a CDR-H3 comprising the amino acid sequence of SEQ ID NO:167, a CDR-L1 comprising the amino acid sequence of SEQ ID NO:168, a CDR-L2 comprising the amino acid sequence of SEQ ID NO:161, and a CDR-L3 comprising the amino acid sequence of SEQ ID NO:169; or
(aa) a CDR-H1 comprising the amino acid sequence of SEQ ID NO:172, a CDR-H2 comprising the amino acid sequence of SEQ ID NO:173, a CDR-H3 comprising the amino acid sequence of SEQ ID NO:174, a CDR-L1 comprising the amino acid sequence of SEQ ID NO:175, a CDR-L2 comprising the amino acid sequence of SEQ ID NO:176, and a CDR-L3 comprising the amino acid sequence of SEQ ID NO:177; or
(bb) a CDR-H1 comprising the amino acid sequence of SEQ ID NO:180, a CDR-H2 comprising the amino acid sequence of SEQ ID NO:181, a CDR-H3 comprising the amino acid sequence of SEQ ID NO:182, a CDR-L1 comprising the amino acid sequence of SEQ ID NO:183, a CDR-L2 comprising the amino acid sequence of SEQ ID NO:184, and a CDR-L3 comprising the amino acid sequence of SEQ ID NO:185; or
(cc) a CDR-H1 comprising the amino acid sequence of SEQ ID NO:188, a CDR-H2 comprising the amino acid sequence of SEQ ID NO:189, a CDR-H3 comprising the amino acid sequence of SEQ ID NO:190, a CDR-L1 comprising the amino acid sequence of SEQ ID NO:191, a CDR-L2 comprising the amino acid sequence of SEQ ID NO:32, and a CDR-L3 comprising the amino acid sequence of SEQ ID NO:146; or
(dd) a CDR-H1 comprising the amino acid sequence of SEQ ID NO:188, a CDR-H2 comprising the amino acid sequence of SEQ ID NO:189, a CDR-H3 comprising the amino acid sequence of SEQ ID NO:190, a CDR-L1 comprising the amino acid sequence of SEQ ID NO:191, a CDR-L2 comprising the amino acid sequence of SEQ ID NO:32, and a CDR-L3 comprising the amino acid sequence of SEQ ID NO:193; or
(ee) a CDR-H1 comprising the amino acid sequence of SEQ ID NO:196, a CDR-H2 comprising the amino acid sequence of SEQ ID NO:197, a CDR-H3 comprising the amino acid sequence of SEQ ID NO:198, a CDR-L1 comprising the amino acid sequence of SEQ ID NO:199, a CDR-L2 comprising the amino acid sequence of SEQ ID NO:89, and a CDR-L3 comprising the amino acid sequence of SEQ ID NO:90; or
(ff) a CDR-H1 comprising the amino acid sequence of SEQ ID NO:202, a CDR-H2 comprising the amino acid sequence of SEQ ID NO:203, a CDR-H3 comprising the amino acid sequence of SEQ ID NO:204, a CDR-L1 comprising the amino acid sequence of SEQ ID NO:205, a CDR-L2 comprising the amino acid sequence of SEQ ID NO:89, and a CDR-L3 comprising the amino acid sequence of SEQ ID NO:206; or
(gg) a CDR-H1 comprising the amino acid sequence of SEQ ID NO:28, a CDR-H2 comprising the amino acid sequence of SEQ ID NO:209, a CDR-H3 comprising the amino acid sequence of SEQ ID NO:210, a CDR-L1 comprising the amino acid sequence of SEQ ID NO:205, a CDR-L2 comprising the amino acid sequence of SEQ ID NO:211, and a CDR-L3 comprising the amino acid sequence of SEQ ID NO:212; or
(hh) a CDR-H1 comprising the amino acid sequence of SEQ ID NO:172, a CDR-H2 comprising the amino acid sequence of SEQ ID NO:214, a CDR-H3 comprising the amino acid sequence of SEQ ID NO:174, a CDR-L1 comprising the amino acid sequence of SEQ ID NO:175, a CDR-L2 comprising the amino acid sequence of SEQ ID NO:176, and a CDR-L3 comprising the amino acid sequence of SEQ ID NO:177; or
(ii) a CDR-H1 comprising the amino acid sequence of SEQ ID NO:149, a CDR-H2 comprising the amino acid sequence of SEQ ID NO:217, a CDR-H3 comprising the amino acid sequence of SEQ ID NO:167, a CDR-L1 comprising the amino acid sequence of SEQ ID NO:218, a CDR-L2 comprising the amino acid sequence of SEQ ID NO:219, and a CDR-L3 comprising the amino acid sequence of SEQ ID NO:169; or
(jj) a CDR-H1 comprising the amino acid sequence of SEQ ID NO:222, a CDR-H2 comprising the amino acid sequence of SEQ ID NO:223, a CDR-H3 comprising the amino acid sequence of SEQ ID NO:22, a CDR-L1 comprising the amino acid sequence of SEQ ID NO:224, a CDR-L2 comprising the amino acid sequence of SEQ ID NO:8, and a CDR-L3 comprising the amino acid sequence of SEQ ID NO:225; or
(kk) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:230, a CDR-L1 comprising the amino acid sequence of SEQ ID NO:231, a CDR-L2 comprising the amino acid sequence of SEQ ID NO:232, and a CDR-L3 comprising the amino acid sequence of SEQ ID NO:233; or
(ll) a CDR-H1 comprising the amino acid sequence of SEQ ID NO:149, a CDR-H2 comprising the amino acid sequence of SEQ ID NO:236, a CDR-H3 comprising the amino acid sequence of SEQ ID NO:151, a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; or
(mm) a CDR-H1 comprising the amino acid sequence of SEQ ID NO:239, a CDR-H2 comprising the amino acid sequence of SEQ ID NO:240, a CDR-H3 comprising the amino acid sequence of SEQ ID NO:241, a CDR-L1 comprising the amino acid sequence of SEQ ID NO:242, a CDR-L2 comprising the amino acid sequence of SEQ ID NO:89, and a CDR-L3 comprising the amino acid sequence of SEQ ID NO:212; or
(nn) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:245, a CDR-L1 comprising the amino acid sequence of SEQ ID NO:246, a CDR-L2 comprising the amino acid sequence of SEQ ID NO:232, and a CDR-L3 comprising the amino acid sequence of SEQ ID NO:233; or
(oo) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:249, a CDR-L1 comprising the amino acid sequence of SEQ ID NO:246, a CDR-L2 comprising the amino acid sequence of SEQ ID NO:250, and a CDR-L3 comprising the amino acid sequence of SEQ ID NO:233; or
(pp) a CDR-H1 comprising the amino acid sequence of SEQ ID NO:253, a CDR-H2 comprising the amino acid sequence of SEQ ID NO:254, a CDR-H3 comprising the amino acid sequence of SEQ ID NO:255, a CDR-L1 comprising the amino acid sequence of SEQ ID NO:256, a CDR-L2 comprising the amino acid sequence of SEQ ID NO:32, and a CDR-L3 comprising the amino acid sequence of SEQ ID NO:257; or
(qq) a CDR-H1 comprising the amino acid sequence of SEQ ID NO:253, a CDR-H2 comprising the amino acid sequence of SEQ ID NO:254, a CDR-H3 comprising the amino acid sequence of SEQ ID NO:260, a CDR-L1 comprising the amino acid sequence of SEQ ID NO:261, a CDR-L2 comprising the amino acid sequence of SEQ ID NO:262, and a CDR-L3 comprising the amino acid sequence of SEQ ID NO:263; or
(rr) a CDR-H1 comprising the amino acid sequence of SEQ ID NO:266, a CDR-H2 comprising the amino acid sequence of SEQ ID NO:267, a CDR-H3 comprising the amino acid sequence of SEQ ID NO:268, a CDR-L1 comprising the amino acid sequence of SEQ ID NO:269, a CDR-L2 comprising the amino acid sequence of SEQ ID NO:270, and a CDR-L3 comprising the amino acid sequence of SEQ ID NO:271; or
(ss) a CDR-H1 comprising the amino acid sequence of SEQ ID NO:274, a CDR-H2 comprising the amino acid sequence of SEQ ID NO:275, a CDR-H3 comprising the amino acid sequence of SEQ ID NO:276, a CDR-L1 comprising the amino acid sequence of SEQ ID NO:277, a CDR-L2 comprising the amino acid sequence of SEQ ID NO:278, and a CDR-L3 comprising the amino acid sequence of SEQ ID NO:279; or
(tt) a CDR-H1 comprising the amino acid sequence of SEQ ID NO:282, a CDR-H2 comprising the amino acid sequence of SEQ ID NO:283, a CDR-H3 comprising the amino acid sequence of SEQ ID NO:284, a CDR-L1 comprising the amino acid sequence of SEQ ID NO:285, a CDR-L2 comprising the amino acid sequence of SEQ ID NO:286, and a CDR-L3 comprising the amino acid sequence of SEQ ID NO:287; or
(uu) a CDR-H1 comprising the amino acid sequence of SEQ ID NO:60, a CDR-H2 comprising the amino acid sequence of SEQ ID NO:289, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:290; or
(vv) a CDR-H1 comprising the amino acid sequence of SEQ ID NO:52, a CDR-H2 comprising the amino acid sequence of SEQ ID NO:53, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:292; or
(ww) a CDR-H1 comprising the amino acid sequence of SEQ ID NO:56, a CDR-H2 comprising the amino acid sequence of SEQ ID NO:57, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49.

In some embodiments, an anti-TREM2 antibody comprises a heavy chain variable region comprising an amino acid sequence that has at least 85%, 90%, 91%, 92%, 93%, 94%, 95%, 96%, 97%, 98%, or 99% sequence identity to any one of SEQ ID NOS:2, 10, 18, 26, 34, 42, 50, 54, 58, 66, 71, 75, 77, 80, 82, 83, 91, 98, 103, 111, 113, 114, 116, 118, 120, 121, 122, 123, 130, 134, 140, 147, 155, 163, 170, 178, 186, 194, 200, 207, 213, 215, 220, 226, 234, 237, 243, 247, 251, 258, 264, 272, 280, 288, and 350. In some embodiments, an anti-TREM2 comprises a heavy chain variable region comprising the amino acid sequence of any one of SEQ ID NOS:2, 10, 18, 26, 34, 42, 50, 54, 58, 66, 71, 75, 77, 80, 82, 83, 91, 98, 103, 111, 113, 114, 116, 118, 120, 121, 122, 123, 130, 134, 140, 147, 155, 163, 170, 178, 186, 194, 200, 207, 213, 215, 220, 226, 234, 237, 243, 247, 251, 258, 264, 272, 280, 288, and 350.

In some embodiments, an anti-TREM2 antibody comprises a light chain variable region comprising an amino acid sequence that has at least 85%, 90%, 91%, 92%, 93%, 94%, 95%, 96%, 97%, 98%, or 99% sequence identity to any one of SEQ ID NOS:3, 11, 19, 27, 35, 43, 51, 55, 59, 67, 72, 76, 78, 84, 92, 99, 104, 112, 124, 131, 135, 141, 148, 156, 164, 171, 179, 187, 192, 195, 201, 208, 216, 221, 227, 235, 238, 244, 248, 252, 259, 265, 273, 281, and 339. In some embodiments, an anti-TREM2 antibody comprises a light chain variable region comprising the amino acid sequence of any one of SEQ ID NOS:3, 11, 19, 27, 35, 43, 51, 55, 59, 67, 72, 76, 78, 84, 92, 99, 104, 112, 124, 131, 135, 141, 148, 156, 164, 171, 179, 187, 192, 195, 201, 208, 216, 221, 227, 235, 238, 244, 248, 252, 259, 265, 273, 281, and 339.

In some embodiments, an anti-TREM2 antibody comprises: a heavy chain variable region comprising an amino acid sequence that has at least 85%, 90%, 91%, 92%, 93%, 94%, 95%, 96%, 97%, 98%, or 99% sequence identity to any one of SEQ ID NOS:2, 10, 18, 26, 34, 42, 50, 54, 58, 66, 71, 75, 77, 80, 82, 83, 91, 98, 103, 111, 113, 114, 116, 118, 120, 121, 122, 123, 130, 134, 140, 147, 155, 163, 170, 178, 186, 194, 200, 207, 213, 215, 220, 226, 234, 237, 243, 247, 251, 258, 264, 272, 280, 288, and 350, and a light chain variable region comprising an amino acid sequence that has at least 85%, 90%, 91%, 92%, 93%, 94%, 95%, 96%, 97%, 98%, or 99% sequence identity to any one of SEQ ID NOS:3, 11, 19, 27, 35, 43, 51, 55, 59, 67, 72, 76, 78, 84, 92, 99, 104, 112, 124, 131, 135, 141, 148, 156, 164, 171, 179, 187, 192, 195, 201, 208, 216, 221, 227, 235, 238, 244, 248, 252, 259, 265, 273, 281, and 339. In some embodiments, an anti-TREM2 comprises: a heavy chain variable region comprising the amino acid sequence of any one of SEQ ID NOS:2, 10, 18, 26, 34, 42, 50, 54, 58, 66, 71, 75, 77, 80, 82, 83, 91, 98, 103, 111, 113, 114, 116, 118, 120, 121, 122, 123, 130, 134, 140, 147, 155, 163, 170, 178, 186, 194, 200, 207, 213, 215, 220, 226, 234, 237, 243, 247, 251, 258, 264, 272, 280, 288, and 350, and a light chain variable region comprising the amino acid sequence of any one of SEQ ID NOS:3, 11, 19, 27, 35, 43, 51, 55, 59, 67, 72, 76, 78, 84, 92, 99, 104, 112, 124, 131, 135, 141, 148, 156, 164, 171, 179, 187, 192, 195, 201, 208, 216, 221, 227, 235, 238, 244, 248, 252, 259, 265, 273, 281, and 339.

In some embodiments, an anti-TREM2 antibody comprises:
(a) a $V_H$ sequence that has at least 85% sequence identity to SEQ ID NO:2 and a $V_L$ sequence that has at least 85% sequence identity to SEQ ID NO:3; or (b) a $V_H$ sequence that has at least 85% sequence identity to SEQ ID NO:10 and a $V_L$ sequence that has at least 85% sequence identity to SEQ ID NO:11; or
(c) a $V_H$ sequence that has at least 85% sequence identity to SEQ ID NO:18 and a $V_L$ sequence that has at least 85% sequence identity to SEQ ID NO:19; or
(d) a $V_H$ sequence that has at least 85% sequence identity to SEQ ID NO:26 and a $V_L$ sequence that has at least 85% sequence identity to SEQ ID NO:27; or
(e) a $V_H$ sequence that has at least 85% sequence identity to SEQ ID NO:34 and a $V_L$ sequence that has at least 85% sequence identity to SEQ ID NO:35; or
(f) a $V_H$ sequence that has at least 85% sequence identity to SEQ ID NO:42 and a $V_L$ sequence that has at least 85% sequence identity to SEQ ID NO:43; or
(g) a $V_H$ sequence that has at least 85% sequence identity to SEQ ID NO:50 and a $V_L$ sequence that has at least 85% sequence identity to SEQ ID NO:51; or
(h) a $V_H$ sequence that has at least 85% sequence identity to SEQ ID NO:54 and a $V_L$ sequence that has at least 85% sequence identity to SEQ ID NO:55; or
(i) a $V_H$ sequence that has at least 85% sequence identity to SEQ ID NO:58 and a $V_L$ sequence that has at least 85% sequence identity to SEQ ID NO:59; or
(j) a $V_H$ sequence that has at least 85% sequence identity to SEQ ID NO:66 and a $V_L$ sequence that has at least 85% sequence identity to SEQ ID NO:67; or
(k) a $V_H$ sequence that has at least 85% sequence identity to SEQ ID NO:71 and a $V_L$ sequence that has at least 85% sequence identity to SEQ ID NO:72; or
(l) a $V_H$ sequence that has at least 85% sequence identity to SEQ ID NO:75 and a $V_L$ sequence that has at least 85% sequence identity to SEQ ID NO:76; or
(m) a $V_H$ sequence that has at least 85% sequence identity to SEQ ID NO:77 and a $V_L$ sequence that has at least 85% sequence identity to SEQ ID NO:76; or
(n) a $V_H$ sequence that has at least 85% sequence identity to SEQ ID NO:75 and a $V_L$ sequence that has at least 85% sequence identity to SEQ ID NO:78; or
(o) a $V_H$ sequence that has at least 85% sequence identity to SEQ ID NO:350 and a $V_L$ sequence that has at least 85% sequence identity to SEQ ID NO:78; or
(p) a $V_H$ sequence that has at least 85% sequence identity to SEQ ID NO:80 and a $V_L$ sequence that has at least 85% sequence identity to SEQ ID NO:76; or
(q) a $V_H$ sequence that has at least 85% sequence identity to SEQ ID NO:82 and a $V_L$ sequence that has at least 85% sequence identity to SEQ ID NO:76; or
(r) a $V_H$ sequence that has at least 85% sequence identity to SEQ ID NO:80 and a $V_L$ sequence that has at least 85% sequence identity to SEQ ID NO:78; or
(s) a $V_H$ sequence that has at least 85% sequence identity to SEQ ID NO:82 and a $V_L$ sequence that has at least 85% sequence identity to SEQ ID NO:78; or
(t) a $V_H$ sequence that has at least 85% sequence identity to SEQ ID NO:83 and a $V_L$ sequence that has at least 85% sequence identity to SEQ ID NO:84; or
(u) a $V_H$ sequence that has at least 85% sequence identity to SEQ ID NO:91 and a $V_L$ sequence that has at least 85% sequence identity to SEQ ID NO:92; or
(v) a $V_H$ sequence that has at least 85% sequence identity to SEQ ID NO:98 and a $V_L$ sequence that has at least 85% sequence identity to SEQ ID NO:99; or
(w) a $V_H$ sequence that has at least 85% sequence identity to SEQ ID NO:103 and a $V_L$ sequence that has at least 85% sequence identity to SEQ ID NO:104; or
(x) a $V_H$ sequence that has at least 85% sequence identity to SEQ ID NO:111 and a $V_L$ sequence that has at least 85% sequence identity to SEQ ID NO:112; or
(y) a $V_H$ sequence that has at least 85% sequence identity to SEQ ID NO:113 and a $V_L$ sequence that has at least 85% sequence identity to SEQ ID NO:112; or
(z) a $V_H$ sequence that has at least 85% sequence identity to SEQ ID NO:114 and a $V_L$ sequence that has at least 85% sequence identity to SEQ ID NO:112; or
(aa) a $V_H$ sequence that has at least 85% sequence identity to SEQ ID NO:116 and a $V_L$ sequence that has at least 85% sequence identity to SEQ ID NO:112; or
(bb) a $V_H$ sequence that has at least 85% sequence identity to SEQ ID NO:118 and a $V_L$ sequence that has at least 85% sequence identity to SEQ ID NO:112; or
(cc) a $V_H$ sequence that has at least 85% sequence identity to SEQ ID NO:120 and a $V_L$ sequence that has at least 85% sequence identity to SEQ ID NO:112; or
(dd) a $V_H$ sequence that has at least 85% sequence identity to SEQ ID NO:121 and a $V_L$ sequence that has at least 85% sequence identity to SEQ ID NO:112; or
(ee) a $V_H$ sequence that has at least 85% sequence identity to SEQ ID NO:122 and a $V_L$ sequence that has at least 85% sequence identity to SEQ ID NO:112; or
(ff) a $V_H$ sequence that has at least 85% sequence identity to SEQ ID NO:123 and a $V_L$ sequence that has at least 85% sequence identity to SEQ ID NO:124; or
(gg) a $V_H$ sequence that has at least 85% sequence identity to SEQ ID NO:130 and a $V_L$ sequence that has at least 85% sequence identity to SEQ ID NO:131; or
(hh) a $V_H$ sequence that has at least 85% sequence identity to SEQ ID NO:134 and a $V_L$ sequence that has at least 85% sequence identity to SEQ ID NO:135; or
(ii) a $V_H$ sequence that has at least 85% sequence identity to SEQ ID NO:140 and a $V_L$ sequence that has at least 85% sequence identity to SEQ ID NO:141; or
(jj) a $V_H$ sequence that has at least 85% sequence identity to SEQ ID NO:147 and a $V_L$ sequence that has at least 85% sequence identity to SEQ ID NO:148; or
(kk) a $V_H$ sequence that has at least 85% sequence identity to SEQ ID NO:155 and a $V_L$ sequence that has at least 85% sequence identity to SEQ ID NO:156; or
(ll) a $V_H$ sequence that has at least 85% sequence identity to SEQ ID NO:163 and a $V_L$ sequence that has at least 85% sequence identity to SEQ ID NO:164; or
(mm) a $V_H$ sequence that has at least 85% sequence identity to SEQ ID NO:170 and a $V_L$ sequence that has at least 85% sequence identity to SEQ ID NO:171; or
(nn) a $V_H$ sequence that has at least 85% sequence identity to SEQ ID NO:178 and a $V_L$ sequence that has at least 85% sequence identity to SEQ ID NO:179; or
(oo) a $V_H$ sequence that has at least 85% sequence identity to SEQ ID NO:186 and a $V_L$ sequence that has at least 85% sequence identity to SEQ ID NO:187; or
(pp) a $V_H$ sequence that has at least 85% sequence identity to SEQ ID NO:186 and a $V_L$ sequence that has at least 85% sequence identity to SEQ ID NO:192; or
(qq) a $V_H$ sequence that has at least 85% sequence identity to SEQ ID NO:194 and a $V_L$ sequence that has at least 85% sequence identity to SEQ ID NO:195; or
(rr) a $V_H$ sequence that has at least 85% sequence identity to SEQ ID NO:200 and a $V_L$ sequence that has at least 85% sequence identity to SEQ ID NO:201; or
(ss) a $V_H$ sequence that has at least 85% sequence identity to SEQ ID NO:207 and a $V_L$ sequence that has at least 85% sequence identity to SEQ ID NO:208; or (tt) a $V_H$ sequence that has at least 85% sequence identity to SEQ ID NO:213 and a $V_L$ sequence that has at least 85% sequence identity to SEQ ID NO:171; or
(uu) a $V_H$ sequence that has at least 85% sequence identity to SEQ ID NO:215 and a $V_L$ sequence that has at least 85% sequence identity to SEQ ID NO:216; or
(vv) a $V_H$ sequence that has at least 85% sequence identity to SEQ ID NO:220 and a $V_L$ sequence that has at least 85% sequence identity to SEQ ID NO:221; or
(ww) a $V_H$ sequence that has at least 85% sequence identity to SEQ ID NO:226 and a $V_L$ sequence that has at least 85% sequence identity to SEQ ID NO:227; or
(xx) a $V_H$ sequence that has at least 85% sequence identity to SEQ ID NO:234 and a $V_L$ sequence that has at least 85% sequence identity to SEQ ID NO:235; or
(yy) a $V_H$ sequence that has at least 85% sequence identity to SEQ ID NO:237 and a $V_L$ sequence that has at least 85% sequence identity to SEQ ID NO:238; or
(zz) a $V_H$ sequence that has at least 85% sequence identity to SEQ ID NO:243 and a $V_L$ sequence that has at least 85% sequence identity to SEQ ID NO:244; or
(aaa) a $V_H$ sequence that has at least 85% sequence identity to SEQ ID NO:247 and a $V_L$ sequence that has at least 85% sequence identity to SEQ ID NO:248; or
(bbb) a $V_H$ sequence that has at least 85% sequence identity to SEQ ID NO:251 and a $V_L$ sequence that has at least 85% sequence identity to SEQ ID NO:252; or
(ccc) a $V_H$ sequence that has at least 85% sequence identity to SEQ ID NO:258 and a $V_L$ sequence that has at least 85% sequence identity to SEQ ID NO:259; or
(ddd) a $V_H$ sequence that has at least 85% sequence identity to SEQ ID NO:264 and a $V_L$ sequence that has at least 85% sequence identity to SEQ ID NO:265; or
(eee) a $V_H$ sequence that has at least 85% sequence identity to SEQ ID NO:272 and a $V_L$ sequence that has at least 85% sequence identity to SEQ ID NO:273; or
(fff) a $V_H$ sequence that has at least 85% sequence identity to SEQ ID NO:280 and a $V_L$ sequence that has at least 85% sequence identity to SEQ ID NO:281; or
(ggg) a $V_H$ sequence that has at least 85% sequence identity to SEQ ID NO:288 and $V_L$ sequence that has at least 85% sequence identity to SEQ ID NO:291; or
(hhh) a $V_H$ sequence that has at least 85% sequence identity to SEQ ID NO:80 and a $V_L$ sequence that has at least 85% sequence identity to SEQ ID NO:339.

In some embodiments, an anti-TREM2 antibody comprises one or more sequences that are encompassed by a consensus sequence disclosed herein. As a non-limiting example, consensus sequences can be identified by aligning heavy chain or light chain sequences (e.g., CDRs) for antibodies that are from the same (or similar) germlines. In some embodiments, consensus sequences may be generated from antibodies that contain sequences that are of the same (or similar) length and/or have at least one highly similar CDR (e.g., a highly similar CDR3). In some embodiments, such sequences in these antibodies may be aligned and compared to identify conserved amino acids or motifs (i.e., where alteration in sequences may alter protein function) and/or regions where variation occurs the sequences (i.e., where variation of sequence is not likely to significantly affect protein function). Alternatively, consensus sequences can be identified by aligning heavy chain or light chain sequences (e.g., CDRs) for antibodies that bind to the same or similar (e.g., overlapping) epitopes to determine conserved amino acids or motifs (i.e., where alteration in sequences may alter protein function) and regions where variation occurs in alignment of sequences (i.e., where variation of sequence is not likely to significantly affect protein function). In some embodiments, one or more consensus sequences can be identified for antibodies that recognize the same or similar epitope as an anti-TREM2 antibody as disclosed herein. Exemplary consensus sequences include SEQ ID NOS:293-323. In the consensus sequences of SEQ ID NOS:293-323, the capitalized letter represents an amino acid residue that is absolutely conserved among the aligned sequences (e.g., aligned CDR sequences), while an "X" or a Greek letter (e.g., "α," "β," "γ," "δ," "ε" or "φ") represents an amino acid residue that is not absolutely conserved among the aligned sequences. It will be appreciated that, when selecting an amino acid to insert at a position marked by an "X" or by a Greek letter, in some embodiments the amino acid is selected from those amino acids found at the corresponding position in the aligned sequences.

Clones CL0020107, CL0020300, CL0020215, CL0020301, and CL0020302

In some embodiments, an anti-TREM2 antibody or antigen-binding fragment thereof comprises:
(a) a CDR-H1 sequence comprising the sequence of G-Y-T-F-T-$\alpha_6$-Y-$\alpha_8$-$\alpha_9$-$\alpha_{10}$ (SEQ ID NO:293), wherein $\alpha_6$ is N, S, or D; $\alpha_8$ is W or N; $\alpha_9$ is I or M; and $\alpha_{10}$ is S, T, M, or H;
(b) a CDR-H2 sequence comprising the sequence of $\beta_1$-I-$\beta_3$-P-$\beta_5$-$\beta_6$-$\beta_7$-$\beta_8$-$\beta_9$-$\beta_{10}$-Y-N-$\beta_{13}$-$\beta_{14}$-F-$\beta_{16}$-$\beta_{17}$ (SEQ ID NO:294), wherein $\beta_1$ is D or Y; $\beta_3$ is Y or F; $\beta_5$ is H, G, S, N, or Y; $\beta_6$ is S or N; $\beta_7$ is T or G; $\beta_8$ is S, N, or G; $\beta_9$ is T or N; $\beta_{10}$ is N or G; $\beta_{13}$ is E or Q; $\beta_{14}$ is R or K; $\beta_{16}$ is R or K; and $\beta_{17}$ is S, G, or N;
(c) a CDR-H3 sequence comprising the sequence of $\gamma_1$-R-$\gamma_3$-G-$\gamma_5$-G-$\gamma_7$-$\gamma_8$-$\gamma_9$ (SEQ ID NO:295), wherein $\gamma_1$ is A or S; $\gamma_3$ is E or S; $\gamma_5$ is F, Y, R, or T; $\gamma_7$ is I or F; $\gamma_8$ is S or A; and $\gamma_9$ is A or Y;
(d) a CDR-L1 sequence comprising:
  (i) the sequence of $\delta_1$-A-$\delta_3$-$\delta_4$-$\delta_5$-Y-$\delta_7$-$\delta_8$-Y-$\delta_{10}$-$\delta_{11}$ (SEQ ID NO:296), wherein $\delta_1$ is S or K; $\delta_3$ is T or S; $\delta_4$ is S or E; $\delta_5$ is S or N; $\delta_7$ is absent or G; $\delta_8$ is S or T; $\delta_{10}$ is M or V; and $\delta_{11}$ is H or S; or
  (ii) the sequence of $\delta_1$-S-S-$\delta_4$-S-L-L-$\delta_8$-S-$\delta_{10}$-N-$\delta_{12}$-$\delta_{13}$-$\delta_{14}$-Y-L-$\delta_{17}$ (SEQ ID NO:297), wherein $\delta_1$ is K or R; $\delta_4$ is Q or K; $\delta_8$ is N or H; $\delta_{10}$ is G or absent; $\delta_{12}$ is Q or G; $\delta_{13}$ is K or N; $\delta_{14}$ is N or T; and $\delta_{17}$ is T or Y;
(e) a CDR-L2 sequence comprising the sequence of $\varepsilon_1$-$\varepsilon_2$-S-$\varepsilon_4$-$\varepsilon_5$-$\varepsilon_6$-$\varepsilon_7$ (SEQ ID NO:298), wherein $\varepsilon_1$ is S, G, W or Q; $\varepsilon_2$ is T, A, or M; $\varepsilon_4$ is N or T; $\varepsilon_5$ is L or R; $\varepsilon_6$ is A, Y, or E; and $\varepsilon_7$ is S or T; and
(f) a CDR-L3 sequence comprising the sequence of $\phi_1$-$\phi_2$-$\phi_3$-$\phi_4$-$\phi_5$-$\phi_6$-P-$\phi_8$-T (SEQ ID NO:299), wherein $\phi_1$ is Q, G, or M; $\phi_2$ is Q or N; $\phi_3$ is R, S, D, or H; $\phi_4$ is S, Y, or L; $\phi_5$ is S or Q; $\phi_6$ is Y or F; and $\phi_8$ is L, F, or Y.

In some embodiments, an anti-TREM2 antibody comprises:
(a) a CDR-H1 sequence comprising the sequence of G-Y-T-F-T-$\alpha_6$-Y-W-I-$\alpha_{10}$ (SEQ ID NO:300), wherein $\alpha_6$ is N or S; and $\alpha_{10}$ is S, T or M;
(b) a CDR-H2 sequence comprising the sequence of D-I-Y-P-$\beta_5$-S-$\beta_7$-$\beta_8$-T-N-Y-N-E-$\beta_{14}$-F-$\beta_{16}$-$\beta_{17}$ (SEQ ID NO:301), wherein $\beta_5$ is H, G, or S; $\beta_7$ is T or G; $\beta_8$ is S or N; $\beta_{14}$ is R or K; $\beta_{16}$ is R or K; and $\beta_{17}$ is S or N;
(c) a CDR-H3 sequence comprising the sequence of $\gamma_1$-R-E-G-$\gamma_5$-G-I-S-A (SEQ ID NO:302), wherein $\gamma_1$ is A or S; and $\gamma_5$ is F or Y;

(d) a CDR-L1 sequence comprising the sequence of $\delta_1$-A-$\delta_3$-$\delta_4$-$\delta_5$-V-$\delta_7$-$\delta_8$-Y-$\delta_{10}$-$\delta_{11}$ (SEQ ID NO:303), wherein $\delta_1$ is S or K; $\delta_3$ is T or S; $\delta_4$ is S or E; $\delta_5$ is S or N; $\delta_7$ is absent or G; $\delta_8$ is absent or T; $\delta_{10}$ is M or V; and $\delta_{11}$ is H or S;

(e) a CDR-L2 sequence comprising the sequence of $\varepsilon_1$-$\varepsilon_2$-S-N-$\varepsilon_5$-$\varepsilon_6$-$\varepsilon_7$ (SEQ ID NO:304), wherein $\varepsilon_1$ is S or G; $\varepsilon_2$ is T or A; $\varepsilon_5$ is L or R; $\varepsilon_6$ is A or Y; and $\varepsilon_7$ is S or T; and (f) a CDR-L3 sequence comprising the sequence of $\phi_1$-Q-$\phi_3$-$\phi_4$-S-$\phi_6$-P-$\phi_8$-T (SEQ ID NO:305), wherein $\phi_1$ is Q or G; $\phi_3$ is R or S; $\phi_4$ is S or Y; $\phi_6$ is Y or F; and $\phi_8$ is L or F.

In some embodiments, an anti-TREM2 antibody comprises a CDR-H1 sequence that is selected from SEQ ID NOS:4, 12, 20, 28, and 36. In some embodiments, an anti-TREM2 antibody comprises a CDR-H2 sequence that is selected from SEQ ID NOS:5, 13, 21, 29, and 37. In some embodiments, an anti-TREM2 antibody comprises a CDR-H3 sequence that is selected from SEQ ID NOS:6, 14, 22, 30, and 38. In some embodiments, an anti-TREM2 antibody comprises a CDR-L1 sequence that is selected from SEQ ID NOS:7, 15, 23, 31, and 39. In some embodiments, an anti-TREM2 antibody comprises a CDR-L2 sequence is selected from SEQ ID NOS:8, 16, 24, 32, and 40. In some embodiments, an anti-TREM2 antibody comprises a CDR-L3 sequence is selected from SEQ ID NOS:9, 17, 25, 33, and 41.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:2, 10, 18, 26, or 34. In some embodiments, an anti-TREM2 antibody comprises a heavy chain variable region comprising the amino acid sequence of any one of SEQ ID NOS:2, 10, 18, 26, or 34.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:3, 11, 19, 27, or 35. In some embodiments, an anti-TREM2 antibody comprises a light chain variable region comprising the amino acid sequence of any one of SEQ ID NOS:3, 11, 19, 27, or 35.

Clone CL0020107

In some embodiments, an anti-TREM2 antibody comprises a CDR-H1 sequence comprising the amino acid sequence of SEQ ID NO:4, a CDR-H2 sequence comprising the amino acid sequence of SEQ ID NO:5, a CDR-H3 sequence comprising the amino acid sequence of SEQ ID NO:6, a CDR-L1 sequence comprising the amino acid sequence of SEQ ID NO:7, a CDR-L2 sequence comprising the amino acid sequence of SEQ ID NO:8, and a CDR-L3 sequence comprising the amino acid sequence of SEQ ID NO:9.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:2. In some embodiments, an anti-TREM2 antibody comprises a heavy chain variable region comprising the amino acid sequence of SEQ ID NO:2.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:3. In some embodiments, an anti-TREM2 antibody comprises a light chain variable region comprising the amino acid sequence of SEQ ID NO:3.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:2 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:3. In some embodiments, an anti-TREM2 antibody comprises a heavy chain variable region comprising the amino acid sequence of SEQ ID NO:2 and a light chain variable region comprising the amino acid sequence of SEQ ID NO:3.

In some embodiments, an anti-TREM2 antibody comprises a heavy chain variable region that comprises a heavy chain CDR1-3 comprising the amino acid sequences of SEQ ID NOS:4, 5, and 6, respectively, and that has at least 85% sequence identity (e.g., at least 90%, 91%, 92%, 93%, 94%, 95%, 96%, 97%, 98%, or 99% sequence identity) to SEQ ID NO:2. In some embodiments, an anti-TREM2 antibody comprises a light chain variable region that comprises a light chain CDR1-3 comprising the amino acid sequences of SEQ ID NOS:7, 8, and 9, respectively, and that has at least 85% sequence identity (e.g., at least 90%, 91%, 92%, 93%, 94%, 95%, 96%, 97%, 98%, or 99% sequence identity) to SEQ ID NO:3.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:4, 5, 6, 7, 8, and 9, respectively, or an antibody comprising a heavy chain variable region comprising the amino acid sequence of SEQ ID NO:2 and a light chain variable region comprising the amino acid sequence of SEQ ID NO:3).

Clone CL0020300

In some embodiments, an anti-TREM2 antibody comprises a CDR-H1 sequence comprising the amino acid sequence of SEQ ID NO:12, a CDR-H2 sequence comprising the amino acid sequence of SEQ ID NO:13, a CDR-H3 sequence comprising the amino acid sequence of SEQ ID NO:14, a CDR-L1 sequence comprising the amino acid sequence of SEQ ID NO:15, a CDR-L2 sequence comprising the amino acid sequence of SEQ ID NO:16, and a CDR-L3 sequence comprising the amino acid sequence of SEQ ID NO:17.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:10. In some embodiments, an anti-TREM2 antibody comprises a heavy chain variable region comprising the amino acid sequence of SEQ ID NO:10.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:11. In some embodiments, an anti-TREM2 antibody comprises a light chain variable region comprising the amino acid sequence of SEQ ID NO:11.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:10 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:11. In some embodiments, an anti-TREM2 antibody comprises a heavy chain variable region comprising the amino acid sequence of SEQ ID NO:10 and a light chain variable region comprising the amino acid sequence of SEQ ID NO:11.

In some embodiments, an anti-TREM2 antibody comprises a heavy chain variable region that comprises a heavy chain CDR1-3 comprising the amino acid sequences of SEQ ID NOS:12, 13, and 14, respectively, and that has at least 85% sequence identity (e.g., at least 90%, 91%, 92%, 93%, 94%, 95%, 96%, 97%, 98%, or 99% sequence identity) to SEQ ID NO:10. In some embodiments, an anti-TREM2 antibody comprises a light chain variable region that comprises a light chain CDR1-3 comprising the amino acid sequences of SEQ ID NOS:15, 16, and 17, respectively, and that has at least 85% sequence identity (e.g., at least 90%, 91%, 92%, 93%, 94%, 95%, 96%, 97%, 98%, or 99% sequence identity) to SEQ ID NO:11.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:12, 13, 14, 15, 16, and 17, respectively, or an antibody comprising a heavy chain variable region comprising the amino acid sequence of SEQ ID NO:10 and a light chain variable region comprising the amino acid sequence of SEQ ID NO:11).

Clone CL0020215

In some embodiments, an anti-TREM2 antibody comprises a CDR-H1 sequence comprising the amino acid sequence of SEQ ID NO:20, a CDR-H2 sequence comprising the amino acid sequence of SEQ ID NO:21, a CDR-H3 sequence comprising the amino acid sequence of SEQ ID NO:22, a CDR-L1 sequence comprising the amino acid sequence of SEQ ID NO:23, a CDR-L2 sequence comprising the amino acid sequence of SEQ ID NO:24, and a CDR-L3 sequence comprising the amino acid sequence of SEQ ID NO:25.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:18. In some embodiments, an anti-TREM2 antibody comprises a heavy chain variable region comprising the amino acid sequence of SEQ ID NO:18.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:19. In some embodiments, an anti-TREM2 antibody comprises a light chain variable region comprising the amino acid sequence of SEQ ID NO:19.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:18 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:19. In some embodiments, an anti-TREM2 antibody comprises a heavy chain variable region comprising the amino acid sequence of SEQ ID NO:18 and a light chain variable region comprising the amino acid sequence of SEQ ID NO:19.

In some embodiments, an anti-TREM2 antibody comprises a heavy chain variable region that comprises a heavy chain CDR1-3 comprising the amino acid sequences of SEQ ID NOS:20, 21, and 22, respectively, and that has at least 85% sequence identity (e.g., at least 90%, 91%, 92%, 93%, 94%, 95%, 96%, 97%, 98%, or 99% sequence identity) to SEQ ID NO:18. In some embodiments, an anti-TREM2 antibody comprises a light chain variable region that comprises a light chain CDR1-3 comprising the amino acid sequences of SEQ ID NOS:23, 24, and 25, respectively, and that has at least 85% sequence identity (e.g., at least 90%, 91%, 92%, 93%, 94%, 95%, 96%, 97%, 98%, or 99% sequence identity) to SEQ ID NO:19.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:20, 21, 22, 23, 24, and 25, respectively, or an antibody comprising a heavy chain variable region comprising the amino acid sequence of SEQ ID NO:18 and a light chain variable region comprising the amino acid sequence of SEQ ID NO:19).

Clone CL0020301

In some embodiments, an anti-TREM2 antibody comprises a CDR-H1 sequence comprising the amino acid sequence of SEQ ID NO:28, a CDR-H2 sequence comprising the amino acid sequence of SEQ ID NO:29, a CDR-H3 sequence comprising the amino acid sequence of SEQ ID NO:30, a CDR-L1 sequence comprising the amino acid sequence of SEQ ID NO:31, a CDR-L2 sequence comprising the amino acid sequence of SEQ ID NO:32, and a CDR-L3 sequence comprising the amino acid sequence of SEQ ID NO:33.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:26. In some embodiments, an anti-TREM2 antibody comprises a heavy chain variable region comprising the amino acid sequence of SEQ ID NO:26.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:27. In some embodiments, an anti-TREM2 antibody comprises a light chain variable region comprising the amino acid sequence of SEQ ID NO:27.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:26 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:27. In some embodiments, an anti-TREM2 antibody comprises a heavy chain variable region comprising the amino acid sequence of SEQ ID NO:26 and a light chain variable region comprising the amino acid sequence of SEQ ID NO:27.

In some embodiments, an anti-TREM2 antibody comprises a heavy chain variable region that comprises a heavy chain CDR1-3 comprising the amino acid sequences of SEQ ID NOS:28, 29, and 30, respectively, and that has at least 85% sequence identity (e.g., at least 90%, 91%, 92%, 93%, 94%, 95%, 96%, 97%, 98%, or 99% sequence identity) to SEQ ID NO:26. In some embodiments, an anti-TREM2 antibody comprises a light chain variable region that comprises a light chain CDR1-3 comprising the amino acid sequences of SEQ ID NOS:31, 32, and 33, respectively, and that has at least 85% sequence identity (e.g., at least 90%, 91%, 92%, 93%, 94%, 95%, 96%, 97%, 98%, or 99% sequence identity) to SEQ ID NO:27.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:28, 29, 30, 31, 32, and 33, respectively, or an antibody comprising a heavy chain variable region comprising the amino acid sequence of SEQ ID NO:26 and a light chain variable region comprising the amino acid sequence of SEQ ID NO:27).

Clone CL0020302

In some embodiments, an anti-TREM2 antibody comprises a CDR-H1 sequence comprising the amino acid sequence of SEQ ID NO:36, a CDR-H2 sequence comprising the amino acid sequence of SEQ ID NO:37, a CDR-H3 sequence comprising the amino acid sequence of SEQ ID NO:38, a CDR-L1 sequence comprising the amino acid sequence of SEQ ID NO:39, a CDR-L2 sequence comprising the amino acid sequence of SEQ ID NO:40, and a CDR-L3 sequence comprising the amino acid sequence of SEQ ID NO:41.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:34. In some embodiments, an anti-TREM2 antibody comprises a heavy chain variable region comprising the amino acid sequence of SEQ ID NO:34.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:35. In some embodiments, an anti-TREM2 antibody comprises a light chain variable region comprising the amino acid sequence of SEQ ID NO:35.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:34 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:35. In some embodiments, an anti-TREM2 antibody comprises a heavy chain variable region comprising the amino acid sequence of SEQ ID NO:34 and a light chain variable region comprising the amino acid sequence of SEQ ID NO:35.

In some embodiments, an anti-TREM2 antibody comprises a heavy chain variable region that comprises a heavy chain CDR1-3 comprising the amino acid sequences of SEQ ID NOS:36, 37, and 38, respectively, and that has at least 85% sequence identity (e.g., at least 90%, 91%, 92%, 93%, 94%, 95%, 96%, 97%, 98%, or 99% sequence identity) to SEQ ID NO:34. In some embodiments, an anti-TREM2 antibody comprises a light chain variable region that comprises a light chain CDR1-3 comprising the amino acid sequences of SEQ ID NOS:39, 40, and 41, respectively, and that has at least 85% sequence identity (e.g., at least 90%, 91%, 92%, 93%, 94%, 95%, 96%, 97%, 98%, or 99% sequence identity) to SEQ ID NO:35.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:36, 37, 38, 39, 40, and 41, respectively, or an antibody comprising a heavy chain variable region comprising the amino acid sequence of SEQ ID NO:34 and a light chain variable region comprising the amino acid sequence of SEQ ID NO:35).

Clones CL0020139, CL0020304, and CL0020305

In some embodiments, an anti-TREM2 antibody or antigen-binding fragment thereof comprises:

(a) a CDR-H1 sequence comprising the sequence of G-Y-$\alpha_3$-F-$\alpha_5$-S-$\alpha_7$-$\alpha_8$-$\alpha_9$-$\alpha_{10}$ (SEQ ID NO:306), wherein $\alpha_3$ is S or K; as is T or P; $\alpha_7$ is Y or F; as is L or I; $\alpha_9$ is M or I; and $\alpha_{10}$ is N or H;

(b) a CDR-H2 sequence comprising the sequence of Y-I-N-P-Y-S-$\beta_7$-G-$\beta_9$-N-Y-N-E-K-F-K-$\beta_{17}$ (SEQ ID NO:307), wherein $\beta_7$ is A or D; $\beta_9$ is S or T; and $\beta_{17}$ is D or G;

(c) a CDR-H3 sequence comprising the sequence of comprising the sequence of ARSSYRYGFDY (SEQ ID NO:46);

(d) a CDR-L1 sequence comprising the sequence of comprising the sequence of KASEDIYNRLA (SEQ ID NO:47);

(e) a CDR-L2 sequence comprising the sequence of comprising the sequence of GATSLET (SEQ ID NO:48); and a CDR-L3 sequence comprising the sequence of comprising the sequence Q-Q-$\phi_3$-W-S-$\phi_6$-P-W-T (SEQ ID NO:308), wherein $\phi_3$ is Y or S; and $\phi_6$ is T or I.

In some embodiments, an anti-TREM2 antibody comprises a CDR-H1 sequence that is selected from SEQ ID NOS:44, 52, and 56. In some embodiments, an anti-TREM2 antibody comprises a CDR-H2 sequence that is selected from SEQ ID NOS:45, 53, and 57. In some embodiments, an anti-TREM2 antibody comprises a CDR-L3 sequence is selected from SEQ ID NOS:49 and 292.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:42, 50, or 54. In some embodiments, an anti-TREM2 antibody comprises a heavy chain variable region comprising the amino acid sequence of any one of SEQ ID NOS:42, 50, or 54.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:43, 51, or 55. In some embodiments, an anti-TREM2 antibody comprises a light chain variable region comprising the amino acid sequence of any one of SEQ ID NOS:43, 51, or 55.

Clone CL0020139

In some embodiments, an anti-TREM2 antibody comprises a CDR-H1 sequence comprising the amino acid sequence of SEQ ID NO:44, a CDR-H2 sequence comprising the amino acid sequence of SEQ ID NO:45, a CDR-H3 sequence comprising the amino acid sequence of SEQ ID NO:46, a CDR-L1 sequence comprising the amino acid sequence of SEQ ID NO:47, a CDR-L2 sequence comprising the amino acid sequence of SEQ ID NO:48, and a CDR-L3 sequence comprising the amino acid sequence of SEQ ID NO:49.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:42. In some embodiments, an anti-TREM2 antibody comprises a heavy chain variable region comprising the amino acid sequence of SEQ ID NO:42.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:43. In some embodiments, an anti-TREM2 antibody comprises a light chain variable region comprising the amino acid sequence of SEQ ID NO:43.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:42 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:43. In some embodiments, an anti-TREM2 antibody comprises a heavy chain variable region comprising the amino acid sequence of SEQ ID NO:42 and a light chain variable region comprising the amino acid sequence of SEQ ID NO:43.

In some embodiments, an anti-TREM2 antibody comprises a heavy chain variable region that comprises a heavy chain CDR1-3 comprising the amino acid sequences of SEQ ID NOS:44, 45, and 46, respectively, and that has at least 85% sequence identity (e.g., at least 90%, 91%, 92%, 93%, 94%, 95%, 96%, 97%, 98%, or 99% sequence identity) to SEQ ID NO:42. In some embodiments, an anti-TREM2 antibody comprises a light chain variable region that comprises a light chain CDR1-3 comprising the amino acid sequences of SEQ ID NOS:47, 48, and 49, respectively, and that has at least 85% sequence identity (e.g., at least 90%, 91%, 92%, 93%, 94%, 95%, 96%, 97%, 98%, or 99% sequence identity) to SEQ ID NO:43.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:44, 45, 46, 47, 48, and 49, respectively, or an antibody comprising a heavy chain variable region comprising the amino acid sequence of SEQ ID NO:42 and a light chain variable region comprising the amino acid sequence of SEQ ID NO:43).

Clone CL0020304

In some embodiments, an anti-TREM2 antibody comprises a CDR-H1 sequence comprising the amino acid sequence of SEQ ID NO:52, a CDR-H2 sequence comprising the amino acid sequence of SEQ ID NO:53, a CDR-H3 sequence comprising the amino acid sequence of SEQ ID NO:46, a CDR-L1 sequence comprising the amino acid sequence of SEQ ID NO:47, a CDR-L2 sequence comprising the amino acid sequence of SEQ ID NO:48, and a CDR-L3 sequence comprising the amino acid sequence of SEQ ID NO:292.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:50. In some embodiments, an anti-TREM2 antibody comprises a heavy chain variable region comprising the amino acid sequence of SEQ ID NO:50.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:51. In some embodiments, an anti-TREM2 antibody comprises a light chain variable region comprising the amino acid sequence of SEQ ID NO:51.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:50 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:51. In some embodiments, an anti-TREM2 antibody comprises a heavy chain variable region comprising the amino acid sequence of SEQ ID NO:50 and a light chain variable region comprising the amino acid sequence of SEQ ID NO:51.

In some embodiments, an anti-TREM2 antibody comprises a heavy chain variable region that comprises a heavy chain CDR1-3 comprising the amino acid sequences of SEQ ID NOS:52, 53, and 46, respectively, and that has at least 85% sequence identity (e.g., at least 90%, 91%, 92%, 93%, 94%, 95%, 96%, 97%, 98%, or 99% sequence identity) to SEQ ID NO:50. In some embodiments, an anti-TREM2 antibody comprises a light chain variable region that comprises a light chain CDR1-3 comprising the amino acid sequences of SEQ ID NOS:47, 48, and 292, respectively, and that has at least 85% sequence identity (e.g., at least 90%, 91%, 92%, 93%, 94%, 95%, 96%, 97%, 98%, or 99% sequence identity) to SEQ ID NO:51.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:52, 53, 46, 47, 48, and 292, respectively, or an antibody comprising a heavy chain variable region comprising the amino acid sequence of SEQ ID NO:50 and a light chain variable region comprising the amino acid sequence of SEQ ID NO:51).

Clone CL0020305

In some embodiments, an anti-TREM2 antibody comprises a CDR-H1 sequence comprising the amino acid sequence of SEQ ID NO:56, a CDR-H2 sequence comprising the amino acid sequence of SEQ ID NO:57, a CDR-H3 sequence comprising the amino acid sequence of SEQ ID NO:46, a CDR-L1 sequence comprising the amino acid sequence of SEQ ID NO:47, a CDR-L2 sequence comprising the amino acid sequence of SEQ ID NO:48, and a CDR-L3 sequence comprising the amino acid sequence of SEQ ID NO:49.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:54. In some embodiments, an anti-TREM2 antibody comprises a heavy chain variable region comprising the amino acid sequence of SEQ ID NO:54.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:55. In some embodiments, an anti-TREM2 antibody comprises a light chain variable region comprising the amino acid sequence of SEQ ID NO:55.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:54 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:55. In some embodiments, an anti-TREM2 antibody comprises a heavy chain variable region comprising the amino acid sequence of SEQ ID NO:54 and a light chain variable region comprising the amino acid sequence of SEQ ID NO:55.

In some embodiments, an anti-TREM2 antibody comprises a heavy chain variable region that comprises a heavy chain CDR1-3 comprising the amino acid sequences of SEQ ID NOS:56, 57, and 46, respectively, and that has at least 85% sequence identity (e.g., at least 90%, 91%, 92%, 93%, 94%, 95%, 96%, 97%, 98%, or 99% sequence identity) to SEQ ID NO:54. In some embodiments, an anti-TREM2 antibody comprises a light chain variable region that comprises a light chain CDR1-3 comprising the amino acid sequences of SEQ ID NOS:47, 48, and 49, respectively, and that has at least 85% sequence identity (e.g., at least 90%, 91%, 92%, 93%, 94%, 95%, 96%, 97%, 98%, or 99% sequence identity) to SEQ ID NO:55.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:56, 57, 46, 47, 48, and 49, respectively, or an antibody comprising a heavy chain variable region comprising the amino acid sequence of SEQ ID NO:54 and a light chain variable region comprising the amino acid sequence of SEQ ID NO:55).

Clone CL0020123 and Variants of CL0020123

In some embodiments, an anti-TREM2 antibody or antigen-binding fragment thereof comprises:
(a) a CDR-H1 sequence comprising the sequence of GFSIEDFYIH (SEQ ID NO:105);
(b) a CDR-H2 sequence comprising the sequence of W-I-D-P-E-$\beta_6$-G-$\beta_8$-S-K-Y-A-P-K-F-Q-G (SEQ ID NO:309), wherein $\beta_6$ is N or Q and $\beta_8$ is D or E;
(c) a CDR-H3 sequence comprising the sequence of HADHGNYGSTMDY (SEQ ID NO:107);
(d) a CDR-L1 sequence comprising the sequence of HASQHINVWLS (SEQ ID NO:108);
(e) a CDR-L2 sequence comprising the sequence of KASNLHT (SEQ ID NO:109); and
(f) a CDR-L3 sequence comprising the sequence of QQGQTYPRT (SEQ ID NO:110).

In some embodiments, an anti-TREM2 antibody comprises a CDR-H2 sequence that is selected from SEQ ID NOS:106, 115, 117, and 119.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:103, 111, 113, 114, 116, 118, 120, 121, or 122. In some embodiments, an anti-TREM2 antibody comprises a heavy chain variable region comprising the amino acid sequence of any one of SEQ ID NOS: 103, 111, 113, 114, 116, 118, 120, 121, or 122.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:104 or 112. In some embodiments, an anti-TREM2 antibody comprises a light chain variable region comprising the amino acid sequence of any one of SEQ ID NOS:104 or 112.

In some embodiments, an anti-TREM2 antibody comprises a CDR-H1 sequence comprising the amino acid sequence of SEQ ID NO:105, a CDR-H2 sequence comprising the amino acid sequence of SEQ ID NO:106, a CDR-H3 sequence comprising the amino acid sequence of SEQ ID NO:107, a CDR-L1 sequence comprising the amino acid sequence of SEQ ID NO:108, a CDR-L2 sequence comprising the amino acid sequence of SEQ ID NO:109, and a CDR-L3 sequence comprising the amino acid sequence of SEQ ID NO:110.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:103. In some embodiments, an anti-TREM2 antibody comprises a heavy chain variable region comprising the amino acid sequence of SEQ ID NO:103.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:104. In some embodiments, an anti-TREM2 antibody comprises a light chain variable region comprising the amino acid sequence of SEQ ID NO:104.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:103 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:104. In some embodiments, an anti-TREM2 antibody comprises a heavy chain variable region comprising the amino acid sequence of SEQ ID NO:103 and a light chain variable region comprising the amino acid sequence of SEQ ID NO:104.

In some embodiments, an anti-TREM2 antibody comprises a heavy chain variable region that comprises a heavy chain CDR1-3 comprising the amino acid sequences of SEQ ID NOS:105, 106, and 107, respectively, and that has at least 85% sequence identity (e.g., at least 90%, 91%, 92%, 93%, 94%, 95%, 96%, 97%, 98%, or 99% sequence identity) to SEQ ID NO:103. In some embodiments, an anti-TREM2 antibody comprises a light chain variable region that comprises a light chain CDR1-3 comprising the amino acid sequences of SEQ ID NOS:108, 109, and 110, respectively, and that has at least 85% sequence identity (e.g., at least 90%, 91%, 92%, 93%, 94%, 95%, 96%, 97%, 98%, or 99% sequence identity) to SEQ ID NO:104.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:105, 106, 107, 108, 109, and 110, respectively, or an antibody comprising a heavy chain variable region comprising the amino acid sequence of SEQ ID NO:103 and a light chain variable region comprising the amino acid sequence of SEQ ID NO:104).

In some embodiments, an anti-TREM2 antibody comprises a CDR-H1 sequence comprising the amino acid sequence of SEQ ID NO:105, a CDR-H2 sequence comprising the amino acid sequence of SEQ ID NO:119, a CDR-H3 sequence comprising the amino acid sequence of SEQ ID NO:107, a CDR-L1 sequence comprising the amino acid sequence of SEQ ID NO:108, a CDR-L2 sequence comprising the amino acid sequence of SEQ ID NO:109, and a CDR-L3 sequence comprising the amino acid sequence of SEQ ID NO:110.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:118. In some embodiments, an anti-TREM2 antibody comprises a heavy chain variable region comprising the amino acid sequence of SEQ ID NO:118.

In some embodiments, an anti-TREM2 antibody comprises a light chain variable region comprising an amino acid sequence that has at least 85% sequence identity (e.g., at least 90%, 95%, or 97% sequence identity) to SEQ ID NO:112. In some embodiments, an anti-TREM2 antibody comprises a light chain variable region comprising the amino acid sequence of SEQ ID NO:112.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:118 and a light chain variable region comprising an amino acid sequence that has at least 85% sequence identity (e.g., at least 90%, 95%, or 97% sequence identity) to SEQ ID NO:112. In some embodiments, an anti-TREM2 antibody comprises a heavy chain variable region comprising the amino acid sequence of SEQ ID NO:118 and a light chain variable region comprising the amino acid sequence of SEQ ID NO:112.

In some embodiments, an anti-TREM2 antibody comprises a heavy chain variable region that comprises a heavy chain CDR1-3 comprising the amino acid sequences of SEQ ID NOs:105, 119, and 107, respectively, and that has at least 85% sequence identity (e.g., at least 90%, 95%, or 97% sequence identity) to SEQ ID NO:118. In some embodiments, an anti-TREM2 antibody comprises a light chain variable region that comprises a light chain CDR1-3 comprising the amino acid sequences of SEQ ID NOs:108, 109, and 110, respectively, and that has at least 85% sequence identity (e.g., at least 90%, 95%, or 97% sequence identity) to SEQ ID NO:112.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:105, 119, 107, 108, 109, and 110, respectively, or an antibody comprising a heavy chain variable region comprising the amino acid sequence of SEQ ID NO:118 and a light chain variable region comprising the amino acid sequence of SEQ ID NO:112).

In some embodiments, an anti-TREM2 antibody comprises a CDR-H1 sequence comprising the amino acid sequence of SEQ ID NO:105, a CDR-H2 sequence comprising the amino acid sequence of SEQ ID NO:117, a CDR-H3 sequence comprising the amino acid sequence of SEQ ID NO:107, a CDR-L1 sequence comprising the amino acid sequence of SEQ ID NO:108, a CDR-L2 sequence comprising the amino acid sequence of SEQ ID NO:109, and a CDR-L3 sequence comprising the amino acid sequence of SEQ ID NO:110.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:121. In some embodiments, an anti-TREM2 antibody comprises a heavy chain variable region comprising the amino acid sequence of SEQ ID NO:121.

In some embodiments, an anti-TREM2 antibody comprises a light chain variable region comprising an amino acid sequence that has at least 85% sequence identity (e.g., at least 90%, 95%, or 97% sequence identity) to SEQ ID NO:112. In some embodiments, an anti-TREM2 antibody comprises a light chain variable region comprising the amino acid sequence of SEQ ID NO:112.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:121 and a light chain variable region comprising an amino acid sequence that has at least 85% sequence identity (e.g., at least 90%, 95%, or 97% sequence identity) to SEQ ID NO:112. In some embodiments, an anti-TREM2 antibody comprises a heavy chain variable region comprising the amino acid sequence of SEQ ID NO:121 and a light chain variable region comprising the amino acid sequence of SEQ ID NO:112.

In some embodiments, an anti-TREM2 antibody comprises a heavy chain variable region that comprises a heavy chain CDR1-3 comprising the amino acid sequences of SEQ ID NOs:105, 117, and 107, respectively, and that has at least 85% sequence identity (e.g., at least 90%, 95%, or 97% sequence identity) to SEQ ID NO:121. In some embodiments, an anti-TREM2 antibody comprises a light chain variable region that comprises a light chain CDR1-3 comprising the amino acid sequences of SEQ ID NOs:108, 109, and 110, respectively, and that has at least 85% sequence identity (e.g., at least 90%, 95%, or 97% sequence identity) to SEQ ID NO:112.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOs: 105, 117, 107, 108, 109, and 110, respectively, or an antibody comprising a heavy chain variable region comprising the amino acid sequence of SEQ ID NO:121 and a light chain variable region comprising the amino acid sequence of SEQ ID NO:112).

Clones CL0020308, CL0020309, and CL0020310

In some embodiments, an anti-TREM2 antibody or antigen-binding fragment thereof comprises:
- (a) a CDR-H1 sequence comprising the sequence of G-F-S-L-T-$\alpha_6$-Y-G-$\alpha_9$-$\alpha_{10}$ (SEQ ID NO:310), wherein $\alpha_6$ is T or S; $\alpha_9$ is I or V; and $\alpha_{10}$ is H or Q;
- (b) a CDR-H2 sequence comprising the sequence of V-I-W-T-G-G-$\beta_7$-T-$\beta_9$-$\beta_{10}$-N-A-A-F-M-S(SEQ ID NO:311), wherein $\beta_7$ is S or T; $\beta_9$ is A or D; and $\beta_{10}$ is F or Y;
- (c) a CDR-H3 sequence comprising the sequence of A-K-$\gamma_3$-G-F-H-S-A-$\gamma_9$-D-Y (SEQ ID NO:312), wherein $\gamma_3$ is V or I; and $\gamma_9$ is T, M, or V;
- (d) a CDR-L1 sequence comprising the sequence of R-S-S-Q-N-$\delta_6$-V-H-S-N-G-N-T-Y-L-E (SEQ ID NO:313), wherein $\delta_6$ is L or I;
- (e) a CDR-L2 sequence comprising the sequence of KVSNRFS (SEQ ID NO:89); and
- (f) a CDR-L3 sequence comprising the sequence of F-Q-G-S-H-$\phi_6$-P-F-T (SEQ ID NO:314), wherein $\phi_6$ is V or I.

In some embodiments, an anti-TREM2 antibody comprises a CDR-H1 sequence that is selected from SEQ ID NOS:85, 93, and 100. In some embodiments, an anti-TREM2 antibody comprises a CDR-H2 sequence that is selected from SEQ ID NOS:86, 94, and 101. In some embodiments, an anti-TREM2 antibody comprises a CDR-H3 sequence that is selected from SEQ ID NOS:87, 95, and 102. In some embodiments, an anti-TREM2 antibody comprises a CDR-L1 sequence that is selected from SEQ ID NOS:88 and 96. In some embodiments, an anti-TREM2 antibody comprises a CDR-L3 sequence is selected from SEQ ID NOS:90 and 97

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:83, 91, or 98. In some embodiments, an anti-TREM2 antibody comprises a heavy chain variable region comprising the amino acid sequence of any one of SEQ ID NOS:83, 91, or 98.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:84, 92, or 99. In some embodiments, an anti-TREM2 antibody comprises a light chain variable region comprising the amino acid sequence of any one of SEQ ID NOS:84, 92, or 99.

Clone CL0020308

In some embodiments, an anti-TREM2 antibody comprises a CDR-H1 sequence comprising the amino acid sequence of SEQ ID NO:85, a CDR-H2 sequence comprising the amino acid sequence of SEQ ID NO:86, a CDR-H3 sequence comprising the amino acid sequence of SEQ ID NO:87, a CDR-L1 sequence comprising the amino acid sequence of SEQ ID NO:88, a CDR-L2 sequence comprising the amino acid sequence of SEQ ID NO:89, and a CDR-L3 sequence comprising the amino acid sequence of SEQ ID NO:90.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:83. In some embodiments, an anti-TREM2 antibody comprises a heavy chain variable region comprising the amino acid sequence of SEQ ID NO:83.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:84. In some embodiments, an anti-TREM2 antibody comprises a light chain variable region comprising the amino acid sequence of SEQ ID NO:84.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:83 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:84. In some embodiments, an anti-TREM2 antibody comprises a heavy chain variable region comprising the amino acid sequence of SEQ ID NO:83 and a light chain variable region comprising the amino acid sequence of SEQ ID NO:84.

In some embodiments, an anti-TREM2 antibody comprises a heavy chain variable region that comprises a heavy chain CDR1-3 comprising the amino acid sequences of SEQ ID NOS:85, 86, and 87, respectively, and that has at least 85% sequence identity (e.g., at least 90%, 91%, 92%, 93%, 94%, 95%, 96%, 97%, 98%, or 99% sequence identity) to SEQ ID NO:83. In some embodiments, an anti-TREM2 antibody comprises a light chain variable region that comprises a light chain CDR1-3 comprising the amino acid sequences of SEQ ID NOS:88, 89, and 90, respectively, and that has at least 85% sequence identity (e.g., at least 90%, 91%, 92%, 93%, 94%, 95%, 96%, 97%, 98%, or 99% sequence identity) to SEQ ID NO:84.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:85, 86, 87, 88, 89, and 90, respectively, or an antibody comprising a heavy chain variable region comprising the amino acid sequence of SEQ ID NO:83 and a light chain variable region comprising the amino acid sequence of SEQ ID NO:84).

Clone CL0020309

In some embodiments, an anti-TREM2 antibody comprises a CDR-H1 sequence comprising the amino acid sequence of SEQ ID NO:93, a CDR-H2 sequence comprising the amino acid sequence of SEQ ID NO:94, a CDR-H3 sequence comprising the amino acid sequence of SEQ ID NO:95, a CDR-L1 sequence comprising the amino acid sequence of SEQ ID NO:96, a CDR-L2 sequence comprising the amino acid sequence of SEQ ID NO:89, and a CDR-L3 sequence comprising the amino acid sequence of SEQ ID NO:97.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:91. In some embodiments, an anti-TREM2 antibody comprises a heavy chain variable region comprising the amino acid sequence of SEQ ID NO:91.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:92. In some embodiments, an anti-TREM2 antibody comprises a light chain variable region comprising the amino acid sequence of SEQ ID NO:92.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:91 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:92. In some embodiments, an anti-TREM2 antibody comprises a heavy chain variable region comprising the amino acid sequence of SEQ ID NO:91 and a light chain variable region comprising the amino acid sequence of SEQ ID NO:92.

In some embodiments, an anti-TREM2 antibody comprises a heavy chain variable region that comprises a heavy chain CDR1-3 comprising the amino acid sequences of SEQ ID NOS:93, 94, and 95, respectively, and that has at least 85% sequence identity (e.g., at least 90%, 91%, 92%, 93%, 94%, 95%, 96%, 97%, 98%, or 99% sequence identity) to SEQ ID NO:91. In some embodiments, an anti-TREM2 antibody comprises a light chain variable region that comprises a light chain CDR1-3 comprising the amino acid sequences of SEQ ID NOS:96, 89, and 97, respectively, and that has at least 85% sequence identity (e.g., at least 90%, 91%, 92%, 93%, 94%, 95%, 96%, 97%, 98%, or 99% sequence identity) to SEQ ID NO:92.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:93, 94, 95, 96, 89, and 97, respectively, or an antibody comprising a heavy chain variable region comprising the amino acid sequence of SEQ ID NO:91 and a light chain variable region comprising the amino acid sequence of SEQ ID NO:92).

Clone CL0020310

In some embodiments, an anti-TREM2 antibody comprises a CDR-H1 sequence comprising the amino acid sequence of SEQ ID NO:100, a CDR-H2 sequence comprising the amino acid sequence of SEQ ID NO:101, a CDR-H3 sequence comprising the amino acid sequence of SEQ ID NO:102, a CDR-L1 sequence comprising the amino acid sequence of SEQ ID NO:96, a CDR-L2 sequence comprising the amino acid sequence of SEQ ID NO:89, and a CDR-L3 sequence comprising the amino acid sequence of SEQ ID NO:90.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:98. In some embodiments, an anti-TREM2 antibody comprises a heavy chain variable region comprising the amino acid sequence of SEQ ID NO:98.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:99. In some embodiments, an anti-TREM2 antibody comprises a light chain variable region comprising the amino acid sequence of SEQ ID NO:99.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:98 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:99. In some embodiments, an anti-TREM2 antibody comprises a heavy chain variable region comprising the amino acid sequence of SEQ ID NO:98 and a light chain variable region comprising the amino acid sequence of SEQ ID NO:99.

In some embodiments, an anti-TREM2 antibody comprises a heavy chain variable region that comprises a heavy chain CDR1-3 comprising the amino acid sequences of SEQ ID NOS:100, 101, and 102, respectively, and that has at least 85% sequence identity (e.g., at least 90%, 91%, 92%, 93%, 94%, 95%, 96%, 97%, 98%, or 99% sequence identity) to SEQ ID NO:98. In some embodiments, an anti-TREM2 antibody comprises a light chain variable region that comprises a light chain CDR1-3 comprising the amino acid sequences of SEQ ID NOS:96, 89, and 90, respectively, and that has at least 85% sequence identity (e.g., at least 90%, 91%, 92%, 93%, 94%, 95%, 96%, 97%, 98%, or 99% sequence identity) to SEQ ID NO:99.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:100, 101, 102, 96, 89, and 90, respectively, or an antibody comprising a heavy chain variable region comprising the amino acid sequence of SEQ ID NO:98 and a light chain variable region comprising the amino acid sequence of SEQ ID NO:99).

Clones CL0020188, CL0020306, CL0020307, and variants of CL0020188

In some embodiments, an anti-TREM2 antibody or antigen-binding fragment thereof comprises:
(a) a CDR-H1 sequence comprising the sequence of G-F-T-F-T-$\alpha_6$-F-Y-M-S(SEQ ID NO:315), wherein $\alpha_6$ is D or N;
(b) a CDR-H2 sequence comprising the sequence of V-I-R-N-$\beta_5$-$\beta_6$-N-$\beta_8$-Y-T-$\beta_{11}$-$\beta_{12}$-Y-N-P-S-V-K-G (SEQ ID NO:316), wherein $\beta_5$ is K or R; $\beta_6$ is A or P; $\beta_8$ is G or A; $\beta_{11}$ is A or T; and $\beta_{12}$ is G or D;
(c) a CDR-H3 sequence comprising the sequence of $\gamma_1$-R-L-$\gamma_4$-Y-G-F-D-Y (SEQ ID NO:317), wherein $\gamma_1$ is A or T; and $\gamma_4$ is T or S;
(d) a CDR-L1 sequence comprising the sequence of Q-S-S-K-S-L-L-H-S-$\delta_{10}$-G-K-T-Y-L-N(SEQ ID NO:318), wherein $\delta_{10}$ is N or T;
(e) a CDR-L2 sequence comprising the sequence of WMSTRAS (SEQ ID NO:64); and
(f) a CDR-L3 sequence comprising the sequence of Q-Q-F-L-E-$\phi_6$-P-F-T (SEQ ID NO:319), wherein $\phi_6$ is Y or F.

In some embodiments, an anti-TREM2 antibody comprises a CDR-H1 sequence that is selected from SEQ ID NOS:60 and 68. In some embodiments, an anti-TREM2 antibody comprises a CDR-H2 sequence that is selected from SEQ ID NOS:61, 69, and 81. In some embodiments, an anti-TREM2 antibody comprises a CDR-H3 sequence that is selected from SEQ ID NOS:62, 70, and 73. In some embodiments, an anti-TREM2 antibody comprises a CDR-L1 sequence that is selected from SEQ ID NOS:63 and 79. In some embodiments, an anti-TREM2 antibody comprises a CDR-L3 sequence is selected from SEQ ID NOS:65 and 74.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:58, 66, 71, 75, 77, 80, 82, and 350. In some embodiments, an anti-TREM2 antibody comprises a heavy chain variable region comprising the amino acid sequence of any one of SEQ ID NOS: 58, 66, 71, 75, 77, 80, 82, and 350.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:59, 67, 72, 76, 78, and 339. In some embodiments, an anti-TREM2 antibody comprises a light chain variable region comprising the amino acid sequence of any one of SEQ ID NOS: 59, 67, 72, 76, 78, and 339.

Clone CL0020188 and Variants of CL0020188

In some embodiments, an anti-TREM2 antibody comprises a CDR-H1 sequence comprising the amino acid sequence of SEQ ID NO:60, a CDR-H2 sequence comprising the amino acid sequence of SEQ ID NO:61, a CDR-H3 sequence comprising the amino acid sequence of SEQ ID NO:73, a CDR-L1 sequence comprising the amino acid sequence of SEQ ID NO:63, a CDR-L2 sequence comprising the amino acid sequence of SEQ ID NO:64, and a CDR-L3 sequence comprising the amino acid sequence of SEQ ID NO:74.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:71. In some embodiments, an anti-TREM2 antibody comprises a heavy chain variable region comprising the amino acid sequence of SEQ ID NO:71.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:72. In some embodiments, an anti-TREM2 antibody comprises a light chain variable region comprising the amino acid sequence of SEQ ID NO:72.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:71 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:72. In some embodiments, an anti-TREM2 antibody comprises a heavy chain variable region comprising the amino acid sequence of SEQ ID NO:71 and a light chain variable region comprising the amino acid sequence of SEQ ID NO:72.

In some embodiments, an anti-TREM2 antibody comprises a heavy chain variable region that comprises a heavy chain CDR1-3 comprising the amino acid sequences of SEQ ID NOS:60, 61, and 73, respectively, and that has at least 85% sequence identity (e.g., at least 90%, 91%, 92%, 93%, 94%, 95%, 96%, 97%, 98%, or 99% sequence identity) to SEQ ID NO:71. In some embodiments, an anti-TREM2 antibody comprises a light chain variable region that comprises a light chain CDR1-3 comprising the amino acid sequences of SEQ ID NOS:63, 64, and 74, respectively, and that has at least 85% sequence identity (e.g., at least 90%, 91%, 92%, 93%, 94%, 95%, 96%, 97%, 98%, or 99% sequence identity) to SEQ ID NO:72.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:0, 61, 73, 63, 64, and 74, respectively, or an antibody comprising a heavy chain variable region comprising the amino acid sequence of SEQ ID NO:71 and a light chain variable region comprising the amino acid sequence of SEQ ID NO:72).

In some embodiments, an anti-TREM2 antibody comprises a CDR-H1 sequence comprising the amino acid sequence of SEQ ID NO:60, a CDR-H2 sequence comprising the amino acid sequence of SEQ ID NO:61, a CDR-H3 sequence comprising the amino acid sequence of SEQ ID NO:73, a CDR-L1 sequence comprising the amino acid sequence of SEQ ID NO:79, a CDR-L2 sequence comprising the amino acid sequence of SEQ ID NO:64, and a CDR-L3 sequence comprising the amino acid sequence of SEQ ID NO:74.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:350. In some embodiments, an anti-TREM2 antibody comprises a heavy chain variable region comprising the amino acid sequence of SEQ ID NO:350.

In some embodiments, an anti-TREM2 antibody comprises a light chain variable region comprising an amino acid sequence that has at least 85% sequence identity (e.g., at least 90%, 95%, or 97% sequence identity) to SEQ ID NO:78. In some embodiments, an anti-TREM2 antibody comprises a light chain variable region comprising the amino acid sequence of SEQ ID NO:78.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:350 and a light chain variable region comprising an amino acid sequence that has at least 85% sequence identity (e.g., at least 90%, 95%, or 97% sequence identity) to SEQ ID NO:78. In some embodiments, an anti-TREM2 antibody comprises a heavy chain variable region comprising the amino acid sequence of SEQ ID NO:350 and a light chain variable region comprising the amino acid sequence of SEQ ID NO:78.

In some embodiments, an anti-TREM2 antibody comprises a heavy chain variable region that comprises a heavy chain CDR1-3 comprising the amino acid sequences of SEQ ID NOs:60, 61, and 73, respectively, and that has at least 85% sequence identity (e.g., at least 90%, 95%, or 97% sequence identity) to SEQ ID NO:350. In some embodiments, an anti-TREM2 antibody comprises a light chain variable region that comprises a light chain CDR1-3 comprising the amino acid sequences of SEQ ID NOs: 79, 64, and 74, respectively, and that has at least 85% sequence identity (e.g., at least 90%, 95%, or 97% sequence identity) to SEQ ID NO:78.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOs: 60, 61, 73, 79, 64, and 74, respectively, or an antibody comprising a heavy chain variable region comprising the amino acid sequence of SEQ ID NO:350 and a light chain variable region comprising the amino acid sequence of SEQ ID NO:78).

In some embodiments, an anti-TREM2 antibody comprises a CDR-H1 sequence comprising the amino acid sequence of SEQ ID NO:60, a CDR-H2 sequence comprising the amino acid sequence of SEQ ID NO:81, a CDR-H3 sequence comprising the amino acid sequence of SEQ ID NO:73, a CDR-L1 sequence comprising the amino acid sequence of SEQ ID NO:79, a CDR-L2 sequence comprising the amino acid sequence of SEQ ID NO:64, and a CDR-L3 sequence comprising the amino acid sequence of SEQ ID NO:74.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:80. In some embodiments, an anti-TREM2 antibody comprises a heavy chain variable region comprising the amino acid sequence of SEQ ID NO:80.

In some embodiments, an anti-TREM2 antibody comprises a light chain variable region comprising an amino acid sequence that has at least 85% sequence identity (e.g., at least 90%, 95%, or 97% sequence identity) to SEQ ID NO:78. In some embodiments, an anti-TREM2 antibody comprises a light chain variable region comprising the amino acid sequence of SEQ ID NO:78.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:80 and a light chain variable region comprising an amino acid sequence that has at least 85% sequence identity (e.g., at least 90%, 95%, or 97% sequence identity) to SEQ ID NO:78. In some embodiments, an anti-TREM2 antibody comprises a heavy chain variable region comprising the amino acid sequence of SEQ ID NO:80 and a light chain variable region comprising the amino acid sequence of SEQ ID NO:78.

In some embodiments, an anti-TREM2 antibody comprises a heavy chain variable region that comprises a heavy chain CDR1-3 comprising the amino acid sequences of SEQ ID NOs:60, 81, and 73, respectively, and that has at least 85% sequence identity (e.g., at least 90%, 95%, or 97% sequence identity) to SEQ ID NO:80. In some embodiments, an anti-TREM2 antibody comprises a light chain variable region that comprises a light chain CDR1-3 comprising the amino acid sequences of SEQ ID NOs:79, 64, and 74, respectively, and that has at least 85% sequence identity (e.g., at least 90%, 95%, or 97% sequence identity) to SEQ ID NO:78.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOs: 60, 81, 73, 79, 64, and 74, respectively, or an antibody comprising a heavy chain variable region comprising the amino acid sequence of SEQ ID NO:80 and a light chain variable region comprising the amino acid sequence of SEQ ID NO:78).

In some embodiments, an anti-TREM2 antibody comprises a CDR-H1 sequence comprising the amino acid sequence of SEQ ID NO:60, a CDR-H2 sequence comprising the amino acid sequence of SEQ ID NO:81, a CDR-H3 sequence comprising the amino acid sequence of SEQ ID NO:73, a CDR-L1 sequence comprising the amino acid sequence of SEQ ID NO:63, a CDR-L2 sequence comprising the amino acid sequence of SEQ ID NO:64, and a CDR-L3 sequence comprising the amino acid sequence of SEQ ID NO:65.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:80. In some embodiments, an anti-TREM2 antibody comprises a heavy chain variable region comprising the amino acid sequence of SEQ ID NO:80.

In some embodiments, an anti-TREM2 antibody comprises a light chain variable region comprising an amino acid sequence that has at least 85% sequence identity (e.g., at least 90%, 95%, or 97% sequence identity) to SEQ ID NO:339. In some embodiments, an anti-TREM2 antibody comprises a light chain variable region comprising the amino acid sequence of SEQ ID NO:339.

In some embodiments, an anti-TREM2 antibody comprises a heavy chain variable region comprising an amino acid sequence that has at least 85% sequence identity (e.g., at least 90%, 95%, or 97% sequence identity) to SEQ ID NO:80 and a light chain variable region comprising an amino acid sequence that has at least 85% sequence identity (e.g., at least 90%, 95%, or 97% sequence identity) to SEQ ID NO:339. In some embodiments, an anti-TREM2 antibody comprises a heavy chain variable region comprising the amino acid sequence of SEQ ID NO:80 and a light chain variable region comprising the amino acid sequence of SEQ ID NO:339.

In some embodiments, an anti-TREM2 antibody comprises a heavy chain variable region that comprises a heavy chain CDR1-3 comprising the amino acid sequences of SEQ ID NOs:60, 81, and 73, respectively, and that has at least 85% sequence identity (e.g., at least 90%, 95%, or 97% sequence identity) to SEQ ID NO:80. In some embodiments, an anti-TREM2 antibody comprises a light chain variable region that comprises a light chain CDR1-3 comprising the amino acid sequences of SEQ ID NOs:63, 64, and 65, respectively, and that has at least 85% sequence identity (e.g., at least 90%, 95%, or 97% sequence identity) to SEQ ID NO:339.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOs: 60, 81, 73, 63, 64, and 65, respectively, or an antibody comprising a heavy chain variable region comprising the amino acid sequence of SEQ ID NO:80 and a light chain variable region comprising the amino acid sequence of SEQ ID NO:339).

Clone CL0020306

In some embodiments, an anti-TREM2 antibody comprises a CDR-H1 sequence comprising the amino acid sequence of SEQ ID NO:60, a CDR-H2 sequence comprising the amino acid sequence of SEQ ID NO:61, a CDR-H3 sequence comprising the amino acid sequence of SEQ ID NO:62, a CDR-L1 sequence comprising the amino acid sequence of SEQ ID NO:63, a CDR-L2 sequence comprising the amino acid sequence of SEQ ID NO:64, and a CDR-L3 sequence comprising the amino acid sequence of SEQ ID NO:65.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:58. In some embodiments, an anti-TREM2 antibody comprises a heavy chain variable region comprising the amino acid sequence of SEQ ID NO:58.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:59. In some embodiments, an anti-TREM2 antibody comprises a light chain variable region comprising the amino acid sequence of SEQ ID NO:59.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:58 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:59. In some embodiments, an anti-TREM2 antibody comprises a heavy chain variable region comprising the amino acid sequence of SEQ ID NO:58 and a light chain variable region comprising the amino acid sequence of SEQ ID NO:59.

In some embodiments, an anti-TREM2 antibody comprises a heavy chain variable region that comprises a heavy chain CDR1-3 comprising the amino acid sequences of SEQ ID NOS:60, 61, and 62, respectively, and that has at least 85% sequence identity (e.g., at least 90%, 91%, 92%, 93%, 94%, 95%, 96%, 97%, 98%, or 99% sequence identity) to SEQ ID NO:58. In some embodiments, an anti-TREM2 antibody comprises a light chain variable region that comprises a light chain CDR1-3 comprising the amino acid sequences of SEQ ID NOS:63, 64, and 65, respectively, and that has at least 85% sequence identity (e.g., at least 90%, 91%, 92%, 93%, 94%, 95%, 96%, 97%, 98%, or 99% sequence identity) to SEQ ID NO:59.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:60, 61, 62, 63, 64, and 65, respectively, or an antibody comprising a heavy chain variable region comprising the amino acid sequence of SEQ ID NO:58 and a light chain variable region comprising the amino acid sequence of SEQ ID NO:59).

Clone CL0020307

In some embodiments, an anti-TREM2 antibody comprises a CDR-H1 sequence comprising the amino acid sequence of SEQ ID NO:68, a CDR-H2 sequence comprising the amino acid sequence of SEQ ID NO:69, a CDR-H3 sequence comprising the amino acid sequence of SEQ ID NO:70, a CDR-L1 sequence comprising the amino acid sequence of SEQ ID NO:63, a CDR-L2 sequence comprising the amino acid sequence of SEQ ID NO:64, and a CDR-L3 sequence comprising the amino acid sequence of SEQ ID NO:65.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:66. In some embodiments, an anti-TREM2 antibody comprises a heavy chain variable region comprising the amino acid sequence of SEQ ID NO:66.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:67. In some embodiments, an anti-TREM2 antibody comprises a light chain variable region comprising the amino acid sequence of SEQ ID NO:67.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:66 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:67. In some embodiments, an anti-TREM2 antibody comprises a heavy chain variable region comprising the amino acid sequence of SEQ ID NO:66 and a light chain variable region comprising the amino acid sequence of SEQ ID NO:67.

In some embodiments, an anti-TREM2 antibody comprises a heavy chain variable region that comprises a heavy chain CDR1-3 comprising the amino acid sequences of SEQ ID NOS:68, 69, and 70, respectively, and that has at least 85% sequence identity (e.g., at least 90%, 91%, 92%, 93%, 94%, 95%, 96%, 97%, 98%, or 99% sequence identity) to SEQ ID NO:66. In some embodiments, an anti-TREM2 antibody comprises a light chain variable region that comprises a light chain CDR1-3 comprising the amino acid sequences of SEQ ID NOS:63, 64, and 65, respectively, and that has at least 85% sequence identity (e.g., at least 90%, 91%, 92%, 93%, 94%, 95%, 96%, 97%, 98%, or 99% sequence identity) to SEQ ID NO:67.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:68, 69, 70, 63, 64, and 65, respectively, or an antibody comprising a heavy chain variable region comprising the amino acid sequence of SEQ ID NO:66 and a light chain variable region comprising the amino acid sequence of SEQ ID NO:67).

Clones CL0020141, CL0020311, and CL0020312

In some embodiments, an anti-TREM2 antibody or antigen-binding fragment thereof comprises:
 (a) a CDR-H1 sequence comprising the sequence of GFTFTDYYMS (SEQ ID NO:125);
 (b) a CDR-H2 sequence comprising the sequence of F-I-R-$\beta_4$-K-A-N-G-Y-T-T-$\beta_{12}$-Y-S-A-S-V-K-G (SEQ ID NO:320), wherein $\beta_4$ is N or D; and $\beta_{12}$ is E or D;
 (c) a CDR-H3 sequence comprising the sequence of $\gamma_1$-R-$\gamma_3$-L-R-A-Q-G-F-A-Y (SEQ ID NO:321), wherein $\gamma_1$ is A or S; $\gamma_3$ is V or L;
 (d) a CDR-L1 sequence comprising the sequence of $\delta_3$-S-$\delta_3$-Q-S-L-L-Y-S-$\delta_{10}$-N-Q-K-N-Y-L-A (SEQ ID NO:322), wherein $\delta_1$ is T or K; $\delta_3$ is G or S; and $\delta_{10}$ is N or S;
 (e) a CDR-L2 sequence comprising the sequence of WASTRES (SEQ ID NO:32); and
 (f) a CDR-L3 sequence comprising the sequence of Q-Q-Y-Y-$\phi_5$-N-P-F-T (SEQ ID NO:323), wherein $\phi_5$ is R or G.

In some embodiments, an anti-TREM2 antibody comprises a CDR-H2 sequence that is selected from SEQ ID NOS:126, 132, and 136. In some embodiments, an anti-TREM2 antibody comprises a CDR-H3 sequence that is selected from SEQ ID NOS:127 and 137. In some embodiments, an anti-TREM2 antibody comprises a CDR-L1 sequence that is selected from SEQ ID NOS:128 and 138. In some embodiments, an anti-TREM2 antibody comprises a CDR-L3 sequence is selected from SEQ ID NOS:129, 133, and 139.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:123, 130, or 134. In some embodiments, an anti-TREM2 antibody comprises a heavy chain variable region comprising the amino acid sequence of any one of SEQ ID NOS:123, 130, or 134.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:124, 131, or 135. In some embodiments, an anti-TREM2 antibody comprises a light chain variable region comprising the amino acid sequence of any one of SEQ ID NOS:124, 131, or 135.

Clone CL0020141

In some embodiments, an anti-TREM2 antibody comprises a CDR-H1 sequence comprising the amino acid sequence of SEQ ID NO:125, a CDR-H2 sequence comprising the amino acid sequence of SEQ ID NO:136, a CDR-H3 sequence comprising the amino acid sequence of SEQ ID NO:137, a CDR-L1 sequence comprising the amino acid sequence of SEQ ID NO:138, a CDR-L2 sequence comprising the amino acid sequence of SEQ ID NO:32, and a CDR-L3 sequence comprising the amino acid sequence of SEQ ID NO:139.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:134. In some embodiments, an anti-TREM2 antibody comprises a heavy chain variable region comprising the amino acid sequence of SEQ ID NO:134.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:135. In some embodiments, an anti-TREM2 antibody comprises a light chain variable region comprising the amino acid sequence of SEQ ID NO:135.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:134 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:135. In some embodiments, an anti-TREM2 antibody comprises a heavy chain variable region comprising the amino acid sequence of SEQ ID NO:134 and a light chain variable region comprising the amino acid sequence of SEQ ID NO:135.

In some embodiments, an anti-TREM2 antibody comprises a heavy chain variable region that comprises a heavy chain CDR1-3 comprising the amino acid sequences of SEQ ID NOS:125, 136, and 137, respectively, and that has at least 85% sequence identity (e.g., at least 90%, 91%, 92%, 93%, 94%, 95%, 96%, 97%, 98%, or 99% sequence identity) to SEQ ID NO:134. In some embodiments, an anti-TREM2 antibody comprises a light chain variable region that comprises a light chain CDR1-3 comprising the amino acid sequences of SEQ ID NOS:138, 32, and 139, respectively, and that has at least 85% sequence identity (e.g., at least 90%, 91%, 92%, 93%, 94%, 95%, 96%, 97%, 98%, or 99% sequence identity) to SEQ ID NO:135.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:125, 136, 137, 138, 32, and 139, respectively, or an antibody comprising a heavy chain variable region comprising the amino acid sequence of SEQ ID NO:134 and a light chain variable region comprising the amino acid sequence of SEQ ID NO:135).

Clone CL0020311

In some embodiments, an anti-TREM2 antibody comprises a CDR-H1 sequence comprising the amino acid sequence of SEQ ID NO:135, a CDR-H2 sequence comprising the amino acid sequence of SEQ ID NO:126, a CDR-H3 sequence comprising the amino acid sequence of SEQ ID NO:127, a CDR-L1 sequence comprising the amino acid sequence of SEQ ID NO:128, a CDR-L2 sequence comprising the amino acid sequence of SEQ ID NO:32, and a CDR-L3 sequence comprising the amino acid sequence of SEQ ID NO:129.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:123. In some embodiments, an anti-TREM2 antibody comprises a heavy chain variable region comprising the amino acid sequence of SEQ ID NO:123.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:124. In some embodiments, an anti-TREM2 antibody comprises a light chain variable region comprising the amino acid sequence of SEQ ID NO:124.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:123 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:124. In some embodiments, an anti-TREM2 antibody comprises a heavy chain variable region comprising the amino acid sequence of SEQ ID NO:123 and a light chain variable region comprising the amino acid sequence of SEQ ID NO:124.

In some embodiments, an anti-TREM2 antibody comprises a heavy chain variable region that comprises a heavy chain CDR1-3 comprising the amino acid sequences of SEQ ID NOS:125, 126, and 127, respectively, and that has at least 85% sequence identity (e.g., at least 90%, 91%, 92%, 93%, 94%, 95%, 96%, 97%, 98%, or 99% sequence identity) to SEQ ID NO:123. In some embodiments, an anti-TREM2 antibody comprises a light chain variable region that comprises a light chain CDR1-3 comprising the amino acid sequences of SEQ ID NOS:128, 32, and 129, respectively, and that has at least 85% sequence identity (e.g., at least 90%, 91%, 92%, 93%, 94%, 95%, 96%, 97%, 98%, or 99% sequence identity) to SEQ ID NO:124.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:125, 126, 127, 128, 32, and 129, respectively, or an antibody comprising a heavy chain variable region comprising the amino acid sequence of SEQ ID NO:123 and a light chain variable region comprising the amino acid sequence of SEQ ID NO:124).

Clone CL0020312

In some embodiments, an anti-TREM2 antibody comprises a CDR-H1 sequence comprising the amino acid sequence of SEQ ID NO:125, a CDR-H2 sequence comprising the amino acid sequence of SEQ ID NO:132, a CDR-H3 sequence comprising the amino acid sequence of SEQ ID NO:127, a CDR-L1 sequence comprising the amino acid sequence of SEQ ID NO:128, a CDR-L2 sequence comprising the amino acid sequence of SEQ ID NO:32, and a CDR-L3 sequence comprising the amino acid sequence of SEQ ID NO:133.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:130. In some embodiments, an anti-TREM2 antibody comprises a heavy chain variable region comprising the amino acid sequence of SEQ ID NO:130.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:131. In some embodiments, an anti-TREM2 antibody comprises a light chain variable region comprising the amino acid sequence of SEQ ID NO:131.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:130 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:131. In some embodiments, an anti-TREM2 antibody comprises a heavy chain variable region comprising the amino acid sequence of SEQ ID NO:130 and a light chain variable region comprising the amino acid sequence of SEQ ID NO:131.

In some embodiments, an anti-TREM2 antibody comprises a heavy chain variable region that comprises a heavy chain CDR1-3 comprising the amino acid sequences of SEQ ID NOS:125, 132, and 127, respectively, and that has at least 85% sequence identity (e.g., at least 90%, 91%, 92%, 93%, 94%, 95%, 96%, 97%, 98%, or 99% sequence identity) to SEQ ID NO:130. In some embodiments, an anti-TREM2 antibody comprises a light chain variable region that comprises a light chain CDR1-3 comprising the amino acid sequences of SEQ ID NOS:128, 32, and 133, respectively, and that has at least 85% sequence identity (e.g., at least 90%, 91%, 92%, 93%, 94%, 95%, 96%, 97%, 98%, or 99% sequence identity) to SEQ ID NO:131.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS:126, 132, 127, 128, 32, and 133, respectively, or an antibody comprising a heavy chain variable region comprising the amino acid sequence of SEQ ID NO:130 and a light chain variable region comprising the amino acid sequence of SEQ ID NO:131).

Binding Characteristics of Anti-TREM2 Antibodies

In some embodiments, an antibody as described herein that specifically binds to a TREM2 protein binds to TREM2 that is expressed on a cell (e.g., a primary cell or cell line that endogenously expresses TREM2, such as human macrophages, or a primary cell or cell line that has been engineered to express TREM2, e.g., as described in the Examples section below). In some embodiments, an antibody that specifically binds to a TREM2 protein as described herein binds to purified or recombinant TREM2 protein of a portion thereof, or to a chimeric protein comprising TREM2 or a portion thereof (e.g., an Fc-fusion protein comprising TREM2 or an Fc-fusion protein comprising the ecto-domain of TREM2).

In some embodiments, some embodiments, an antibody that specifically binds to human TREM2 protein exhibits cross-reactivity with one or more other TREM2 proteins of another species. In some embodiments, an antibody that specifically binds to human TREM2 protein exhibits cross-reactivity with a cynomolgus monkey ("cyno") TREM2 protein. In some embodiments, an antibody that specifically binds to human TREM2 protein exhibits cross-reactivity with a mouse TREM2 protein. In some embodiments, an anti-TREM2 antibody exhibits cross-reactivity with human TREM2, cyno TREM2, and mouse TREM2.

Methods for analyzing binding affinity, binding kinetics, and cross-reactivity are known in the art. These methods include, but are not limited to, solid-phase binding assays (e.g., ELISA assay), immunoprecipitation, surface plasmon resonance (e.g., Biacore™ (GE Healthcare, Piscataway, NJ)), kinetic exclusion assays (e.g., KinExA®)), flow cytometry, fluorescence-activated cell sorting (FACS), Bio-Layer interferometry (e.g., Octet™ (FortéBio, Inc., Menlo Park, CA)), and western blot analysis. In some embodiments, ELISA is used to determine binding affinity and/or cross-reactivity. Methods for performing ELISA assays are known in the art, and are also described in the Examples section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity.

Epitopes Recognized by Anti-TREM2 Antibodies

In some embodiments, an anti-TREM2 antibody recognizes an epitope of human TREM2 that is the same or substantially the same as the epitope recognized by an antibody clone as described herein. As used herein, the term "substantially the same," as used with reference to an epitope recognized by an antibody clone as described herein, means that the anti-TREM2 antibody recognizes an epitope that is identical, within, or nearly identical to (e.g., has at least 90% sequence identity to, or has one, two, or three amino acid substitutions, e.g., conservative substitutions, relative to), or has substantial overlap with (e.g., at least 50%, 60%, 70%, 80%, 90%, or 95% overlap with) the epitope recognized by the antibody clone as described herein.

In some embodiments, an anti-TREM2 antibody recognizes an epitope of human TREM2 that is the same or substantially the same as the epitope recognized by an antibody clone selected from the group consisting of Clone CL0020107, Clone CL0020300, Clone CL0020215, Clone CL0020301, Clone CL0020302, Clone CL0020139, Clone CL0020304, Clone CL0020305, Clone CL0020306, Clone CL0020188, Clone CL0020307, Clone CL0020308, Clone CL0020309, Clone CL0020310, Clone CL0020123, Clone CL0020311, Clone CL0020312, Clone CL0020141, Clone CL0020103, Clone CL0020201, Clone CL0020120, Clone CL0020127, Clone CL0020109, Clone CL0020214, Clone CL0020096, Clone CL0020210, Clone CL0020313, Clone CL0020314, Clone CL0020315, Clone CL0020205, Clone CL0020206, Clone CL0020111, Clone CL0020112, Clone CL0020124, Clone CL0020125, Clone CL0220183, Clone CL0020186, Clone CL0020113, Clone CL0020162, Clone CL0020195, Clone CL0020161, Clone CL0020173, and Clone CL0020164.

In some embodiments, an anti-TREM2 antibody binds to human TREM2 at an epitope within the stalk region of TREM2. In some embodiments, an anti-TREM2 antibody recognizes an epitope of human TREM2 comprising, within, or consisting of residues 129-172 or residues 131-169 of SEQ ID NO:1. In some embodiments, an anti-TREM2 antibody recognizes an epitope of human TREM2 comprising, within, or consisting of residues 129-148 of SEQ ID NO:1. In some embodiments, anti-TREM2 antibody recognizes an epitope of human TREM2 comprising, within, or consisting of amino acid residues 143-149 of SEQ ID NO: 1. In some embodiments, an anti-TREM2 antibody is an agonist that activates TREM2/DAP12 signaling (e.g., by inducing phosphorylation of a kinase such as Syk) and binds to human TREM2 at an epitope within the stalk region of TREM2. In some embodiments, an anti-TREM2 antibody binds to human TREM2 at an epitope within the stalk region of TREM2 and inhibits cleavage of TREM2 by a protease (e.g., ADAM17).

In some embodiments, an anti-TREM2 antibody binds to human TREM2 at an epitope within the Ig variable (IgV) domain of TREM2. In some embodiments, an anti-TREM2 antibody is an agonist that activates TREM2/DAP12 signaling (e.g., by inducing phosphorylation of a kinase such as Syk) and binds to human TREM2 at an epitope within the IgV domain of TREM2. In some embodiments, an anti-TREM2 antibody binds to human TREM2 at an epitope comprising or consisting of one or more of the following: (i) amino acid residues 55-63 (GEKGPCQRV (SEQ ID NO:341)) of SEQ ID NO:1, (ii) amino acids 96-107 (TLRNLQPHDAGL (SEQ ID NO:342)) of SEQ ID NO:1, and (iii) amino acid residues 126-129 (VEVL (SEQ ID NO:343)) of SEQ ID NO:1.

Functional Characteristics of Anti-TREM2 Antibodies

In some embodiments, an anti-TREM2 antibody (e.g., an antibody having one or more CDR, heavy chain variable region, and/or light chain variable region sequences as disclosed herein) functions in one or more TREM2 activities as disclosed herein. For example, in some embodiments an anti-TREM2 antibody is an antibody that modulates levels of sTREM2 protein (e.g., levels of sTREM2 that are shed from the cell surface into an extracellular sample), modulates recruitment or phosphorylation of a kinase that interacts with a TREM2/DAP12 signaling complex (e.g., Syk kinase), and/or modulates one or more activities downstream of the signaling complex, such as phagocytosis, cell growth, cell survival, cell differentiation, cytokine secretion, or cell migration. In some embodiments, an anti-TREM2 antibody as disclosed herein binds soluble TREM2 protein (sTREM2) in healthy human CSF or cynomolgus CSF with better potency compared to a reference antibody. In some embodiments, the reference antibody is represented by a combination of sequences selected from the group consisting of: SEQ ID NOS:344 and 345; SEQ ID NOS:346 and 347; and SEQ ID NOS:348 and 349. In some embodiments, the potency assay is carried out substantially as described in Example 11.

In some embodiments, an anti-TREM2 antibody enhances one or more TREM2 activities (e.g., those described herein) that are induced by a ligand. In some embodiments, the ligand is a lipid ligand. Examples of TREM2 lipid ligands include, but are not limited to, 1-palmitoyl-2-(5'-oxo-valeroyl)-sn-glycero-3-phosphocholine (POVPC), 2-Arachidonoylglycerol (2-AG), 7-ketocholesterol (7-KC), 24(S)hydroxycholesterol (24OHC), 25(S)hydroxycholesterol (25OHC), 27-hydroxycholesterol (27OHC), Acyl Carnitine (AC), alkylacylglycerophosphocholine (PAF), α-galactosylceramide (KRN7000), Bis(monoacylglycero)phosphate (BMP), Cardiolipin (CL), Ceramide, Ceramide-1-phosphate (C1P), Cholesteryl ester (CE), Cholesterol phosphate (CP), Diacylglycerol 34:1 (DG 34:1), Diacylglycerol 38:4 (DG 38:4), Diacylglycerol pyrophosphate (DGPP), Dihyrdoceramide (DhCer), Dihydrosphingomyelin (DhSM), Ether phosphatidylcholine (PCe), Free cholesterol (FC), Galactosylceramide (GalCer), Galactosyl sphingosine (GalSo), Ganglioside GM1, Ganglioside GM3, Glucosylsphingosine (GlcSo), Hank's Balanced Salt Solution (HBSS), Kdo2-Lipid A (KLA), Lactosylceramide (LacCer), lysoalkylacylglycerophosphocholine (LPAF), Lysophosphatidic acid (LPA), Lysophosphatidylcholine (LPC), Lysophosphatidylethanolamine (LPE), Lysophosphatidylglycerol (LPG), Lysophosphatidylinositol (LPI), Lysosphingomyelin (LSM), Lysophosphatidylserine (LPS), N-Acyl-phosphatidylethanolamine (NAPE), N-Acyl-Serine (NSer), Oxidized phosphatidylcholine (oxPC), Palmitic-acid-9-hydroxy-stearic-acid (PAHSA), Phosphatidylethanolamine (PE), Phosphatidylethanol (PEtOH), Phosphatidic acid (PA), Phosphatidylcholine (PC), Phosphatidylglycerol (PG), Phosphatidylinositol (PI), Phosphatidylserine (PS), Sphinganine, Sphinganine-1-phosphate (Sa1P), Sphingomyelin (SM), Sphingosine, Sphingosine-1-phosphate (So1P), and Sulfatide.

Modulation of sTREM2 Shedding

In some embodiments, an anti-TREM2 antibody alters levels of sTREM2 protein in a sample, e.g., levels of sTREM2 that are shed from the cell surface into an extracellular sample. In some embodiments, an anti-TREM2 antibody decreases levels of sTREM2.

In some embodiments, an anti-TREM2 antibody decreases levels of sTREM2 if the amount of sTREM2 in a treated sample is decreased by at least 10%, at least 20%, at least 30%, at least 40%, at least 50%, at least 60%, at least 70%, at least 80%, at least 90% or more as compared to a control value. In some embodiments, an anti-TREM2 antibody decreases levels of sTREM2 if the amount of sTREM2 in a treated sample is decreased by at least 2-fold, 3-fold, 4-fold, 5-fold, 6-fold, 7-fold, 8-fold, 9-fold, 10-fold or more as compared to a control value. In some embodiments, the control value is the amount of sTREM2 in an untreated sample (e.g., a supernatant from a TREM2-expressing cell that has not been treated with an anti-TREM2 antibody, or a sample from a subject that has not been treated with an anti-TREM2 antibody) or a sample treated with an appropriate non-TREM2-binding antibody.

In some embodiments, sTREM2 shedding is measured using a sample that comprises a fluid, e.g., blood, plasma, serum, urine, or cerebrospinal fluid. In some embodiments, the sample comprises cerebrospinal fluid. In some embodiments, the sample comprises supernatant from cell cultures (e.g., supernatant from a primary cell or cell line that endogenously expresses TREM2, such as human macrophages, or a primary cell or cell line that has been engineered to express TREM2, e.g., as described in the Examples section below).

In some embodiments, the level of sTREM2 in a sample is measured using an immunoassay. Immunoassays are known in the art and include, but are not limited to, enzyme immunoassays (EIA) such as enzyme multiplied immunoassay (EMIA), enzyme-linked immunosorbent assay (ELISA), microparticle enzyme immunoassay (META), immunohistochemistry (IHC), immunocytochemistry, capillary electrophoresis immunoassays (CEIA), radioimmunoassays (MA), immunofluorescence, chemiluminescence immunoassays (CL), and electrochemiluminescence immunoassays (ECL). In some embodiments, sTREM2 levels are measuring using an ELISA assay. In some embodiments, sTREM2 levels are measured using an ELISA assay as described in the Examples section below.

Modulation of Kinase Recruitment or Phosphorylation

In some embodiments, an anti-TREM2 antibody induces phosphorylation of a kinase that interacts with the TREM2/DAP12 signaling complex (such as, but not limited to, Syk, ZAP70, PI3K, Erk, AKT, or GSK3b). In some embodiments, an anti-TREM2 antibody induces phosphorylation of a kinase that interacts with the TREM2/DAP12 signaling complex without blocking binding of a native TREM2 ligand. In some embodiments, an anti-TREM2 antibody enhances phosphorylation of a kinase that interacts with the TREM2/DAP12 signaling complex that is induced by a TREM2 ligand (e.g., a lipid ligand). In some embodiments, an anti-TREM2 antibody induces or enhances phosphorylation of Syk. In some embodiments, an anti-TREM2 antibody induces or enhances phosphorylation of Syk if the level of Syk phosphorylation in a sample treated with the anti-TREM2 antibody is increased by at least 10%, at least 20%, at least 30%, at least 40%, at least 50%, at least 60%, at least 70%, at least 80%, at least 90% or more as compared to a control value. In some embodiments, an anti-TREM2 antibody induces phosphorylation of Syk if the level of Syk phosphorylation in a sample treated with the anti-TREM2 antibody is increased by at least 2-fold, 3-fold, 4-fold, 5-fold, 6-fold, 7-fold, 8-fold, 9-fold, 10-fold, or more as compared to a control value. In some embodiments, the control value is the level of Syk phosphorylation in an untreated sample (e.g., a sample comprising a TREM2-expressing cell that has not been treated with an anti-TREM2 antibody, or a sample from a subject that has not been treated with an anti-TREM2 antibody), or a sample that has been treated with a TREM2 ligand but not an anti-TREM2 antibody, or a sample treated with an appropriate non-TREM2-binding antibody.

For detecting and/or quantifying phosphorylation (e.g., Syk phosphorylation) in a sample, in some embodiments, an immunoassay is used. In some embodiments, the immunoassay is an enzyme immunoassay (EIA), enzyme multiplied immunoassay (EMIA), enzyme-linked immunosorbent assay (ELISA), microparticle enzyme immunoassay (MEIA), immunohistochemistry (IHC), immunocytochemistry, capillary electrophoresis immunoassay (CEIA), radioimmunoassay (MA), immunofluorescence, chemiluminescence immunoassay (CL), or electrochemiluminescence immunoassay (ECL). In some embodiments, phosphorylation is detected and/or quantified using an immunoassay that utilizes an amplified luminescent proximity homogenous assay (AlphaLISA®, PerkinElmer Inc.).

In some embodiments, phosphorylation is measured using a sample that comprises one or more cells, e.g., one or more TREM2-expressing cells (e.g., a primary cell or cell line that endogenously expresses TREM2, such as human macrophages or iPSC-derived microglia, or a primary cell or cell line that has been engineered to express TREM2, e.g., as described in the Examples section below). In some embodiments, the sample comprises a fluid, e.g., blood, plasma, serum, urine, or cerebrospinal fluid. In some embodiments, the sample comprises tissue (e.g., lung, brain, kidney, spleen, nervous tissue, or skeletal muscle) or cells from such tissue. In some embodiments, the sample comprises endogenous fluid, tissue, or cells (e.g., from a human or non-human subject).

Modulation of Phagocytosis

In some embodiments, an anti-TREM2 antibody enhances phagocytosis of dead cell debris, tissue debris, amyloid beta particles, or foreign material. In some embodiments, an anti-TREM2 antibody enhances phagocytosis without blocking binding of a native TREM2 ligand. In some embodiments, an anti-TREM2 antibody enhances phagocytosis that is induced by a TREM2 ligand (e.g., a lipid ligand). In some embodiments, an anti-TREM2 antibody enhances phagocytosis if the level of phagocytosis in a sample treated with the anti-TREM2 antibody is increased by at least 10%, at least 20%, at least 30%, at least 40%, at least 50%, at least 60%, at least 70%, at least 80%, at least 90% or more as compared to a control value. In some embodiments, an anti-TREM2 antibody enhances phagocytosis if the level of phagocytosis in a sample treated with the anti-TREM2 antibody is increased by at least 2-fold, 3-fold, 4-fold, 5-fold, 6-fold, 7-fold, 8-fold, 9-fold, 10-fold, or more as compared to a control value. In some embodiments, the control value is the level of phagocytosis in an untreated sample, a sample that has been treated with a TREM2 ligand but not an anti-TREM2 antibody, or a sample treated with an appropriate non-TREM2-binding antibody.

In some embodiments, phagocytosis is measured using a phagocytosis assay with a labeled substrate. Phagocytosis assays are known in the art. In some embodiments, the phagocytosis assay is performed on a sample comprising cells that endogenously express TREM2, such as human macrophages or microglia. In some embodiments, the phagocytosis assay is performed on a sample comprising cells that have been engineered to express TREM2. In some embodiments, phagocytosis is measured using a human macrophage phagocytosis assay as described in the Examples section below.

Modulation of Cell Differentiation, Function, Migration, and Survival

In some embodiments, an anti-TREM2 antibody enhances cell migration, cell survival, cell function, or cell differentiation (e.g., for myeloid cells, macrophages, and microglia, including iPSC-derived microglia and disease-associated microglia). Disease-associated microglia and methods of detecting disease-associated microglia are described in Keren-Shaul et al., *Cell,* 2017, 169:1276-1290. In some embodiments, an anti-TREM2 antibody enhances cell migration of one or more cell types (e.g., myeloid cells, macrophages, or microglia). In some embodiments, an anti-TREM2 antibody enhances cell survival of one or more cell types (e.g., myeloid cells, macrophages, or microglia). In some embodiments, an anti-TREM2 antibody enhances cell function of one or more cell types (e.g., myeloid cells, macrophages, or microglia). In some embodiments, an anti-TREM2 antibody enhances cell differentiation of one or more cell types (e.g., myeloid cells, macrophages, or microglia). In some embodiments, an anti-TREM2 antibody enhances the migration, survival, function, and/or differentiation of myeloid cells. In some embodiments, an anti-TREM2 antibody enhances the migration, survival, function, and/or differentiation of macrophages. In some embodiments, an anti-TREM2 antibody enhances the migration, survival, function, and/or differentiation of microglia. In some embodiments, an anti-TREM2 antibody enhances microglia activation. In some embodiments, an anti-TREM2 antibody enhances the migration, survival, function, and/or differentiation of disease-associated microglia. In some embodiments, an anti-TREM2 antibody enhances cell migration, cell survival, cell function, or cell differentiation without blocking binding of a native TREM2 ligand. In some embodiments, an anti-TREM2 antibody enhances cell migration, cell survival, cell function, or cell differentiation that is induced by a TREM2 ligand (e.g., a lipid ligand).

In some embodiments, an anti-TREM2 antibody enhances cell migration, cell survival, cell function, or cell differentiation if the level of activity (e.g., migration, survival, function, or differentiation) in a sample treated with the anti-TREM2 antibody is increased by at least 10%, at least 20%, at least 30%, at least 40%, at least 50%, at least 60%, at least 70%, at least 80%, at least 90% or more as compared to a control value. In some embodiments, an anti-TREM2 antibody enhances cell migration, cell survival, cell function, or cell differentiation if the level of activity (e.g., migration, survival, function, or differentiation) in a sample treated with the anti-TREM2 antibody is increased by at least 2-fold, 3-fold, 4-fold, 5-fold, 6-fold, 7-fold, 8-fold, 9-fold, 10-fold, or more as compared to a control value. In some embodiments, the control value is the level of activity (e.g., migration, survival, function, or differentiation) in an untreated sample (e.g., a sample that has not been treated with an anti-TREM2 antibody), a sample that has been treated with a TREM2 ligand but not an anti-TREM2 antibody, or a sample treated with an appropriate non-TREM2-binding antibody.

In some embodiments, cell migration is measured using a chemotaxis assay. Chemotaxis assays are known in the art. In some embodiments, the cell migration assay (e.g., chemotaxis assay) is performed on a sample comprising cells that endogenously express TREM2, such as human macrophages. In some embodiments, the cell migration assay (e.g., chemotaxis assay) is performed on a sample comprising cells that have been engineered to express TREM2. In some embodiments, cell migration is measured using a human macrophage chemotaxis assay as described in the Examples section below.

In some embodiments, cell survival is measured using a cell viability assay. Cell viability assays are known in the art. In some embodiments, the cell survival assay (e.g., cell viability assay) is performed on a sample comprising cells that endogenously express TREM2, such as human macrophages. In some embodiments, the cell survival assay (e.g., cell viability assay) is performed on a sample comprising cells that have been engineered to express TREM2. In some embodiments, cell survival is measured using a human macrophage viability assay as described in the Examples section below.

In some embodiments, cell function is measured using a functional assay that is appropriate for that cell. For example, in some embodiments, macrophage cell function is evaluated using a phagocytosis assay, e.g., as described in the Examples section below.

In some embodiments, cell differentiation is measured by evaluating the ability of cells that endogenously express TREM2 to differentiate. For example, in some embodiments, cell differentiation is measured by evaluating the ability of macrophages to differentiate from monocytes, e.g., as described in the Examples section below.

In some embodiments, activation of microglia is measured in vivo. In some embodiments, microglia activation is measured using TSPO-PET imaging. TSPO-PET imaging methods are known in the art.

In some embodiments, an anti-TREM2 antibody enhances microglia function without increasing neuroinflammation. Levels of neuroinflammation can be determined by measuring levels of cytokines (e.g., inflammatory cytokines), such as but not limited to TNF-α, IL-1β, IL-6, IL-1ra, TGFβ, IL-15, or IFN-γ. In some embodiments, cytokine levels are measured using immunoassays, for example, an enzyme immunoassay (EIA), enzyme multiplied immunoassay (EMIA), enzyme-linked immunosorbent assay (ELISA), microparticle enzyme immunoassay (META), immunohistochemistry (IHC), immunocytochemistry, capillary electrophoresis immunoassay (CEIA), radioimmunoassay (MA), immunofluorescence, chemiluminescence immunoassay (CL), or electrochemiluminescence immunoassay (ECL).

IV. Preparation of Antibodies

In some embodiments, antibodies are prepared by immunizing an animal or animals (e.g., mice, rabbits, or rats) with an antigen or a mixture of antigens for the induction of an antibody response. In some embodiments, the antigen or mixture of antigens is administered in conjugation with an adjuvant (e.g., Freund's adjuvant). After an initial immunization, one or more subsequent booster injections of the antigen or antigens may be administered to improve antibody production. Following immunization, antigen-specific B cells are harvested, e.g., from the spleen and/or lymphoid tissue. For generating monoclonal antibodies, the B cells are fused with myeloma cells, which are subsequently screened for antigen specificity. Methods of preparing antibodies are also described in the Examples section below.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Alternatively, phage or yeast display technology can be used to identify antibodies and Fab fragments that specifically bind to selected antigens. Antibodies can also be made bispecific, i.e., able to recognize two different antigens. Antibodies can also be heteroconjugates, e.g., two covalently joined antibodies, or immunotoxins.

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a VH and VL region, the VH and VL regions may be expressed using a single vector, e.g., in a di-cistronic expression unit, or under the control of different promoters. In other embodiments, the VH and VL region may be expressed using separate vectors. A VH or VL region as described herein may optionally comprise a methionine at the N-terminus.

In some embodiments, the antibody is a chimeric antibody. Methods for making chimeric antibodies are known in the art. For example, chimeric antibodies can be made in which the antigen binding region (heavy chain variable region and light chain variable region) from one species, such as a mouse, is fused to the effector region (constant domain) of another species, such as a human. As another example, "class switched" chimeric antibodies can be made in which the effector region of an antibody is substituted with an effector region of a different immunoglobulin class or subclass.

In some embodiments, the antibody is a humanized antibody. Generally, a non-human antibody is humanized in order to reduce its immunogenicity. Humanized antibodies typically comprise one or more variable regions (e.g., CDRs) or portions thereof that are non-human (e.g., derived from a mouse variable region sequence), and possibly some framework regions or portions thereof that are non-human, and further comprise one or more constant regions that are derived from human antibody sequences. Methods for humanizing non-human antibodies are known in the art. Transgenic mice, or other organisms such as other mammals, can be used to express humanized or human antibodies. Other methods of humanizing antibodies include, for example, variable domain resurfacing, CDR grafting, grafting specificity-determining residues (SDR), guided selection, and framework shuffling.

As an alternative to humanization, fully human antibodies can be generated. As a non-limiting example, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. As another example, human antibodies can be produced by hybridoma-based methods, such as by using primary human B cells for generating cell lines producing human monoclonal antibodies.

Human antibodies can also be produced using phage display or yeast display technology. In phage display, repertoires of variable heavy chain and variable light chain genes are amplified and expressed in phage display vectors. In some embodiments, the antibody library is a natural repertoire amplified from a human source. In some embodiments, the antibody library is a synthetic library made by cloning heavy chain and light chain sequences and recombining to generate a large pool of antibodies with different antigenic specificity. Phage typically display antibody fragments (e.g., Fab fragments or scFv fragments), which are then screened for binding to an antigen of interest.

In some embodiments, antibody fragments (such as a Fab, a Fab', a F(ab')$_2$, a scFv, a $V_H$, or a $V_{HH}$) are generated. Various techniques have been developed for the production of antibody fragments. Traditionally, these fragments were derived via proteolytic digestion of intact antibodies. However, these fragments can now be produced directly using recombinant host cells. For example, antibody fragments can be isolated from antibody phage libraries. Alternatively, Fab'-SH fragments can be directly recovered from *E. coli* cells and chemically coupled to form F(ab')$_2$ fragments. According to another approach, F(ab')$_2$ fragments can be isolated directly from recombinant host cell culture. Other techniques for the production of antibody fragments will be apparent to those skilled in the art.

In some embodiments, an antibody or an antibody fragment is conjugated to another molecule, e.g., polyethylene glycol (PEGylation) or serum albumin, to provide an extended half-life in vivo.

In some embodiments, multispecific antibodies comprising an anti-TREM2 antibody (or antigen-binding fragment thereof) as described herein are provided, e.g., a bispecific antibody. Multispecific antibodies are antibodies that have binding specificities for at least two different sites. In some embodiments, a multispecific antibody (e.g., a bispecific antibody) has a binding specificity for TREM2 and has a binding specificity for at least one other antigen. In some embodiments, a multispecific antibody (e.g., a bispecific antibody) binds to two different TREM2 epitopes. In some embodiments, a multispecific antibody (e.g., a bispecific antibody) is capable of inducing TREM2 clustering at the cell surface. An illustrative method for measuring receptor clustering using confocal FRET microscopy is described in Wallrabe et al., *Biophys. J.,* 2003, 85:559-571. Methods of making multispecific antibodies (e.g., bispecific antibodies) include, but are not limited to, recombinant co-expression of two pairs of heavy chain and light chain in a host cell, "knobs-into-holes" engineering, intramolecular trimerization, and fusion of an antibody fragment to the N-terminus or C-terminus of another antibody, e.g., tandem variable domains.

V. Nucleic Acids, Vectors, and Host Cells

In some embodiments, the anti-TREM2 antibodies as disclosed herein are prepared using recombinant methods. Accordingly, in some aspects, the disclosure provides isolated nucleic acids comprising a nucleic acid sequence encoding any of the anti-TREM2 antibodies as described herein (e.g., any one or more of the CDRs, heavy chain variable regions, and light chain variable regions described herein); vectors comprising such nucleic acids; and host cells into which the nucleic acids are introduced that are used to replicate the antibody-encoding nucleic acids and/or to express the antibodies.

In some embodiments, a polynucleotide (e.g., an isolated polynucleotide) comprises a nucleotide sequence encoding an antibody or antigen-binding portion thereof as described herein (e.g., as described in the Section above entitled "Anti-TREM2 Antibody Sequences"). In some embodiments, the polynucleotide comprises a nucleotide sequence encoding one or more amino acid sequences (e.g., CDR, heavy chain, or light chain sequences) disclosed in the Informal Sequence Listing below. In some embodiments, the polynucleotide comprises a nucleotide sequence encoding an amino acid sequence having at least 85% sequence identity (e.g., at least 85%, at least 90%, at least 91%, at least 92%, at least 93%, at least 94%, at least 95%, at least 96%, at least 97%, at least 98%, or at least 99% sequence identity) to a sequence (e.g., a CDR, heavy chain, or light chain sequence) disclosed in the Informal Sequence Listing below.

In some embodiments, a polynucleotide as described herein is operably linked to a heterologous nucleic acid, e.g., a heterologous promoter.

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicate in the host cells either as episomes or as an integral part of the chromosomal DNA. Suitable expression vectors include but are not limited to plasmids, viral vectors, including adenoviruses, adeno-associated viruses, retroviruses, and any other vector.

Suitable host cells for cloning or expressing a polynucleotide or vector as described herein include prokaryotic or eukaryotic cells. In some embodiments, the host cell is prokaryotic. In some embodiments, the host cell is eukaryotic, e.g., Chinese Hamster Ovary (CHO) cells or lymphoid cells. In some embodiments, the host cell is a human cell, e.g., a Human Embryonic Kidney (HEK) cell.

In another aspect, methods of making an anti-TREM2 antibody as described herein are provided. In some embodiments, the method includes culturing a host cell as described herein (e.g., a host cell expressing a polynucleotide or vector as described herein) under conditions suitable for expression of the antibody. In some embodiments, the antibody is subsequently recovered from the host cell (or host cell culture medium).

VI. Therapeutic Methods Using Anti-Trem2 Antibodies

In another aspect, therapeutic methods using an anti-TREM2 antibody as disclosed herein (e.g., an anti-TREM2 antibody as described in Section III above) are provided. In some embodiments, methods of treating a neurodegenerative disease are provided. In some embodiments, methods of modulating one or more TREM2 activities (e.g., in a subject having a neurodegenerative disease) are provided.

In some embodiments, methods of treating a neurodegenerative disease are provided. In some embodiments, the neurodegenerative disease is selected from the group consisting of Alzheimer's disease, primary age-related tauopathy, progressive supranuclear palsy (PSP), frontotemporal dementia, frontotemporal dementia with parkinsonism linked to chromosome 17, argyrophilic grain dementia, amyotrophic lateral sclerosis, amyotrophic lateral sclerosis/parkinsonism-dementia complex of Guam (ALS-PDC), corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, Gerstmann-Straussler-Scheinker disease, globular glial tauopathy, Guadeloupean parkinsonism with dementia, Guadeloupean PSP, Hallevorden-Spatz disease, hereditary diffuse leukoencephalopathy with spheroids (HDLS), Huntington's disease, inclusion-body myositis, multiple system atrophy, myotonic dystrophy, Nasu-Hakola disease, neurofibrillary tangle-predominant dementia, Niemann-Pick disease type C, pallidoponto-nigral degeneration, Parkinson's disease, Pick's disease, postencephalitic parkinsonism, prion protein cerebral amyloid angiopathy, progressive subcortical gliosis, subacute sclerosing panencephalitis, and tangle only dementia. In some embodiments, the neurodegenerative disease is Alzheimer's disease. In some embodiments, the neurodegenerative disease is Nasu-Hakola disease. In some embodiments, the neurodegenerative disease is frontotemporal dementia. In some embodiments, the neurodegenerative disease is Parkinson's disease. In some embodiments, the method comprises administering to the subject an isolated antibody or an antigen-binding fragment thereof that specifically binds to a human TREM2 protein, e.g., an anti-TREM2 antibody as described herein, or a pharmaceutical composition comprising an anti-TREM2 antibody as described herein.

In some embodiments, an anti-TREM2 antibody (or antigen-binding portion or pharmaceutical composition thereof) as described herein is used in treating a neurodegenerative disease that is characterized by a mutation in TREM2. In some embodiments, the neurodegenerative disease that is characterized by a mutation in TREM2 is Alzheimer's disease, e.g., Alzheimer's disease that is characterized by a R47H mutation in TREM2.

In some embodiments, methods of modulating one or more TREM2 activities in a subject (e.g., a subject having a neurodegenerative disease) are provided. In some embodiments, the method comprises modulating levels of sTREM2; modulating recruitment or phosphorylation of a kinase that interacts with a TREM2/DAP12 signaling complex (e.g., Syk kinase); modulating phagocytosis (e.g., phagocytosis of cell debris, amyloid beta particles, etc.); modulating cell migration (e.g., migration of myeloid cells, macrophages, microglia, and disease associated microglia); and/or modulating cell differentiation (e.g., for myeloid cells, macrophages, microglia, and disease associated microglia). In some embodiments, methods of enhancing one or more TREM2 activities in a subject having a neurodegenerative disease are provided. In some embodiments, methods of decreasing levels of sTREM2 in a subject having a neurodegenerative disease are provided. In some embodiments, the method of modulating one or more TREM2 activities in a subject comprises administering to the subject an isolated antibody or an antigen-binding portion thereof that specifically binds to a human TREM2 protein, e.g., an anti-TREM2 antibody as describe herein, or a pharmaceutical composition comprising an anti-TREM2 antibody as described herein.

In some embodiments, the subject to be treated is a human, e.g., a human adult or a human child.

In some embodiments, methods of reducing plaque accumulation in a subject having a neurodegenerative disease are provided. In some embodiments, the method comprises administering to the subject an antibody or pharmaceutical composition as described herein. In some embodiments, the subject has Alzheimer's disease. In some embodiments, the subject is an animal model of a neurodegenerative disease (e.g., a 5XFAD or APP/PS1 mouse model). In some embodiments, plaque accumulation is measured by amyloid plaque imaging and/or Tau imaging, e.g., using positron emission tomography (PET) scanning. In some embodiments, administration of an anti-TREM2 antibody reduces plaque accumulation by at least 20%, at least 30%, at least 40%, at least 50%, at least 60%, at least 70%, at least 80%, or at least 90% as compared to a baseline value (e.g., the level of plaque accumulation in the subject prior to administration of the anti-TREM2 antibody).

In some embodiments, an anti-TREM2 antibody is administered to a subject at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

The route of administration of an anti-TREM2 antibody as described herein can be oral, intraperitoneal, transdermal, subcutaneous, intravenous, intramuscular, intrathecal, inhalational, topical, intralesional, rectal, intrabronchial, nasal, transmucosal, intestinal, ocular or otic delivery, or any other methods known in the art. In some embodiments, the antibody is administered orally, intravenously, or intraperitoneally.

In some embodiments, the anti-TREM2 antibody (and optionally another therapeutic agent) is administered to the subject over an extended period of time, e.g., for at least 30, 40, 50, 60, 70, 80, 90, 100, 150, 200, 250, 300, 350 days or longer.

VII. Pharmaceutical Compositions and Kits

In another aspect, pharmaceutical compositions and kits comprising an antibody that specifically binds to a human TREM2 protein are provided. In some embodiments, the pharmaceutical compositions and kits are for use in treating a neurodegenerative disease. In some embodiments, the pharmaceutical compositions and kits are for use in modulating (e.g., enhancing or inhibiting) one or more TREM2 activities, e.g., Syk phosphorylation. In some embodiments, the pharmaceutical compositions and kits are for use in modulating (e.g., decreasing) sTREM2 levels.

Pharmaceutical Compositions

In some embodiments, pharmaceutical compositions comprising an anti-TREM2 antibody or an antigen-binding fragment thereof are provided. In some embodiments, the anti-TREM2 antibody is an antibody as described in Section III above or an antigen-binding fragment thereof.

In some embodiments, a pharmaceutical composition comprises an anti-TREM2 antibody as described herein and further comprises one or more pharmaceutically acceptable carriers and/or excipients. A pharmaceutically acceptable carrier includes any solvents, dispersion media, or coatings that are physiologically compatible and that does not interfere with or otherwise inhibit the activity of the active agent. Various pharmaceutically acceptable excipients are well-known in the art.

In some embodiments, the carrier is suitable for intravenous, intramuscular, oral, intraperitoneal, intrathecal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known in the art.

The pharmaceutical compositions described herein can be manufactured in a manner that is known to those of skill in the art, e.g., by means of conventional mixing, dissolving, granulating, dragee-making, emulsifying, encapsulating, entrapping or lyophilizing processes. The following methods and excipients are merely exemplary and are in no way limiting.

For oral administration, an anti-TREM2 antibody can be formulated by combining it with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

An anti-TREM2 antibody can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, compounds can be formulated in aqueous solutions, e.g., in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

In some embodiments, an anti-TREM2 antibody is prepared for delivery in a sustained-release, controlled release, extended-release, timed-release or delayed-release formulation, for example, in semi-permeable matrices of solid hydrophobic polymers containing the active agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients. Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions of the disclosure may vary depending on the particular use envisioned. The determination of the appropriate dosage or route of administration is well within the skill of one in the art. Suitable dosages are also described in Section VI above.

Kits

In some embodiments, kits comprising an anti-TREM2 antibody or an antigen-binding fragment thereof are provided. In some embodiments, the anti-TREM2 antibody is an antibody as described in Section III above or an antigen-binding fragment thereof.

In some embodiments, the kit further comprises one or more additional therapeutic agents. For example, in some embodiments, the kit comprises an anti-TREM2 antibody as described herein and further comprises one or more additional therapeutic agents for use in the treatment of a neurodegenerative disease, e.g., Alzheimer's disease. In some embodiments, the therapeutic agent is an agent for use in treating a cognitive or behavioral symptom of a neurodegenerative disease (e.g., an antidepressant, a dopamine agonist, or an anti-psychotic). In some embodiments, the therapeutic agent is a neuroprotective agent (e.g., carbidopa/levodopa, an anticholinergic agent, a dopaminergic agent, a monoamine oxidase B (MAO-B) inhibitor, a catechol-O-methyl transferase (COMT) inhibitor, a glutamatergic agent, a histone deacetylase (HDAC) inhibitor, a cannabinoid, a caspase inhibitor, melatonin, an anti-inflammatory agent, a hormone (e.g., estrogen or progesterone), or a vitamin).

In some embodiments, the kit comprises an anti-TREM antibody as described herein and further comprises one or more reagents for measuring sTREM2 levels. In some embodiments, the kit comprises an anti-TREM antibody as described herein and further comprises one or more reagents for measuring TREM2 activity (e.g., for measuring Syk phosphorylation).

In some embodiments, the kit further comprises instructional materials containing directions (i.e., protocols) for the practice of the methods described herein (e.g., instructions for using the kit for a therapeutic method as described in Section VI above). While the instructional materials typically comprise written or printed materials, they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD-ROM), and the like. Such media may include addresses to internet sites that provide such instructional materials.

VIII. Examples

The present invention will be described in greater detail by way of specific examples. The following examples are offered for illustrative purposes only, and are not intended to limit the invention in any manner.

Example 1. Generation and Initial Characterization of Anti-TREM2 Antibodies

Recombinant Expression and Purification of Mouse Fc Fused Human TREM2 ECD

The ecto domain (residues 19-172) of human TREM2 (UniProtKB ID—Q9NZC2) was subcloned into pRK vector with the secretion signal from mouse IgG kappa chain V-III, amino acids 1-20 (UniProtKB ID—P01661) at the N-terminal region, and a mouse Fc tag at the C-terminal region with a GGGGS (SEQ ID NO:335) between TREM2 ECD and Fc.

Purified plasmid was transfected into Expi293F™ cells (Thermo Fisher) using the Expi293F™ Expression System Kit according to the manufacturer's instructions. To inhibit maturation of N-linked glycans and reduce glycosylation heterogeneity, kifunensine (Sigma), an inhibitor of high mannosidase I was added to the culture at 1 µg/mL concentration immediately after transfection. Transfected cells were incubated in an orbital shaker (Infors HT Multitron) at 125 rpm and 37° C. in a humidified atmosphere of 6% $CO_2$. ExpiFectamine™ 293 Transfection Enhancer 1 and 2 were added to the cells 16 hours post transfection and the media supernatant was harvested 96 hours post transfection. The clarified supernatant was supplemented with EDTA-free protease inhibitor (Roche) and was stored at −80° C.

For rhTREM2-Fc isolation, clarified media supernatant was loaded on HiTrap Mab Select SuRe Protein A affinity column (GE Healthcare Life Sciences) and washed with 200 mM arginine and 137 mM succinate buffer pH 5.0. The fusion protein was eluted in 100 mM QB citrate buffer pH 3.0 and 50 mM NaCl. Immediately after elution, 1M Tris-HCl buffer pH 8.0 was added to the protein solution to neutralize the pH. Protein aggregates were separated by size exclusion chromatography (SEC) on Superdex 200 increase 10/300 GL column (GE Healthcare Life Sciences). The SEC mobile phase buffer was kept at 20 mM Tris-HCl pH 8.0, 100 mM NaCl and 50 mM arginine, which was also the protein storage buffer. All chromatography steps were performed on AKTA pure or AKTA Avant systems (GE Healthcare Life Sciences).

Recombinant Expression and Purification of His-tagged TREM2 ECD

The ecto domain (residues 19-172) of TREM2 (UniProtKB—Q9NZC2) was subcloned in the pRK vector with the secretion signal from mouse Ig kappa chain V-III, amino acids 1-20 (UniProtKB ID—P01661) at the N-terminal region, and a 6×-His tag (SEQ ID NO:336) at the C-terminal region. The insert was verified by sequencing and maxi prep plasmid purification was performed.

Purified plasmid was transfected into Expi293F™ cells (Thermo Fisher) using the Expi293F™ Expression System Kit according to the manufacturer's instructions. Transfected cells were incubated in an orbital shaker (Infors HT Multitron) at 125 rpm and 37° C. in a humidified atmosphere of 6% $CO_2$. ExpiFectamine™ 293 Transfection Enhancer 1 and 2 were added to the cells 16 hours post transfection and the media supernatant was harvested 96 hours post transfection.

Harvested media was supplemented with 1M imidazole pH 8.0 to a final concentration of 10 mM and filtered using the Nalgene™ Rapid-Flow™ disposable filter units (Thermo Fisher) with a pore size of 0.4 microns. HisPur™ Ni-NTA Resin (Thermo Fisher) was washed with MQ water and equilibrated with load buffer (20 mM Tris pH 8.0, 150 mM NaCl, and 10 mM imidazole). Affinity purification was performed using the gravity flow method. The harvested media was loaded onto the resin and nonspecifically bound proteins were washed with load buffer supplemented with 50 mM and 100 mM imidazole. The bound His-tagged TREM2 eco domain was eluted with 20 mM Tris pH 8.0, 150 mM NaCl, and 200 mM imidazole. Eluted protein was concentrated using Amicon 10 kDa concentrators and the concentrated protein was further purified by gel filtration chromatography using the AKTA Avant system (GE Healthcare Life Sciences). The protein was loaded onto a HiLoad Superdex 200 16/600 (GE Healthcare Life Sciences) column equilibrated with 1×PBS and eluted and fractionated using 1×PBS as the running buffer. Eluted fractions were analyzed by electrophoresis on polyacrylamide (PAGE) gels under denaturing and native conditions. Eluted fractions were further characterized by analytical size exclusion chromatography and the intact protein mass determination. Results from the PAGE and analytical characterization were used to pool the heavily glycosylated protein fractions and these were aliquoted and stored at −80° C.

Generation of Antibodies

Rodents (mice and rats) were immunized using standard protocols with rhTREM2-Fc immunogen or BWZ cells expressing full length Trem2 receptor. Titers were measured throughout immunization using sera collected at different time points. The detection of an antigen specific immune response was performed using flow cytometry with the rhTREM2-Fc immunogen and live BWZ cells expressing full-length TREM2. Selection criteria of candidate antibodies included rodent antibody production and specificity of binding to TREM2 as detected by flow cytometry. Antibody-secreting cells were isolated from animal immune tissues including spleen, lymph nodes and bone marrow.

Single cell suspensions were analyzed to determine the binding properties of secreted antibodies. Antibody-secreting cells were loaded into microfluidic devices and isolated in nanoliter volume reaction chambers to enable the detection of secreted antibodies using fluorescent and brightfield image-based microscopy assays (see, e.g., U.S. Pat. No. 9,188,593). Binding assays involving detection of antibodies binding to antigen-coated micro-beads, detection of soluble fluorescently-labeled antigen binding to antibodies immobilized on beads, and detection of antibody binding to cell surface-expressed antigens were carried out. Cell surface-expressed antigens included both recombinant form and the native forms of antigens presented on the surface of cells.

Image analysis was used to identify chambers exhibiting positive fluorescent signals, indicating the presence of a single cell producing antibodies with the desired properties, and the contents of chambers were recovered and lysed in 384 well plates (see, e.g., U.S. Pat. No. 10,087,408). Single cell lysates were then subjected to RT-PCR to amplify the heavy and light chain variable region sequences. The resulting amplicons were then sequenced to determine the cDNA sequence of paired heavy and light chain variable regions from the selected single cells. The resulting sequences were manually inspected and analyzed to determine sequence diversity and somatic hypermutation. Sequences were selected for expression based on screening data and sequence diversity. Expressed antibodies were tested to confirm antigen binding specificity.

Primary Screening of Anti-TREM2 Antibodies

Primary screening of antibodies was performed in HEK 293 cells expressing TREM2, wild-type iPSC, and TREM2 knockout iPSC as follows.

1. Screening for TREM2 Binding in TREM2-Expressing HEK Cells

A HEK 293 cell line stably expressing human TREM2/DAP12 was generated by transfecting the cells with a vector expressing wild type human TREM2 and DAP12, and DAP12 alone, respectively. Stable expressing clones were selected, and the cell surface TREM2 expression was evaluated by flow cytometry. APC-conjugated rat anti-human/mouse-TREM2 monoclonal antibody (R&D, Catalog No. MAB17291) was used to detect surface TREM2 expression. The clone showing the highest wild type TREM2 expression level was selected and named "HEK293-H6." The clones stably expressing DAP12 were analyzed by Western blot, and the selected clone was named "HEK293-DAP12 #1."

HEK 293 overexpressing human TREM2 (HEK293-H6) and HEK 293 overexpressing GFP (B5) were harvested by 0.05% trypsin and incubated at 37° C. for 2 hours. After incubation, the cells were centrifuged and washed in FACS buffer (PBS+0.5% BSA) twice. Mixed cells were resuspended in FACS buffer with human Trustain FcX solution (Biolegend, Catalog No. 422302) at a density of $10^6$/mL per cell line. The mixed cell lines were seeded at 200,000 cells per well in a 96-well round-bottom plate and incubated for 20 minutes at room temperature. After incubation, the cells were centrifuged and incubated with anti-TREM2 antibodies of about 0-200 nM dose titration for 45 minutes on ice. After incubation, the cells were centrifuged and washed with FACS buffer three times. The cells were then incubated with secondary antibody (Alexa Fluor 647 AffiniPure F(ab')2 Fragment Goat Anti-human IgG(H+L), Jackson ImmunoResearch Laboratories, Catalog No. 109-606-088, 1:800 dilution) for 30 minutes on ice. After incubation, the cells were washed with FACS buffer three times, resuspended in 100 μL of FACS buffer, and analyzed by flow cytometry (BD FACSCanto II, San Jose, CA), for which 30,000 events were obtained for each sample. Mean fluorescence intensity per cells were calculated by FlowJo software and used for generating dose response binding curve.

FIG. 1 illustrates a representative result for an exemplary antibody that binds cell surface receptor TREM2 in HEK293-H6 cells.

Evaluation of Activation of TREM2-Dependent pSyk Signaling

Activation of TREM2-dependent pSyk signaling was measured in human macrophage cells or in HEK293-H6 cells using a commercial AlphaLisa assay from Perkin-Elmer.

For all experiments involving use of lipid vesicles containing 70% DOPC and 30% POPS, the lipid vesicles were prepared within two weeks of experiments as follows: 7 mg DOPC (1,2-dioleoyl-sn-glycero-3-phosphocholine) and 3 mg POPS (1-palmitoyl-2-oleoyl-sn-glycero-3-phospho-L-serine) were combined in chloroform in a glass vial and dried under a stream of N2 gas for 1-2 hours, or until completely dry. The lipid mixture was re-suspended in 1 mL HBSS (for a final lipid concentration of about 10 mg/mL) and vortexed for 2-3 minutes. Subsequently, the lipid suspension was extruded using an Avanti mini-extruder constructed with one 100-nm pore size membrane to form small unilamellar vesicles at 10 mg/mL.

1. Dosing of Antibodies in Cells

The day before assay, human macrophage cells or HEK293-H6 cells were plated at 100,000 cells/well or 40,000 cells/well, respectively, on a 96-well plate coated with poly-D-lysine. Antibodies were diluted into PBS starting at 300 nM and proceeding in a 10-point serial dilution titration with 3-fold dilutions between points. For antagonist dose-response curves, lipid vesicles containing 70% DOPC and 30% POPS at 1 mg/mL final concentration were also included in the antibody/PBS mixture. The cells were washed 3 times with HBSS using a Biotek 405/406 plate washer, after which 50 μL per well of the antibody/PBS (with or without vesicles) solution was added using a Hamilton Nimbus liquid handler. The cell plate was then transferred to a 37° C. incubator for 5 minutes. The liposome/antibody solution was removed by flicking the plate, and 40 μL lysis buffer (Cell Signaling Technologies, CST) containing 1 μM PMSF was added using the liquid handler. The lysate was then either frozen at −80° C. or immediately assayed in the AlphaLisa assay.

Human macrophage cells were prepared for assay as follows. Human monocytes were isolated following the RosetteSep human monocyte enrichment cocktail protocol (Stemcell Technologies, REF #15068) from fresh blood. Isolated monocytes were washed in wash buffer (PBS+2% FBS) and resuspended in 10 mL ACK lysis buffer (ThermoFisher Scientific, Catalog No. A10492) to lyse red blood cells. Twenty (20) mL of wash buffer was added to stop cell lysis, and the sample was centrifuged and washed once more with culture media (RPMI, 10% Hyclone FBS, 1% Sodium Pyruvate, 1% Glutamax, 1% non-essential amino acids, and 1% Penicillin-streptomycin). Human monocytes were then differentiated into macrophage cells in culture media in the presence of 50 ng/mL human recombinant M-CSF (Gibco, Catalog No. PHC9501) at 250-mL flask. Fresh human M-CSF was spiked on day 3 and human macrophages were subsequently harvested on day 5 and used for assay.

2. AlphaLisa Assay

Cell lysates were assayed for pSyk using the standard protocol for the Perkin Elmer pSyk AlphaLisa kit. In brief, 10 μL of lysate/well was transferred to a white opaque 384 well Optiplate (Perkin Elmer). Next, 5 μL of Acceptor Mix (containing the working solution of acceptor beads) was added per well, followed by sealing of plates with foil seals and incubation for 1 hour at room temperature. Subsequently, 5 μL of Donor Mix (containing the working solution of donor beads) was added to each well under reduced light conditions. Plates were again sealed and incubated for 1 hour at room temperature. Finally, the plates were read using AlphaLisa settings on a Perkin Elmer EnVision plate reader.

Figure 2:
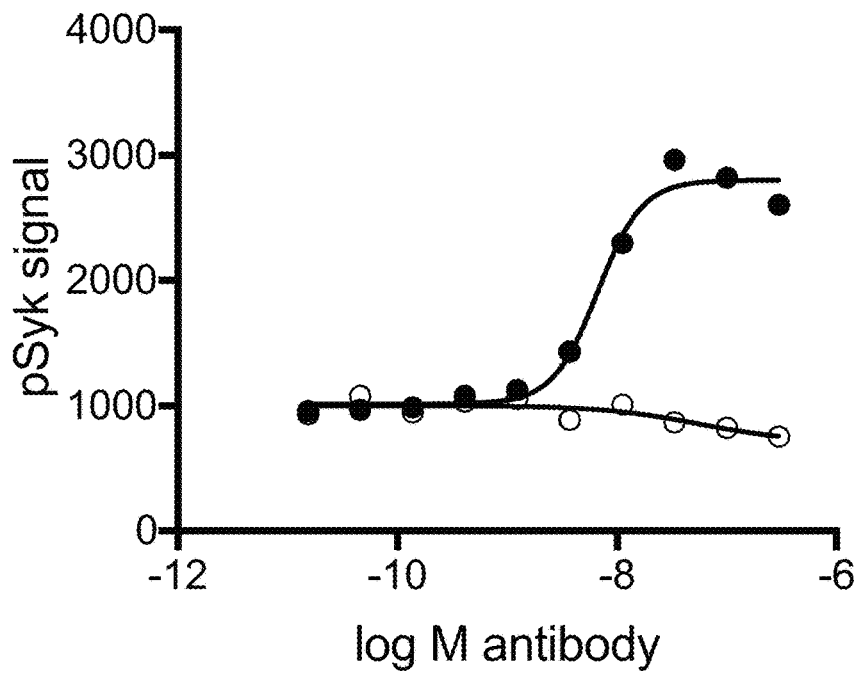
FIG. 2 includes a representative dose-response curves of pSyk signal activation by an exemplary anti-TREM2 antibody in primary human macrophage cells (FIG. 2A) and HEK293-H6 cells (FIG. 2B). Solid black circles (●) represent anti-TREM2 antibody, and open white circles (○) represent isotype control.
Figure 2:
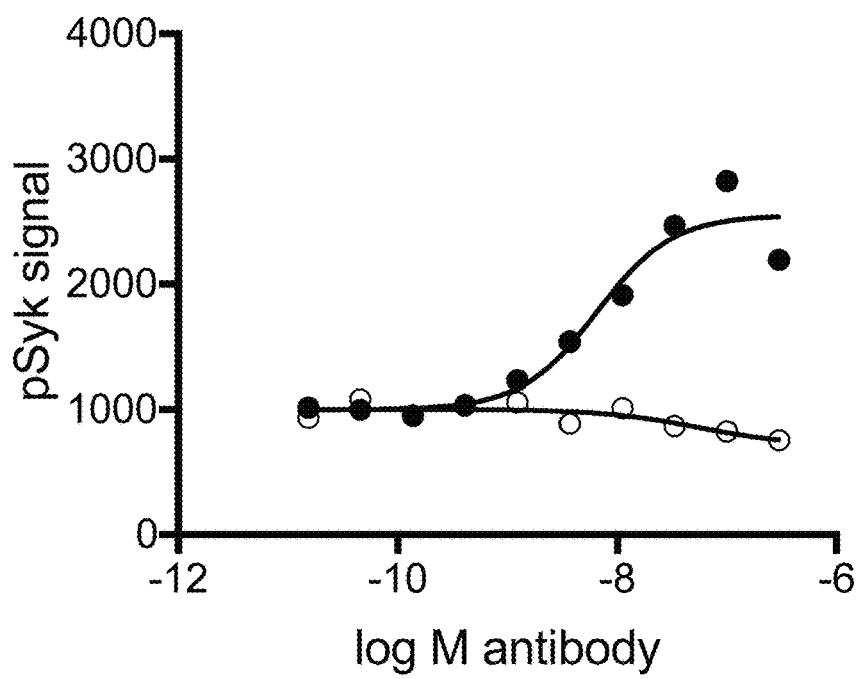

FIG. 2 illustrates representative anti-TREM2 antibody dose response curves for pSyk signal activation in primary human macrophage cells. Solid black circles (●) represent anti-TREM2 antibody, and open white circles (○) represent isotype control. Each curve represents the mean of three independent experiments, and $EC_{50}$ values are provided in Table 1 below. The results indicate that anti-TREM2 antibodies are able to activate TREM2-DAP12 ITAM signaling in primary human macrophages.

Liposome Response Assay in iPSC Microglia

TREM2 agonist antibodies and phosphotidylserine-containing liposomes activate pSyk via TREM2. In order to understand the effect of anti-TREM2 antibodies on Syk signaling in the presence of liposomes, iPSC microglia were pre-treated with anti-TREM2 antibody, followed by assessment of the liposome response in the cells.

Prior to assay, iPSCs were first differentiated into hematopoietic progenitor cells (HPCs) using a commercially available kit (STEMdiff Hematopoietic Kit from StemCell Technologies). HPCs were transferred to a plate containing primary human astrocytes and co-cultured for 14-21 days. Once floating cells in co-culture were predominantly identified as mature microglia (>80%), the microglia were used for assay.

Two days prior to assay, human iPSC microglia were plated at 30,000 cells/well on a 96-well plate coated with poly-D-lysine. Antibodies were diluted to 100 nM into media containing IMDM, 10% Hyclone FBS, and 1% Penstrep, and the cells were dosed with the antibody solution for 24 hours or 5 minutes at 37° C. Subsequently, the cells were washed once with HBSS and then dosed with lipid vesicles containing 70% DOPC and 30% POPS at 1 mg/mL for 5 minutes at 37° C. The liposome solution was removed by flicking the plate, and 30 μL lysis buffer (Cell Signaling Technologies, CST) containing 1 μM PMSF was added. The lysate was then either frozen at −80° C. or immediately assayed in the AlphaLisa assay. The cell lysates were assayed for pSyk using the standard protocol for the Perkin Elmer pSyk AlphaLisa kit as described above.

Figure 3B:
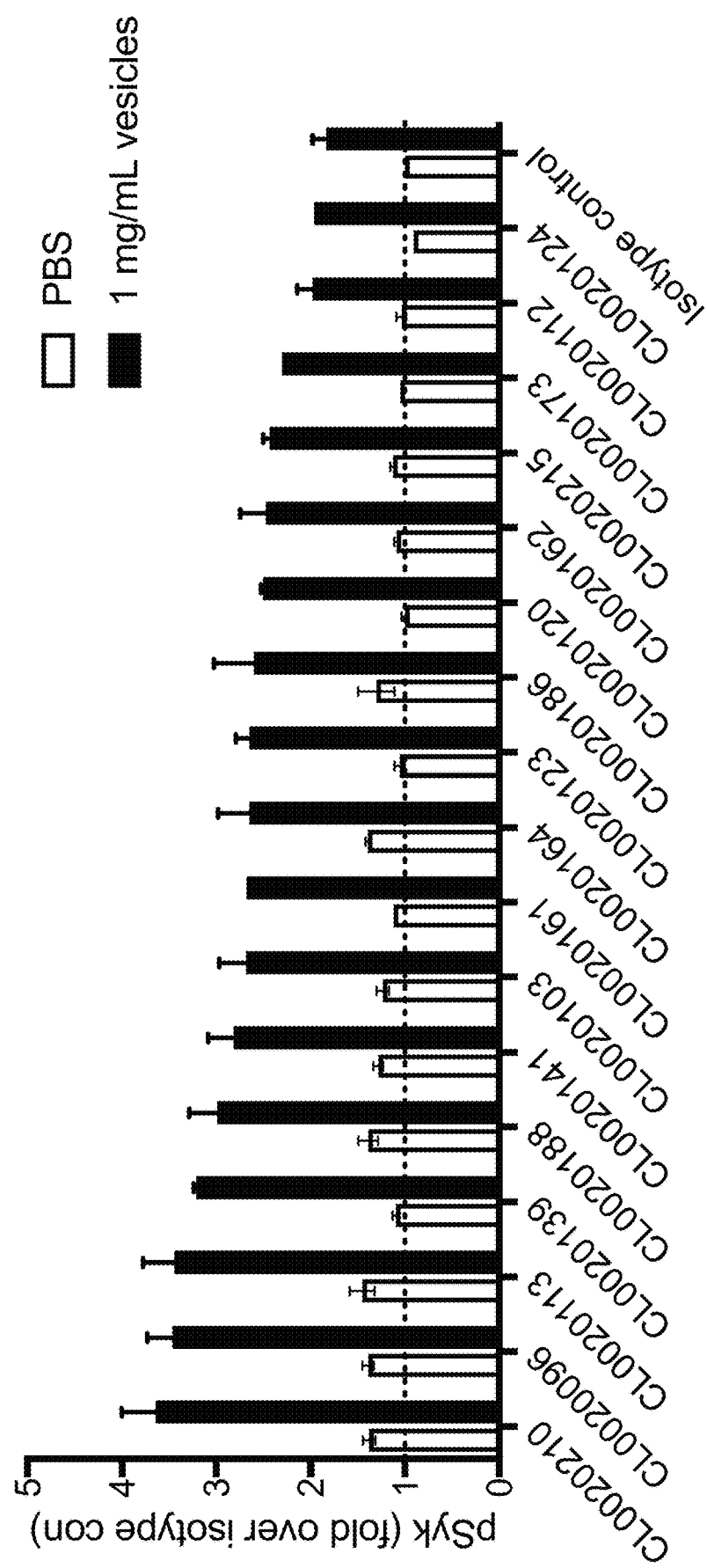

FIGS. 3A and 3B illustrate the activation of pSyk signal in human iPSC microglia incubated with anti-TREM2 antibodies, followed by dosing with lipid vesicles and assessment of the liposome response in the cells. White bars indicate incubation with PBS instead of lipid vesicles as a control. The data represent the mean and standard error of 2-7 independent experiments. FIG. 3A illustrates data for iPSC microglia pre-treated with antibody for 5 minutes, and FIG. 3B illustrates data for iPSC microglia pre-treated with antibody for 24 hours. The results show that pre-treatment of human iPSC microglia with anti-TREM2 antibodies produces an increase in the phospho-Syk signal elicited by liposomes compared to isotype control, indicating that the anti-TREM2 antibodies do not interfere with, but instead enhance, lipid activation of pSyk signaling in cells.

Human TREM2 NFAT Reporter Assay

Human TREM2/DAP12-expressing Jurkat NFAT cell lines were generated as follows. Jurkat NFAT reporter cells were infected with lentiviral vector expression of human TREM2 and DAP12 and cultured in RPMI containing 10% Hyclone FBS and 1% penicillin/streptomycin. Stable expressing clones were selected in the presence of puromycin and Zeocin. The cell surface TREM2 expression was evaluated by flow cytometer using a biotinylated anti-TREM2 antibody (SEQ ID NOS:337 and 338). The clone that illustrated the highest wild type TREM2 expression level was selected and named as hTrem2/NFAT Jurkat reporter cells for the assay described below.

The day prior to the assay, 96-well plates were pre-coated with anti-TREM2 antibody or isotype control at a 0-500 nM dose titration (45 μL/well, total 12 points) and incubated overnight at 4° C. After overnight incubation, the pre-coated plate was washed twice with PBS and then loaded with hTrem2/NFAT Jurkat reporter cells ($10^6$ cells/well) in 200 μL fresh culture media (RPMI with 10% Hyclone FBS and 1% penicillin/streptomycin). The plate was incubated at 37° C. for 24 hours, after which 50 μL/well of quantlucia solution were added to each well and mixed well. For analysis, 20 μL of solution were removed from each well and transferred to a 384-well white plate for measurement of signal by luminometer (Perkin Elmer Envision).

Figure 4:
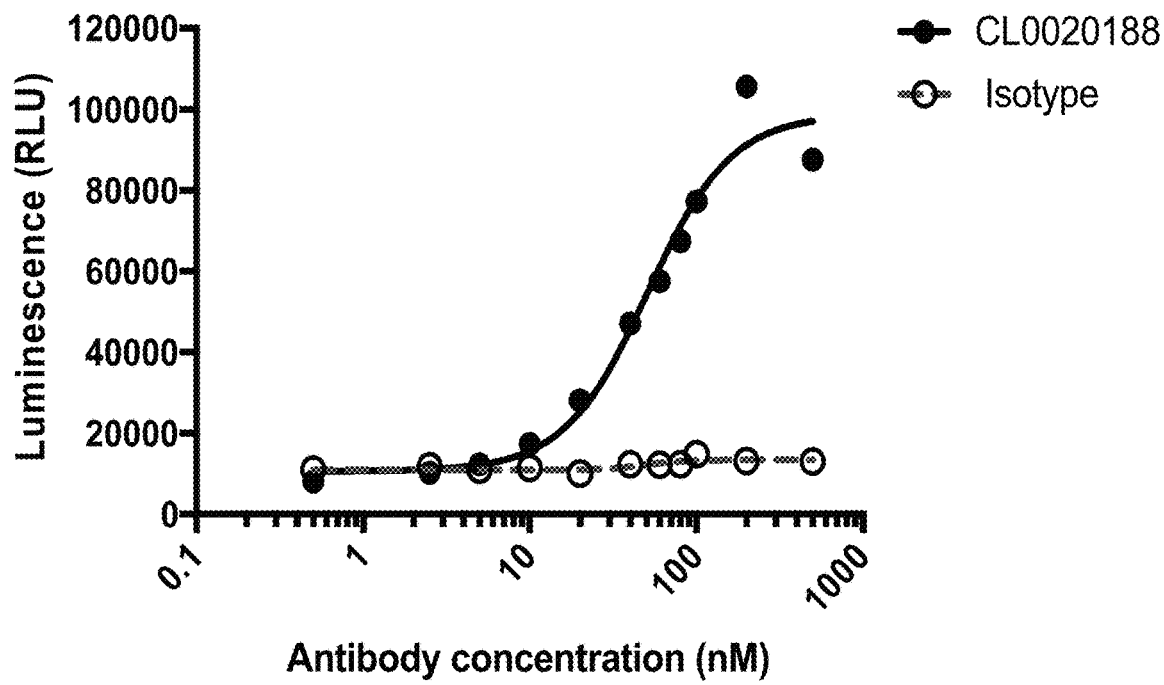
FIG. 4 includes representative dose-response curves of NFAT-luciferase reporter activity in Jurkat NFAT cells expressing human TREM2/DAP12 in response to stimulation by exemplary anti-TREM2 antibodies. Solid black circles (●) represent anti-TREM2 antibody, and open white circles (○) represent isotype control.
Figure 4:
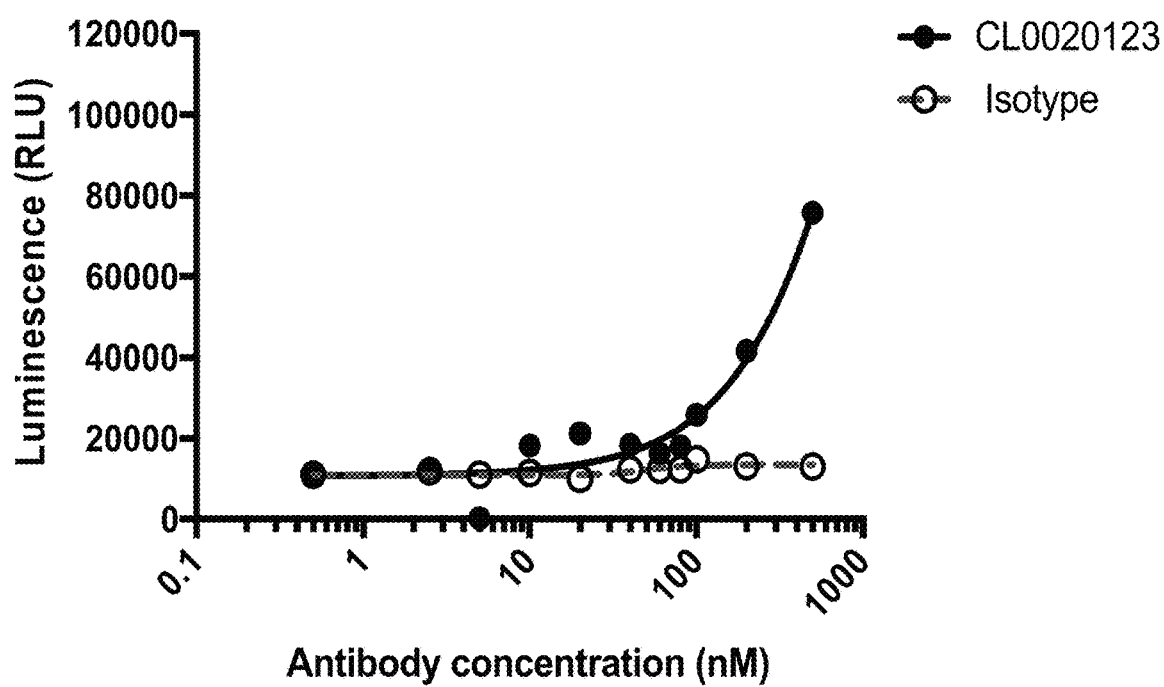

FIG. 4 includes representative anti-TREM2 antibody dose-response curves for activation of NFAT as measured by detection of the reporter gene luciferase, and $EC_{50}$ values for activation are provided in Table 1 below. The results in FIG. 4 illustrate that relative to isotype control, candidate anti-TREM2 antibodies were capable of inducing NFAT activation and sufficient downstream signaling to activate a transcriptional response.

Survival Assay in Human Macrophage Cells

Human monocytes were isolated following the RosetteSep human monocyte enrichment cocktail protocol (Stemcell Technologies, Catalog No. 15068). Isolated monocytes were washed in wash buffer (PBS+2% FBS) and resuspended in 10 mL ACK lysis solution (ThermoFisher Scientific, Catalog No. A10492) to lyse red blood cells. Twenty (20) mL wash buffer was added to stop lysis. The cell suspension was centrifuged and washed once with culture media (RPMI 1640+10% FBS+penicillin/streptomycin). Cells were resuspended in culture media at a density of $10^6$ cells μL/mL and used in the survival assay described below.

The day prior to assay, 96-well plates were pre-coated with anti-TREM2 antibody or isotype control at a 0-200 nM dose titration (45 μL/well, total 12 points) and incubated overnight at 4° C. After overnight incubation, the pre-coated plate was washed twice with PBS and then loaded with human monocyte ($10^5$ cells/well) in the presence of low concentration human M-CSF (5 ng/mL, Gibco, Catalog No. PHC9501). After 5 days at 37° C., the media was aspirated, and 100 μL PBS+100 μL Celltiter-glo media (Promega, Catalog No. G7571) was added to each well. After 10 minutes of incubation, the cell media was transferred to multiwell plates compatible for luminometer use, and luminescence for cell viability was recorded.

Figure 5:
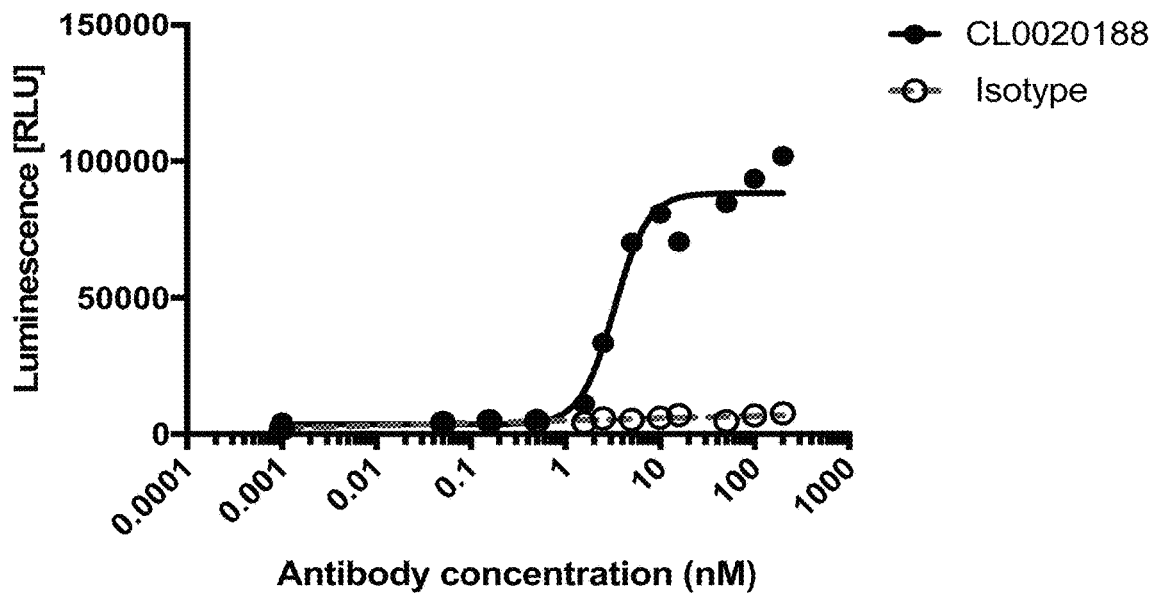
FIG. 5 illustrates representative dose-response curves of cell survival in human macrophage cells in response to treatment with exemplary anti-TREM2 antibodies.
Figure 5:
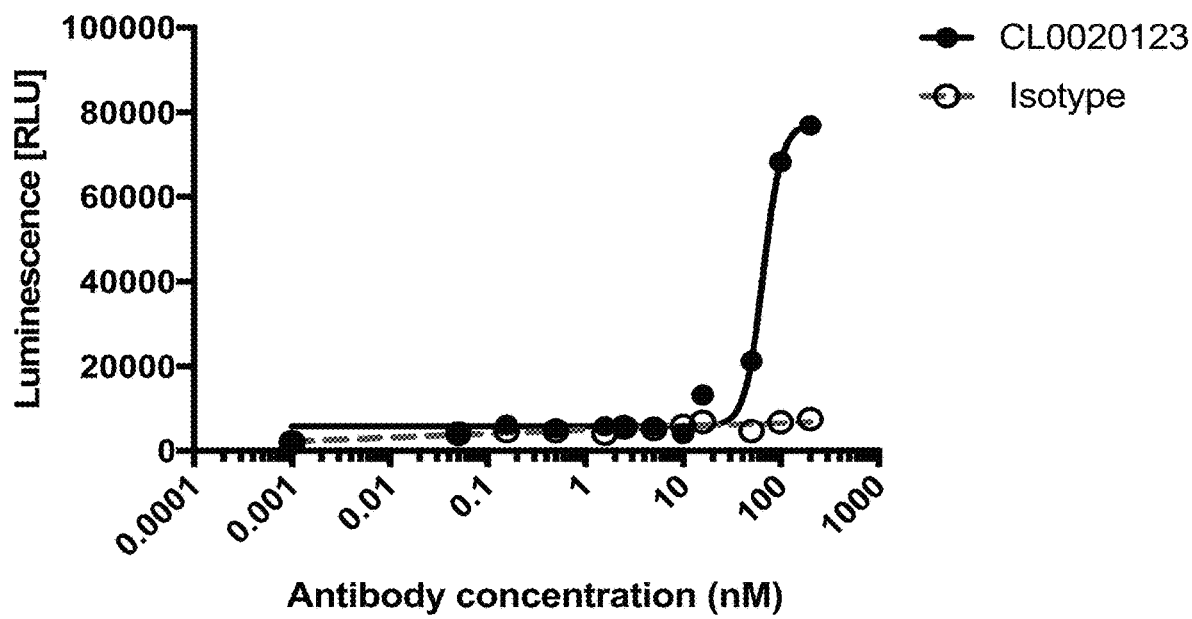

FIG. 5 illustrates representative anti-TREM2 antibody dose-response curves of cell survival in human macrophage cells under low M-CSF conditions, and $EC_{50}$ values for survival are provided in Table 1 below. The results indicate that TREM2 agonist antibodies have sufficient receptor activating capacity to induce a transcriptional response for modulating cellular function and promoting survival of human macrophage cells under low M-CSF conditions.

Biacore Kinetic Measurement of Antibodies

Surface plasmon resonance (Biacore™ 8K instrument) was used to measure anti-TREM2 antibody affinities for human and cynomolgus TREM2 ECD. Anti-TREM2 antibodies were captured using Human Fab Capture Kit (GE Healthcare Life Sciences, Catalog No. 28958325) on a Biacore Series S CM5 sensor chip (GE Healthcare Life Sciences, Catalog No. 29149604). Serial 3-fold dilutions of recombinant human or cynomolgus TREM2 were injected at a flow rate of 30 μL/min. Antibody binding was monitored for 300 seconds, followed by monitoring of antibody dissociation for 600+ seconds in HBS-EP+ running buffer (GE Healthcare Life Sciences, Catalog No. BR100669). The binding response was corrected by subtracting the RU value from a blank flow cell. A 1:1 Languir model of simultaneous fitting of $k_{on}$ and $k_{off}$ was used for kinetics analysis. $K_D$ binding values are provided in Table 1 below.

TABLE 1

In Vitro Characteristics of Antibodies

| Antibody | Biacore hTREM2 $K_D$(nM) | Biacore cyno TREM2 $K_D$(nM) | pSyk activation (human macrophages) EC50 (nM) | pSyk activation (HEK293-H6) EC50 (nM) | Cell binding (human macrophages) EC50 (nM) | NFAT EC50 (nM)* *Plate coated mAb | Survival EC50 (nM)* *Plate coated mAb |
|---|---|---|---|---|---|---|---|
| CL0020141 | 4.6 | NB | 5.9 ± 0.5 | | 0.6 | 25.5 ± 3.4 | 2.0 ± 1.2 |
| CL0020123 | 0.068 | 5.7 | 7 ± 2.7 | | 0.3 | Not Calculable | 44.7 ± 30.3 |
| CL0020188 | 5.2 | 2.0 | 7.7 ± 1.5 | | 0.5 | 91.2 ± 47.0 | 2.4 ± 1.3 |
| CL0020201 | 0.54 | 13.4 | 9.5 ± 2.5 | | ND | 81.7 ± 73.8 | 6.6 ± 1.9 |
| CL0020127 | 3.37 | | 11.9 ± 1.7 | | 11 | 20.5 ± 2.0 | ND |
| CL0020195 | 25.7 | | 12 ± 1.8 | | 1.3 | 98.3 ± 4.3 | ND |
| CL0020205 | 1.52 | | 14.3 ± 1.9 | | 2.1 | 67.7 ± 2.0 | 5.70 ± 3.4 |
| CL0020206 | 1.82 | | 20.7 ± 6.9 | | 4.8 | 69.9 ± 5.3 | ND |
| CL0020139 | 1.60 | 0.3 | 23.8 ± 2.8 | | 1.6 | 30.8 ± 4.3 | 1.8 ± 0.8 |
| CL0020120 | 4.04 | | 24.2 ± 5.6 | | 1.6 | 195.1 ± 21.4 | 17.8 ± 5.5 |
| CL0020113 | 7.81 | | 24.8 ± 2.3 | | 2.1 | 185 ± 101 | 24.8 ± 2.3 |
| CL0020107 | 1.47 | 104 | 28.5 ± 2.2 | | 4.4 | 10.9 ± 2.3 | 0.53 ± 0.2 |
| CL0020096 | 5.54 | | 30.9 ± 1.8 | | 14 | 16.2 ± 4.7 | 1.8 ± 0.2 |
| CL0020210 | 6.27 | | 37.4 ± 20.1 | | 0.9 | 11.7 ± 0.3 | ND |
| CL0020313 | 14.00 | 13.8 | | 46.61 | 1.2 | No Activity | 30.7 ± 3.6 |
| CL0020308 | 2.31 | 2.28 | | 33.36 | 0.6 | 51.9 | 8.9 ± 0.8 |
| CL0020309 | 5.31 | 5.33 | | 40.58 | 0.7 | Not Calculable | 2.69 ± 0.68 |
| CL0020314 | 0.33 | 56.9 | | 18.83 | 0.05 | Not Calculable | 1.6 ± 0.1 |
| CL0020315 | 0.0259 | 2.52 | | ND | 5.6 | 72.7 | 10.1 ± 2.1 |

NB: no binding detected
ND: not determined

Example 2. Modulation of Soluble TREM2 Levels and Phagocytosis Behavior in Human Macrophage Cells Soluble TREM2 Dose Response Assay in Human Macrophages Human macrophage cells were generated as described above. One day prior to assay, human macrophage cells were plated at 100,000 cells/well on a 96 well plate coated with poly-D-lysine. Antibodies were diluted in human macrophage media (RPMI, 10% Hyclone FBS, 1% Sodium Pyruvate, 1% Glutamax, 1% non-essential amino acids, and 1% Penicillin-streptomycin) starting from 300 nM and proceeding in a 10-point serial dilution titration with 3-fold dilutions between points. The cells were dosed with the antibodies and incubated for 24 hours. After incubation with the antibodies, the plate was spun down to remove debris, and the supernatants collected for soluble TREM2 measurement.

Soluble TREM2 was measured as follows. Briefly, MSD small spot streptavidin plates (Meso Scale Discovery) were coated with biotinylated anti-hTREM2 polyclonal antibody (R&D Systems) overnight at 4° C. The plates were then blocked with 3% BSA/TBST for 1 hour at room temperature. Samples and standards were prepared by heating to 95° C. for 5 minutes in SDS-containing buffer. The prepared samples and standards were diluted 1:10 in 3% BSA/TBST in the assay plate after blocking. A TREM2-His protein diluted in 3% BSA/TBST was used as a standard for absolute quantification. Following a two-hour incubation at room temperature, the plates were washed with TBST. The primary detection antibody, sulfo-tagged goat anti-human TREM2 (R&D Systems), was diluted in 3% BSA/TBST, added to the plates, and incubated for one hour at room temperature. After washing with TBST, the MSD plates were developed using 2×MSD read buffer T, followed by detection using an MSD Sector plate reader. MSD values were converted to absolute quantities of sTREM2 by fitting a standard curve using Prism 7.0 software (Graphpad). Modulation of TREM2 shedding was represented as a ratio of soluble TREM2 from cells incubated with test anti-TREM2 antibodies normalized to soluble TREM2 from cells cultured with no specific anti-TREM2 antibody in the media.

Figure 6:
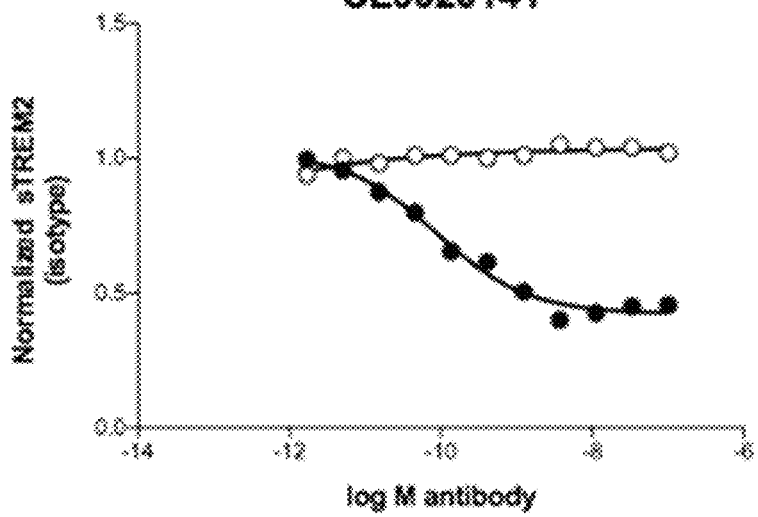
FIG. 6 illustrates representative soluble TREM2 levels (sTREM2) as a function of the anti-TREM2 antibody concentration for exemplary anti-TREM2 antibodies.
Figure 6:
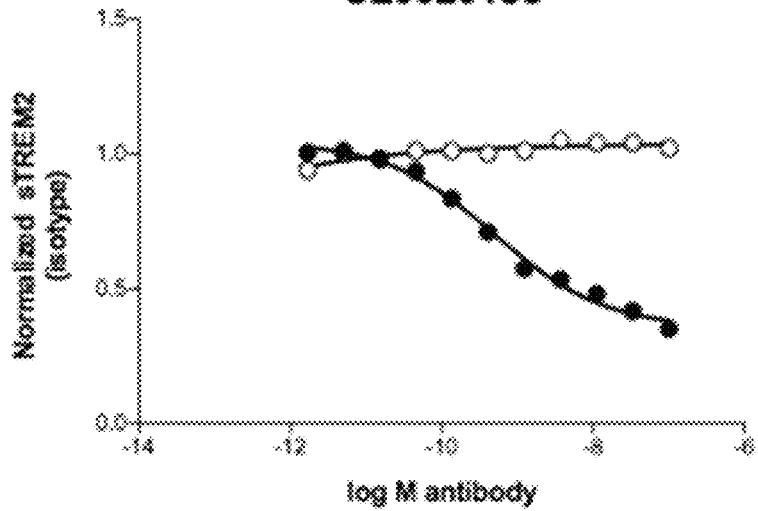
Figure 6:
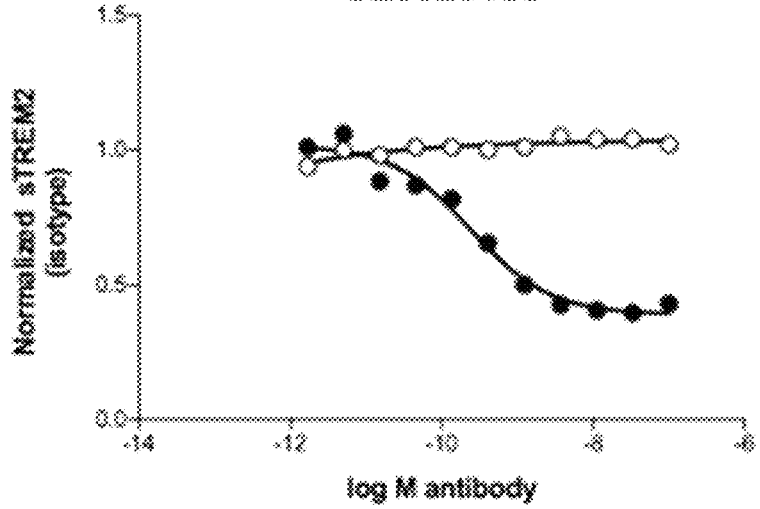
Figure 6:
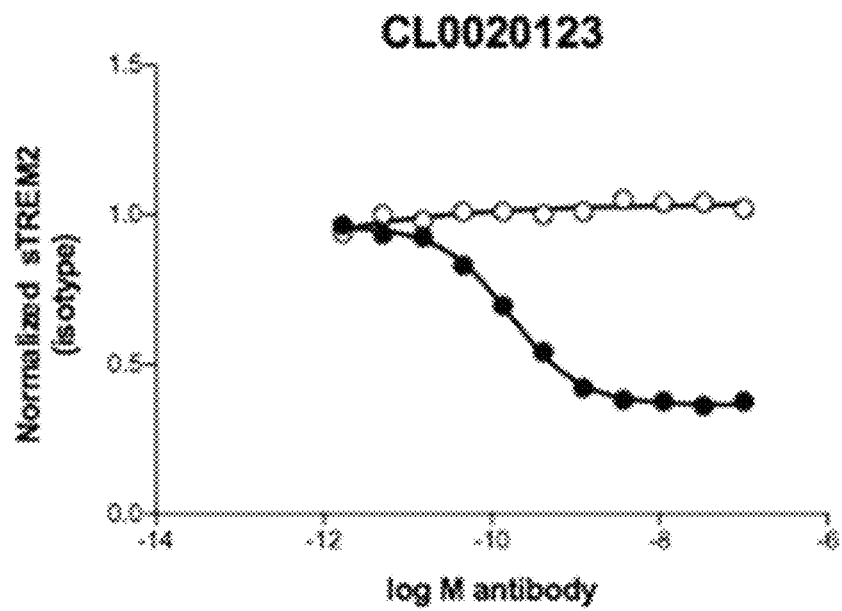
Figure 6:
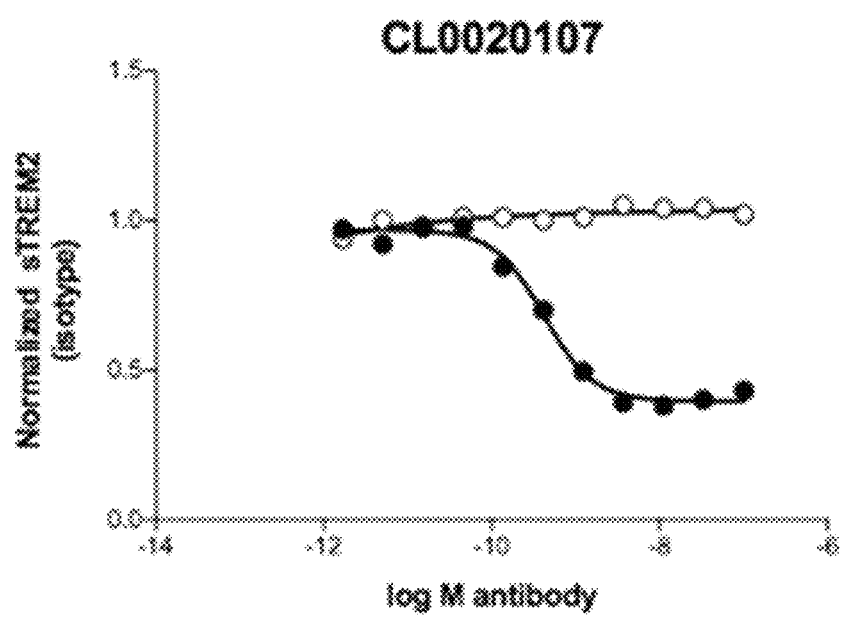

FIG. 6 illustrates representative soluble TREM2 levels (sTREM2) as a function of the anti-TREM2 antibody concentration. The results indicate the anti-TREM2 antibodies are capable of decreasing sTREM2 levels in human macrophage cells in a dose-dependent manner after overnight treatment.

Phagocytosis Assay in Human Macrophages

Human macrophage cells were generated as described above. Two days prior to assay, human macrophage cells were plated at 80,000 cells/well on a 96 well plate coated with poly-D-lysine. Antibodies were diluted at 100 nM into media containing RPMI, 10% Hyclone FBS, 1% Sodium Pyruvate, 1% Glutamax, 1% non-essential amino acids, and 1% Penicillin-streptomycin. The cells were then dosed with antibody solution for 24 hours at 37° C. The cell nuclei and cell membrane were then stained for 10 minutes, after which pHrodo-myelin was added at 5 µg/mL. The cells were then incubated for 4 hours at 37° C. The pHrodo fluorescence was measured per cell on a high content confocal microscope (Opera Phoenix), and the fluorescence intensity quantified on the instrument software.

pHrodo-myelin was prepared by purifying myelin from wildtype C57Bl/6 mouse brain (Jackson Laboratories) using methods described in Safaiyan et al. (2016, Nature Neuroscience 19(8):995-998). Following purification, myelin was resuspended in PBS and adjusted to 1 mg/mL protein concentration using the DC Protein Assay Kit 2 (BioRad, Catalog No. 5000112). Myelin was tagged with pHrodo-red using a microscale labeling kit (ThermoFisher, Catalog No. P35363) according to manufacturer instructions. Excess label was removed by pelleting the myelin at 10,000 g for 5 min, removing the supernatant, and repeating these steps 3-5 times.

Figure 7:
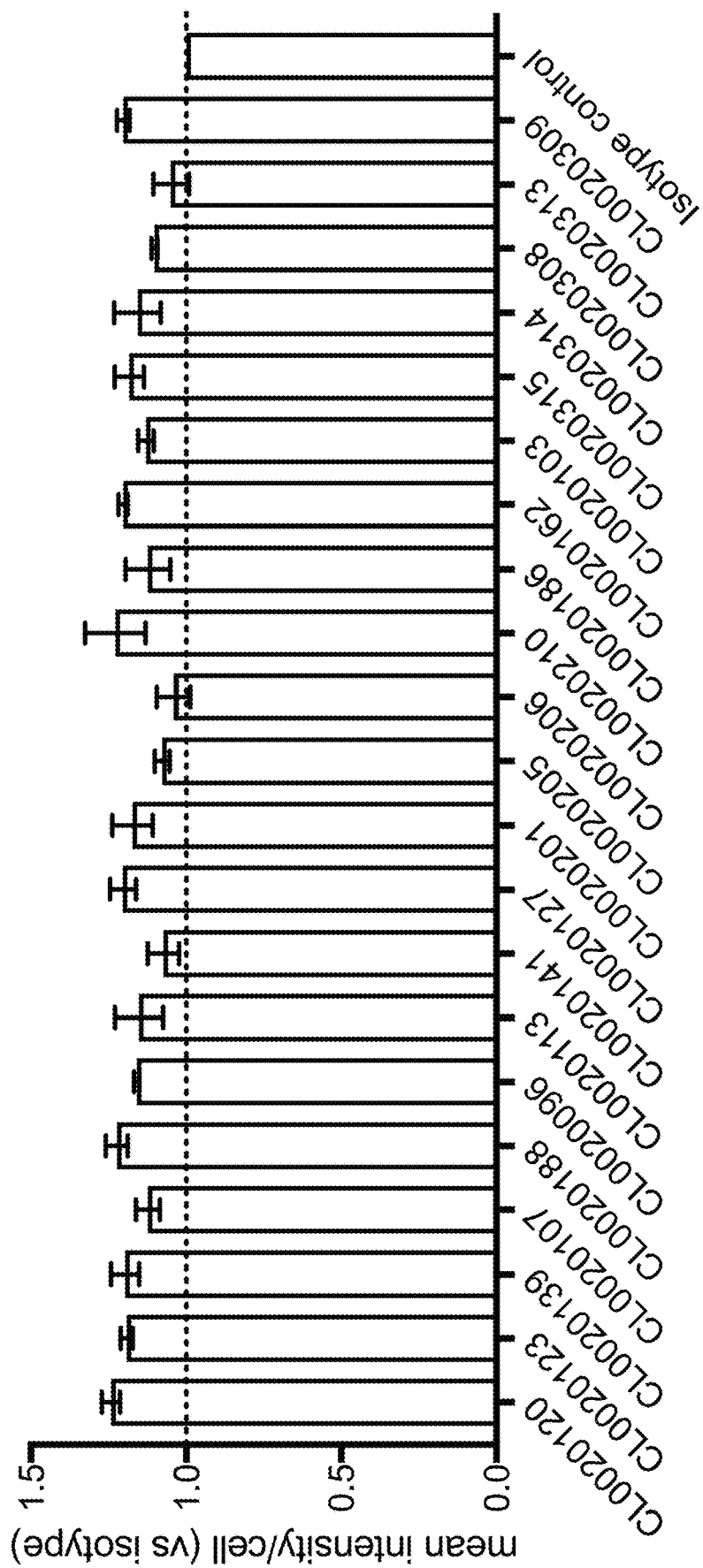
FIG. 7 is a bar chart indicating mean pHrodo fluorescence intensity per cell in human macrophages treated with exemplary anti-TREM2 antibodies.

FIG. 7 illustrates the results of the phagocytosis assay in human macrophage cells. Myelin phagocytosis was measured by detecting and quantifying pHrodo fluorescence in microscopic images of TREM2-treated macrophage cells and comparing the measured values to those of an isotype control. The results show that human macrophages treated with TREM2 agonist antibodies increase pHrodo-myelin phagocytosis relative to isotype control, indicating that the anti-TREM2 antibodies can enable beneficial clearance of myelin debris in cells.

Example 3. Modulation of Lipid Accumulation in iPSC Microglia

Lipid Storage Assay

Prior to assay, iPSCs were first differentiated into hematopoietic progenitor cells (HPCs) using a commercially available kit (STEMdiff Hematopoietic Kit from StemCell Technologies). HPCs were transferred to a plate containing primary human astrocytes and co-cultured for 14-21 days. Once floating cells in co-culture were predominantly identified as mature microglia (>80%), the microglia were used for assay.

Cells (iPSC microglia, 30,000 cells/well) were plated on PDL-coated 96-well plates in full serum media. After 24 hours at 37° C., purified unlabeled myelin (50 µg/mL final concentration, purified from wildtype C57Bl/6 mouse brain (Jackson Laboratories) using methods described in Safaiyan et al. (2016, Nature Neuroscience 19(8):995-998)) was spiked into the wells. After 24 hours at 37° C. of lipid treatment, anti-TREM2 antibody or RSV control was spiked into the wells to a final concentration of 100 nM. The cells were incubated for another 48-72 hours at 37° C. before collecting or imaging cells. For myelin washout experiments, myelin was removed after the 24-hour incubation period and replaced with antibody-containing media for a subsequent 24-48 hours of incubation.

Figure 8A:
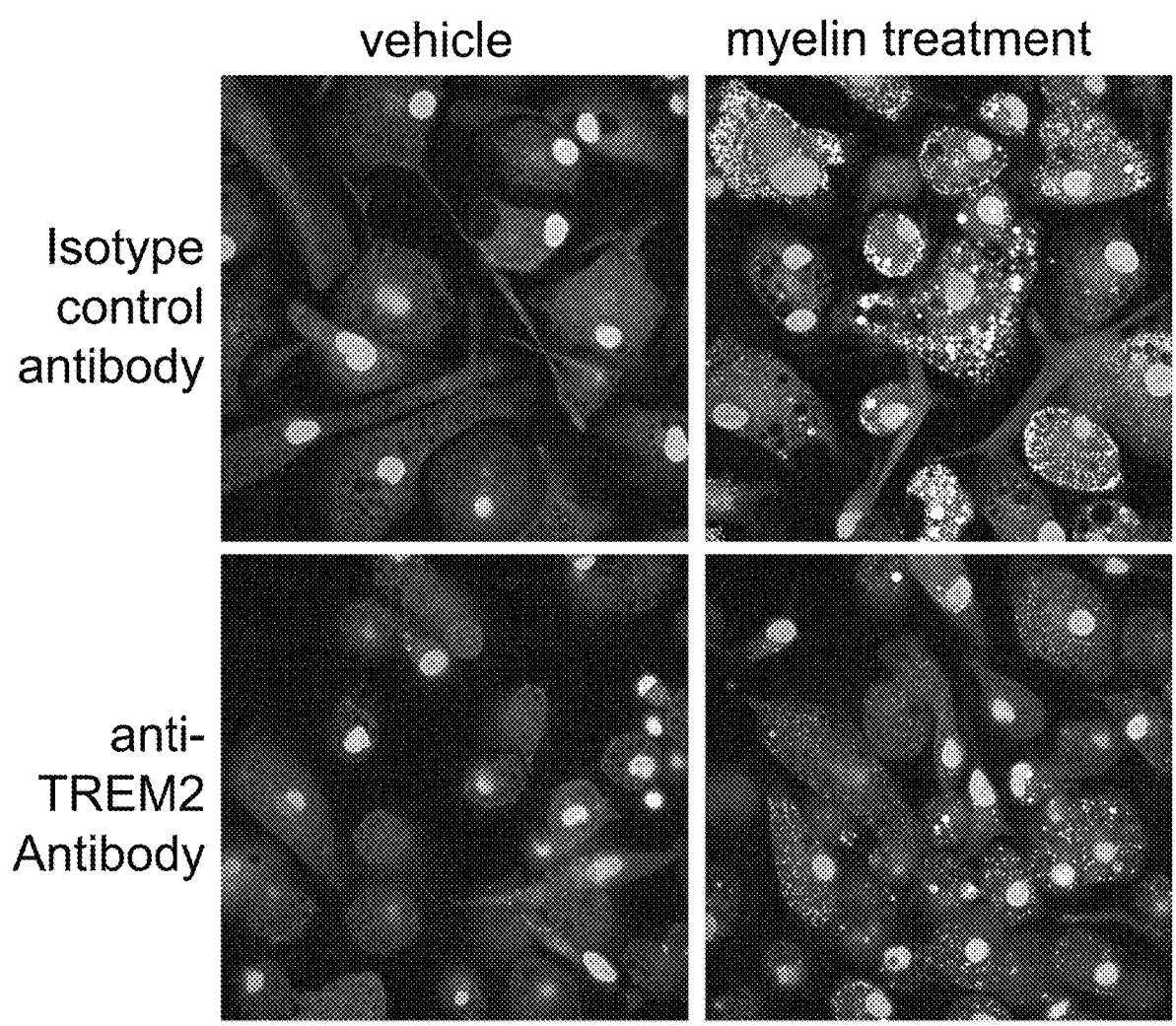
FIG. 8A is a representative microscopy image of lipid accumulation in iPSC microglia treated with myelin, followed by incubation with exemplary anti-TREM2 antibody or isotype control.
Figure 8B:
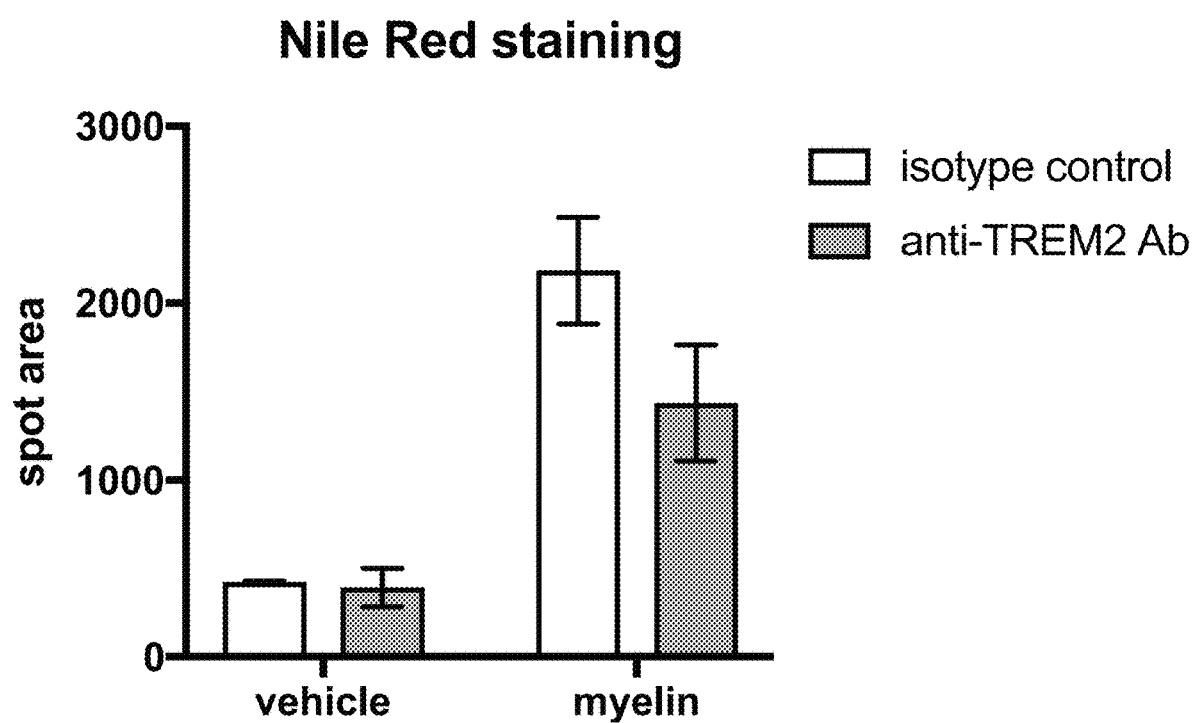
FIG. 8B is a representative bar chart of Nile Red staining (indicating lipid accumulation) of iPSC microglia that were imaged in FIG. 8A.

For Nile Red imaging, the supernatant was removed, and cells were incubated at 37° C. for 30 minutes in live cell imaging buffer (Life Technologies, Catalog No. A14291DJ) containing 1 µM Nile Red (ThermoFisher, Catalog No. N1142) and 1 drop/mL of Nucblue (ThermoFisher, Catalog No. R37605). After the incubation period, the staining solution was removed, and the cells were fixed in 4% paraformaldehyde. The cells were then imaged using Alexa 568 and DAPI illumination settings on an Opera Phoenix high content confocal imager. Lipid spots were analyzed using a spot-finding algorithm on the Harmony software supplied with the instrument. FIG. 8A includes a representative microscopy image of iPSC microglia treated with either vehicle or myelin (50 µg/mL final concentration) for 24 hours, followed by incubation with an isotype control or an exemplary anti-TREM2 antibody (CL0020123) for 72 hours. FIG. 8B is a representative bar chart for the same anti-TREM2 antibody used in the microscopy image of FIG. 8A. Quantification of Nile Red staining was performed by total spot intensity per cell, and data is shown as the mean and standard deviation of three technical replicates in different fields of the same microscopy sample.

For lipidomic analysis, cells were washed once with PBS while kept on ice. A volume of 70 µL of a 9:1 methanol:water solution containing 1:100 internal standards was added to the cells in the 96-well plate. The plate was agitated on a shaker at 4° C. and 1200 rpm for 20 minutes and then centrifuged for 5 minutes at 300×g. A 50 µL sample of supernatant was transferred to LCMS vials and kept at −80° C. until analyzed on the instrument.

Lipid levels were analyzed by liquid chromatography (Shimadzu Nexera X2 system, Shimadzu Scientific Instrument, Columbia, MD, USA) coupled to electrospray mass spectrometry (QTRAP 6500+, Sciex, Framingham, MA, USA). For each analysis, 5 µL of sample was injected on a BEH C18 1.7 µm, 2.1×100 mm column (Waters Corporation, Milford, Massachusetts, USA) using a flow rate of 0.25 mL/min at 55° C. For positive ionization mode, mobile phase A consisted of 60:40 acetonitrile/water (v/v) with 10 mM ammonium formate+0.1% formic acid; mobile phase B consisted of 90:10 isopropyl alcohol/acetonitrile (v/v) with 10 mM ammonium formate+0.1% formic acid. For negative ionization mode, mobile phase A consisted of 60:40 acetonitrile/water (v/v) with 10 mM ammonium acetate; mobile phase B consisted of 90:10 isopropyl alcohol/acetonitrile (v/v) with 10 mM ammonium acetate. The gradient was programmed as follows: 0.0-8.0 min from 45% B to 99% B, 8.0-9.0 min at 99% B, 9.0-9.1 min to 45% B, and 9.1-10.0 min at 45% B. Electrospray ionization was performed in either positive or negative ion mode applying the following settings: curtain gas at 30; collision gas set at medium; ion spray voltage at 5500 (positive mode) or 4500 (negative mode); temperature at 250° C. (positive mode) or 600° C. (negative mode); ion source Gas 1 at 50; ion source Gas 2 at 60. Data acquisition was performed using Analyst 1.6.3 (Sciex) in multiple reaction monitoring mode (MRM), with the following parameters: dwell time (msec) and collision energy (CE); declustering potential (DP) at 80; entrance potential (EP) at 10 (positive mode) or −10 (negative mode), and collision cell exit potential (CXP) at 12.5 (positive mode) or −12.5 (negative mode). Lipids were quantified using a mixture of non-endogenous internal standards. Lipids were identified based on their retention times and MRM properties of commercially available reference standards (Avanti Polar Lipids, Birmingham, AL, USA).

Figure 8D:
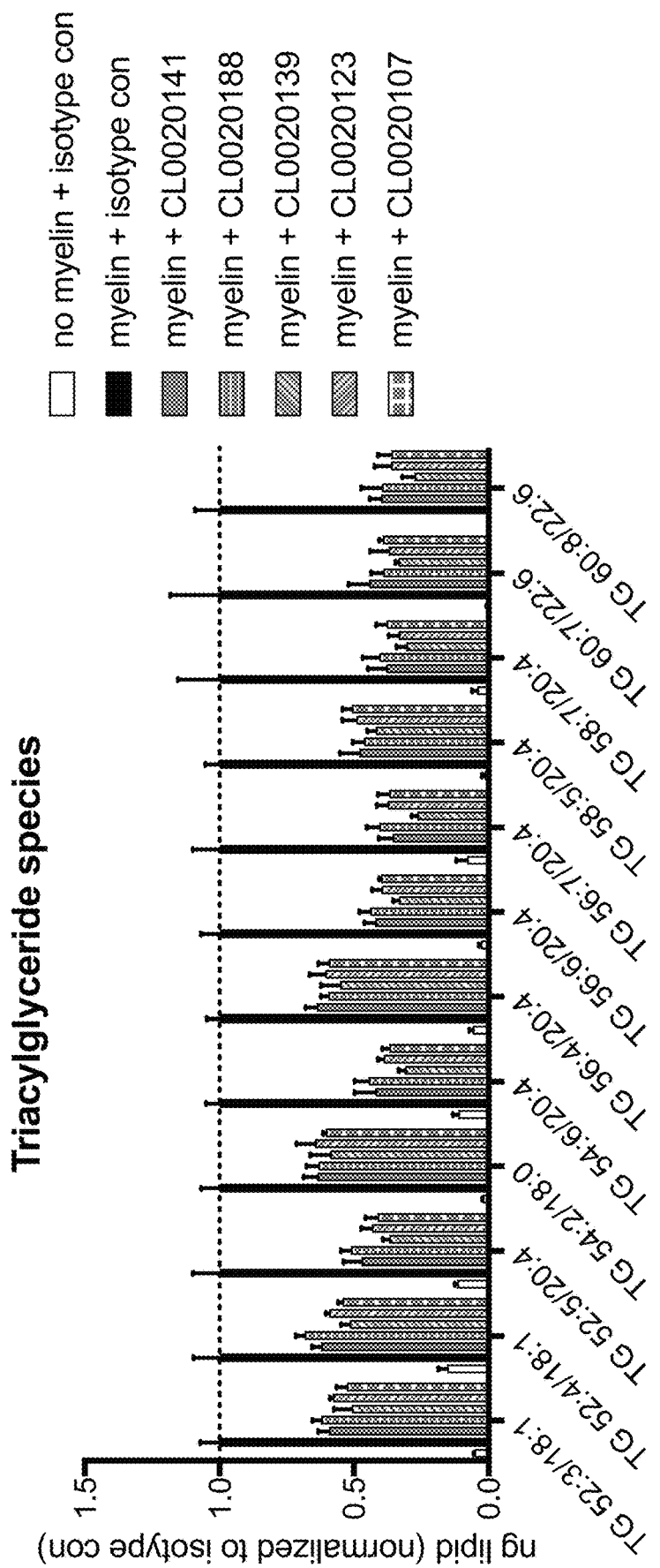
Figure 8E:
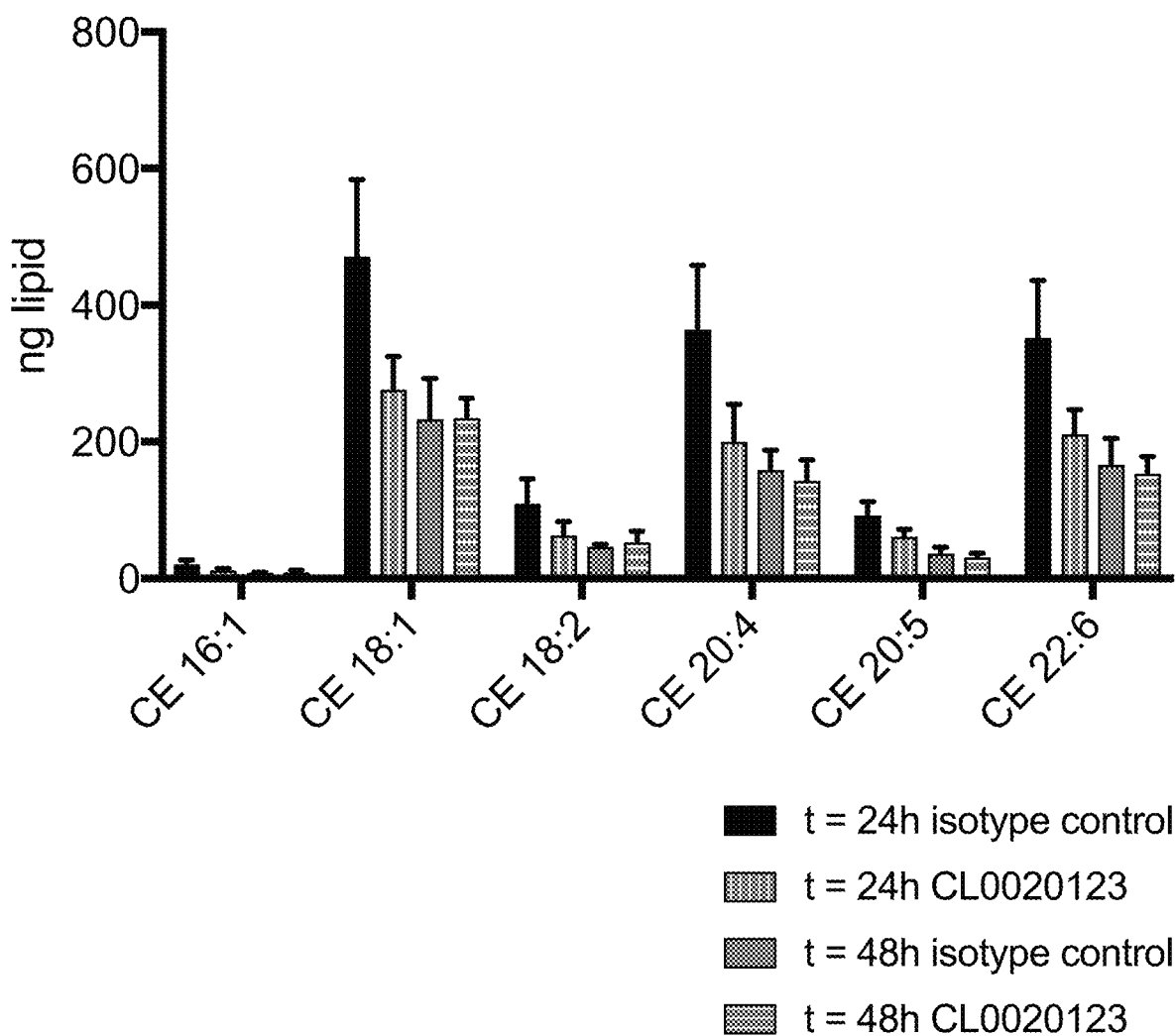

FIGS. 8C and 8D illustrate levels of cholesterol ester (CE) (FIG. 8C) and triacylglyceride (TAG) lipid species (FIG. 8D) as detected by mass spectrometry in cell lysates of iPSC microglia cells treated with anti-TREM2 antibodies for 72 hours after a 24-hour myelin treatment. FIGS. 8E and 8F illustrates levels of cholesterol ester (CE) (FIG. 8E) and triacylglyceride (TAG) lipid species (FIG. 8F) as detected by mass spectrometry in cell lysates of iPSC microglia cells which underwent myelin washout experiments with anti-TREM2 antibodies. LC/MS data generated in FIGS. 8C-8F were normalized to the internal standards for CE data and normalized to myelin+isotype control for each individual lipid species for TAG data.

Lipid accumulation in iPSC microglia is induced by myelin treatment, which is reflected by an increase in neutral lipid staining (Nile Red) and by LC/MS for detection of specific lipid species in cellular lysates. The data illustrated in FIGS. 8A-8F collectively indicate that treatment of iPSC microglia cells post-myelin challenge with anti-TREM2 antibodies reduced accumulation of lipid species, as indicated by the decrease in neutral lipid staining in cells and by the decrease of CE and TAG lipid species levels measured by LC/MS. The reduction of lipid levels as a result of antibody treatment was observed at different timepoints ranging from 24 hours to 72 hours. To eliminate the possibility that the reduction in lipid levels is caused by blocking of lipid uptake, myelin washout experiments in which myelin was removed prior to anti-TREM2 antibody addition were carried out. FIG. 8F illustrates that anti-TREM2 antibodies also reduced lipid levels in iPSC microglia with myelin washout prior to antibody treatment relative to isotype control.

Example 4. Functional Epitope Binning of Antibodies

TREM2 antibody epitope bins were determined by competition binding on TREM2 protein. Epitope binning experiment was performed on a Carterra LSA instrument using a classical sandwich epitope binning configuration method at 25° C. All test antibodies were immobilized onto a HC30M chip by amine coupling. Multiple cycles of sandwich competition binding were then carried out for the test antibodies. Each cycle consisted of antigen (His-tagged TREM2 ECD) injection followed by analyte antibody injection to the immobilized antibodies. At the end of each cycle, the surface of immobilized antibodies were regenerated by injecting a low pH buffer (pH=3) containing 1.25 M NaCl. Epitope binding data was evaluated by Carterra software to create competition matrix and epitope bins. Results are provided in Table 2.

Two agonist bins were identified by epitope binning of the anti-TREM2 antibodies: (1) stalk binding agonists, and (2) IgV domain binding agonists. Antibodies within the same bins demonstrated the same function, e.g., inhibition of TREM2-DAP12 pSyk activation by lipid ligand (antagonist antibodies), activation of pSyk with antibody alone (stalk binding agonists, IgV domain binding agonists).

TABLE 2

Anti-TREM2 Antibody Bins, Annotated by Functional Class

| Bin 1<br>Stalk Agonist | Bin 2<br>IgV Agonist |
|---|---|
| CL0020164 | CL0020123 |
| CL0020141 | CL0020107 |
| CL0020210 | CL0020120 |
| CL0020096 | CL0020139 |
| CL0020103 | CL0020161 |
| CL0020162 | CL0020186 |
| CL0020113 | CL0020206 |
| CL0020188 | CL0020112 |
|  | CL0020215 |
|  | CL0020127 |
|  | CL0020214 |
|  | CL0020205 |
|  | CL0020109 |
|  | CL0020111 |
|  | CL0020124 |
|  | CL0020201 |
|  | CL0020173 |

Example 5. Antibody Binding to TREM2 Stalk Peptide

TREM2 antibodies were evaluated for binding to human and mouse TREM2 stalk region peptides. The tested peptides included: (1) full length stalk region (amino acids 129-172 of human TREM2, UniProtKB Q9NZC2; amino acids 131-169 of mouse TREM2, UniProtKB Q99NH8) and (2) a truncated stalk peptide containing the ADAM10/17 cleavage site (amino acids 149-163 of human/mouse TREM2). Antibody binding to TREM2 stalk peptides was detected using standard sandwich ELISA. Briefly, a 96-well half-area ELISA plate was coated with streptavidin overnight at 4° C. The following day, biotinylated TREM2 stalk peptides diluted in 1% BSA/PBS were added to the plate and incubated for 1 hour. Antibodies diluted in 1% BSA/PBS were then added and incubated for 1 hour. Antibodies bound to peptide were detected with anti-human kappa-HRP secondary antibody (Bethyl Laboratories, Inc.) diluted in 1% BSA/PBS. Plates were assayed by reaction with a detection reagent (One-step TMB Ultra, Thermo) and measurement of absorbance at 450 nm (A450) by standard spectrophotometry instrumentation (BioTek®). The results are provided in Tables 3A, 3B, and 3C, below. Data are shown as normalized values (fold over background where background=isotype control).

TABLE 3A

Anti-TREM2 Antibody Binding to TREM2 Stalk Peptides

|  | Isotype | CL0020188 | CL0020096 | CL0020141 | CL0020113 | CL0020162 |
|---|---|---|---|---|---|---|
| Human TREM2 peptide binding (aa 149-163) | 1.0 | 3.0 | 2.2 | 2.1 | 1.4 | 1.3 |
| Human TREM2 peptide binding (aa 129-172) | 1.0 | 51 | 45 | 45 | 47 | 49 |
| Mouse TREM2 peptide binding (aa 149-163) | 1.0 | 0.9 | 1.3 | 1.4 | 1.3 | 1.4 |
| Mouse TREM2 peptide binding (aa 131-169) | 1.0 | 33 | 45 | 4.5 | 2.9 | 10 |

|  | CL0020210 | CL0020103 | CL0020164 | CL0020139 | CL0020107 |
|---|---|---|---|---|---|
| Human TREM2 peptide binding (aa 149-163) | 1.5 | 1.8 | 1.4 | 1.3 | 1.4 |
| Human TREM2 peptide binding (aa 129-172) | 50 | 56 | 50 | 1.6 | 1.7 |
| Mouse TREM2 peptide binding (aa 149-163) | 1.6 | 1.8 | 1.5 | 1.6 | 1.6 |
| Mouse TREM2 peptide binding (aa 131-169) | 25 | 4.1 | 51 | 1.4 | 1.3 |

TABLE 3B

Anti-TREM2 Antibody Binding to TREM2 Stalk Peptides

|  | CL0020123 | CL0020120 | CL0020201 | CL0020127 | CL0020109 |
|---|---|---|---|---|---|
| Human TREM2 peptide binding (aa 149-163) | 1.2 | 1.2 | 1.7 | 1.2 | 1.5 |
| Human TREM2 peptide binding (aa 129-172) | 1.2 | 1.2 | 14 | 1.4 | 1.7 |
| Mouse TREM2 peptide binding (aa 149-163) | 0.9 | 1.2 | 1.8 | 1.2 | 1.7 |
| Mouse TREM2 peptide binding (aa 131-169) | 1.0 | 1.2 | 5.4 | 1.3 | 1.7 |

|  | CL0020215 | CL0020173 | CL0020195 | CL0020186 | CL0020205 |
|---|---|---|---|---|---|
| Human TREM2 peptide binding (aa 149-163) | 1.1 | 1.2 | 1.1 | 1.3 | 1.2 |
| Human TREM2 peptide binding (aa 129-172) | 1.2 | 1.6 | 1.3 | 4.9 | 1.3 |
| Mouse TREM2 peptide binding (aa 149-163) | 1.2 | 1.2 | 1.2 | 1.3 | 1.1 |
| Mouse TREM2 peptide binding (aa 131-169) | 1.1 | 1.2 | 1.1 | 7.0 | 1.1 |

TABLE 3C

Anti-TREM2 Antibody Binding to TREM2 Stalk Peptides

| | CL0020206 | CL0020111 | CL0020214 | CL0020161 | CL0020124 |
|---|---|---|---|---|---|
| Human TREM2 peptide binding (aa 149-163) | 1.6 | 1.6 | 1.3 | 1.0 | 1.5 |
| Human TREM2 peptide binding (aa 129-172) | 1.8 | 1.3 | 1.5 | 1.4 | 2.1 |
| Mouse TREM2 peptide binding (aa 149-163) | 1.6 | 1.5 | 1.3 | 1.1 | 1.7 |
| Mouse TREM2 peptide binding (aa 131-169) | 1.6 | 1.1 | 1.3 | 1.2 | 1.6 |

| | CL0020313 | CL0020308 | CL0020309 | CL0020314 | CL0020315 |
|---|---|---|---|---|---|
| Human TREM2 peptide binding (aa 149-163) | 1.2 | 2.5 | 2.2 | 1.2 | 1.3 |
| Human TREM2 peptide binding (aa 129-172) | 12 | 11 | 11 | 11 | 8.7 |
| Mouse TREM2 peptide binding (aa 149-163) | 1.1 | 1.1 | 1.3 | 1.4 | 1.5 |
| Mouse TREM2 peptide binding (aa 131-169) | 2.3 | 7.9 | 6.6 | 1.0 | 6.8 |

Tables 3A, 3B and 3C depict human and mouse stalk region peptide-antibody binding interactions which support the epitope binning data in Table 2. Based on the data in Tables 3A, 3B, and 3C, the site at which certain anti-TREM2 antibodies appear to bind corresponds to amino acids 129-148 in the TREM2 extracellular stalk region.

The ability of anti-TREM2 antibodies to inhibit TREM2 stalk peptide cleavage by ADAM17 was also analyzed using a fluorescence polarization assay. TREM2 stalk peptides were first prepared in assay buffer (25 mM Tris pH 7.5, 2.5 µM $ZnCl_2$, 0.005% Brij-35) with streptavidin. Anti-TREM2 antibodies were then pre-incubated with TREM2 stalk peptides for 30 minutes at room temperature. After the pre-incubation period, ADAM17 (R&D systems, Catalog No. 930-ADB) was added and incubated with the peptides for 20 hours at 37° C. The following day, samples were further diluted in assay buffer and transferred to a black opaque 384-well plate. Fluorescence polarization was subsequently measured on Perkin Elmer EnVision plate reader. The fluorescence polarization of TREM2 stalk peptides pre-incubated with anti-TREM2 antibody was compared to fluorescence polarization of full-length TREM2 stalk peptide and enzyme control (full-length TREM2 stalk peptide with ADAM17).

TREM2 stalk-binding antibodies significantly increased fluorescence polarization, demonstrating partial inhibition of stalk peptide cleavage by ADAM17 (clones CL0020141, CL0020188, CL0020313, CL0020308). IgV binding antibody CL0020107 did not bind TREM2 stalk region peptide and thus did not show an effect on peptide cleavage in the fluorescence polarization assay.

Example 6. Pharmacokinetic Analysis of Anti-TREM2 Antibodies

The pharmacokinetic profiles of the anti-TREM2 antibodies were evaluated in mice. C57BL/6J mice were purchased from Jackson Laboratory (Stock No. 000664) at 2 months of age used for a 7-day pharmacokinetic (PK) study and target engagement study. Human Trem2 cDNA KI homozygous mice (huTrem2$^{KI/KI}$) were used for 24-hour target engagement study at 3 months of age. Generation and breeding of the human Trem2 cDNA KI mice are described below.

Generation of Human Trem2 cDNA KI Mouse Model

A human TREM2 cDNA KI mouse (huTrem2$^{KI/KI}$) was generated as follows. Human Trem2 cDNA-pA sequence was inserted at the mouse Trem2 endogenous ATG start site. The insertion of human Trem2 cDNA-pA resulted in replacement of the exon1 sequence of mouse Trem2, which allows expression of human Trem2 cDNA driven by the endogenous mouse promoter and disruption of the expression of endogenous mouse Trem2. The huTrem2$^{KI/KI}$ mouse was generated in C57BL/6 genetic background using homologous recombination.

For the huTrem2$^{KI/KI}$ targeting vector, the long homology arm (LA) extends about 3.6 kb upstream of the 5' end of the human Trem2 cDNA-pA sequence, and the short homology arm (SA) extends about 2.3 kb downstream of the 3' to the FRT-flanked Neo cassette. Both the long and short homology arms were amplified from a C57BL/6 BAC clone (RP23: 358G22) and then sub-cloned into a ~2.4 kb pSP72 (Promega) backbone vector containing an ampicillin selection cassette. A hUBS-gb2 FRT-flanked Neomycin cassette was inserted immediately downstream of the hTrem2-pA cassette, resulting in a targeting vector of about 13.6 kb in size. Ten (10)µg of the targeting vector was linearized with restriction enzyme Not I (New England Biolabs) and then transfected into FLP C57Bl/6 (B6) embryonic stem (ES) cells by electroporation. After selection with G418 antibiotic, surviving clones were expanded for PCR analysis to identify positive recombinant ES clones. The primer sequences for PCR screening (SEQ ID NO:324=5'-AGG AAT GTG GGG AGC ACG GAG-3' and SEQ ID NO:325=5'-TGC ATC GCA TTG TCT GAG TAG GTG-3') amplified a 2.81-kb fragment containing the region from the bghpA element to the downstream of the short homology arm (SA) outside the 3' region. Five clones were identified as positive and selected for further expansion. The Neo cassette was removed by F1p transgene during ES clone expansion.

Genomic DNA extracted from the five positive clones were first characterized by sequencing analysis. A 1.19-kb product was amplified and sequenced by primers (SEQ ID NO:326=5'-ACC CTA GTC CTG ACT GTT GCT C-3'; SEQ ID NO:327=5'-TAT AGG AAC TTC GCG ACA CGG ACA C-3') to confirm the 5' genome/neo cassette junction and 3' KI cassette junctions. The sequencing results confirmed the introduction of human Trem2 cDNA-pA sequence in all of the five clones.

The five positive clones were further characterized by Southern Blotting analysis using probes targeted against short arm and long arm. ES cell genomic DNA digested with Ssp I and Bam HI were hybridized with short arm and long arm probe respectively. All five ES clones were confirmed to carry the correct homologous recombination events in both long and short arms. The primer sequences for amplifying the short arm probe (658 bp) are (SEQ ID NO:328=5'-ACA GGA GGG ACC TAC CTT CAG 3'; SEQ ID NO:329=5'-GCC TGC CTT TCA GAG ACC TCA GTC-3). The primer sequences for amplifying the long arm probe (681 bp) are (SEQ ID NO:330=5'-CCT CTC CGG CTG CTC ATC TTA CTC—3'; SEQ ID NO:331=5'-GTC TCT CAG CCC TGG CAG AGT TTG-3').

All five ES cell clones were then injected into C57BL/6 blastocysts. The pups from one clone were confirmed with germline transmission by PCR genotyping. The primers for genotyping are (SEQ ID NO:332=pr1: 5'-CGC CTA CCC TAG TCC TGA CTG TTG-3', SEQ ID NO:333=pr2: 5'-AAA GCC TAC AGC ATC CTC ACC TC-3'; and SEQ ID NO:334=pr3: 5'-GCA TCA TGG GGT TGT AGA TTC CG-3'). The PCR product for the pr1/pr2 on the wild-type is 658 bp. The PCR product for pr1/pr3 on the KI allele is 469 bp.

Antibody Dosing and Plasma/CSF Collection

For PK analysis, the C57BL/6J mice were dosed with anti-TREM2 antibodies or control IgG at 10 mg/kg through intravenous (IV) tail vein injection (dosing volume of about 200 µL/mouse, n=3 for each group). Blood samples were collected at 1 hour, 24 hours, 4 days, and 7 days after dosing. The blood samples at the first three time points were collected through submandibular bleeding by using 3-mm lancets (GoldenRod animal lancets). The last and terminal blood sample at day 7 was collected through cardiac puncture. Blood was collected in EDTA tubes (Sarstedt Microvette 500 K3E, Catalog No. 201341102), inverted slowly to mix, and centrifuged at 4° C. The plasma (top) layer was transferred to 1.5-mL Eppendorf tubes and stored at −80° C. until analysis.

For the 24-hour target engagement study, C57BL/6J mice were used to test mouse surrogate anti-TREM2 antibodies, and huTrem2$^{KI/KI}$ mice were used to test human anti-TREM2 antibodies. The mice were dosed with anti-TREM2 antibodies or control IgG at 100 mg/kg through intravenous (IV) tail vein injection (dosing volume of about 200 µL/mouse, n=5 for each group). Blood samples were collected 24 hours before dosing to determine baseline levels of TREM2. Terminal blood and CSF samples were collected 24 hours after dosing. Plasma preparation was prepared as described above. For collection of the CSF sample, a sagittal incision was made at the back of the skull, and subcutaneous tissue and muscles were separated to expose the cisterna magna. A pre-pulled glass capillary tube was used to puncture the cisterna magna and collect the CSF sample. The CSF was then centrifuged at 4° C. to remove blood residue, and the CSF supernatant was transferred to a 0.5-mL Low Protein LoBind Eppendorf tube (Eppendorf, Catalog No. 022431064) for storage at −80° C. until analysis.

Analysis of in Vivo Anti-TREM2 Antibody Plasma Levels

For anti-TREM2 antibody PK analysis, total antibody concentrations in mouse plasma were quantified using a generic human anti-Fc sandwich ELISA. A 384-well MaxiSorp plate was coated overnight with 1 µg/mL anti-huFc donkey polyclonal (Jackson Immunoresearch). Following incubation with plasma diluted 1:2,000 or 1:20,000 in assay buffer (PBST, 1% BSA), an anti-huFc donkey antibody conjugated to HRP (Jackson Immunoresearch) was added as the detection reagent. Standard curves were generated for each individual antibody, from 2 nM to 2.7 pM using 3-fold dilutions, using a five-parameter logistic regression.

Figure 9:
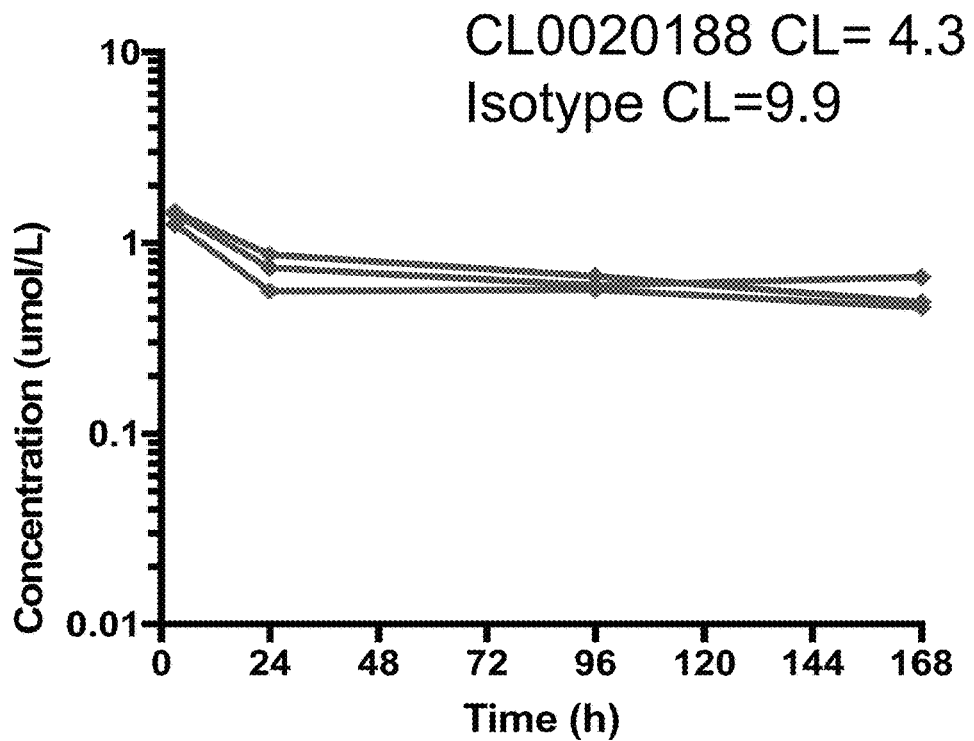
FIG. 9 includes representative mouse plasma pharmacokinetic profiles of exemplary anti-TREM2 antibodies.
Figure 9:
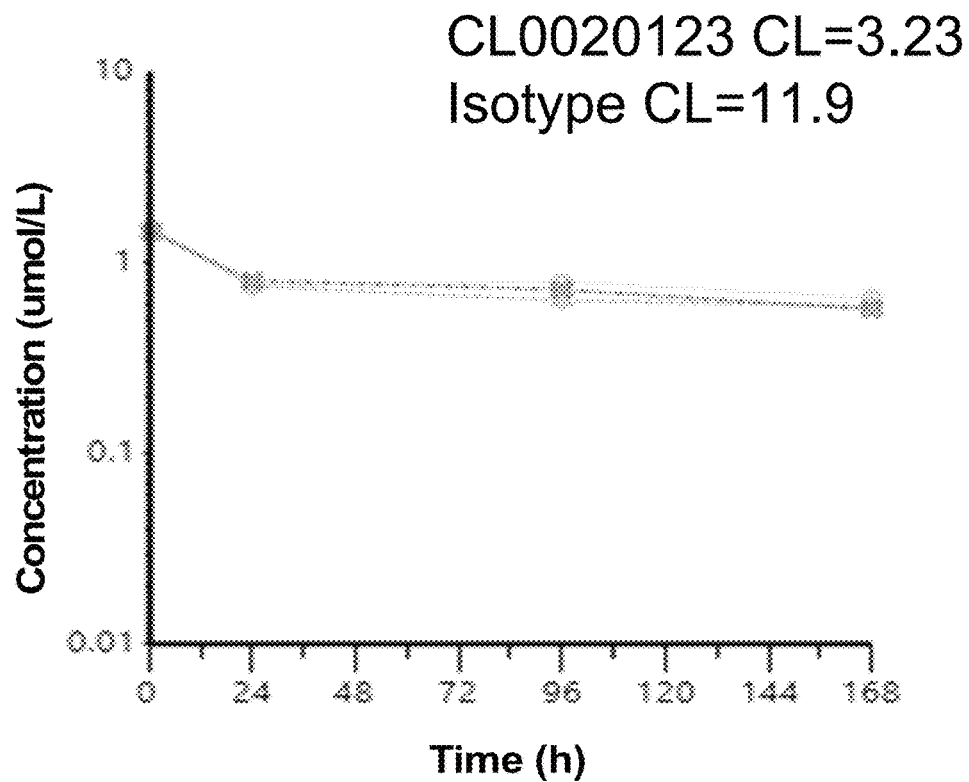

FIG. 9 illustrates representative mouse PK profiles for exemplary anti-TREM2 antibodies. Antibody clearance rates (CL [mL/day/kg]) are provided for each exemplary antibody over a 7-day period and are compared to normal effectorless isotype control. Each antibody illustrated in FIG. 9 exhibited comparable clearance rates relative to isotype control. Table 4 below further lists the antibody clearance rates for additional anti-TREM2 antibodies, with each antibody compared its corresponding effectorless isotype control.

TABLE 4

Anti-TREM2 Antibody Clearance Rates (CL [mL/day/kg])

| | Clearance Rate (CL [mL/day/kg]) | |
|---|---|---|
| Antibody | Antibody | Isotype |
| CL0020123 | 3.23 | 11.9 |
| CL0020188 | 4.3 | 9.9 |
| CL0020141 | 4.5 | 9.9 |
| CL0020139 | 5.12 | 11.9 |
| CL0020096 | 6.49 | 11.9 |
| CL0020120 | 19.4 | 18.2 |
| CL0020107 | 38.2 | 18.2 |

In Vivo Target Engagement: sTREM2 Plasma Levels

For measurement of soluble TREM2 (sTREM2) plasma levels, human TREM2 cDNA KI mice (huTrem2$^{KI/KI}$) were bled and then intravenously treated with 100 mg/kg of test anti-TREM2 antibody or isotype control. Mice were bled 24 hours post-dosing. Plasma were obtained from blood samples and evaluated in an MSD assay conducted as follows. MSD SECTOR Plates were coated with 1 µg/mL capture antibody (R+D anti-TREM2 antibody, Catalog No. MAB17291-100) diluted in PBS and incubated overnight at 4° C. The sample wells were blocked for 1 hour with undiluted MSD Blocker A. Plasma samples were diluted 1:20 in 25% MSD Blocker A in Tris-buffered saline containing 0.05% Tween-20 (TBST) and added to each sample well on the plate, which was then incubated for 2 hours at room temperature. Detection antibody (MSD sulfo-tagged goat anti-human, Catalog No. R32AJ-1, 1:1000) was subsequently added to each sample well, and the plate was incubated for 1 hour at room temperature. TBST washes were performed for each sample well with a Biotek plate washer. Detection reagent (MSD Read buffer) was added and measured using a MSD Meso Sector S600 reader to obtain the results of sTREM2 binding to the antibodies.

Figure 10A:
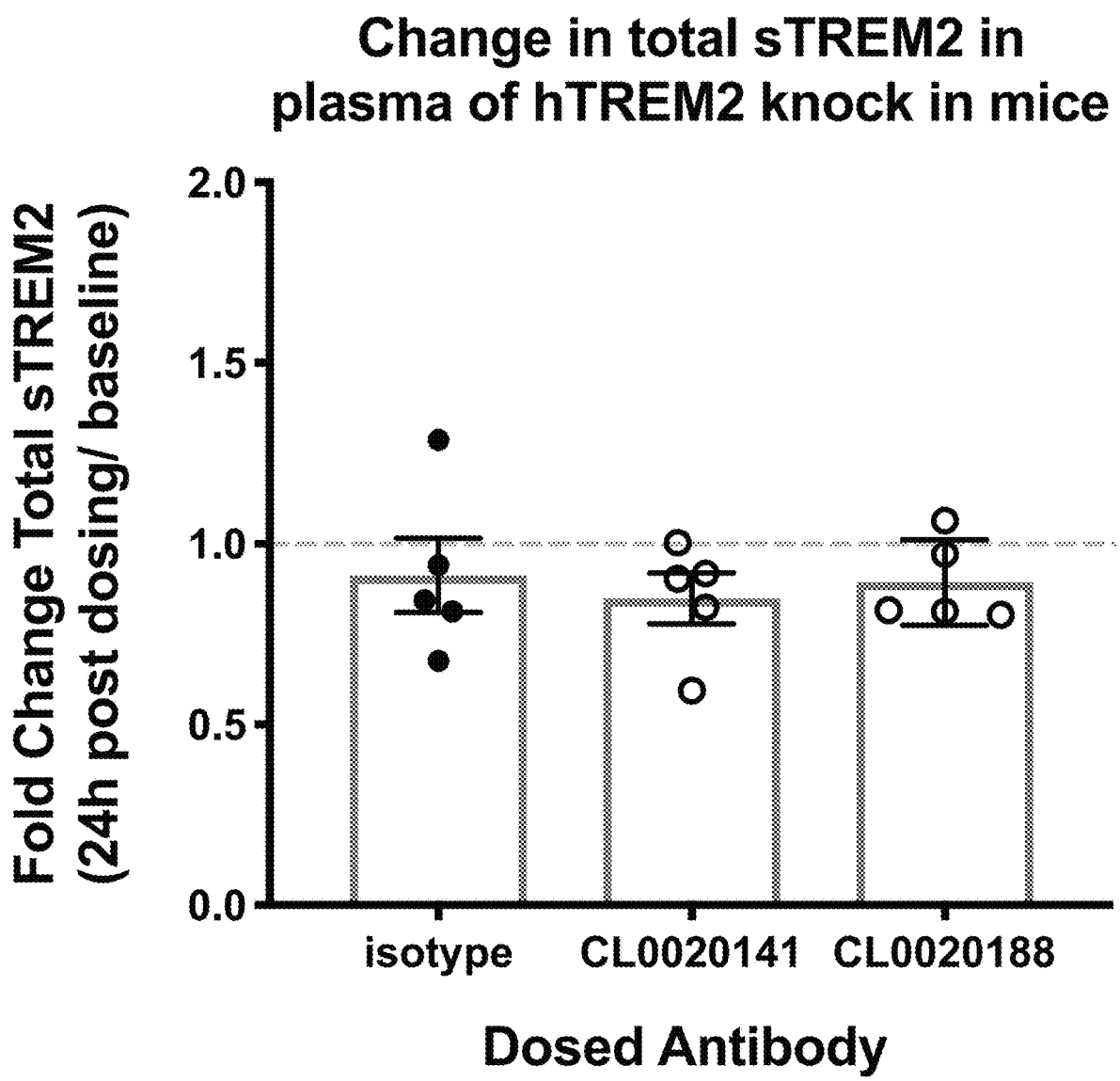
FIGS. 10A and 10B includes bar charts illustrating change in total soluble TREM2 (sTREM2) (FIG. 10A) and antibody-bound TREM2 (FIG. 10B) in mouse plasma for exemplary anti-TREM2 antibodies, which were injected into TREM2 cDNA KI (huTrem2$^{KI/KI}$) mice.
Figure 10B:
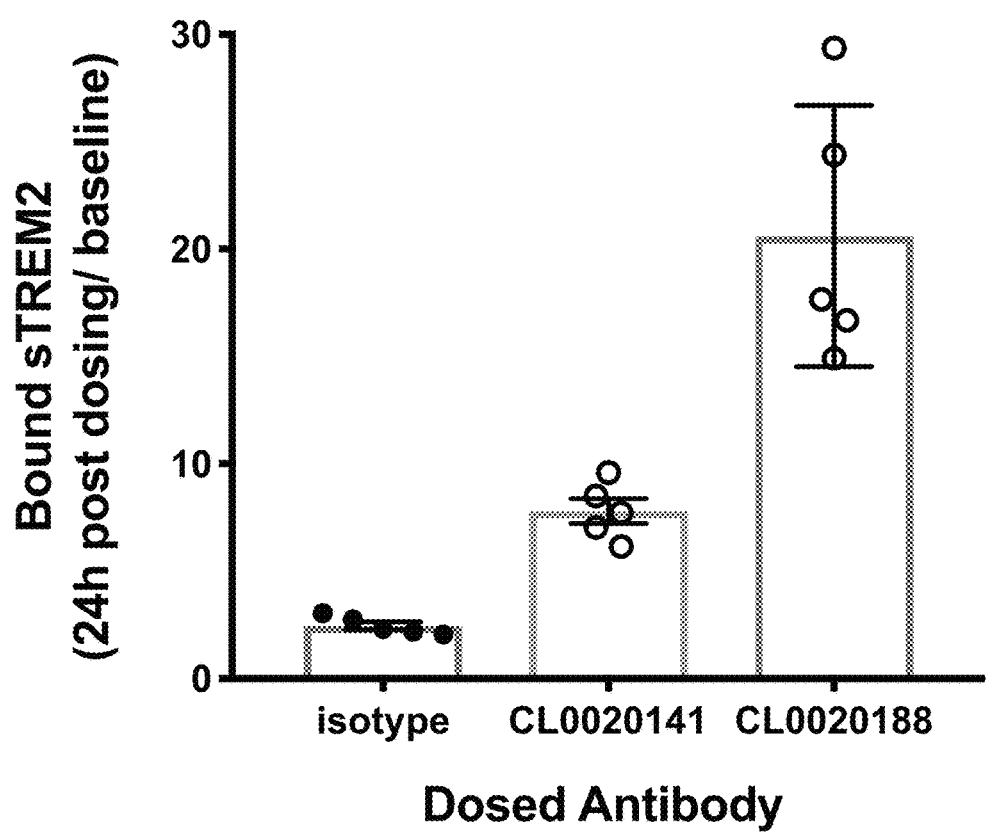

FIGS. 10A and 10B illustrate total sTREM2 levels (FIG. 10A) and antibody-bound sTREM2 levels (FIG. 10B) in huTrem2' plasma for two exemplary anti-TREM2 antibodies (CL0020141, CL0020188). Data were normalized to pre-dose baseline levels of sTREM2 for total and bound sTREM2 assays. The results indicate that total circulating sTREM2 levels did not significantly change between mice treated with anti-TREM2 antibodies compared to isotype control after 24-hour treatment with the antibodies, which suggests that total circulating sTREM2 levels are unaffected at early timepoints post-antibody dose. In contrast, antibody-bound sTREM2 levels were higher in mice injected with anti-TREM2 antibodies relative to isotype control.

Example 7. Sequence Optimization and Humanization of Anti-TREM2 Antibodies

Exemplary anti-TREM2 antibodies were sequence optimized and humanized, followed by characterization for binding kinetics and binding specificity.

Sequence optimization was conducted by searching within CDR sequences for residues that are susceptible to chemical modification (e.g., asparagine deamidation motifs (NG), aspartic acid isomerization motifs (DS), and potential oxidation residues (tryptophan (W) and methionine (M)) and making amino acid substitutions with conservative and germline residues to remove such sequence liabilities. Humanized and sequence-optimized variants of anti-TREM2 antibodies were then analyzed for binding kinetics using Biacore and dose-titrated cell binding to HEK293-H6 cells (see, Example 1 for representative protocols).

Results for an analysis of the binding characteristics of humanized and sequence-optimized variants of antibody CL0020188 are provided in Table 5. NG motifs in the CL0020188 CDR-H2 sequence (SEQ ID NO:61) and CDR-L1 sequence (SEQ ID NO:63) were modified, grafted onto human framework regions, and analyzed. Table 5 provides $K_D$ values as measured by Biacore and $EC_{50}$ values as measured by dose-titrated binding assay in HEK293-H6 cells.

TABLE 5

Binding Characteristics of Sequence-Optimized and Humanized Variants of CL0020188

| Clone | $hV_H$ | $hV_L$ | $K_D$ | $EC_{50}$ |
| --- | --- | --- | --- | --- |
| CL0020188-1 | NG/graft | NG/graft | 2.3 nM | 0.42 nM |
| CL0020188-2 | NG/3 m | NG/graft | 3.4 nM | 0.26 nM |
| CL0020188-3 | NG/graft | TG/graft | 6.8 nM | 0.64 nM |
| CL0020188-4 | NG/3 m | TG/graft | 4.8 nM | 0.44 nM |
| CL0020188-5 | NA/graft | NG/graft | 5.1 nM | 0.45 nM |
| CL0020188-6 | NA/3 m | NG/graft | 4.0 nM | 0.31 nM |
| CL0020188-7 | NA/graft | TG/graft | 10 nM | 0.68 nM |
| CL0020188-8 | NA/3 m | TG/graft | 7.3 nM | 0.51 nM |
| Parent | | | 9.5 nM | 0.44 nM |

3 m = A24G/L45P/V48L in $V_H$

As illustrated in Table 5, humanized and sequence-optimized clones of CL00201088 exhibited similar affinity values for hTREM2 compared to the parent antibody ($K_D$=9.5 nM), as measured by Biacore. This was consistent with cell-binding results in HEK293-H6 cells, which are illustrated in Table 5. Compared to the parent antibody ($EC_{50}$=0.44 nM), humanized and sequence-optimized clones exhibited comparable and sub-nanomolar affinity for TREM2 expressed in HEK293-H6 cells. Taken together, the results indicate comparable binding kinetics between the parent antibody and the humanized and sequence-optimized variants.

Results for an analysis of the binding characteristics of humanized and sequence-optimized variants of antibody CL0020123 are provided in Table 6. NG and DS motifs in the CL0020123 CDR-H2 sequence (SEQ ID NO:106) were modified, grafted onto human framework regions, and analyzed. Table 6 provides $K_D$ values as measured by Biacore and $EC_{50}$ values as measured by dose-titrated binding assay in HEK293-H6 cells.

TABLE 6

Binding Characteristics of Sequence-Optimized and Humanized Variants of CL0020123

| Clone | $hV_H$ | $hV_L$ | $K_D$ | $EC_{50}$ |
| --- | --- | --- | --- | --- |
| CL0020123-1 | NGDS/2 m (SEQ ID NO: 351) | Vκ graft | 0.14 nM | 0.25 nM |
| CL0020123-2 | NGDS/1 m (SEQ ID NO: 351) | Vκ graft | 0.18 nM | 0.23 nM |
| CL0020123-3 | QGDS/2 m (SEQ ID NO: 352) | Vκ graft | 0.40 nM | 0.24 nM |
| CL0020123-4 | NGES/2 m (SEQ ID NO: 353) | Vκ graft | 0.17 nM | 0.17 nM |
| CL0020123-5 | QGES/2 m (SEQ ID NO: 354) | Vκ graft | 0.44 nM | 0.37 nM |
| CL0020123-6 | QGDS/1 m (SEQ ID NO: 352) | Vκ graft | 0.32 nM | 0.29 nM |
| CL0020123-7 | NGES/1 m (SEQ ID NO: 353) | Vκ graft | 0.15 nM | 0.19 nM |
| CL0020123-8 | QGES/1 m (SEQ ID NO: 354) | Vκ graft | 0.39 nM | 0.38 nM |
| Parent | | | 0.10 nM | 0.26 nM |

1 m = R71A in $V_H$
2 m = V67A/R71A in $V_H$

Compared to the parent antibody ($K_D$=0.10 nM), the humanized and sequence-optimized clones exhibited about 4-fold higher $K_D$ values for binding to hTREM2 as measured by Biacore. On the other hand, in dose-titrated cell-binding assays in HEK293-H6 cells, the humanized and sequence-optimized clones exhibited comparable and sub-nanomolar affinity for TREM2.

Figure 11A:
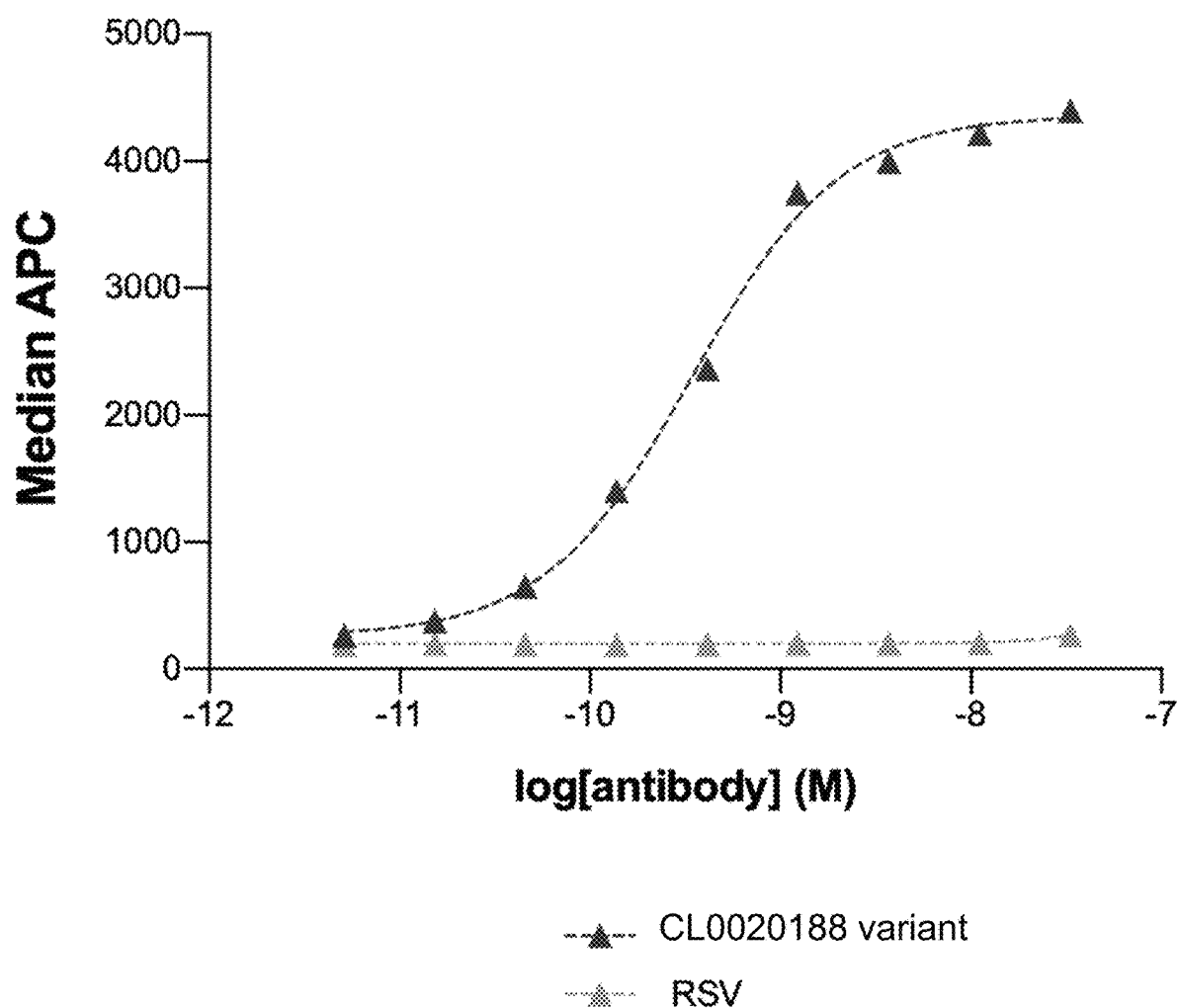
FIGS. 11A and 11B include dose-response binding curves to human TREM2 in HEK cells for exemplary humanized and sequence-optimized anti-TREM2 antibodies.
Figure 11B:
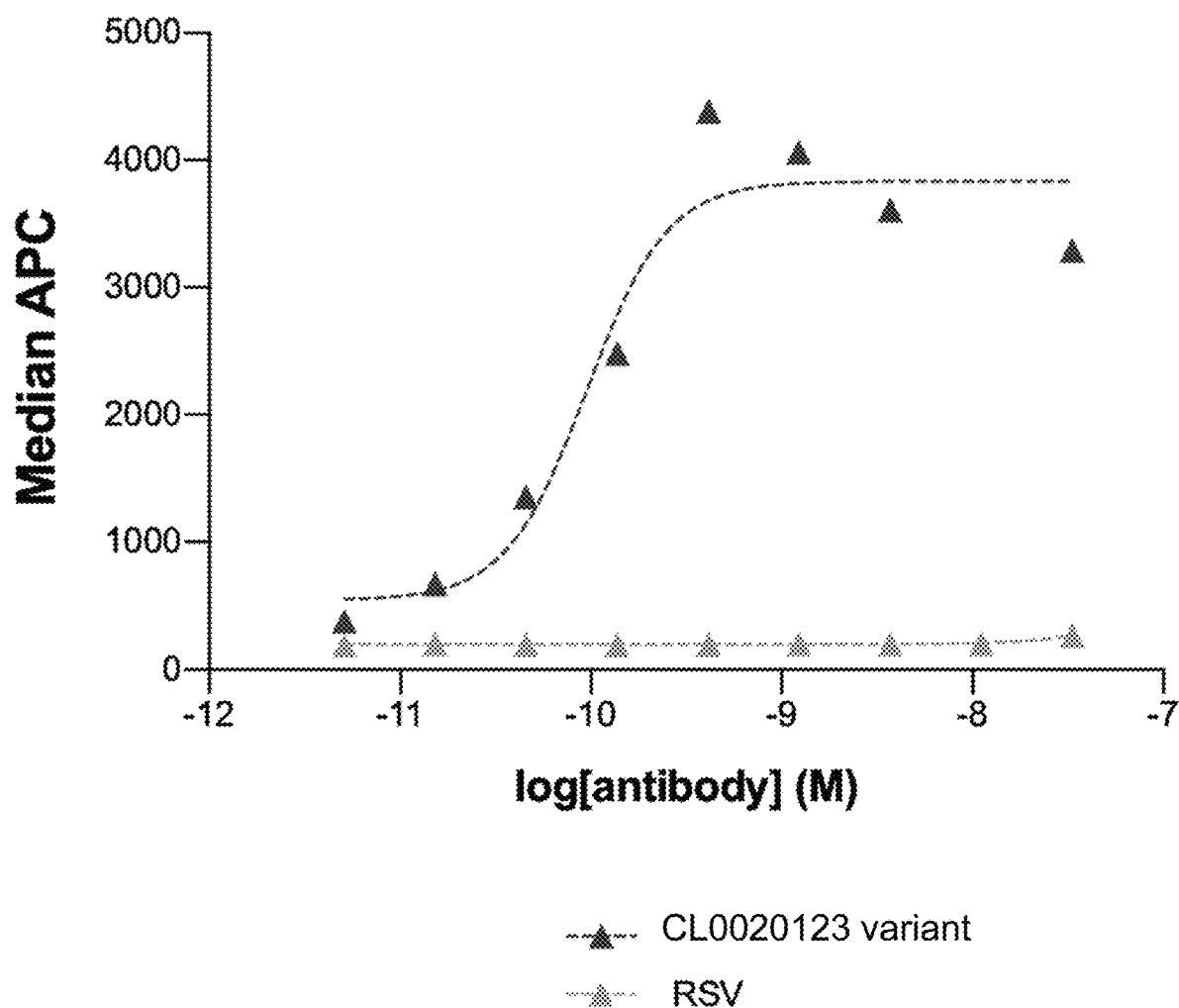
Figure 12B:
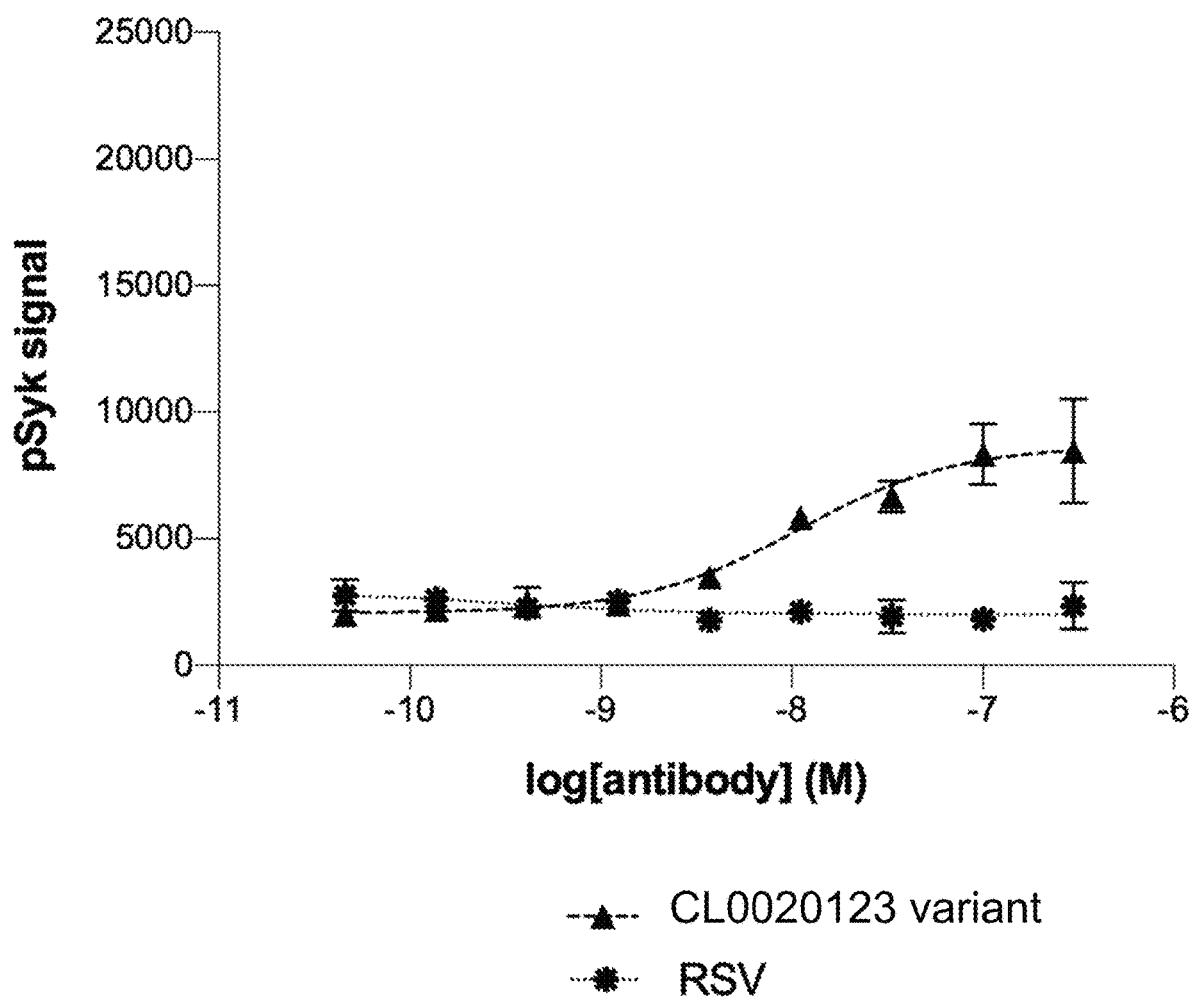
Figure 13:
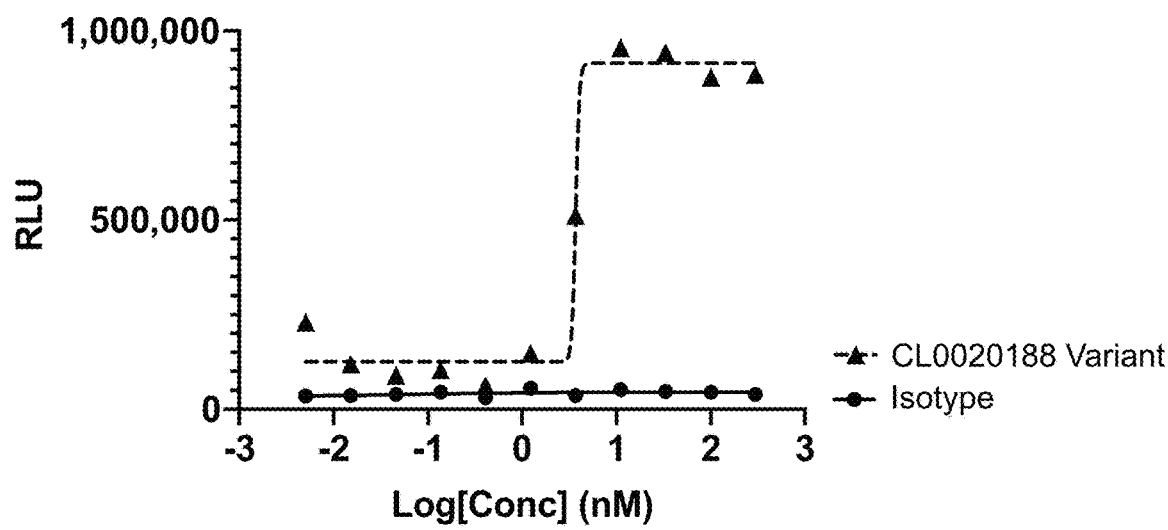
FIG. 13 illustrates dose-response curves of cell survival in human macrophage cells in response to treatment with exemplary humanized and sequence-optimized anti-TREM2 antibodies.
Figure 13:
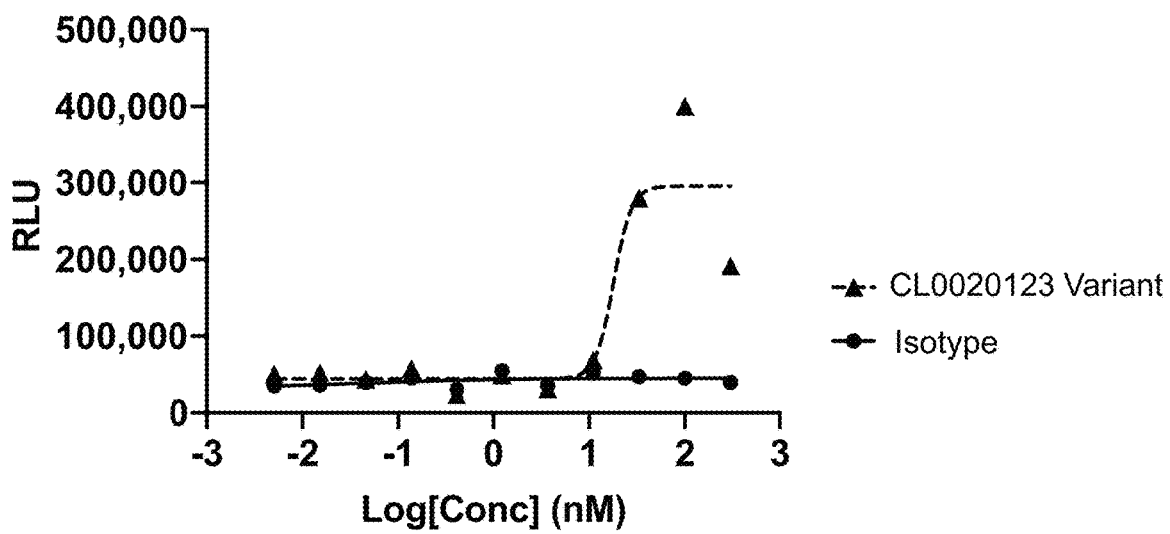
Figure 14A:
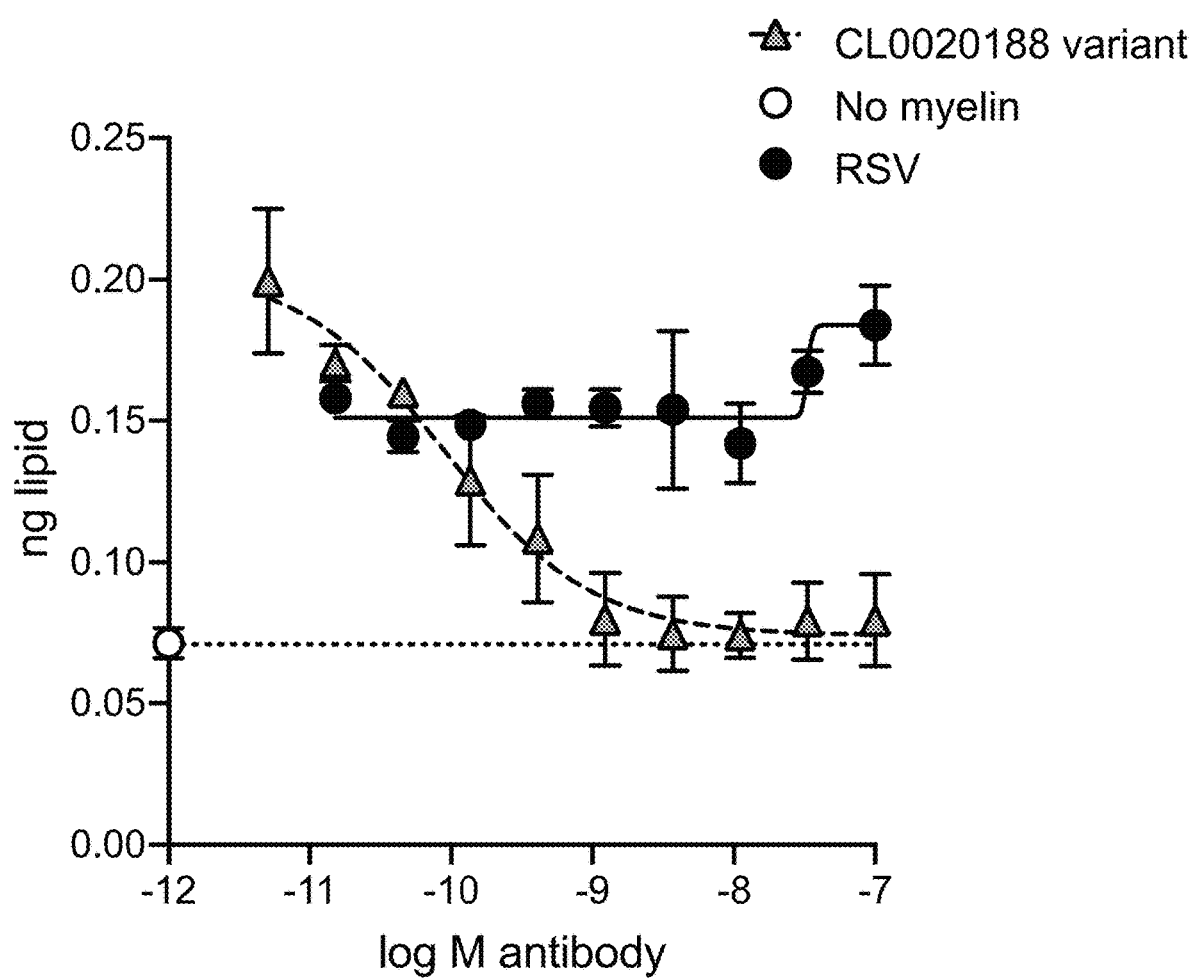
FIGS. 14A and 14B include dose-response curves of lipid clearance in iPSC microglia in response to treatment with exemplary humanized and sequence-optimized anti-TREM2 antibodies.
Figure 14B:
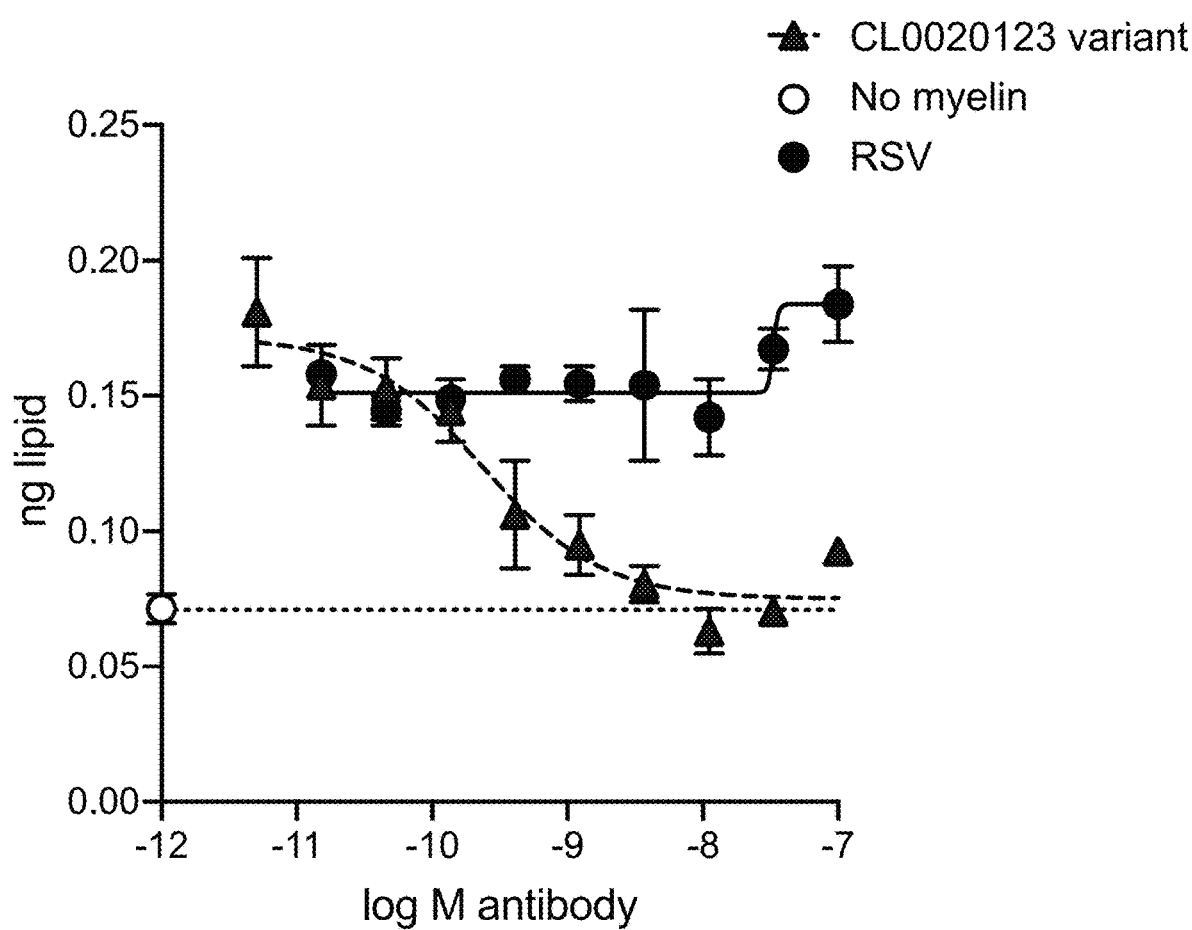

Example 8. In Vitro Characterization of Sequence-Optimized, Humanized Anti-TREM2 Antibodies Exemplary sequence-optimized and humanized anti-TREM2 antibodies (Example 7) were evaluated by in vitro methods as described in Examples 1 and 3. The antibodies were assessed for TREM2 binding in TREM2-expressing HEK cells, TREM2-dependent pSyk signaling in HEK-H6 cells, capability for promoting survival of human macrophage cells, and ability to modulate lipid accumulation in iPSC microglia. FIGS. 11 to 14 illustrate the results for representative anti-TREM2 antibodies. The anti-TREM2 antibodies exhibited good cell binding in assays with TREM2-expressing HEK293-H6 cells (EC50 values of 0.34 nM (FIG. 11A) and 0.08 nM (FIG. 11B). The anti-TREM2 antibodies also activated pSyk signaling in TREM2-expressing HEK293-H6 cells (FIGS. 12A and 12B). In addition, the anti-TREM2 antibodies induced macrophage survival, with better survival activity observed for a CL0020188 variant antibody (FIG. 13). Finally, the anti-TREM2 antibodies demonstrated capability in reducing lipid accumulation in myelin-treated iPSC microglia (FIGS. 14A and 14B).

Example 9. Mouse PK of Sequence-Optimized, Humanized Anti-TREM2 Antibodies

The pharmacokinetic profiles of certain sequence-optimized, humanized anti-TREM2 antibodies (Example 7)

were evaluated in wild-type mice for a 7-day pharmacokinetic (PK) study similar to that described in Example 6. Each dose group contained n=3 mice. Table 7 provides the PK properties of exemplary sequence-optimized and humanized anti-TREM2 antibodies (Example 7).

TABLE 7

Mouse PK Properties of Anti-TREM2 Antibodies

| Clone | Dose (mg/kg) | $C_0$ (µM) | $AUC_{0\text{-}inf}$ (µM*hr) | CL (mL/day/kg) |
|---|---|---|---|---|
| CL0020188 variant | 10 | 1.14 ± 0.05 | 207.78 ± 43.30 | 8.14 ± 1.80 |
| CL0020188 variant | 50 | 6.48 ± 0.61 | 236.49 ± 2.67 | 34.58 ± 0.39 |
| CL0020123 variant | 10 | 1.4999 | 223.1 | 13.2 |
| Anti-BACE reference | 10 | 1.017 | 60.19 | 33.3 |

Example 10. Cyno PK of Sequence-Optimized, Humanized Anti-TREM2 Antibodies

The pharmacokinetic profiles of the anti-TREM2 antibodies were evaluated in naïve cynomolgus monkeys. Naïve cynomolgus monkeys of 2-4 years of age (approximately 2-3 kg in weight) were injected with anti-TREM2 antibody via intravenous bolus injection. Administered doses included 3 mg/kg and 25 mg/kg, with n=3 monkeys per dose group. Blood samples (about 1 mL) were collected pre-dose and at 10 minutes, 30 minutes, at 1, 6, 12, and 24 hours, and at 3, 7, 10, 14, 17, 21, 24, and 28 days post-dose. The samples were chilled at about 5° C. prior to centrifugation to obtain plasma, and the obtained plasma was maintained on dry ice prior to storage at −70° C. until analysis. The plasma samples were analyzed for anti-TREM2 antibody levels as follows.

For anti-TREM2 antibody PK analysis, the total antibody concentrations in monkey plasma were quantified using a generic anti-human IgG sandwich electrochemiluminescence immunoassay (ECLIA) on a Meso Scale Discovery (MSD) platform. Briefly, 1% casein-based PBS blocking buffer (Thermo Scientific, MA) was added to an MSD GOLD 96-well small-spot streptavidin-coated microtiter plate (Meso Scale Discovery, MD) and incubated for approximately 1 hr. Following the plate blocking and wash steps, a biotinylated anti-human IgG goat antibody (SouthernBiotech, AL) at a working solution of 0.5 µg/mL was added to the assay plate and allowed to incubate for 1-2 hrs. Following the incubation and wash steps, plasma test samples (i.e., samples with anti-TREM2 humanized antibodies) were added to the assay plate and incubated for 1-2 hrs. Note that the test samples must be diluted at the assay minimum-required-dilution (MRD) of 1:100 in 0.5% casein-based PBS assay buffer (Thermo Scientific, MA), resulting in the final 1% plasma matrix, prior to adding to the assay plate. Following the capture of anti-TREM2 antibody analyte and wash steps, a secondary ruthenylated (SULFO-TAG) anti-human IgG goat antibody (Meso Scale Discovery, MD) at a working solution of 0.4 µg/mL was added to the assay plate and incubated for approximately 1 hr. Lastly, following the incubation and wash steps, an assay read buffer (1xMSD Read Buffer T) was added to the assay plate to generate assay sample signals. The sample signal readouts from an MSD plate reader was in a form of electrochemiluminescence (ECL) signals and expressed in ECL units (ECLU). All of the assay reaction steps previously described were done at the ambient temperature and with shaking on a plate shaker (where appropriate). The assay had a dynamic calibration standard range of 19.5-2500 ng/mL (or 0.195-25 ng/mL in post-MRD of 1:100) with 8 standard points serially-diluted at 1:2 plus a blank plasma sample. Plasma sample concentration was back-calculated off the assay calibration standard curve which was fitted with a weighed four-parameter non-linear logistic regression. Table 8 provides the pharmacokinetic (PK) properties of an exemplary sequence-optimized and humanized anti-TREM2 antibody (Example 7).

TABLE 8

Cynomolgus PK Properties of Anti-TREM2 Antibodies

| Clone | Dose (mg/kg) | $AUC_{0\text{-}inf}$ (µM*hr) | CL (mL/day/kg) |
|---|---|---|---|
| CL0020188 variant | 25 | 899.0 ± 53 | 4.46 ± 0.26 |
| CL0020188 variant | 3 | 61.2 ± 6.3 | 7.90 ± 0.77 |

The CL0020188 variant exhibited similar low clearance levels between different dose levels and a linear pharmacokinetic profile in cynomolgus monkeys. In addition, there were no clinical pathology findings related to administration of the variant in cynomolgus monkeys (data not shown).

Example 11. Comparison of Anti-TREM2 Antibodies

The affinity of anti-TREM2 antibodies to human TREM2 and cynomolgus TREM2 were measured by Biacore (described in Example 1). The potency of anti-TREM2 antibodies were measured in healthy human volunteer CSF samples (Innovative Research) and healthy cynomolgus monkey CSF samples (Worldwide Primates), by MSD assay. The potency of each antibody was determined by its EC50. Briefly, MSD GOLD 96-well small spot streptavidin plates (MSD, Cat. No. L45SA) coated with capture antibody (biotinylated goat anti-human TREM2, R&D Systems, Cat. No. BAF1828) was incubated with biofluid samples diluted 1:3 in Assay Buffer (25% (v/v) MSD Blocker A (MSD, Cat. No. R93BA-A), 75% (v/v) TBST) for one hour at room temperature. After rinsing the wells with TBST, sulfo-tagged anti-TREM2 antibody was added in a serial dilution (4x dilution over 11 points) to the wells of the plate and incubated for one hour at room temperature. The wells were washed with TBST, and MSD Read Buffer (MSD, Cat. No. R92TC-3) was added to the wells. Signal from the samples were measured using an MSD Meso Sector 5600 device. EC50 values for each antibody was determined by four-parameter variable slope non-linear regression. The variable regions of reference antibody #1 are represented by SEQ ID NOS:344 and 345. The variable regions of reference antibody #2 are represented by SEQ ID NOS:346 and 347. The variable regions of reference antibody #3 are represented by SEQ ID NOS:348 and 349. Results are provided in Table 9.

As illustrated in Table 9, the CL0020188 and CL0020123 variants, relative to reference antibodies, have stronger affinity for human TREM2 and are more potent in binding sTREM2 in CSF samples isolated from healthy human volunteer subjects. In addition, the CL0020188 variants, relative to reference antibodies, have stronger affinity for cynomolgus TREM2 and are more potent in binding sTREM2 in CSF samples isolated from healthy cynomolgus monkey subjects. This is demonstrated by the relative amount of antibody needed to reach the half maximal effective concentration for binding a given amount of sTREM2 under the same conditions (EC50). As illustrated in Table 9, higher relative amounts of reference antibodies #1, #2, and #3 are needed to achieve EC50 compared to the CL0020188 and CL0020123 antibodies.

TABLE 9

Comparison of Properties of Anti-TREM2 Antibodies

| Antibody | $K_D$ (nM) Human TREM2 | $K_D$ (nM) Cyno TREM2 | EC50, bound sTREM2 in Human CSF [nM] | EC50, bound sTREM2 in Cyno CSF [nM] |
|---|---|---|---|---|
| CL0020188-4 | 1.4 | 1.5 | 0.29 | 0.28 |
| CL0020188-7 | 3.3 | 2.8 | 0.75 | 0.72 |
| CL0020123-5 | 0.63 | 9.3 | 1.00 | 49.41 |
| CL0020123-7 | 0.08 | 9.4 | 0.54 | 16.88 |
| Reference antibody #1 | 5.9 | 14 | 32.6 | 81.6 |
| Reference antibody #2 | 4.3 | 9.2 | 7.4 | 6.5 |
| Reference antibody #3 | 8.7 | 9.2 | 7.25 | 33.72 |

Example 12. Epitope Mapping of Anti-TREM2 Antibodies

To identify the epitopes of the anti-TREM2 antibodies at the peptide level, hydrogen deuterium exchange (HDX) mass spectrometry was used. Recombinant human TREM2 alone or mixed with anti-TREM2 antibody was incubated with deuterium oxide labeling buffer (50 mM sodium phosphate, 100 mM sodium chloride, pH 7.0) for 0, 60, 600, and 3600 seconds at 20° C. Hydrogen/deuterium exchange was quenched by adding an equal volume of 4 M guanidine hydrochloride, 0.85 M TCEP buffer (final pH 2.5). The quenched samples were then subjected to pepsin/protease XIII digestion and LC-MS analysis. Briefly, the quenched samples were injected onto a packed pepsin/protease XIII column (2.1×30 mm) held at 20° C., and the resultant peptides were analyzed using an UPLC-MS system comprised of a Waters Acquity UPLC (Waters Corporation) coupled to a Q Exactive™ HF-Hybrid Quadrupole-Orbitrap Mass Spectrometer (Thermo Fisher). The peptides were separated on a 50 mm×1 mm C8 column held at −6° C. using a 16.5-minute gradient from 2% to 31% solvent B (solvent B: 0.2% formic acid in acetonitrile; solvent A: 0.2% formic acid in water). The mass spectra were recorded in MS only mode. Raw MS data was processed using HDX Workbench (Pascal et al. 2012. *Journal of The American Society for Mass Spectrometry* 23:1512-1521). The deuterium levels were calculated using the average mass difference between the deuterated peptide and its native form at t0. Peptide identification was carried out through searching MS/MS data against the human TREM2 sequence with Mascot softward (Matrix Science). The mass tolerance for precursor and product ions were 10 ppm and 0.02 Da, respectively.

Based on the HDX mass spectrometry results, CL0020188 and variants of CL0020188 bind to human TREM2 (SEQ ID NO:1) at amino acid residues 143-149 (FPGESES (SEQ ID NO:340)), while CL0020123 and variants of CL0020123 bind to human TREM2 at (i) amino acid residues 55-63 (GEKGPCQRV (SEQ ID NO:341)), (ii) amino acids 96-107 (TLRNLQPHDAGL (SEQ ID NO:342)), and (iii) amino acid residues 126-129 (VEVL (SEQ ID NO:343)).

INFORMAL SEQUENCE LISTING

| SEQ ID NO | Sequence | Description |
|---|---|---|
| 1 | MEPLRLLILLFVTELSGAHNTTVFQGVAGQSLQVSCPYDSMKH WGRRKAWCRQLGEKGPCQRVVSTHNLWLLSFLRRWNGSTAITD DTLGGTLTITLRNLQPHDAGLYQCQSLHGSEADTLRKVLVEVL ADPLDHRDAGDLWFPGESESFEDAHVEHSISRSLLEGEIPFPP TSILLLLACIFLIKILAASALWAAAWHGQKPGTHPPSELDCGH DPGYQLQTLPGLRDT | Human TREM2 protein |
| 2 | QVQLQQPGAELVKPGASVKMSCRASGYTFTNYWISWVKQRPGQ GLEWIGDIYPHSTSTNYNERFRSKATLTVDKSSTTAYMQLSSL TSEDSAVYYCAREGFGISAWGQGTTLTVSS | CL0020107 VH |
| 3 | QIVLTQSPAIMSASPGEKVTITCSATSSVSYMHWFQQKPGTSP KLWIYSTSNLASGVPARFSGSGSGTSHSLTISRMEAEDAATYY CQQRSSYPLTFGSGTKLELK | CL0020107 VL |
| 4 | GYTFTNYWIS | CL0020107 CDR-H1 |
| 5 | DIYPHSTSTNYNERFRS | CL0020107 CDR-H2 |
| 6 | AREGFGISA | CL0020107 CDR-H3 |
| 7 | SATSSVSYMH | CL0020107 CDR-L1 |
| 8 | STSNLAS | CL0020107 CDR-L2; CL0020111 CDR-L2 |
| 9 | QQRSSYPLT | CL0020107 CDR-L3 |
| 10 | QVQLQQPGAELVKPGASVKMSCKASGYTFTSYWITWVKQRPGQ GLEWIGDIYPGSGNTNYNEKFKSKATLTVDTSSTTAYMQLSSL TSEDSAVYYCAREGYGISAWGQGTTLTVSS | CL0020300 VH |

INFORMAL SEQUENCE LISTING

| SEQ ID NO | Sequence | Description |
|---|---|---|
| 11 | NIVMTQSPKSMSMSVGERVTLSCKASENVGTYVSWYQQKPEQS PKLLIYGASNRYTGVPDRFTGSGSATDFTLTISSVQAEDLADY HCGQSYSYPFTFGSGTKLEIK | CL0020300 VL |
| 12 | GYTFTSYWIT | CL0020300 CDR-H1 |
| 13 | DIYPGSGNTNYNEKFKS | CL0020300 CDR-H2 |
| 14 | AREGYGISA | CL0020300 CDR-H3 |
| 15 | KASENVGTYVS | CL0020300 CDR-L1 |
| 16 | GASNRYT | CL0020300 CDR-L2 |
| 17 | GQSYSYPFT | CL0020300 CDR-L3 |
| 18 | QVQLQQPGAELVKPGASVKMSCKASGYTFTNYWIMWVKQRPGQ GLEWIGDIYPSSGSTNYNEKFKNRATLTVDTSSNTAYMQLSSL TSEDSAVYFCSREGYGISAWGQGTTLTVSS | CL0020215 VH |
| 19 | QIVLTQSPAIMSASPGEKVTITCSASSSVSYMHWFQQKPGTSP KLWIYSTSNLASGVPARFSGSGSGTSCSLTISRMEAEDAATYY CQQRSSFPLTFGAGTKLELK | CL0020215 VL |
| 20 | GYTFTNYWIM | CL0020215 CDR-H1 |
| 21 | DIYPSSGSTNYNEKFKN | CL0020215 CDR-H2 |
| 22 | SREGYGISA | CL0020215 CDR-H3; CL0020111 CDR-H3 |
| 23 | SASSSVSYMH | CL0020215 CDR-L1 |
| 24 | STSNLAS | CL0020215 CDR-L2 |
| 25 | QQRSSFPLT | CL0020215 CDR-L3 |
| 26 | EVQLQQSGPELVKPGASVKMSCKASGYTFTDYNIHWVKQSHGK SLEWIGYIFPNNGNNGYNQKFKGKATMTEDKSSSTAYMELRSL TSEDSAVYYCARSGRGFAYWGQGTLVTVSA | CL0020301 VH |
| 27 | DIVMTQSPSSLTVTAGEKVTLSCKSSQSLLNSGNQKNYLTWYQ QKPGQPPKLLIFWASTRESGVPHRFTGSGSGTDFTLTISSVQA EDLAFYYCQNDYSYPYTFGGGTKLEIR | CL0020301 VL |
| 28 | GYTFTDYNIH | CL0020301 CDR-H1; CL0020315 CDR-H1 |
| 29 | YIFPNNGNNGYNQKFKG | CL0020301 CDR-H2 |
| 30 | ARSGRGFAY | CL0020301 CDR-H3 |
| 31 | KSSQSLLNSGNQKNYLT | CL0020301 CDR-L1 |
| 32 | WASTRES | CL0020301 CDR-L2, CL0020311 CDR-L2; CL0020312 CDR-L2; CL0020141 CDR-L2; CL0020103 CDR-L2; CL0020096 CDR-L2; CL0020210 CDR-L2; CL0020113 CDR-L2 |
| 33 | QNDYSYPYT | CL0020301 CDR-L3 |
| 34 | EVQLQQSGPELVKPGASVKISCKASGYTFTDYNMHWVKQSHGK SLEWIGYIYPYNGGTGYNQKFKNKATLTVDNSSSTAYMELRSL TSEDSAVYYCARSGTGFAYWGQGTLVTVSA | CL0020302 VH |
| 35 | DIVMTQAAPSVPVTPGESVSISCRSSKSLLHSNGNTYLYWFLQ RPGQSPQLLIYQMSNLASGVPDRFSGSGSGTAFTLRLSRVEAE DVGVYYCMQHLQYPFTFGGGTKLEIK | CL0020302 VL |
| 36 | GYTFTDYNMH | CL0020302 CDR-H1 |

INFORMAL SEQUENCE LISTING

| SEQ ID NO | Sequence | Description |
|---|---|---|
| 37 | YIYPYNGGTGYNQKFKN | CL0020302 CDR-H2 |
| 38 | ARSGTGFAY | CL0020302 CDR-H3 |
| 39 | RSSKSLLHSNGNTYLY | CL0020302 CDR-L1 |
| 40 | QMSNLAS | CL0020302 CDR-L2 |
| 41 | MQHLQYPFT | CL0020302 CDR-L3 |
| 42 | EVQLQQSGPELVKPGASVKMSCKAPGYSFTSYLMNWVKQKPGQ GLEWIGYINPYSAGSNYNEKFKDKATLTSDKSSSTAYMELRSL TSEDSAVYFCARSSYRYGFDYWGQGTTLTVSS | CL0020139 VH |
| 43 | DIQMTQSSSSFSVSLGDRVTITCKASEDIYNRLAWYQQKPGNA PRLLISGATSLETGVPSRFSGSGSGKDYTLSITSLQTEDVATY SCQQYVVSTPWTFGGGTKLEIK | CL0020139 VL |
| 44 | GYSFTSYLMN | CL0020139 CDR-H1 |
| 45 | YINPYSAGSNYNEKFKD | CL0020139 CDR-H2 |
| 46 | ARSSYRYGFDY | CL0020139 CDR-H3; CL0020304 CDR-H3; CL0020305 CDR-H3 |
| 47 | KASEDIYNRLA | CL0020139 CDR-L1; CL0020304 CDR-L1; CL0020305 CDR-L1 |
| 48 | GATSLET | CL0020139 CDR-L2; CL0020304 CDR-L2; CL0020305 CDR-L2 |
| 49 | QQYWSTPWT | CL0020139 CDR-L3; CL0020305 CDR-L3 |
| 50 | EVQLQQSGPELVKPGTSVKMSCKASGYSFPSFLIHWVKQKPGQ GLEWIGYINPYSDGSNYNEKFKGKATLTSDKSSSTAYMELSSL TSEDSAVYNCARSSYRYGFDYWGQGTTLSVSS | CL0020304 VH |
| 51 | DIQMTQSSSSFSVSLGDRVTITCKASEDIYNRLAWYQQKPGNA PRLLISGATSLETGVPSRFSGSGSGKNYTLSITSLQIEDVATY YCQQSWSIPWTFGGGTNLEIK | CL0020304 VL |
| 52 | GYSFPSFLIH | CL0020304 CDR-H1 |
| 53 | YINPYSDGSNYNEKFKG | CL0020304 CDR-H2 |
| 54 | GVQLQQSGPELVKPGASVKMSCKASGYKFTSYIIHWVNQKPGQ GLEWIGYINPYSDGTNYNEKFKGKATLTSDKSSSTAYMELSSL TSEDSAVYYCARSSYRYGFDYWGQGTTLTVSS | CL0020305 VH |
| 55 | DIQMTQSSSSFSVSLGDRVTITCKASEDIYNRLAWYQQKPGNA PRLLISGATSLETGVPSRFNGSGSGKDYTLSITSLQIEDVATY YCQQYWSTPWTFGGGTKLEIK | CL0020305 VH |
| 56 | GYKFTSYIIH | CL0020305 CDR-H1 |
| 57 | YINPYSDGTNYNEKFKG | CL0020305 CDR-H2 |
| 58 | EVKLLDSGGGLVQAGGSLRLSCAGSGFTFTDFYMSWIRQPPGK APEWLGVIRNKANGYTAGYNPSVKGRFTISRDNTQNILYLQMN TLRAEDTAIYYCARLSYGFDYWGQGVMVTVSS | CL0020306 VH |
| 59 | DIVMTQGALPNPVPSGESASITCQSSKSLLHSNGKTYLNWYLQ RPGQSPQLLIYWMSTRASGVSDRFSGSGSGTDFTLKISSVEAE DVGVYYCQQFLEFPFTFGSGTKLEIK | CL0020306 VL |
| 60 | GFTFTDFYMS | CL0020306 CDR-H1; CL0020164 CDR-H1; CDR-H1 for CL0020188 and variants CL0020188-1, |

| SEQ ID NO | Sequence | Description |
|---|---|---|
| | | CL0020188-2, CL0020188-3, CL0020188-4, CL0020188-5, CL0020188-6, CL0020188-7, and CL0020188-8 |
| 61 | VIRNKANGYTAGYNPSVKG | CL0020306 CDR-H2; CDR-H2 for CL0020188 and variants CL0020188-1, CL0020188-2, CL0020188-3, and CL0020188-4 |
| 62 | ARLSYGFDY | CL0020306 CDR-H3 |
| 63 | QSSKSLLHSNGKTYLN | CL0020306 CDR-L1; CL0020164 CDR-L1; CL0020307 CDR-L1; CL0020307-1 CDR-L1; CDR-L1 for CL0020188 and variants CL0020188-1, CL0020188-2, CL0020188-5, and CL0020188-6 |
| 64 | WMSTRAS | CL0020306 CDR-L2; CL0020307 CDR-L2; CL0020307-1 CDR-L2; CL0020164 CDR-L2; CDR-L2 for CL0020188 and variants CL0020188-1, CL0020188-2, CL0020188-3, CL0020188-4, CL0020188-5, CL0020188-6, CL0020188-7, and CL0020188-8 |
| 65 | QQFLEFPFT | CL0020306 CDR-L3; CL0020307 CDR-L3; CL0020307-1 CDR-L3 |
| 66 | EVKLLESGGGLVQPGGSLRLSCAASGFTFTNFYMSWIRQPPGR APEWLGVIRNRPNGYTTDYNPSVKGRFTISRDNTQNILYLQMS TLRADDTAFYYCTRLTYGFDYWGQGVMVTVSS | CL0020307 VH |
| 67 | DIVMTQGALPNPVPSGESASITCQSSKSLLHSNGKTYLNWYLQ RPGQSPQLLIYWMSTRASGVSDRFSGSGSGTDFTLKISSVEAE VVGVYYCQQFLEFPFTFGSGTKLEIK | CL0020307 VL |
| 68 | GFTFTNFYMS | CL0020307 CDR-H1 |
| 69 | VIRNRPNGYTTDYNPSVKG | CL0020307 CDR-H2 |
| 70 | TRLTYGFDY | CL0020307 CDR-H3 |
| 71 | EVKLLDSGGGLVQAGGSLRLSCAGSGFTFTDFYMSWIRQPPGK APEWLGVIRNKANGYTAGYNPSVKGRFTISRDNTQNILYLQMN TLRAEDTAIYYCARLTYGFDYWGQGVMVTVSS | CL0020188 VH |
| 72 | DIVMTQGALPNPVPSGESASITCQSSKSLLHSNGKTYLNWYLQ RPGQSPQLLIYWMSTRASGVSDRFSGSGSGTDFTLKISSVEAE DVGVYYCQQFLEYPFTFGSGTKLEIK | CL0020188 VL |
| 73 | ARLTYGFDY | CDR-H3 for CL0020188 and variants CL0020188-1, CL0020188-2, CL0020188-3, CL0020188-4, CL0020188-5, CL0020188-6, CL0020188-7, and CL0020188-8; CL0020164 CDR-H3 |
| 74 | QQFLEYPFT | CDR-L3 for CL0020188 and variants CL0020188-1, CL0020188-2, CL0020188-3, CL0020188-4, CL0020188-5, CL0020188-6, CL0020188-7, and CL0020188-8 |

INFORMAL SEQUENCE LISTING

| SEQ ID NO | Sequence | Description |
|---|---|---|
| 75 | EVQLVESGGGLVQPGGSLRLSCAASGFTFTDFYMSWVRQAPGKGLEWVSVIRNKANGYTAGYNPSVKGRFTISRDNSKNTLYLQMNSLRAEDTAVYYCARLTYGFDYWGQGTLVTVSS | CL0020188-1 VH; CL0020188-3 VH |
| 76 | DIVMTQTPLSLPVTPGEPASISCQSSKSLLHSNGKTYLNWYLQKPGQSPQLLIYWMSTRASGVPDRFSGSGSGTDFTLKISRVEAEDVGVYYCQQFLEYPFTFGQGTKVEIK | CL0020188-1 VL; CL0020188-2 VL; CL0020188-5 VL; CL0020188-6 VL |
| 77 | EVQLVESGGGLVQPGGSLRLSCAGSGFTFTDFYMSWVRQAPGKGLEWVSVIRNKANGYTAGYNPSVKGRFTISRDNSKNTLYLQMNSLRAEDTAVYYCARLTYGFDYWGQGTLVTVSS | CL0020188-2 VH |
| 78 | DIVMTQTPLSLPVTPGEPASISCQSSKSLLHSTGKTYLNWYLQKPGQSPQLLIYWMSTRASGVPDRFSGSGSGTDFTLKISRVEAEDVGVYYCQQFLEYPFTFGQGTKVEIK | CL0020188-3 VL; CL0020188-4 VL; CL0020188-7 VL; CL0020188-8 VL |
| 79 | QSSKSLLHSTGKTYLN | CDR-L1 for variants CL0020188-3, CL0020188-4, CL0020188-7, and CL0020188-8 |
| 80 | EVQLVESGGGLVQPGGSLRLSCAASGFTFTDFYMSWVRQAPGKGLEWVSVIRNKANAYTAGYNPSVKGRFTISRDNSKNTLYLQMNSLRAEDTAVYYCARLTYGFDYWGQGTLVTVSS | CL0020188-5 VH; CL0020188-7 VH |
| 81 | VIRNKANAYTAGYNPSVKG | CDR-H2 for variants CL0020188-5, CL0020188-6, CL0020188-7, and CL0020188-8 |
| 82 | EVQLVESGGGLVQPGGSLRLSCAGSGFTFTDFYMSWVRQAPGKGPEWLSVIRNKANAYTAGYNPSVKGRFTISRDNSKNTLYLQMNSLRAEDTAVYYCARLTYGFDYWGQGTLVTVSS | CL0020188-6 VH; CL0020188-8 VH |
| 83 | QVQLKQSGPSLVQPSQSLSITCTVSGFSLTTYGIHWVRQSPGKGLEWLGVIWTGGSTAFNAAFMSRLSITKDNSKSQVFFKMNSLQADDTAIYYCAKVGFHSATDYWGQGTSVTVSS | CL0020308 VH |
| 84 | DVLMTQTPLSLPVTLGDQASISCRSSQNLVHSNGNTYLEWYLQKPGQSPKLLIYKVSNRFSGVPDRFSGSGSGTDFTLKISRVEAEDLGLYYCFQGSHVPFTFGSGTKLEIK | CL0020308 VL |
| 85 | GFSLTTYGIH | CL0020308 CDR-H1 |
| 86 | VIWTGGSTAFNAAFMS | CL0020308 CDR-H2 |
| 87 | AKVGFHSATDY | CL0020308 CDR-H3 |
| 88 | RSSQNLVHSNGNTYLE | CL0020308 CDR-L1 |
| 89 | KVSNRFS | CL0020308 CDR-L2; CL0020309 CDR-L2; CL0020310 CDR-L2; CL0020313 CDR-L2; CL0020314 CDR-L2; CL0020125 CDR-L2 |
| 90 | FQGSHVPFT | CL0020308 CDR-L3; CL0020310 CDR-L3; CL0020313 CDR-L3 |
| 91 | QVQLKQSGPSLVQPSQSLSITCTVSGFSLTSYGVQWVRQSPGKGLEWLGVIWTGGTTDFNAAFKSRLSITKDNSKSQVFFKMNSLQADDSAIYYCAKIGFHSAVDYWGQGTSVTVSS | CL0020309 VH |
| 92 | DVLMTQTPLSLPVSLGDQASISCRSSQNIVHSNGNTYLEWYLQKPGQSPKLLIYKVSNRFSGVPDRFSGSGSGTDFTLKINRVEAEDLGLYYCFQGSHIPFTFGSGTQLEIK | CL0020309 VL |
| 93 | GFSLTSYGVQ | CL0020309 CDR-H1 |
| 94 | VIWTGGTTDFNAAFKS | CL0020309 CDR-H2 |

-continued

INFORMAL SEQUENCE LISTING

| SEQ ID NO | Sequence | Description |
|---|---|---|
| 95 | AKIGFHSAVDY | CL0020309 CDR-H3 |
| 96 | RSSQNIVHSNGNTYLE | CL0020309 CDR-L1; CL0020310 CDR-L1 |
| 97 | FQGSHIPFT | CL0020309 CDR-L3 |
| 98 | QVQLKQSGPSLVQPSQSLSITCTVSGFSLTTYGVHWVRQSPGK GLEWLGVIWTGGSTAYNAAFMSRLSITKDNSKSQVFFKMNSLQ ADDTAIYYCAKVGFHSAMDYWDQGTSVTVSS | CL0020310 VH |
| 99 | DVLMTQTPLSLPVSLGDQASISCRSSQNIVHSNGNTYLEWYLQ KPGQSPKLLIYKVSNRFSGVPDRFSGSGSGTDFTLKISRVEAE DLGVYYCFQGSHVPFTFGSGTKLEIK | CL0020310 VL |
| 100 | GFSLTTYGVH | CL0020310 CDR-H1 |
| 101 | VIWTGGSTAYNAAFMS | CL0020310 CDR-H2 |
| 102 | AKVGFHSAMDY | CL0020310 CDR-H3 |
| 103 | EVQLQQSGAELVRSGASVKLSCTASGFSIEDFYIHWVKQRPEQ GLEWIGWIDPENGDSKYAPKFQGKATMTADTSSNTAYLHLSSL TSEDTAVYYCHADHGNYGSTMDYWGQGTSVTVSS | CL0020123 VH |
| 104 | DIQMNQSPSSLSASLGDTVTITCHASQHINVWLSWYQQKPGDH PKLLIYKASNLHTGVPSRFSGSGSGTGFTLTISSLQPEDIATY YCQQGQTYPRTFGGGTKLEIK | CL0020123 VL |
| 105 | GFSIEDFYIH | CDR-H1 for CL0020123 and variants CL0020123-1, CL0020123-2, CL0020123-3, CL0020123-4, CL0020123-5, CL0020123-6, CL0020123-7, and CL0020123-8 |
| 106 | WIDPENGDSKYAPKFQG | CDR-H2 for CL0020123 and variants CL0020123-1 and CL0020123-2 |
| 107 | HADHGNYGSTMDY | CDR-H3 for CL0020123 and variants CL0020123-1, CL0020123-2, CL0020123-3, CL0020123-4, CL0020123-5, CL0020123-6, CL0020123-7, and CL0020123-8 |
| 108 | HASQHINVWLS | CDR-L1 for CL0020123 and variants CL0020123-1, CL0020123-2, CL0020123-3, CL0020123-4, CL0020123-5, CL0020123-6, CL0020123-7, and CL0020123-8 |
| 109 | KASNLHT | CDR-L2 for CL0020123 and variants CL0020123-1, CL0020123-2, CL0020123-3, CL0020123-4, CL0020123-5, CL0020123-6, CL0020123-7, and CL0020123-8 |
| 110 | QQGQTYPRT | CDR-L3 for CL0020123 and variants CL0020123-1, CL0020123-2, CL0020123-3, CL0020123-4, CL0020123-5, CL0020123-6, CL0020123-7, and CL0020123-8 |
| 111 | QVQLVQSGAEVKKPGASVKVSCKASGFSIEDFYIHWVRQAPGQ GLEWMGWIDPENGDSKYAPKFQGRATITADTSTSTAYMELSSL RSEDTAVYYCHADHGNYGSTMDYWGQGTLVTVSS | CL0020123-1 VH |

-continued

INFORMAL SEQUENCE LISTING

| SEQ ID NO | Sequence | Description |
|---|---|---|
| 112 | DIQMTQSPSSLSASVGDRVTITCHASQHINVWLSWYQQKPGKA PKLLIYKASNLHTGVPSRFSGSGSGTDFTLTISSLQPEDFATY YCQQGQTYPRTFGQGTKVEIK | CL0020123-1 VL; CL0020123-2 VL; CL0020123-3 VL; CL0020123-4 VL CL0020123-5 VL; CL0020123-6 VL; CL0020123-7 VL; CL0020123-8 VL |
| 113 | QVQLVQSGAEVKKPGASVKVSCKASGFSIEDFYIHWVRQAPGQ GLEWMGWIDPENGDSKYAPKFQGRVTITADTSTSTAYMELSSL RSEDTAVYYCHADHGNYGSTMDYWGQGTLVTVSS | CL0020123-2 VH |
| 114 | QVQLVQSGAEVKKPGASVKVSCKASGFSIEDFYIHWVRQAPGQ GLEWMGWIDPEQGDSKYAPKFQGRATITADTSTSTAYMELSSL RSEDTAVYYCHADHGNYGSTMDYWGQGTLVTVSS | CL0020123-3 VH |
| 115 | WIDPEQGDSKYAPKFQG | CDR-H2 for variants CL0020123-3 and CL0020123-6 |
| 116 | QVQLVQSGAEVKKPGASVKVSCKASGFSIEDFYIHWVRQAPGQ GLEWMGWIDPENGESKYAPKFQGRATITADTSTSTAYMELSSL RSEDTAVYYCHADHGNYGSTMDYWGQGTLVTVSS | CL0020123-4 VH |
| 117 | WIDPENGESKYAPKFQG | CDR-H2 for variants CL0020123-4 and CL0020123-7 |
| 118 | QVQLVQSGAEVKKPGASVKVSCKASGFSIEDFYIHWVRQAPGQ GLEWMGWIDPEQGESKYAPKFQGRATITADTSTSTAYMELSSL RSEDTAVYYCHADHGNYGSTMDYWGQGTLVTVSS | CL0020123-5 VH |
| 119 | WIDPEQGESKYAPKFQG | CDR-H2 for variants CL0020123-5 and CL0020123-8 |
| 120 | QVQLVQSGAEVKKPGASVKVSCKASGFSIEDFYIHWVRQAPGQ GLEWMGWIDPEQGDSKYAPKFQGRVTITADTSTSTAYMELSSL RSEDTAVYYCHADHGNYGSTMDYWGQGTLVTVSS | CL0020123-6 VH |
| 121 | QVQLVQSGAEVKKPGASVKVSCKASGFSIEDFYIHWVRQAPGQ GLEWMGWIDPENGESKYAPKFQGRVTITADTSTSTAYMELSSL RSEDTAVYYCHADHGNYGSTMDYWGQGTLVTVSS | CL0020123-7 VH |
| 122 | QVQLVQSGAEVKKPGASVKVSCKASGFSIEDFYIHWVRQAPGQ GLEWMGWIDPEQGESKYAPKFQGRVTITADTSTSTAYMELSSL RSEDTAVYYCHADHGNYGSTMDYWGQGTLVTVSS | CL0020123-8 VH |
| 123 | EVKLVESGGGLVQPGGSLRLSCATSGFTFTDYYMSWVRQPPGK ALEWLGFIRNKANGYTTEYSASVKGRFTISRDISQSILYLQMN TLRAEDSATYYCARVLRAQGFAYWGQGTLVTVSA | CL0020311 VH |
| 124 | DIVMSQSPSSLAVSVGEKVTMSCKSSQSLLYSSNQKNYLAWYQ QKPGQSPKLLIYWASTRESGVPDRFTGSGSGTDFTLTISSVKA EDLAVYYCQQYYGYPFTFGSGTKLEIK | CL0020311 VL |
| 125 | GFTFTDYYMS | CL0020311 CDR-H1; CL0020312 CDR-H1; CL0020141 CDR-H1 |
| 126 | FIRNKANGYTTEYSASVKG | CL0020311 CDR-H2 |
| 127 | ARVLRAQGFAY | CL0020311 CDR-H3; CL0020312 CDR-H3 |
| 128 | KSSQSLLYSSNQKNYLA | CL0020311 CDR-L1; CL0020312 CDR-L1 |
| 129 | QQYYGYPFT | CL0020311 CDR-L3 |

| INFORMAL SEQUENCE LISTING | | |
|---|---|---|
| SEQ ID NO | Sequence | Description |
| 130 | EVKLVESGGGLVQPGGSLRLSCSTSGFTFTDYYMSWVRQPPGK ALEWLGFIRNKANGYTTDYSASVKGRFTISRDNSQNILYLQMN TLRAEDSATYYCARVLRAQGFAYWGQGTLVAVSA | CL0020312 VH |
| 131 | DIVMSQSPSSLAVPVGEKVTMSCKSSQSLLYSSNQKNYLAWYQ QKPGQSPKLLIYWASTRESGVPDRFTGSGSGTDFTLTISSVKA EDLAIYYCQQYYGNPFTFGSGTKLDIK | CL0020312 VL |
| 132 | FIRNKANGYTTDYSASVKG | CL0020312 CDR-H2 |
| 133 | QQYYGNPFT | CL0020312 CDR-L3 |
| 134 | EVTLVESGGGLVQPGGSLRLSCATSGFTFTDYYMSWVRQPPGK ALEWLGFIRDKANGYTTDYSASVKGRFTISRDNSQNILYLQMN TLRAEDSATYYCSRLLRAQGFAYWGQGTLVTVSA | CL0020141 VH |
| 135 | DIVMSQSPSSLGVSIGEKVIMSCTSGQSLLYSNNQKNYLAWYQ QKPGQSPKLLIYWASTRESGVPDRFTGSGSGTDFTLTINSVKA EDLAVYYCQQYRNPFTFGSGTKLEIK | CL0020141 VL |
| 136 | FIRDKANGYTTDYSASVKG | CL0020141 CDR-H2 |
| 137 | SRLLRAQGFAY | CL0020141 CDR-H3 |
| 138 | TSGQSLLYSNNQKNYLA | CL0020141 CDR-L1 |
| 139 | QQYYRNPFT | CL0020141 CDR-L3 |
| 140 | EVQLQQSGPELVKPGASVKISCKTSGYTFTEYTMHWVKESHGK SLEWIGGINPNKGGSSYNQKFKGKATLTVDKSSSTAYMDLRRL TSEDSAVYYCARGGYEYYALDYWGQGTSVTVSS | CL0020103 VH |
| 141 | DIVMSQSPSSLTVSVGERVTMSCKSSQSLLYSRNQKNYLAWYQ QKPGQSPKLLIYWASTRESGVPDRFTGSGSGTDFSLTISSVKA EDLAVYYCQQYSYPPTFGGGTKLEIK | CL0020103 VL |
| 142 | GYTFTEYTMH | CL0020103 CDR-H1 |
| 143 | GINPNKGGSSYNQKFKG | CL0020103 CDR-H2 |
| 144 | ARGGYEYYALDY | CL0020103 CDR-H3 |
| 145 | KSSQSLLYSRNQKNYLA | CL0020103 CDR-L1 |
| 146 | QQYSYPPT | CL0020103 CDR-L3; CL0020096 CDR-L3 |
| 147 | EVQLQQSGPVLVKPGASVRMSCKPSGYTFTDYYMNWVKQSHGK SLEWIGSINPYTGGSSYNQNFRGKATLTVDKSSSTAYMELNSL TSEDSAVYYCARGSYYSNLGFAYWGQGTLVTVSA | CL0020201 VH |
| 148 | DVQLTQSPSFLTASPGETITINCRASKSISKYLAWYQEKPGKT NKLLISSGSTLQSGIPSRFSGSGSGTDFTLTISSLEPEDFAMY YCQQYSEYPFTFGSGTKLEIK | CL0020201 VL |
| 149 | GYTFTDYYMN | CL0020201 CDR-H1; CL0020206 CDR-H1; CL0020124 CDR-H1 |
| 150 | SINPYTGGSSYNQNFRG | CL0020201 CDR-H2 |
| 151 | ARGSYYSNLGFAY | CL0020201 CDR-H3; CL0020124 CDR-H3 |
| 152 | RASKSISKYLA | CL0020201 CDR-L1; CL0020124 CDR-L1 |
| 153 | SGSTLQS | CL0020201 CDR-L2; CL0020124 CDR-L2 |
| 154 | QQYSEYPFT | CL0020201 CDR-L3; CL0020124 CDR-L3 |

INFORMAL SEQUENCE LISTING

| SEQ ID NO | Sequence | Description |
|---|---|---|
| 155 | EVQLQQSGPELVRTGASVKISCRASSYSFTDNYIHWVKQTHGR SLEWIGYISGYTGATSYNQKFKGKATFTVDTSSSTAYMQFNSL TSEDSAVYYCARSTMIAPYGMDYWGQGTSVTSS | CL0020120 VH |
| 156 | DIVMTQSHKFMSTSVGDRVNITCKASQDVVTAVAWYQQKPGQS PKLLIYWASTRHTGVPDRFTGSGSGTDFTLTISNVQSEDLADY FCQQYSRYPLTFGAGTKLELK | CL0020120 VL |
| 157 | SYSFTDNYIH | CL0020120 CDR-H1 |
| 158 | YISGYTGATSYNQKFKG | CL0020120 CDR-H2 |
| 159 | ARSTMIAPYGMDY | CL0020120 CDR-H3 |
| 160 | KASQDVVTAVA | CL0020120 CDR-L1 |
| 161 | WASTRHT | CL0020120 CDR-L2; CL0020127 CDR-L2 |
| 162 | QQYSRYPLT | CL0020120 CDR-L3 |
| 163 | EVQLQQSGPVLVKPGASVKMSCKASGYKFTDYYMNWVKQSHGK SLEWIGTINPYSGGISYNQKFKGKATLTVDKSSSTAYMELNSL TSEASAVYYCTRRNWDGRYAMDYWGQGTSVTSS | CL0020127 VH |
| 164 | DIVMTQSHKFMSTSVGDRVSITCKASQDVSTAVAWYQQKPGQS PKLLIYWASTRHTGVPDRFTGSGSGTDFTLTISNVQSEDLAEY FCQQYSSYPFTFGGGTKLEIK | CL0020127 VL |
| 165 | GYKFTDYYMN | CL0020127 CDR-H1 |
| 166 | TINPYSGGISYNQKFKG | CL0020127 CDR-H2 |
| 167 | TRRNWDGRYAMDY | CL0020127 CDR-H3; CL0020206 CDR-H3 |
| 168 | KASQDVSTAVA | CL0020127 CDR-L1 |
| 169 | QQYSSYPFT | CL0020127 CDR-L3; CL0020206 CDR-L3 |
| 170 | EVQLQQSGPVLVKPGASLKMSCRASGYTFTDYYVHWVKQSHGK SLEWIGLINPYTGTTSYNQRFKGKATLTVDKSSSTAYMEVNSL TSEDSAVYYCARSRVYYGSSLFAFWGQGTLVTVSA | CL0020109 VH |
| 171 | DIVMTQSPSSLSVSAGEKVTMSCKSSQSLLNSGNQKNYLAWYQ QKPGQPPKLLIYGASTRESGVPDRFTGSGSGTDFTLTISSVQA EDLAVYYCQNDHSYPYTFGGGTKLEIK | CL0020109 VL; CL0020205 VH |
| 172 | GYTFTDYYVH | CL0020109 CDR-H1; CL0020205 CDR-H1 |
| 173 | LINPYTGTTSYNQRFKG | CL0020109 CDR-H2 |
| 174 | ARSRVYYGSSLFAF | CL0020109 CDR-H3; CL0020205 CDR-H3 |
| 175 | KSSQSLLNSGNQKNYLA | CL0020109 CDR-L1; CL0020205 CDR-L1 |
| 176 | GASTRES | CL0020109 CDR-L2; CL0020205 CDR-L2 |
| 177 | QNDHSYPYT | CL0020109 CDR-L3; CL0020205 CDR-L3 |
| 178 | QVRLQQSGAELVRPGSSVKLSCKASGYAFSSYWMNWVKQRPGQ GLEWIGQIYPGDGDTNYNGNFKGKATLTADNSSSTAYMQLSSL TSEDSAVYFCARRRNGDFGDYAMDYWGQGTSVTSS | CL0020214 VH |
| 179 | QIVLTQSPAIMSASPGEKVTISCSASSSVSYMCWYQQKPGSSP KPWIYRTSTLASGVPARFSGSGSGTSYSLTISSMEAADAATYY CQHYSYPFTFGAGTKLELK | CL0020214 VL |

-continued

INFORMAL SEQUENCE LISTING

| SEQ ID NO | Sequence | Description |
|---|---|---|
| 180 | GYAFSSYWMN | CL0020214 CDR-H1 |
| 181 | QIYPGDGDTNYNGNFKG | CL0020214 CDR-H2 |
| 182 | ARRRNGDFGDYAMDY | CL0020214 CDR-H3 |
| 183 | SASSSVSYMC | CL0020214 CDR-L1 |
| 184 | WIYRTST | CL0020214 CDR-L2 |
| 185 | YYCQHYHSY | CL0020214 CDR-L3 |
| 186 | QIQLVQSGPELRKPGETVKISCKASGYTFTTYGMSWVKQAPGKGLKWMGWINTYSGLPRHSDDFKGRFAFSLETSASTAYLQINNLKNEDTATYFCAREVYYGSRKTAWFAYWGQGTLVTVSA | CL0020096 VH; CL0020210 VH |
| 187 | DLVMSQSPSSLAVSVGERVTMSCKSSQSLLYSNDQKNYLAWYQQIPGQSPKLLIYWASTRESGVPDRFTGSGSGTDFTLTISSVKAEDLAVYFCQQYYSYPPTFGAGTKLELK | CL0020096 VL |
| 188 | GYTFTTYGMS | CL0020096 CDR-H1; CL0020210 CDR-H1 |
| 189 | WINTYSGLPRHSDDFKG | CL0020096 CDR-H2; CL0020210 CDR-H2 |
| 190 | AREVYYGSRKTAWFAY | CL0020096 CDR-H3; CL0020210 CDR-H3 |
| 191 | KSSQSLLYSNDQKNYLA | CL0020096 CDR-L1; CL0020210 CDR-L1 |
| 192 | DLVMSQSPSSLAVSVGERITMTCKSSQSLLYSNDQKNYLAWYQQIPGQSPKLLLYWASTRESGVPDRFTGSGSGTDFTLTISSVKAEDLAVYFCQQYYNYPPTFGAGTKLELK | CL020210 VL |
| 193 | QQYYNYPPT | CL0020210 CDR-L3 |
| 194 | QVQLKQSGPGLLQPSQSLSITCTVSGFSLTSYGVHWVRQSPGKGLEWLGVIWSGGITLYNAAFMSRLSITKDNSKSQVFFKMNSLQADDTAIYYCAKVGYGSSSDYWGQGTTLTVSS | CL0020313 VH |
| 195 | DVLMTQSPLSLPVSLGDQASFSCRSSQSIVHSNGNTYLEWYLQKPGQSPKLLIYKVSNRFSGVPDRFSGSGSGTDFTLKISRVEAEDLGVYYCFQGSHVPFTFGSGTKLEIK | CL0020313 VL |
| 196 | GFSLTSYGVH | CL0020313 CDR-H1 |
| 197 | VIWSGGITLYNAAFMS | CL0020313 CDR-H2 |
| 198 | AKVGYGSSSDY | CL0020313 CDR-H3 |
| 199 | RSSQSIVHSNGNTYLE | CL0020313 CDR-L1 |
| 200 | DVKLVESGGGLVKLGGSLKLSCAASGFTFSSYYMSWVRQTPEKRLELVAAINTNGGRTYYPDTVKGRFTISRDNAKNTLYLQMSSLKSEDTALYYCARESDGGAFAYWGQGTLVTVSA | CL0020314 VH |
| 201 | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQNTHVPLTFGAGTKLELK | CL0020314 VL |
| 202 | GFTFSSYYMS | CL0020314 CDR-H1 |
| 203 | AINTNGGRTYYPDTVKG | CL0020314 CDR-H2 |
| 204 | ARESDGGAFAY | CL0020314 CDR-H3 |
| 205 | RSSQSLVHSNGNTYLH | CL0020314 CDR-L1; CL0020315 CDR-L1 |
| 206 | SQNTHVPLT | CL0020314 CDR-L3 |

INFORMAL SEQUENCE LISTING

| SEQ ID NO | Sequence | Description |
|---|---|---|
| 207 | EVQLQQSGPELVKPGASVKISCKASGYTFTDYNIHWVKQSHGK SLEWIGYIYPYNGVTGYNQKFKSKATLTVDNSSSTAYMELRSL TSEDSAVYYCARSRVDGDYWGQGTTLTVSS | CL0020315 VH |
| 208 | DVVMTQTPLSLPVSLGDQASISCRSSQSLVHSNGNTYLHWYLQ KPGQSPKLLIYKISNRFSGVPDRFSGSGSGTDFTLKISRVEAE DLGVYFCSQSTHVPLTFGAGTKLELK | CL0020315 VL |
| 209 | YIYPYNGVTGYNQKFKS | CL0020315 CDR-H2 |
| 210 | ARSRVDGDY | CL0020315 CDR-H3 |
| 211 | KISNRFS | CL0020315 CDR-L2 |
| 212 | SQSTHVPLT | CL0020315 CDR-L3; CL0020125 CDR-L3 |
| 213 | EVQLQQSGPVLVKPGASVKMSCKASGYTFTDYYVHWVKQSHGK SLEWIGLINPYTGTTSYNQRFRVKATLTVDKSSSTAYMEVNSL TSEDSAVYYCARSRVYYGSSLFAFWGQGTLVTVSA | CL0020205 VH |
| 214 | GLINPYTGTTSYNQRFRV | CL0020205 CDR-H2 |
| 215 | EVQLQQSGPVLVKPGASVKMSCKASGYTFTDYYMNWVKQSHGK SLEWIGIINPYSGGISYNQKFKGKAILTVDKSSSTAYMELNSL TSEASAVYYCTRRNWDGRYAMDYWGQGTSVTVSS | CL0020206 VH |
| 216 | DIVMTQSHKFMSTSVGDRVSITYKASQDVGSAVAWYQQKPGQS PKLLIYWTSTRHTGVPDRFTGSGSGTDFTLTISNVQSEDLADY FCQQYSSYPFTFGGGTKLEIK | CL0020206 VL |
| 217 | IINPYSGGISYNQKFKG | CL0020206 CDR-H2 |
| 218 | KASQDVGSAVA | CL0020206 CDR-L1 |
| 219 | WTSTRHT | CL0020206 CDR-L2 |
| 220 | QVQLQQPGADLVKPGASVKMSCKASGYTFTNYWITWVQQRPGQ GLEWIGDIYPGSGNTNYNEKFRSKATLTVDTSSNTAYMQLSSL TSEDSAVYYCSREGYGISAWGQGTTLTVSS | CL0020111 VH |
| 221 | QIVLTQSPAFMSASPGEKVTITCRASSSVSYMHWFQQKPGTSP KLWIFSTSNLASGVPARFSGSGSGTSHSLTISRMEAEDAATYY CQQRSGYPLTFGAGTKLELK | CL0020111 VL |
| 222 | GYTFTNYWIT | CL0020111 CDR-H1 |
| 223 | DIYPGSGNTNYNEKFRS | CL0020111 CDR-H2 |
| 224 | RASSSVSYMH | CL0020111 CDR-L1 |
| 225 | QQRSGYPLT | CL0020111 CDR-L3 |
| 226 | EVQLVESGGGLVQPGKSLKLSCAASGFTFSYYGMAWVRQAPTK GLEWVASISTGGGNTYYRDSVKGRFTISRGNAKNTLYLQMDSL RSEDTATYYCARGDIGTSYWFTYWGQGTLVTVSS | CL0020112 VH |
| 227 | DIQLTQSPSLLSASVGDRVTLSCKGSQTINNYLAWYQQKLGEA PKLLIYKTNSLQTGIPSRFSGSGSGTDYTLTISSLHSEDLATY YCYQYNNGWTFGGGTKLELK | CL0020112 VL |
| 228 | GFTFSYYGMA | CL0020112 CDR-H1; CL0020183 CDR-H1; CL0020186 CDR-H1 |
| 229 | SISTGGGNTYYRDSVKG | CL0020112 CDR-H2; CL0020183 CDR-H2; CL0020186 CDR-H2 |
| 230 | ARGDIGTSYWFTY | CL0020112 CDR-H3 |
| 231 | KGSQTINNYLA | CL0020112 CDR-L1 |

INFORMAL SEQUENCE LISTING

| SEQ ID NO | Sequence | Description |
|---|---|---|
| 232 | KTNSLQT | CL0020112 CDR-L2; CL0020183 CDR-L2 |
| 233 | YQYNNGWT | CL0020112 CDR-L3; CL0020183 CDR-L3; CL0020186 CDR-L3 |
| 234 | EVQLQQSGPVLVKPGASVKMSCKPSGYTFTDYYMNWVKQSHGK SLEWIGSINPYTGGSSYNQKFRGKATLTVDKSSSTAYMELNSL TSEDSAVYYCARGSYYSNLGFAYWGQGTLVTVSA | CL0020124 VH |
| 235 | DVQLTQSPSYLTASPGETITINCRASKSISKYLAWYQEKPGKT NKLLISSGSTLQSGIPSRFSGSGSGTDFTLTISSLEPEDFAMY YCQQYSEYPFTFGSGTKLEIK | CL0020124 VL |
| 236 | SINPYTGGSSYNQKFRG | CL0020124 CDR-H2 |
| 237 | QVQLQQSGAELARPGASVKLSCKASGYTFTSYALSWVKQRTGQ GLEWIGEIYPRSGNTYSNEKFKGKATLTADKSSSTAYMELRSL TSEDSAVYFCAKGGVYYGSSYWYFDVWGTGTTVTSS | CL0020125 VH |
| 238 | DVVMTQTPLSLPVSLGDQASISCSSSQSLVHSNGNTYLHWYLQ KPGQSPKLLIYKVSNRFSGVPDRFSGTESGTDFTLKISRVEAE DLGVYFCSQSTHVPLTFGAGTKLELK | CL0020125 VL |
| 239 | GYTFTSYALS | CL0020125 CDR-H1 |
| 240 | EIYPRSGNTYSNEKFKG | CL0020125 CDR-H2 |
| 241 | AKGGVYYGSSYWYFDV | CL0020125 CDR-H3 |
| 242 | SSSQSLVHSNGNTYLH | CL0020125 CDR-L1 |
| 243 | EVQLVESGGGLVQPGRSLKLSCAASGFTFSYYGMAWVRQAPTK GLEWVASISTGGGNTYYRDSVKGRFTISRDNAKNTLYLQMDSL RSEDTATYYCARGDIGTTYWFTYWGQGTLVTVSS | CL0020183 VH |
| 244 | NIQLTQSPSLLSASVGDRVTLSCKGSQNINNYLAWYQQKLGEA PKLLIYKTNSLQTGIPSRFSGSGSGTDYTLTISSLHSEDLATY YCYQYNNGWTFGGGTKLELK | CL0020183 VL |
| 245 | ARGDIGTTYWFTY | CL0020183 CDR-H3 |
| 246 | KGSQNINNYLA | CL0020183 CDR-L1; CL0020186 CDR-L1 |
| 247 | EVQLVESGGGLVQPGRSLKLSCPASGFTFSYYGMAWVRQAPTK GLEWVASISTGGGNTYYRDSVKGRFTISRDNAKNTLYLQMDSL RSEDTATYYCARGDIGTAYWFTYWGQGTLVTVSS | CL0020186 VH |
| 248 | NIQLTQSPSLLSASVGDRVTLSCKGSQNINNYLAWYQQKLGEA PKLLIYKTNSLLTGIPSRFSGSGSGTDYTLTISSLHSEDLATY YCYQYNNGWTFGGGTKLELK | CL0020186 VL |
| 249 | ARGDIGTAYWFTY | CL0020186 CDR-H3 |
| 250 | KTNSLLT | CL0020186 CDR-L2 |
| 251 | QIQLVQSGPELKKPGESLKISCKASGYTFTDYAMQWVKQAPGK GLQYMGWINTQTGKPTYADDFKERFVFSLETSASTAYLKINNL KNDDMATYLCARSYGGEYNWIAYWGQGTLVTVSS | CL0020113 VH |
| 252 | DIVMTQTPSSQAVSAGEKVTMNCKSSQSLLYNENKKNYLAWYQ QKPGQSPKLLIYWASTRESGVPDRFIGSGSGTDFTLTISSVQA EDLAVYYCQQSYNFPPTFGGGTKLELK | CL0020113 VL |
| 253 | GYTFTDYAMQ | CL0020113 CDR-H1; CL0020162 CDR-H1 |
| 254 | WINTQTGKPTYADDFKE | CL0020113 CDR-H2; CL0020162 CDR-H2 |
| 255 | ARSYGGEYNWIAY | CL0020113 CDR-H3 |

INFORMAL SEQUENCE LISTING

| SEQ ID NO | Sequence | Description |
|---|---|---|
| 256 | KSSQSLLYNENKKNYLA | CL0020113 CDR-L1 |
| 257 | QQSYNFPPT | CL0020113 CDR-L3 |
| 258 | QIQLVQSGPELKKPGESLKISCKASGYTFTDYAMQWVKQAPEKGLQYMGWINTQTGKPTYADDFKERFVFSLETSATTAYLQINNLKNEDMATYFCVRSYNNYENWFAYWGQGTLVTVSS | CL0020162 VH |
| 259 | DIVMTQSPSSLAVSAGETVTINCKSSQSLLYSGNQKNYLAWYQQKPGQSPKVLIYWASTRQFGVPDRFIGSGSGTDFTLTISSVQAEDLAIYYCQQYYNSPITFGSGTKLEIK | CL0020162 VL |
| 260 | VRSYNNYENWFAY | CL0020162 CDR-H3 |
| 261 | KSSQSLLYSGNQKNYLA | CL0020162 CDR-L1 |
| 262 | WASTRQF | CL0020162 CDR-L2 |
| 263 | QQYYNSPIT | CL0020162 CDR-L3 |
| 264 | EVQLVESGGGLVQPGRSMMLSCSASGFTFSNYHMAWVRQAPTTGLEWVASITTGSGNTYYRHSVKGRFTISRDNAKSTLYLQMDSLRSEDTASYYCARRWYGGYEGYYFDYWGQGVMVTVSS | CL0020195 VH |
| 265 | DIQMTQSPSLLSASVGDRVTLSCKAGQNVNNYLAWYQQKLGEAPKLLIYNANILQTGFPSRFSGTGSGTDFTLTISSLQPEDVATYFCQQYNSWTTFGGGTKLELK | CL0020195 VL |
| 266 | GFTFSNYHMA | CL0020195 CDR-H1 |
| 267 | SITTGSGNTYYRHSVKG | CL0020195 CDR-H2 |
| 268 | ARRWYGGYEGYYFDY | CL0020195 CDR-H3 |
| 269 | KAGQNVNNYLA | CL0020195 CDR-L1 |
| 270 | NANILQT | CL0020195 CDR-L2 |
| 271 | QQYNSWTT | CL0020195 CDR-L3 |
| 272 | EVQLVESGGGLVQPGRSMKLSCAALGFTFSNYYMAWVRQAPRKGLEWVASISTGGDNTYYRDSVKGRFTISRDNAKSTLYMQMDSLRSEDTATYYCVRSFIVGTTGYYFDYWGQGVMVTVSS | CL0020161 VH |
| 273 | DIVLTQSPALAVSLGQRATISCKTNQNVDYYGNNYMHWYQQTPGQQPKLLIYFASNLASGIPARFSGRGSGTDFTLTIDPVEADDTATYYCQQSRNLPTFGGGTKLELK | CL0020161 VL |
| 274 | GFTFSNYYMA | CL0020161 CDR-H1 |
| 275 | SISTGGDNTYYRDSVKG | CL0020161 CDR-H2 |
| 276 | VRSFIVGTTGYYFDY | CL0020161 CDR-H3 |
| 277 | KTNQNVDYYGNNYMH | CL0020161 CDR-L1 |
| 278 | FASNLAS | CL0020161 CDR-L2 |
| 279 | QQSRNLPT | CL0020161 CDR-L3 |
| 280 | EVKLLESGGGLVQPGSSMRLSCAASGFTFTDFYMNWIRQPAGRAPEWLGFFRNIVDGYTTEYNPSVKGRFTISRDNTQNMLYLQMNTLRAEDTATYYCARSGYSSYIYGGTFAYWGQGTLVTVSS | CL0020173 VH |
| 281 | ETVMTQSPTSMSTSIGERVTLNCKASQSVGIHVDWYQQTPGQSPKLLIYGASNRHTGVPDRFTGSGFGRDFTLTISNVEAEDLAVYYCLQYGSIPWTFGGGTKLELK | CL0020173 VL |
| 282 | GFTFTDFYMN | CL0020173 CDR-H1 |
| 283 | FFRNIVDGYTTEYNPSVKG | CL0020173 CDR-H2 |
| 284 | ARSGYSSYIYGGTFAY | CL0020173 CDR-H3 |

INFORMAL SEQUENCE LISTING

| SEQ ID NO | Sequence | Description |
|---|---|---|
| 285 | KASQSVGIHVD | CL0020173 CDR-L1 |
| 286 | GASNRHT | CL0020173 CDR-L2 |
| 287 | LQYGSIPWT | CL0020173 CDR-L3 |
| 288 | EVKLLESGGGLVQPGGSLRLSCAASGFTFTDFYMSWIRQPPGK APEWLGVIRNKANGFTIEYNTSVKGRFTISRDYTQNILHLQTN TLRAEDTAIYYCARLTYGFDYWGQGVMVTVSS | CL0020164 VH |
| 289 | VIRNKANGFTTEYNTSVKG | CL0020164 CDR-H2 |
| 290 | QQFLELPFT | CL0020164 CDR-L3 |
| 291 | DIVMTQGALPNPVPSGESASITCQSSKSLLHSNGKTYLNWYLQ RPGQSPQFLIYWMSTRASGVSDRFSGSGSGTDFTLKISSVEAE DVGVYYCQQFLELPFTFGSGTKLEIK | CL0020164 VL |
| 292 | QQSWSIPWT | CL0020304 CDR-L3 |
| 293 | G-Y-T-F-T-$\alpha_6$-Y-$\alpha_8$-$\alpha_9$-$\alpha_{10}$, wherein $\alpha_6$ is N, S, or D; $\alpha_8$ is W or N; $\alpha_9$ is I or M; and $\alpha_{10}$ is S, T, M, or H | CDR-H1 consensus sequence |
| 294 | $\beta_1$-I-$\beta_3$-P-$\beta_5$-$\beta_6$-$\beta_7$-$\beta_8$-$\beta_9$-$\beta_{10}$-Y-N-$\beta_{13}$-$\beta_{14}$-F-$\beta_{16}$-$\beta_{17}$, wherein $\beta_1$ is D or Y; $\beta_3$ is Y or F; $\beta_5$ is H, G, S, N, or Y; $\beta_6$ is S or N; $\beta_7$ is T or G; $\beta_8$ is S, N, or G; $\beta_9$ is T or N; $\beta_{10}$ is N or G; $\beta_{13}$ is E or Q; $\beta_{14}$ is R or K; $\beta_{16}$ is R or K; and $\beta_{17}$ is S, G, or N | CDR-H2 consensus sequence |
| 295 | $\gamma_1$-R-$\gamma_3$-G-$\gamma_5$-G-$\gamma_7$-$\gamma_8$-$\gamma_9$, wherein $\gamma_1$ is A or S; $\gamma_3$ is E or S; $\gamma_5$ is F, Y, R, or T; $\gamma_7$ is I or F; $\gamma_8$ is S or A; and $\gamma_9$ is A or Y | CDR-H3 consensus sequence |
| 296 | $\delta_1$-A-$\delta_3$-$\delta_4$-$\delta_5$-V-$\delta_7$-$\delta_8$-Y-$\delta_{10}$-$\delta_{11}$, wherein $\delta_1$ is S or K; $\delta_3$ is T or S; $\delta_4$ is S or E; $\delta_5$ is S or N; $\delta_7$ is absent or G; $\delta_8$ is S or T; $\delta_{10}$ is M or V; and $\delta_{11}$ is H or S | CDR-L1 consensus sequence |
| 297 | $\delta_1$-S-S-$\delta_4$-S-L-L-$\delta_8$-S-$\delta_{10}$-N-$\delta_{12}$-$\delta_{13}$-$\delta_{14}$-Y-L-$\delta_{17}$, wherein $\delta_1$ is K or R; $\delta_4$ is Q or K; $\delta_8$ is N or H; $\delta_{10}$ is G or absent; $\delta_{12}$ is Q or G; $\delta_{13}$ is K or N; $\delta_{14}$ is N or T; and $\delta_{17}$ is T or Y | CDR-L1 consensus sequence |
| 298 | $\epsilon_1$-$\epsilon_2$-S-$\epsilon_4$-$\epsilon_5$-$\epsilon_6$-$\epsilon_7$, wherein $\epsilon_1$ is S, G, W or Q; $\epsilon_2$ is T, A, or M; $\epsilon_4$ is N or T; $\epsilon_5$ is L or R; $\epsilon_6$ is A, Y, or E; and $\epsilon_7$ is S or T | CDR-L2 consensus sequence |
| 299 | $\phi_1$-$\phi_2$-$\phi_3$-$\phi_4$-$\phi_5$-$\phi_6$-P-$\phi_8$-T, wherein $\phi_1$ is Q, G, or M; $\phi_2$ is Q or N; $\phi_3$ is R, S, D, or H; $\phi_4$ is S, Y, or L; $\phi_5$ is S or Q; $\phi_6$ is Y or F; and $\phi_8$ is L, F, or Y | CDR-L3 consensus sequence |
| 300 | G-Y-T-F-T-$\alpha_6$-Y-W-I-$\alpha_{10}$ wherein $\alpha_6$ is N or S; and $\alpha_{10}$ is S, T or M | CDR-H1 consensus sequence |
| 301 | D-I-Y-P-$\beta_5$-S-$\beta_7$-$\beta_8$-T-N-Y-N-E-$\beta_{14}$-F-$\beta_{16}$-$\beta_{17}$, wherein $\beta_5$ is H, G, or S; $\beta_7$ is T or G; $\beta_8$ is S or N; $\beta_{14}$ is R or K; $\beta_{16}$ is R or K; and $\beta_{17}$ is S or N | CDR-H2 consensus sequence |
| 302 | $\gamma_1$-R-E-G-$\gamma_5$-G-I-S-A, wherein $\gamma_1$ is A or S; and $\gamma_5$ is F or Y | CDR-H3 consensus sequence |
| 303 | $\delta_1$-A-$\delta_3$-$\delta_4$-$\delta_5$-V-$\delta_7$-$\delta_8$-Y-$\delta_{10}$-$\delta_{11}$, wherein $\delta_1$ is S or K; $\delta_3$ is T or S; $\delta_4$ is S or E; $\delta_5$ is S or N; $\delta_7$ is absent or G; $\delta_8$ is absent or T; $\delta_{10}$ is M or V; and $\delta_{11}$ is H or S | CDR-L1 consensus sequence |

-continued

INFORMAL SEQUENCE LISTING

| SEQ ID NO | Sequence | Description |
|---|---|---|
| 304 | $\epsilon_1$-$\epsilon_2$-S-N-$\epsilon_5$-$\epsilon_6$-$\epsilon_7$, wherein $\epsilon_1$ is S or G; $\epsilon_2$ is T or A; $\epsilon_5$ is L or R; $\epsilon_6$ is A or Y; and $\epsilon_7$ is S or T | CDR-L2 consensus sequence |
| 305 | $\phi_1$-Q-$\phi_3$-$\phi_4$-S-$\phi_6$-P-$\phi_8$-T, wherein $\phi_1$ is Q or G; $\phi_3$ is R or S; $\phi_4$ is S or Y; $\phi_6$ is Y or F; and $\phi_8$ is L or F | CDR-L3 consensus sequence |
| 306 | G-Y-$\alpha_3$-F-$\alpha_5$-S-$\alpha_7$-$\alpha_8$-$\alpha_9$-$\alpha_{10}$, wherein $\alpha_3$ is S or K; $\alpha_5$ is T or P; $\alpha_7$ is Y or F; $\alpha_8$ is L or I; $\alpha_9$ is M or I; and $\alpha_{10}$ is N or H | CDR-H1 consensus sequence |
| 307 | Y-I-N-P-Y-S-$\beta_7$-G-$\beta_9$-N-Y-N-E-K-F-K-$\beta_{17}$, wherein $\beta_7$ is A or D; $\beta_9$ is S or T; and $\beta_{17}$ is D or G | CDR-H2 consensus sequence |
| 308 | Q-Q-$\phi_3$-W-S-$\phi_6$-P-W-T, wherein $\phi_3$ is Y or S; and $\phi_6$ is T or I | CDR-L3 consensus sequence |
| 309 | W-I-D-P-E-$\beta_6$-G-$\beta_8$-S-K-Y-A-P-K-F-Q-G, wherein $\beta_6$ is N or Q and $\beta_8$ is D or E | CDR-H2 consensus sequence |
| 310 | G-F-S-L-T-$\alpha_6$-Y-G-$\alpha_9$-$\alpha_{10}$, wherein $\alpha_6$ is T or S; $\alpha_9$ is I or V; and $\alpha_{10}$ is H or Q; | CDR-H1 consensus sequence |
| 311 | V-I-W-T-G-G-$\beta_7$-T-$\beta_9$-$\beta_{10}$-N-A-A-F-M-S, wherein $\beta_7$ is S or T; $\beta_9$ is A or D; and $\beta_{10}$ is F or Y | CDR-H2 consensus sequence |
| 312 | A-K-$\gamma_3$-G-F-H-S-A-$\gamma_9$-D-Y, wherein $\gamma_3$ is V or I; and $\gamma_9$ is T, M, or V | CDR-H3 consensus sequence |
| 313 | R-S-S-Q-N-$\delta_6$-V-H-S-N-G-N-T-Y-L-E, wherein $\delta_6$ is L or I | CDR-L1 consensus sequence |
| 314 | F-Q-G-S-H-$\phi_6$-P-F-T, wherein $\phi_6$ is V or I | CDR-L3 consensus sequence |
| 315 | G-F-T-F-T-$\alpha_6$-F-Y-M-S, wherein $\alpha_6$ is D or N | CDR-H1 consensus sequence |
| 316 | V-I-R-N-$\beta_5$-$\beta_6$-N-$\beta_8$-Y-T-$\beta_{11}$-$\beta_{12}$-Y-N-P-S-V-K-G, wherein $\beta_5$ is K or R; $\beta_6$ is A or P; $\beta_8$ is G or A; $\beta_{11}$ is A or T; and $\beta_{12}$ is G or D | CDR-H2 consensus sequence |
| 317 | $\gamma_1$-R-L-$\gamma_4$-Y-G-F-D-Y, wherein $\gamma_1$ is A or T; and $\gamma_4$ is T or S | CDR-H3 consensus sequence |
| 318 | Q-S-S-K-S-L-L-H-S-$\delta_{10}$-G-K-T-Y-L-N, wherein $\delta_{10}$ is N or T | CDR-L1 consensus sequence |
| 319 | Q-Q-F-L-E-$\phi_6$-P-F-T, wherein $\phi_6$ is Y or F | CDR-L3 consensus sequence |
| 320 | F-I-R-$\beta_4$-K-A-N-G-Y-T-T-$\beta_{12}$-Y-S-A-S-V-K-G, wherein $\beta_4$ is N or D; and $\beta_{12}$ is E or D | CDR-H2 consensus sequence |
| 321 | $\gamma_1$-R-$\gamma_3$-L-R-A-Q-G-F-A-Y, wherein $\gamma_1$ is A or S; $\gamma_3$ is V or L | CDR-H3 consensus sequence |
| 322 | $\delta_1$-S-$\delta_3$-Q-S-L-L-Y-S-$\delta_{10}$-N-Q-K-N-Y-L-A, wherein $\delta_1$ is T or K; $\delta_3$ is G or S; and $\delta_{10}$ is N or S | CDR-L1 consensus sequence |
| 323 | Q-Q-Y-Y-$\phi_5$-N-P-F-T, wherein $\phi_5$ is R or G | CDR-L3 consensus sequence |
| 324 | AGGAATGTGGGGAGCACGGAG | Primer sequence |
| 325 | TGCATCGCATTGTCTGAGTAGGTG | Primer sequence |
| 326 | ACCCTAGTCCTGACTGTTGCTC | Primer sequence |
| 327 | TATAGGAACTTCGCGACACGGACAC | Primer sequence |
| 328 | ACAGGAGGGACCTACCTTCAG | Primer sequence |

| SEQ ID NO | Sequence | Description |
|---|---|---|
| 329 | GCCTGCCTTTCAGAGACCTCAGTC | Primer sequence |
| 330 | CCTCTCCGGCTGCTCATCTTACTC | Primer sequence |
| 331 | GTCTCTCAGCCCTGGCAGAGTTTG | Primer sequence |
| 332 | CGCCTACCCTAGTCCTGACTGTTG | Primer sequence |
| 333 | AAAGCCTACAGCATCCTCACCTC | Primer sequence |
| 334 | GCATCATGGGGTTGTAGATTCCG | Primer sequence |
| 335 | GGGGS | Linker sequence |
| 336 | HHHHHH | 6X-His tag |
| 337 | QVQLQQPGAELVKPGASVKLSCKASGYTFTSYWMHWVKQSPGRGLEWIGRSDPTTGGTNYNEKFKTKATLTVDKPSSTAYMQLSSLTSDDSAVYYCVRTSGTGDYWGQGTSLTVSSAKTTAPSVYPLAPVCGGTTGSSVT | VH for anti-TREM2 antibody RS9.F6 |
| 338 | DVVMTQTPLSLPVSLGDQASISCRSSQSLVHNNGNTFLHWYLQKPGQSPKLLIYKVSNRFSGVPDRFSGSGSGTDFTLKISRVEAEDLGVYFCSQTTHVPPTFGGGTKLEIKRADAAPTVSIFPPSSEQLTSGGASVVCF | VL for anti-TREM2 antibody RS9.F6 |
| 339 | DIVMTQSPDSLAVSLGERATINCQSSKSLLHSNGKTYLNWYQQKPGQPPKLLIYWMSTRASGVPDRFSGSGSGTDFTLTISSLQAEDVAVYYCQQFLEFPFTFGQGTKVEIK | Humanized CL0020307 VL |
| 340 | FPGESES | TREM2 epitope |
| 341 | GEKGPCQRV | TREM2 epitope |
| 342 | TLRNLQPHDAGL | TREM2 epitope |
| 343 | VEVL | TREM2 epitope |
| 344 | DIQMTQSPSSVSASVGDRVTITCRASQGISNWLAWYQQKPGKAPKLLIYAASSLQVGVPLRFSGSGSGTDFTLTISSLQPEDFATYYCQQADSFPRNFGQGTKLEIK | Reference antibody #1 VL |
| 345 | EVQLVQSGAEVKKPGESLKISCKGSGHSFTNYWIAWVRQMPGKGLEWMGIIYPGDSDTRYSPSFQGQVTISADKSISTAYLQWSSLKASDTAVYFCARQRTFYYDSSGYFDYWGQGTLVTVSS | Reference antibody #1 VH |
| 346 | DIQMTQSPSSVSASVGDRVTITCRASQGISSWLAWYQQKPGKAPKLLIYAASSLQNGVPSRFSGSGSGTDFTLTISSLQPEDFATYFCQQADSFPRTFGQGTKLEIK | Reference antibody #2 VL |
| 347 | EVQLVQSGAEVKKPGESLKISCKGSGYSFTSYWIAWVRQMPGKGLEWMGIIYPGDSDTRYSPSFQGQVTISADKSISTAYLQWSSLKASDTAMYFCARQRTFYYDSSDYFDYWGQGTLVTVSS | Reference antibody #2 VH |
| 348 | DVVMTQSPDSLAVSLGERATINCRSSQSLVHSNRYTYLHWYQQKPGQSPKLLIYKVSNRFSGVPDRFSGSGSGTDFTLKISRVEAEDVGVYYCSQSTRVPYTFGQGTKLEIK | Reference antibody #3 VL |
| 349 | QVQLVQSGAEVKKPGASVKVSCKASGYAFSSQWMNWVRQAPGQRLEWIGRIYPGGGDTNYAGKFQGRVTITADTSASTAYMELSSLRSEDTAVYYCARLLRNQPGESYAMDYWGQGTLVTVSS | Reference antibody #3 VH |
| 350 | EVQLVESGGGLVQPGGSLRLSCAGSGFTFTDFYMSWVRQAPGKGPEWLSVIRNKANGYTAGYNPSVKGRFTISRDNSKNTLYLQMNSLRAEDTAVYYCARLTYGFDYWGQGTLVTVSS | CL0020188-4 VH |

What is claimed is:

1. An isolated antibody or antigen-binding fragment thereof that specifically binds to a human triggering receptor expressed on myeloid cells 2 (TREM2), wherein the antibody or antigen-binding fragment thereof comprises:

(a) a CDR-H1 sequence comprising the sequence of G-Y-T-F-T-α6-Y-α8-α9-α10 (SEQ ID NO:293), wherein α6 is N, S, or D; α8 is W or N; α9 is I or M; and α10 is S, T, M, or H;

(b) a CDR-H2 sequence comprising the sequence of β1-I-β3-P-β5-β6-β7-β8-β9-β10-Y-N-β13-β14-F-β16-β17 (SEQ ID NO:294), wherein β1 is D or Y; β3 is Y or F; β5 is H, G, S, N, or β6 is S or N; β7 is T or G; β8 is S, N, or G; β9 is T or N; β10 is N or G; β13 is E or Q; β14 is R or K; β16 is R or K; and β17 is S, G, or N;

(c) a CDR-H3 sequence comprising the sequence of γ1-R-γ3-G-γ5-G-γ7-γ8-γ9 (SEQ ID NO:295), wherein γ1 is A or S; γ3 is E or S; γ5 is F, Y, R, or T; γ7 is I or F; γ8 is S or A; and γ9 is A or Y;
(d) a CDR-L1 sequence comprising:
(i) the sequence of δ1-A-δ3-δ4-δ5-V-δ7-δ8-Y-δ10-δ11 (SEQ ID NO:296), wherein δ1 is S or K; δ3 is T or S; δ4 is S or E; δ5 is S or N; δ7 is absent or G; δ8 is S or T; δ10 is M or V; and δ11 is H or S; or
(ii) the sequence of δ1-S-S-δ4-S-L-L-δ8-S-δ10-N-δ12-δ13-δ14-Y-L-δ17 (SEQ ID NO:297), wherein δ1 is K or R; δ4 is Q or K; δ8 is N or H; δ10 is G or absent; δ12 is Q or G; δ13 is K or N; δ14 is N or T; and δ17 is T or Y;
(e) a CDR-L2 sequence comprising the sequence of ε1-ε2-S-ε4-ε5-ε6-ε7 (SEQ ID NO:298), wherein ε1 is S, G, W or Q; ε2 is T, A, or M; ε4 is N or T; ε5 is L or R; ε6 is A, Y, or E; and ε7 is S or T; and
(f) a CDR-L3 sequence comprising the sequence of φ1-φ2-φ3-φ4-φ5-φ6-P-φ8-T (SEQ ID NO:299), wherein φ1 is Q, G, or M; φ2 is Q or N; φ3 is R, S, D, or H; φ4 is S, Y, or L; φ5 is S or Q; φ6 is Y or F; and φ8 is L, F, or Y.

2. The isolated antibody or antigen-binding fragment of claim 1, wherein:
(a) the CDR-H1 sequence is selected from SEQ ID NOS:4, 12, 20, 28, and 36; and/or
(b) the CDR-H2 sequence is selected from SEQ ID NOS:5, 13, 21, 29, and 37; and/or
(c) the CDR-H3 sequence is selected from SEQ ID NOS:6, 14, 22, 30, and 38; and/or
(d) the CDR-L1 sequence is selected from SEQ ID NOS:7, 15, 23, 31, and 39; and/or
(e) the CDR-L2 sequence is selected from SEQ ID NOS:8, 16, 24, 32, and 40; and/or
(f) the CDR-L3 sequence is selected from SEQ ID NOS:9, 17, 25, 33, and 41.

3. The isolated antibody or antigen-binding fragment of claim 1, wherein the antibody or antigen-binding fragment comprises:
(a) a CDR-H1 comprising the amino acid sequence of SEQ ID NO:28, a CDR-H2 comprising the amino acid sequence of SEQ ID NO:29, a CDR-H3 comprising the amino acid sequence of SEQ ID NO:30, a CDR-L1 comprising the amino acid sequence of SEQ ID NO:31, a CDR-L2 comprising the amino acid sequence of SEQ ID NO:32, and a CDR-L3 comprising the amino acid sequence of SEQ ID NO:33; or
(b) a CDR-H1 comprising the amino acid sequence of SEQ ID NO:36, a CDR-H2 comprising the amino acid sequence of SEQ ID NO:37, a CDR-H3 comprising the amino acid sequence of SEQ ID NO:38, a CDR-L1 comprising the amino acid sequence of SEQ ID NO:39, a CDR-L2 comprising the amino acid sequence of SEQ ID NO:40, and a CDR-L3 comprising the amino acid sequence of SEQ ID NO:41.

4. The isolated antibody or antigen-binding fragment of claim 1, comprising:
(a) a heavy chain variable region ($V_H$) sequence that has at least 85% sequence identity to any one of SEQ ID NOS:2, 10, 18, 26, or 34; and/or
(b) a light chain variable region ($V_L$) sequence that has at least 85% sequence identity to any one of SEQ ID NOS:3, 11, 19, 27, or 35.

5. The isolated antibody or antigen-binding fragment of claim 1, wherein the antibody or antigen-binding fragment comprises:
(a) a $V_H$ sequence comprising SEQ ID NO:26 and a $V_L$ sequence comprising SEQ ID NO:27; or
(b) a $V_H$ sequence comprising SEQ ID NO:34 and a $V_L$ sequence comprising SEQ ID NO:35.

6. The isolated antibody or antigen-binding fragment of claim 1, wherein the antibody or antigen-binding fragment thereof comprises:
(a) a CDR-H1 sequence comprising the sequence of G-Y-T-F-T-α6-Y-W-I-α10 (SEQ ID NO:300), wherein α6 is N or S; and α10 is S, T or M;
(b) a CDR-H2 sequence comprising the sequence of D-I-Y-P-β5-S-β7-β8-T-N-Y-N-E-β14-F-β16-β17 (SEQ ID NO:301), wherein β5 is H, G, or S; β7 is T or G; β8 is S or N; β14 is R or K; β16 is R or K; and β17 is S or N;
(c) a CDR-H3 sequence comprising the sequence of γ1-R-E-G-γ5-G-I-S-A (SEQ ID NO:302), wherein γ1 is A or S; and γ5 is F or Y;
(d) a CDR-L1 sequence comprising the sequence of δ1-A-δ3-δ4-δ5-V-δ7-δ8-Y-δ10-δ11 (SEQ ID NO:296), wherein δ1 is S or K; δ3 is T or S; δ4 is S or E; δ5 is S or N; δ7 is absent or G; δ8 is S or T; δ10 is M or V; and δ11 is H or S;
(e) a CDR-L2 sequence comprising the sequence of ε1-ε2-S-N-ε5-ε6-ε7 (SEQ ID NO:304), wherein ε1 is S or G; ε2 is T or A; ε5 is L or R; ε6 is A or Y; and ε7 is S or T; and
(f) a CDR-L3 sequence comprising the sequence of φ1-Q-φ3-φ4-S-φ6-P-φ8-T (SEQ ID NO:305), wherein φ1 is Q or G; φ3 is R or S; φ4 is S or Y; φ6 is Y or F; and φ8 is L or F.

7. The isolated antibody or antigen-binding fragment of claim 6, wherein:
(a) the CDR-H1 sequence is selected from SEQ ID NOS:4, 12, and 20; and/or
(b) the CDR-H2 sequence is selected from SEQ ID NOS:5, 13, and 21; and/or
(c) the CDR-H3 sequence is selected from SEQ ID NOS:6, 14, and 22; and/or
(d) the CDR-L1 sequence is selected from SEQ ID NOS:7, 15, and 23; and/or
(e) the CDR-L2 sequence is selected from SEQ ID NOS:8, 16, and 24; and/or
(f) the CDR-L3 sequence is selected from SEQ ID NOS:9, 17, and 25.

8. The isolated antibody or antigen-binding fragment of claim 6, wherein the antibody or antigen-binding fragment comprises:
(a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO:6, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO:9; or
(b) a CDR-H1 comprising the amino acid sequence of SEQ ID NO:12, a CDR-H2 comprising the amino acid sequence of SEQ ID NO:13, a CDR-H3 comprising the amino acid sequence of SEQ ID NO:14, a CDR-L1 comprising the amino acid sequence of SEQ ID NO:15, a CDR-L2 comprising the amino acid sequence of SEQ ID NO:16, and a CDR-L3 comprising the amino acid sequence of SEQ ID NO:17; or
(c) a CDR-H1 comprising the amino acid sequence of SEQ ID NO:20, a CDR-H2 comprising the amino acid sequence of SEQ ID NO:21, a CDR-H3 comprising the amino acid sequence of SEQ ID NO:22, a CDR-L1 comprising the amino acid sequence of SEQ ID NO:23, a CDR-L2 comprising the amino acid sequence of SEQ ID NO:24, and a CDR-L3 comprising the amino acid sequence of SEQ ID NO:25.

9. The isolated antibody or antigen-binding fragment of claim 8, wherein the antibody or antigen-binding fragment comprises:
   (a) a $V_H$ sequence comprising SEQ ID NO:2 and a $V_L$ sequence comprising SEQ ID NO:3; or
   (b) a $V_H$ sequence comprising SEQ ID NO: 10 and a $V_L$ sequence comprising SEQ ID NO:11; or
   (c) a $V_H$ sequence comprising SEQ ID NO: 18 and a $V_L$ sequence comprising SEQ ID NO:19.

10. A pharmaceutical composition comprising the isolated antibody or antigen-binding fragment thereof of claim 1 and a pharmaceutically acceptable carrier.

11. A method of treating a neurodegenerative disease in a subject, comprising administering to the subject the isolated antibody or antigen-binding fragment thereof of claim 1.

12. The method of claim 11, wherein the neurodegenerative disease is selected from the group consisting of: Alzheimer's disease, primary age-related tauopathy, progressive supranuclear palsy (PSP), frontotemporal dementia, frontotemporal dementia with parkinsonism linked to chromosome 17, argyrophilic grain dementia, amyotrophic lateral sclerosis, amyotrophic lateral sclerosis/parkinsonism-dementia complex of Guam (ALS-PDC), corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, Gerstmann-Straussler-Scheinker disease, globular glial tauopathy, Guadeloupean parkinsonism with dementia, Guadelopean PSP, Hallevorden-Spatz disease, hereditary diffuse leukoencephalopathy with spheroids (HDLS), Huntington's disease, inclusion-body myositis, multiple system atrophy, myotonic dystrophy, Nasu-Hakola disease, neurofibrillary tangle-predominant dementia, Niemann-Pick disease type C, pallido-ponto-nigral degeneration, Parkinson's disease, Pick's disease, postencephalitic parkinsonism, prion protein cerebral amyloid angiopathy, progressive subcortical gliosis, subacute sclerosing panencephalitis, and tangle only dementia.

13. An isolated antibody or antigen-binding fragment thereof that specifically binds to a human TREM2, wherein the antibody or antigen-binding fragment thereof comprises:
   (a) a CDR-H1 sequence comprising the sequence of G-Y-$\alpha_3$-F-$\alpha_5$-S-$\alpha_7$-$\alpha_8$-$\alpha_9$-$\alpha_{10}$ (SEQ ID NO:306), wherein $\alpha_3$ is S or K; $\alpha_5$ is T or P; $\alpha_7$ is Y or F; $\alpha_8$ is L or I; $\alpha_9$ is M or I; and $\alpha_{10}$ is N or H;
   (b) a CDR-H2 sequence comprising the sequence of Y-I-N-P-Y-S-$\beta_7$-G-$\beta_9$-N-Y-N-E-K-F-K-$\beta_{17}$ (SEQ ID NO:307), wherein $\beta_7$ is A or D; $\beta_9$ is S or T; and $\beta_{17}$ is D or G;
   (c) a CDR-H3 sequence comprising the sequence of comprising the sequence of ARSSYRYGFDY (SEQ ID NO:46);
   (d) a CDR-L1 sequence comprising the sequence of comprising the sequence of KASEDIYNRLA (SEQ ID NO:47);
   (e) a CDR-L2 sequence comprising the sequence of comprising the sequence of GATSLET (SEQ ID NO:48); and
   (f) a CDR-L3 sequence comprising the sequence of comprising the sequence Q-Q-$\phi_3$-W-S-$\phi_6$-P-W-T (SEQ ID NO:308), wherein $\phi_3$ is Y or S; and $\phi_6$ is T or I.

14. The isolated antibody or antigen-binding fragment of claim 13, wherein the antibody or antigen-binding fragment comprises:
   (a) a CDR-H1 comprising the amino acid sequence of SEQ ID NO:44, a CDR-H2 comprising the amino acid sequence of SEQ ID NO:45, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49; or
   (b) a CDR-H1 comprising the amino acid sequence of SEQ ID NO:52, a CDR-H2 comprising the amino acid sequence of SEQ ID NO:53, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:292; or
   (c) a CDR-H1 comprising the amino acid sequence of SEQ ID NO:56, a CDR-H2 comprising the amino acid sequence of SEQ ID NO:57, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49.

15. An isolated antibody or antigen-binding fragment thereof that specifically binds to a human TREM2, wherein the antibody or antigen-binding fragment thereof comprises:
   (a) a CDR-H1 sequence comprising the sequence of G-F-S-L-T-$\alpha_6$-Y-G-$\alpha_9$-$\alpha_{10}$ (SEQ ID NO:310), wherein $\alpha_6$ is T or S; $\alpha_9$ is I or V; and $\alpha_{10}$ is H or Q;
   (b) a CDR-H2 sequence comprising the sequence of V-I-W-T-G-G-$\beta_7$-T-$\beta_9$-$\beta_{10}$-N-A-A-F-M-S(SEQ ID NO:311), wherein $\beta_7$ is S or T; $\beta_9$ is A or D; and $\beta_{10}$ is F or Y;
   (c) a CDR-H3 sequence comprising the sequence of A-K-$\gamma_3$-G-F-H-S-A-$\gamma_9$-D-Y (SEQ ID NO:312), wherein $\gamma_3$ is V or I; and $\gamma_9$ is T, M, or V;
   (d) a CDR-L1 sequence comprising the sequence of R-S-S-Q-N-$\delta_6$-V-H-S-N-G-N-T-Y-L-E (SEQ ID NO:313), wherein $\delta_6$ is L or I;
   (e) a CDR-L2 sequence comprising the sequence of KVSNRFS (SEQ ID NO:89); and
   (f) a CDR-L3 sequence comprising the sequence of F-Q-G-S-H-$\phi_6$-P-F-T (SEQ ID NO:314), wherein $\phi_6$ is V or I.

16. The isolated antibody or antigen-binding fragment of claim 15, wherein the antibody or antigen-binding fragment comprises:
   (a) a CDR-H1 comprising the amino acid sequence of SEQ ID NO:85, a CDR-H2 comprising the amino acid sequence of SEQ ID NO:86, a CDR-H3 comprising the amino acid sequence of SEQ ID NO:87, a CDR-L1 comprising the amino acid sequence of SEQ ID NO:88, a CDR-L2 comprising the amino acid sequence of SEQ ID NO:89, and a CDR-L3 comprising the amino acid sequence of SEQ ID NO:90; or
   (b) a CDR-H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:97; or
   (c) a CDR-H1 comprising the amino acid sequence of SEQ ID NO:100, a CDR-H2 comprising the amino acid sequence of SEQ ID NO:101 a CDR-H3 comprising the amino acid sequence of SEQ ID NO:102, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:90.

17. An isolated antibody or antigen-binding fragment thereof that specifically binds to a human TREM2, wherein the antibody or antigen-binding fragment thereof comprises:
   (a) a CDR-H1 sequence comprising the sequence of GFTFTDYYMS (SEQ ID NO:125);
   (b) a CDR-H2 sequence comprising the sequence of F-I-R-$\beta_4$-K-A-N-G-Y-T-T-$\beta_{12}$-Y-S-A-S-V-K-G (SEQ ID NO:320), wherein $\beta_4$ is N or D; and $\beta_{12}$ is E or D;
   (c) a CDR-H3 sequence comprising the sequence of $\gamma_1$-R-$\gamma_3$-L-R-A-Q-G-F-A-Y (SEQ ID NO:321), wherein $\gamma_1$ is A or S; $\gamma_3$ is V or L;
   (d) a CDR-L1 sequence comprising the sequence of $\delta_1$-S-$\delta_3$-Q-S-L-L-Y-S-$\delta_{10}$-N-Q-K-N-Y-L-A (SEQ ID NO:322), wherein $\delta_1$ is T or K; $\delta_3$ is G or S; and $\delta_{10}$ is N or S;
   (e) a CDR-L2 sequence comprising the sequence of WASTRES (SEQ ID NO:32); and
   (f) a CDR-L3 sequence comprising the sequence of Q-Q-Y-Y-$\phi_5$-N-P-F-T (SEQ ID NO:323), wherein $\phi_5$ is R or G.

18. The isolated antibody or antigen-binding fragment of claim 17, wherein the antibody or antigen-binding fragment comprises:
   (a) a CDR-H1 comprising the amino acid sequence of SEQ ID NO: 125, a CDR-H2 comprising the amino acid sequence of SEQ ID NO:136, a CDR-H3 comprising the amino acid sequence of SEQ ID NO:137, a CDR-L1 comprising the amino acid sequence of SEQ ID NO:138, a CDR-L2 comprising the amino acid sequence of SEQ ID NO:32, and a CDR-L3 comprising the amino acid sequence of SEQ ID NO:139; or
   (b) a CDR-H1 comprising the amino acid sequence of SEQ ID NO:125, a CDR-H2 comprising the amino acid sequence of SEQ ID NO: 126, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:129; or
   (c) a CDR-H1 comprising the amino acid sequence of SEQ ID NO:125, a CDR-H2 comprising the amino acid sequence of SEQ ID NO:132, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO: 133.

19. An isolated antibody or antigen-binding fragment thereof that specifically binds to a human TREM2, wherein the antibody or antigen-binding fragment thereof comprises:
   (a) a CDR-H1 sequence comprising the amino acid sequence of any one of SEQ ID NOS:4, 12, 20, 28, 36, 44, 52, 56, 60, 68, 85, 93, 100, 105, 125, 142, 149, 157, 165, 172, 180, 188, 196, 202, 222, 228, 239, 253, 266, 274, and 282;
   (b) a CDR-H2 sequence comprising the amino acid sequence of any one of SEQ ID NOS:5, 13, 21, 29, 37, 45, 53, 57, 61, 69, 81, 86, 94, 101, 106, 115, 117, 119, 126, 132, 136, 143, 150, 158, 166, 173, 181, 189, 197, 203, 209, 214, 217, 223, 229, 236, 240, 254, 267, 275, 283, and 289;
   (c) a CDR-H3 sequence comprising the amino acid sequence of any one of SEQ ID NOS:6, 14, 22, 30, 38, 46, 62, 70, 73, 87, 95, 102, 107, 127, 137, 144, 151, 159, 167, 174, 182, 190, 198, 204, 210, 230, 241, 245, 249, 255, 260, 268, 276, and 284;
   (d) a CDR-L1 sequence comprising the amino acid sequence of any one of SEQ ID NOS:7, 15, 23, 31, 39, 47, 63, 79, 88, 96, 108, 128, 138, 145, 152, 160, 168, 175, 183, 191, 199, 205, 218, 224, 231, 242, 246, 256, 261, 269, 277, and 285;
   (e) a CDR-L2 sequence comprising the amino acid sequence of any one of SEQ ID NOS:8, 16, 24, 32, 40, 48, 64, 89, 109, 153, 161, 176, 184, 211, 219, 232, 250, 262, 270, 278, and 286; and
   (f) a CDR-L3 sequence comprising the amino acid sequence of any one of SEQ ID NOS:9, 17, 25, 33, 41, 49, 65, 74, 90, 97, 110, 129, 133, 139, 146, 154, 162, 169, 177, 185, 193, 206, 212, 225, 233, 257, 263, 271, 279, 287, and 290.

20. The isolated antibody or antigen-binding fragment of claim 19, wherein the antibody or antigen-binding fragment comprises:
   (a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO:6, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO:9; or
   (b) a CDR-H1 comprising the amino acid sequence of SEQ ID NO:12, a CDR-H2 comprising the amino acid sequence of SEQ ID NO:13, a CDR-H3 comprising the amino acid sequence of SEQ ID NO:14, a CDR-L1 comprising the amino acid sequence of SEQ ID NO:15, a CDR-L2 comprising the amino acid sequence of SEQ ID NO:16, and a CDR-L3 comprising the amino acid sequence of SEQ ID NO:17; or
   (c) a CDR-H1 comprising the amino acid sequence of SEQ ID NO:20, a CDR-H2 comprising the amino acid sequence of SEQ ID NO:21, a CDR-H3 comprising the amino acid sequence of SEQ ID NO:22, a CDR-L1 comprising the amino acid sequence of SEQ ID NO:23, a CDR-L2 comprising the amino acid sequence of SEQ ID NO:24, and a CDR-L3 comprising the amino acid sequence of SEQ ID NO:25; or
   (d) a CDR-H1 comprising the amino acid sequence of SEQ ID NO:28, a CDR-H2 comprising the amino acid sequence of SEQ ID NO:29, a CDR-H3 comprising the amino acid sequence of SEQ ID NO:30, a CDR-L1 comprising the amino acid sequence of SEQ ID NO:31, a CDR-L2 comprising the amino acid sequence of SEQ ID NO:32, and a CDR-L3 comprising the amino acid sequence of SEQ ID NO:33; or
   (e) a CDR-H1 comprising the amino acid sequence of SEQ ID NO:36, a CDR-H2 comprising the amino acid sequence of SEQ ID NO:37, a CDR-H3 comprising the amino acid sequence of SEQ ID NO:38, a CDR-L1 comprising the amino acid sequence of SEQ ID NO:39, a CDR-L2 comprising the amino acid sequence of SEQ ID NO:40, and a CDR-L3 comprising the amino acid sequence of SEQ ID NO:41; or
   (f) a CDR-H1 comprising the amino acid sequence of SEQ ID NO:44, a CDR-H2 comprising the amino acid sequence of SEQ ID NO:45, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49; or
(g) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:62, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or
(h) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or
(i) a CDR-H1 comprising the amino acid sequence of SEQ ID NO:60, a CDR-H2 comprising the amino acid sequence of SEQ ID NO:61, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or
(j) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:74; or
(k) a CDR-H1 comprising the amino acid sequence of SEQ ID NO:60, a CDR-H2 comprising the amino acid sequence of SEQ ID NO:81, a CDR-H3 comprising the amino acid sequence of SEQ ID NO:73, a CDR-L1 comprising the amino acid sequence of SEQ ID NO:79, a CDR-L2 comprising the amino acid sequence of SEQ ID NO:64, and a CDR-L3 comprising the amino acid sequence of SEQ ID NO:74; or
(l) a CDR-H1 comprising the amino acid sequence of SEQ ID NO:68, a CDR-H2 comprising the amino acid sequence of SEQ ID NO:69, a CDR-H3 comprising the amino acid sequence of SEQ ID NO:70, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:65; or
(m) a CDR-H1 comprising the amino acid sequence of SEQ ID NO:85, a CDR-H2 comprising the amino acid sequence of SEQ ID NO:86, a CDR-H3 comprising the amino acid sequence of SEQ ID NO:87, a CDR-L1 comprising the amino acid sequence of SEQ ID NO:88, a CDR-L2 comprising the amino acid sequence of SEQ ID NO:89, and a CDR-L3 comprising the amino acid sequence of SEQ ID NO:90; or
(n) a CDR-H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:97; or
(o) a CDR-H1 comprising the amino acid sequence of SEQ ID NO:100, a CDR-H2 comprising the amino acid sequence of SEQ ID NO:101, a CDR-H3 comprising the amino acid sequence of SEQ ID NO:102, a CDR-L1 comprising the amino acid sequence of SEQ ID NO:96, a CDR-L2 comprising the amino acid sequence of SEQ ID NO:89, and a CDR-L3 comprising the amino acid sequence of SEQ ID NO:90; or
(p) a CDR-H1 comprising the amino acid sequence of SEQ ID NO:105, a CDR-H2 comprising the amino acid sequence of SEQ ID NO:106, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(q) a CDR-H1 comprising the amino acid sequence of SEQ ID NO:105, a CDR-H2 comprising the amino acid sequence of SEQ ID NO:115, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(r) a CDR-H1 comprising the amino acid sequence of SEQ ID NO:105, a CDR-H2 comprising the amino acid sequence of SEQ ID NO:117, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(s) a CDR-H1 comprising the amino acid sequence of SEQ ID NO:105, a CDR-H2 comprising the amino acid sequence of SEQ ID NO:119, a CDR-H3 comprising the amino acid sequence of SEQ ID NO:107, a CDR-L1 comprising the amino acid sequence of SEQ ID NO:108, a CDR-L2 comprising the amino acid sequence of SEQ ID NO:109, and a CDR-L3 comprising the amino acid sequence of SEQ ID NO:110; or
(t) a CDR-H1 comprising the amino acid sequence of SEQ ID NO:125, a CDR-H2 comprising the amino acid sequence of SEQ ID NO:126, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO: 129; or
u) a CDR-H1 comprising the amino acid sequence of SEQ ID NO:125, a CDR-H2 comprising the amino acid sequence of SEQ ID NO:132, a CDR-H3 comprising the amino acid sequence of SEQ ID NO:127, a CDR-L1 comprising the amino acid sequence of SEQ ID NO:128, a CDR-L2 comprising the amino acid sequence of SEQ ID NO:32, and a CDR-L3 comprising the amino acid sequence of SEQ ID NO:133; or
(v) a CDR-H1 comprising the amino acid sequence of SEQ ID NO:125, a CDR-H2 comprising the amino acid sequence of SEQ ID NO:136, a CDR-H3 comprising the amino acid sequence of SEQ ID NO:137, a CDR-L1 comprising the amino acid sequence of SEQ ID NO:138, a CDR-L2 comprising the amino acid sequence of SEQ ID NO:32, and a CDR-L3 comprising the amino acid sequence of SEQ ID NO: 139; or
(w) a CDR-H1 comprising the amino acid sequence of SEQ ID NO:142, a CDR-H2 comprising the amino acid sequence of SEQ ID NO:143, a CDR-H3 comprising the amino acid sequence of SEQ ID NO:144, a CDR-L1 comprising the amino acid sequence of SEQ ID NO:145, a CDR-L2 comprising the amino acid sequence of SEQ ID NO:32, and a CDR-L3 comprising the amino acid sequence of SEQ ID NO:146; or (x) a CDR-H1 comprising the amino acid sequence of SEQ ID NO:149, a CDR-H2 comprising the amino acid sequence of SEQ ID NO:150, a CDR-H3 comprising the amino acid sequence of SEQ ID NO:151, a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; or (y) a CDR-H1 comprising the amino acid sequence of SEQ ID NO:157, a CDR-H2 comprising the amino acid sequence of SEQ ID NO:158, a CDR-H3 comprising the amino acid sequence of SEQ ID NO:159, a CDR-L1 comprising the amino acid sequence of SEQ ID NO:160, a CDR-L2 comprising the amino acid sequence of SEQ ID NO:161, and a CDR-L3 comprising the amino acid sequence of SEQ ID NO:162; or (z) a CDR-H1 comprising the amino acid sequence of SEQ ID NO:165, a CDR-H2 comprising the amino acid sequence of SEQ ID NO: 166, a CDR-H3 comprising the amino acid sequence of SEQ ID NO:167, a CDR-L1 comprising the amino acid sequence of SEQ ID NO:168, a CDR-L2 comprising the amino acid sequence of SEQ ID NO:161, and a CDR-L3 comprising the amino acid sequence of SEQ ID NO: 169; or (aa) a CDR-H1 comprising the amino acid sequence of SEQ ID NO:172, a CDR-H2 comprising the amino acid sequence of SEQ ID NO:173, a CDR-H3 comprising the amino acid sequence of SEQ ID NO:174, a CDR-L1 comprising the amino acid sequence of SEQ ID NO:175, a CDR-L2 comprising the amino acid sequence of SEQ ID NO:176, and a CDR-L3 comprising the amino acid sequence of SEQ ID NO:177; or (bb) a CDR-H1 comprising the amino acid sequence of SEQ ID NO:180, a CDR-H2 comprising the amino acid sequence of SEQ ID NO:181, a CDR-H3 comprising the amino acid sequence of SEQ ID NO:182, a CDR-L1 comprising the amino acid sequence of SEQ ID NO:183, a CDR-L2 comprising the amino acid sequence of SEQ ID NO:184, and a CDR-L3 comprising the amino acid sequence of SEQ ID NO:185; or (cc) a CDR-H1 comprising the amino acid sequence of SEQ ID NO:188, a CDR-H2 comprising the amino acid sequence of SEQ ID NO: 189, a CDR-H3 comprising the amino acid sequence of SEQ ID NO:190, a CDR-L1 comprising the amino acid sequence of SEQ ID NO:191, a CDR-L2 comprising the amino acid sequence of SEQ ID NO:32, and a CDR-L3 comprising the amino acid sequence of SEQ ID NO: 146; or (dd) a CDR-H1 comprising the amino acid sequence of SEQ ID NO:188, a CDR-H2 comprising the amino acid sequence of SEQ ID NO:189, a CDR-H3 comprising the amino acid sequence of SEQ ID NO:190, a CDR-L1 comprising the amino acid sequence of SEQ ID NO:191, a CDR-L2 comprising the amino acid sequence of SEQ ID NO:32, and a CDR-L3 comprising the amino acid sequence of SEQ ID NO:193; or (ee) a CDR-H1 comprising the amino acid sequence of SEQ ID NO:196, a CDR-H2 comprising the amino acid sequence of SEQ ID NO:197, a CDR-H3 comprising the amino acid sequence of SEQ ID NO:198, a CDR-L1 comprising the amino acid sequence of SEQ ID NO:199, a CDR-L2 comprising the amino acid sequence of SEQ ID NO:89, and a CDR-L3 comprising the amino acid sequence of SEQ ID NO:90; or (ff) a CDR-H1 comprising the amino acid sequence of SEQ ID NO:202, a CDR-H2 comprising the amino acid sequence of SEQ ID NO:203, a CDR-H3 comprising the amino acid sequence of SEQ ID NO:204, a CDR-L1 comprising the amino acid sequence of SEQ ID NO:205, a CDR-L2 comprising the amino acid sequence of SEQ ID NO:89, and a CDR-L3 comprising the amino acid sequence of SEQ ID NO:206; or (gg) a CDR-H1 comprising the amino acid sequence of SEQ ID NO:28, a CDR-H2 comprising the amino acid sequence of SEQ ID NO:209, a CDR-H3 comprising the amino acid sequence of SEQ ID NO:210, a CDR-L1 comprising the amino acid sequence of SEQ ID NO:205, a CDR-L2 comprising the amino acid sequence of SEQ ID NO:211, and a CDR-L3 comprising the amino acid sequence of SEQ ID NO:212; or (hh) a CDR-H1 comprising the amino acid sequence of SEQ ID NO:172, a CDR-H2 comprising the amino acid sequence of SEQ ID NO:214, a CDR-H3 comprising the amino acid sequence of SEQ ID NO:174, a CDR-L1 comprising the amino acid sequence of SEQ ID NO:175, a CDR-L2 comprising the amino acid sequence of SEQ ID NO:176, and a CDR-L3 comprising the amino acid sequence of SEQ ID NO:177; or (ii) a CDR-H1 comprising the amino acid sequence of SEQ ID NO:149, a CDR-H2 comprising the amino acid sequence of SEQ ID NO:217, a CDR-H3 comprising the amino acid sequence of SEQ ID NO:167, a CDR-L1 comprising the amino acid sequence of SEQ ID NO:218, a CDR-L2 comprising the amino acid sequence of SEQ ID NO:219, and a CDR-L3 comprising the amino acid sequence of SEQ ID NO:169; or (jj) a CDR-H1 comprising the amino acid sequence of SEQ ID NO:222, a CDR-H2 comprising the amino acid sequence of SEQ ID NO:223, a CDR-H3 comprising the amino acid sequence of SEQ ID NO:22, a CDR-L1 comprising the amino acid sequence of SEQ ID NO:224, a CDR-L2 comprising the amino acid sequence of SEQ ID NO:8, and a CDR-L3 comprising the amino acid sequence of SEQ ID NO:225; or (kk) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:230, a CDR-L1 comprising the amino acid sequence of SEQ ID NO:231, a CDR-L2 comprising the amino acid sequence of SEQ ID NO:232, and a CDR-L3 comprising the amino acid sequence of SEQ ID NO:233; or

(11) a CDR-H1 comprising the amino acid sequence of SEQ ID NO:149, a CDR-H2 comprising the amino acid sequence of SEQ ID NO:236, a CDR-H3 comprising the amino acid sequence of SEQ ID NO:151, a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; or (mm) a CDR-H1 comprising the amino acid sequence of SEQ ID NO:239, a CDR-H2 comprising the amino acid sequence of SEQ ID NO:240, a CDR-H3 comprising the amino acid sequence of SEQ ID NO:241, a CDR-L1 comprising the amino acid sequence of SEQ ID NO:242, a CDR-L2 comprising the amino acid sequence of SEQ ID NO:89, and a CDR-L3 comprising the amino acid sequence of SEQ ID NO:212; or (nn) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:245, a CDR-L1 comprising the amino acid sequence of SEQ ID NO:246, a CDR-L2 comprising the amino acid sequence of SEQ ID NO:232, and a CDR-L3 comprising the amino acid sequence of SEQ ID NO:233; or (oo) a CDR-H1 comprising the amino acid sequence of SEQ ID NO:228, a CDR-H2 comprising the amino acid sequence of SEQ ID NO:229, a CDR-H3 comprising the amino acid sequence of SEQ ID NO:249, a CDR-L1 comprising the amino acid sequence of SEQ ID NO:246, a CDR-L2 comprising the amino acid sequence of SEQ ID NO:250, and a CDR-L3 comprising the amino acid sequence of SEQ ID NO:233; or (pp) a CDR-H1 comprising the amino acid sequence of SEQ ID NO:253, a CDR-H2 comprising the amino acid sequence of SEQ ID NO:254, a CDR-H3 comprising the amino acid sequence of SEQ ID NO:255, a CDR-L1 comprising the amino acid sequence of SEQ ID NO:256, a CDR-L2 comprising the amino acid sequence of SEQ ID NO:32, and a CDR-L3 comprising the amino acid sequence of SEQ ID NO:257; or a CDR-H1 comprising the amino acid sequence of SEQ ID NO:253, a CDR-H2 (qq) comprising the amino acid sequence of SEQ ID NO:254, a CDR-H3 comprising the amino acid sequence of SEQ ID NO:260, a CDR-L1 comprising the amino acid sequence of SEQ ID NO:261, a CDR-L2 comprising the amino acid sequence of SEQ ID NO:262, and a CDR-L3 comprising the amino acid sequence of SEQ ID NO:263; or (rr) a CDR-H1 comprising the amino acid sequence of SEQ ID NO:266, a CDR-H2 comprising the amino acid sequence of SEQ ID NO:267, a CDR-H3 comprising the amino acid sequence of SEQ ID NO:268, a CDR-L1 comprising the amino acid sequence of SEQ ID NO:269, a CDR-L2 comprising the amino acid sequence of SEQ ID NO:270, and a CDR-L3 comprising the amino acid sequence of SEQ ID NO:271; or (ss) a CDR-H1 comprising the amino acid sequence of SEQ ID NO:274, a CDR-H2 comprising the amino acid sequence of SEQ ID NO:275, a CDR-H3 comprising the amino acid sequence of SEQ ID NO:276, a CDR-L1 comprising the amino acid sequence of SEQ ID NO:277, a CDR-L2 comprising the amino acid sequence of SEQ ID NO:278, and a CDR-L3 comprising the amino acid sequence of SEQ ID NO:279; or (tt) a CDR-H1 comprising the amino acid sequence of SEQ ID NO:282, a CDR-H2 comprising the amino acid sequence of SEQ ID NO:283, a CDR-H3 comprising the amino acid sequence of SEQ ID NO:284, a CDR-L1 comprising the amino acid sequence of SEQ ID NO:285, a CDR-L2 comprising the amino acid sequence of SEQ ID NO:286, and a CDR-L3 comprising the amino acid sequence of SEQ ID NO:287; or (uu) a CDR-H1 comprising the amino acid sequence of SEQ ID NO:60, a CDR-H2 comprising the amino acid sequence of SEQ ID NO:289, a CDR-H3 comprising the amino acid sequence of SEQ ID NO:73, a CDR-L1 comprising the amino acid sequence of SEQ ID NO:63, a CDR-L2 comprising the amino acid sequence of SEQ ID NO:64, and a CDR-L3 comprising the amino acid sequence of SEQ ID NO:290; or (vv) a CDR-H1 comprising the amino acid sequence of SEQ ID NO:52, a CDR-H2 comprising the amino acid sequence of SEQ ID NO:53, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:292; or (ww) a CDR-H1 comprising the amino acid sequence of SEQ ID NO:56, a CDR-H2 comprising the amino acid sequence of SEQ ID NO:57, a CDR-H3 comprising the amino acid sequence of SEQ ID NO:46, a CDR-L1 comprising the amino acid sequence of SEQ ID NO:47, a CDR-L2 comprising the amino acid sequence of SEQ ID NO:48, and a CDR-L3 comprising the amino acid sequence of SEQ ID NO:49.

\* \* \* \* \*

SEQUENCE LISTING

<160> NUMBER OF SEQ ID NOS: 354

<210> SEQ ID NO 1
<211> LENGTH: 230
<212> TYPE: PRT
<213> ORGANISM: Homo sapiens

<400> SEQUENCE: 1

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230

<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Pro Gly Ala Glu Leu Val Lys Pro Gly Ala
1               5                   10                  15

Ser Val Lys Met Ser Cys Arg Ala Ser Gly Tyr Thr Phe Thr Asn Tyr
            20                  25                  30

Trp Ile Ser Trp Val Lys Gln Arg Pro Gly Gln Gly Leu Glu Trp Ile
        35                  40                  45

Gly Asp Ile Tyr Pro His Ser Thr Ser Thr Asn Tyr Asn Glu Arg Phe
    50                  55                  60

Arg Ser Lys Ala Thr Leu Thr Val Asp Lys Ser Ser Thr Thr Ala Tyr

```
                65                  70                  75                  80
Met Gln Leu Ser Ser Leu Thr Ser Glu Asp Ser Ala Val Tyr Tyr Cys
                        85                  90                  95
Ala Arg Glu Gly Phe Gly Ile Ser Ala Trp Gly Gln Gly Thr Thr Leu
                100                 105                 110
Thr Val Ser Ser
        115
```

```
<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ile Val Leu Thr Gln Ser Pro Ala Ile Met Ser Ala Ser Pro Gly
1               5                   10                  15
Glu Lys Val Thr Ile Thr Cys Ser Ala Thr Ser Ser Val Ser Tyr Met
                20                  25                  30
His Trp Phe Gln Gln Lys Pro Gly Thr Ser Pro Lys Leu Trp Ile Tyr
            35                  40                  45
Ser Thr Ser Asn Leu Ala Ser Gly Val Pro Ala Arg Phe Ser Gly Ser
        50                  55                  60
Gly Ser Gly Thr Ser His Ser Leu Thr Ile Ser Arg Met Glu Ala Glu
65                  70                  75                  80
Asp Ala Ala Thr Tyr Tyr Cys Gln Gln Arg Ser Ser Tyr Pro Leu Thr
                85                  90                  95
Phe Gly Ser Gly Thr Lys Leu Glu Leu Lys
                100                 105
```

```
<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Asn Tyr Trp Ile Ser
1               5                   10
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ile Tyr Pro His Ser Thr Ser Thr Asn Tyr Asn Glu Arg Phe Arg
1               5                   10                  15
Ser
```

```
<210> SEQ ID NO 6
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 6

Ala Arg Glu Gly Phe Gly Ile Ser Ala
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Thr Ser Ser Val Ser Tyr Met His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Thr Ser Asn Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Arg Ser Ser Tyr Pro Leu Thr
1               5

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Asn Thr Asn Tyr Asn Glu Lys Phe
    50                  55                  60

Lys Ser Lys Ala Thr Leu Thr Val Asp Thr Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Gly Tyr Gly Ile Ser Ala Trp Gly Gln Gly Thr Thr Leu
            100                 105                 110

Thr Val Ser Ser
        115

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Tyr Thr Phe Thr Ser Tyr Trp Ile Thr
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Tyr Pro Gly Ser Gly Asn Thr Asn Tyr Asn Glu Lys Phe Lys
1               5                   10                  15

Ser

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Ala Arg Glu Gly Tyr Gly Ile Ser Ala
1               5
```

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Lys Ala Ser Glu Asn Val Gly Thr Tyr Val Ser
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gly Ala Ser Asn Arg Tyr Thr
1               5
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Gly Gln Ser Tyr Ser Tyr Pro Phe Thr
1               5
```

<210> SEQ ID NO 18
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Met Trp Val Lys Gln Arg Pro Gly Gln Gly Leu Glu Trp Ile
        35                  40                  45

Gly Asp Ile Tyr Pro Ser Ser Gly Ser Thr Asn Tyr Asn Glu Lys Phe
    50                  55                  60

Lys Asn Arg Ala Thr Leu Thr Val Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ser Arg Glu Gly Tyr Gly Ile Ser Ala Trp Gly Gln Gly Thr Thr Leu
            100                 105                 110

Thr Val Ser Ser
            115
```

```
<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Cys Ser Leu Thr Ile Ser Arg Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys
            100                 105

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Thr Phe Thr Asn Tyr Trp Ile Met
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Ile Tyr Pro Ser Ser Gly Ser Thr Asn Tyr Asn Glu Lys Phe Lys
1               5                   10                  15

Asn

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Arg Glu Gly Tyr Gly Ile Ser Ala
1               5

<210> SEQ ID NO 23
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Ser Ser Ser Val Ser Tyr Met His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Thr Ser Asn Leu Ala Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Gln Arg Ser Ser Phe Pro Leu Thr
1               5

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Phe Pro Asn Asn Gly Asn Asn Gly Tyr Asn Gln Lys Phe
    50                  55                  60

Lys Gly Lys Ala Thr Met Thr Glu Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Gly Arg Gly Phe Ala Tyr Trp Gly Gln Gly Thr Leu Val
            100                 105                 110

Thr Val Ser Ala
        115

<210> SEQ ID NO 27
<211> LENGTH: 113
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro His Arg Phe Thr Gly Ser Gly Ser Gly Thr Asp Phe Thr Leu Thr
65                  70                  75                  80

Ile Ser Ser Val Gln Ala Glu Asp Leu Ala Phe Tyr Tyr Cys Gln Asn
                85                  90                  95

Asp Tyr Ser Tyr Pro Tyr Thr Phe Gly Gly Gly Thr Lys Leu Glu Ile
            100                 105                 110

Arg

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Thr Phe Thr Asp Tyr Asn Ile His
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Ile Phe Pro Asn Asn Gly Asn Asn Gly Tyr Asn Gln Lys Phe Lys
1               5                   10                  15

Gly

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Ser Gly Arg Gly Phe Ala Tyr
1               5

<210> SEQ ID NO 31
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 31

Lys Ser Ser Gln Ser Leu Leu Asn Ser Gly Asn Gln Lys Asn Tyr Leu
1               5                   10                  15

Thr

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Ala Ser Thr Arg Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Asn Asp Tyr Ser Tyr Pro Tyr Thr
1               5

<210> SEQ ID NO 34
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Asn Lys Ala Thr Leu Thr Val Asp Asn Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Gly Thr Gly Phe Ala Tyr Trp Gly Gln Gly Thr Leu Val
            100                 105                 110

Thr Val Ser Ala
        115

<210> SEQ ID NO 35
<211> LENGTH: 112
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 35

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Ala Phe Thr Leu Arg Leu
65                  70                  75                  80

Ser Arg Val Glu Ala Glu Asp Val Gly Val Tyr Tyr Cys Met Gln His
                85                  90                  95

Leu Gln Tyr Pro Phe Thr Phe Gly Gly Gly Thr Lys Leu Glu Ile Lys
            100                 105                 110

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Tyr Thr Phe Thr Asp Tyr Asn Met His
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Ile Tyr Pro Tyr Asn Gly Gly Thr Gly Tyr Asn Gln Lys Phe Lys
1               5                   10                  15

Asn

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Arg Ser Gly Thr Gly Phe Ala Tyr
1               5

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 39

Arg Ser Ser Lys Ser Leu Leu His Ser Asn Gly Asn Thr Tyr Leu Tyr
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Met Ser Asn Leu Ala Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Gln His Leu Gln Tyr Pro Phe Thr
1               5

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Gln Gln Ser Gly Pro Glu Leu Val Lys Pro Gly Ala
1               5                   10                  15

Ser Val Lys Met Ser Cys Lys Ala Pro Gly Tyr Ser Phe Thr Ser Tyr
            20                  25                  30

Leu Met Asn Trp Val Lys Gln Lys Pro Gly Gln Gly Leu Glu Trp Ile
        35                  40                  45

Gly Tyr Ile Asn Pro Tyr Ser Ala Gly Ser Asn Tyr Asn Glu Lys Phe
    50                  55                  60

Lys Asp Lys Ala Thr Leu Thr Ser Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Ser Ser Tyr Arg Tyr Gly Phe Asp Tyr Trp Gly Gln Gly Thr
            100                 105                 110

Thr Leu Thr Val Ser Ser
        115

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Tyr Thr Leu Ser Ile Thr Ser Leu Gln Thr
65              70                  75                  80

Glu Asp Val Ala Thr Tyr Ser Cys Gln Gln Tyr Trp Ser Thr Pro Trp
                85                  90                  95

Thr Phe Gly Gly Gly Thr Lys Leu Glu Ile Lys
            100                 105
```

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Gly Tyr Ser Phe Thr Ser Tyr Leu Met Asn
1               5                   10
```

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Tyr Ile Asn Pro Tyr Ser Ala Gly Ser Asn Tyr Asn Glu Lys Phe Lys
1               5                   10                  15

Asp
```

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ala Arg Ser Ser Tyr Arg Tyr Gly Phe Asp Tyr
1               5                   10
```

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Lys Ala Ser Glu Asp Ile Tyr Asn Arg Leu Ala
1               5                   10
```

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ala Thr Ser Leu Glu Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Gln Tyr Trp Ser Thr Pro Trp Thr
1               5

<210> SEQ ID NO 50
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Ser Phe Pro Ser Phe
            20                  25                  30

Leu Ile His Trp Val Lys Gln Lys Pro Gly Gln Gly Leu Glu Trp Ile
        35                  40                  45

Gly Tyr Ile Asn Pro Tyr Ser Asp Gly Ser Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Asn Cys
                85                  90                  95

Ala Arg Ser Ser Tyr Arg Tyr Gly Phe Asp Tyr Trp Gly Gln Gly Thr
            100                 105                 110

Thr Leu Ser Val Ser Ser
        115

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg

```
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asn Tyr Thr Leu Ser Ile Thr Ser Leu Gln Thr
65                  70                  75                  80

Glu Asp Val Ala Thr Tyr Tyr Cys Gln Gln Ser Trp Ser Ile Pro Trp
                85                  90                  95

Thr Phe Gly Gly Gly Thr Asn Leu Glu Ile Lys
            100                 105

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Tyr Ser Phe Pro Ser Phe Leu Ile His
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Ile Asn Pro Tyr Ser Asp Gly Ser Asn Tyr Asn Glu Lys Phe Lys
1               5                   10                  15

Gly

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Ile Ile His Trp Val Asn Gln Lys Pro Gly Gln Gly Leu Glu Trp Ile
        35                  40                  45

Gly Tyr Ile Asn Pro Tyr Ser Asp Gly Thr Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Ser Tyr Arg Tyr Gly Phe Asp Tyr Trp Gly Gln Gly Thr
            100                 105                 110
```

Thr Leu Thr Val Ser Ser
        115

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Asn Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Trp
                85                  90                  95

Thr Phe Gly Gly Gly Thr Lys Leu Glu Ile Lys
            100                 105

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Tyr Lys Phe Thr Ser Tyr Ile Ile His
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Ile Asn Pro Tyr Ser Asp Gly Thr Asn Tyr Asn Glu Lys Phe Lys
1               5                   10                  15

Gly

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Lys Leu Leu Asp Ser Gly Gly Gly Leu Val Gln Ala Gly Gly
1               5                   10                  15

```
Ser Leu Arg Leu Ser Cys Ala Gly Ser Gly Phe Thr Phe Thr Asp Phe
         20                  25                  30

Tyr Met Ser Trp Ile Arg Gln Pro Pro Gly Lys Ala Pro Glu Trp Leu
         35                  40                  45

Gly Val Ile Arg Asn Lys Ala Asn Gly Tyr Thr Ala Gly Tyr Asn Pro
 50                  55                  60

Ser Val Lys Gly Arg Phe Thr Ile Ser Arg Asp Asn Thr Gln Asn Ile
65                  70                  75                  80

Leu Tyr Leu Gln Met Asn Thr Leu Arg Ala Glu Asp Thr Ala Ile Tyr
                 85                  90                  95

Tyr Cys Ala Arg Leu Ser Tyr Gly Phe Asp Tyr Trp Gly Gln Gly Val
                100                 105                 110

Met Val Thr Val Ser Ser
            115

<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
         35                  40                  45

Pro Gln Leu Leu Ile Tyr Trp Met Ser Thr Arg Ala Ser Gly Val Ser
     50                  55                  60

Asp Arg Phe Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                 85                  90                  95

Leu Glu Phe Pro Phe Thr Phe Gly Ser Gly Thr Lys Leu Glu Ile Lys
                100                 105                 110

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Phe Thr Phe Thr Asp Phe Tyr Met Ser
1               5                   10

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Ile Arg Asn Lys Ala Asn Gly Tyr Thr Ala Gly Tyr Asn Pro Ser
```

Val Lys Gly

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Arg Leu Ser Tyr Gly Phe Asp Tyr
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Ser Lys Ser Leu Leu His Ser Asn Gly Lys Thr Tyr Leu Asn
1               5                   10                  15

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Met Ser Thr Arg Ala Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Phe Leu Glu Phe Pro Phe Thr
1               5

<210> SEQ ID NO 66
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Phe
                20                  25                  30

Tyr Met Ser Trp Ile Arg Gln Pro Pro Gly Arg Ala Pro Glu Trp Leu
        35                  40                  45

```
Gly Val Ile Arg Asn Arg Pro Asn Gly Tyr Thr Thr Asp Tyr Asn Pro
                50                  55                  60

Ser Val Lys Gly Arg Phe Thr Ile Ser Arg Asp Asn Thr Gln Asn Ile
 65                  70                  75                  80

Leu Tyr Leu Gln Met Ser Thr Leu Arg Ala Asp Asp Thr Ala Phe Tyr
                    85                  90                  95

Tyr Cys Thr Arg Leu Thr Tyr Gly Phe Asp Tyr Trp Gly Gln Gly Val
                100                 105                 110

Met Val Thr Val Ser Ser
                115

<210> SEQ ID NO 67
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Val Met Thr Gln Gly Ala Leu Pro Asn Pro Val Pro Ser Gly
 1               5                  10                  15

Glu Ser Ala Ser Ile Thr Cys Gln Ser Ser Lys Ser Leu Leu His Ser
                20                  25                  30

Asn Gly Lys Thr Tyr Leu Asn Trp Tyr Leu Gln Arg Pro Gly Gln Ser
            35                  40                  45

Pro Gln Leu Leu Ile Tyr Trp Met Ser Thr Arg Ala Ser Gly Val Ser
 50                  55                  60

Asp Arg Phe Ser Gly Ser Gly Ser Gly Thr Asp Phe Thr Leu Lys Ile
 65                  70                  75                  80

Ser Ser Val Glu Ala Glu Val Val Gly Val Tyr Tyr Cys Gln Gln Phe
                85                  90                  95

Leu Glu Phe Pro Phe Thr Phe Gly Ser Gly Thr Lys Leu Glu Ile Lys
                100                 105                 110

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Thr Phe Thr Asn Phe Tyr Met Ser
 1               5                  10

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Ile Arg Asn Arg Pro Asn Gly Tyr Thr Thr Asp Tyr Asn Pro Ser
 1               5                  10                  15

Val Lys Gly
```

```
<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Arg Leu Thr Tyr Gly Phe Asp Tyr
1               5

<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Lys Leu Leu Asp Ser Gly Gly Gly Leu Val Gln Ala Gly Gly
1               5                   10                  15

Ser Leu Arg Leu Ser Cys Ala Gly Ser Gly Phe Thr Phe Thr Asp Phe
            20                  25                  30

Tyr Met Ser Trp Ile Arg Gln Pro Pro Gly Lys Ala Pro Glu Trp Leu
        35                  40                  45

Gly Val Ile Arg Asn Lys Ala Asn Gly Tyr Thr Ala Gly Tyr Asn Pro
    50                  55                  60

Ser Val Lys Gly Arg Phe Thr Ile Ser Arg Asp Asn Thr Gln Asn Ile
65                  70                  75                  80

Leu Tyr Leu Gln Met Asn Thr Leu Arg Ala Glu Asp Thr Ala Ile Tyr
                85                  90                  95

Tyr Cys Ala Arg Leu Thr Tyr Gly Phe Asp Tyr Trp Gly Gln Gly Val
            100                 105                 110

Met Val Thr Val Ser Ser
        115

<210> SEQ ID NO 72
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Tyr Pro Phe Thr Phe Gly Ser Gly Thr Lys Leu Glu Ile Lys
            100                 105                 110
```

```
<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Leu Thr Tyr Gly Phe Asp Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Phe Leu Glu Tyr Pro Phe Thr
1               5

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Gly Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser
        115

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Thr Pro Leu Ser Leu Pro Val Thr Pro Gly
1               5                   10                  15

Glu Pro Ala Ser Ile Ser Cys Gln Ser Ser Lys Ser Leu Leu His Ser
```

```
            20                  25                  30

Asn Gly Lys Thr Tyr Leu Asn Trp Tyr Leu Gln Lys Pro Gly Gln Ser
            35                  40                  45

Pro Gln Leu Leu Ile Tyr Trp Met Ser Thr Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Phe
                85                  90                  95

Leu Glu Tyr Pro Phe Thr Phe Gly Gln Gly Thr Lys Val Glu Ile Lys
            100                 105                 110

<210> SEQ ID NO 77
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Ser Trp Val Arg Gln Ala Pro Gly Lys Gly Leu Glu Trp Val
            35                  40                  45

Ser Val Ile Arg Asn Lys Ala Asn Gly Tyr Thr Ala Gly Tyr Asn Pro
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser
            115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Thr Pro Leu Ser Leu Pro Val Thr Pro Gly
1               5                   10                  15

Glu Pro Ala Ser Ile Ser Cys Gln Ser Ser Lys Ser Leu Leu His Ser
            20                  25                  30

Thr Gly Lys Thr Tyr Leu Asn Trp Tyr Leu Gln Lys Pro Gly Gln Ser
            35                  40                  45

Pro Gln Leu Leu Ile Tyr Trp Met Ser Thr Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Phe
```

```
                    85                  90                  95
Leu Glu Tyr Pro Phe Thr Phe Gly Gln Gly Thr Lys Val Glu Ile Lys
                100                 105                 110

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Ser Ser Lys Ser Leu Leu His Ser Thr Gly Lys Thr Tyr Leu Asn
1               5                   10                  15

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser
        115

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Ile Arg Asn Lys Ala Asn Ala Tyr Thr Ala Gly Tyr Asn Pro Ser
1               5                   10                  15

Val Lys Gly

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Ser Trp Val Arg Gln Ala Pro Gly Lys Gly Pro Glu Trp Leu
        35                  40                  45

Ser Val Ile Arg Asn Lys Ala Asn Ala Tyr Thr Ala Gly Tyr Asn Pro
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser
        115

<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Ile His Trp Val Arg Gln Ser Pro Gly Lys Gly Leu Glu Trp Leu
        35                  40                  45

Gly Val Ile Trp Thr Gly Gly Ser Thr Ala Phe Asn Ala Ala Phe Met
50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Val Gly Phe His Ser Ala Thr Asp Tyr Trp Gly Gln Gly Thr Ser
            100                 105                 110

Val Thr Val Ser Ser
        115

<210> SEQ ID NO 84
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Val Leu Met Thr Gln Thr Pro Leu Ser Leu Pro Val Thr Leu Gly
1               5                   10                  15

Asp Gln Ala Ser Ile Ser Cys Arg Ser Ser Gln Asn Leu Val His Ser
            20                  25                  30

Asn Gly Asn Thr Tyr Leu Glu Trp Tyr Leu Gln Lys Pro Gly Gln Ser

```
                35                  40                  45
Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Leu Tyr Tyr Cys Phe Gln Gly
                 85                  90                  95

Ser His Val Pro Phe Thr Phe Gly Ser Gly Thr Lys Leu Glu Ile Lys
            100                 105                 110

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Phe Ser Leu Thr Thr Tyr Gly Ile His
 1               5                  10

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Ile Trp Thr Gly Gly Ser Thr Ala Phe Asn Ala Ala Phe Met Ser
 1               5                  10                  15

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Lys Val Gly Phe His Ser Ala Thr Asp Tyr
 1               5                  10

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ser Ser Gln Asn Leu Val His Ser Asn Gly Asn Thr Tyr Leu Glu
 1               5                  10                  15

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 89

Lys Val Ser Asn Arg Phe Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Gln Gly Ser His Val Pro Phe Thr
1               5

<210> SEQ ID NO 91
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Ser Pro Gly Lys Gly Leu Glu Trp Leu
        35                  40                  45

Gly Val Ile Trp Thr Gly Gly Thr Thr Asp Phe Asn Ala Ala Phe Lys
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Ser Ala Ile Tyr Tyr Cys Ala
                85                  90                  95

Lys Ile Gly Phe His Ser Ala Val Asp Tyr Trp Gly Gln Gly Thr Ser
            100                 105                 110

Val Thr Val Ser Ser
        115

<210> SEQ ID NO 92
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Asn Arg Val Glu Ala Glu Asp Leu Gly Leu Tyr Tyr Cys Phe Gln Gly
            85                  90                  95

Ser His Ile Pro Phe Thr Phe Gly Ser Gly Thr Gln Leu Glu Ile Lys
        100                 105                 110

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Phe Ser Leu Thr Ser Tyr Gly Val Gln
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Ile Trp Thr Gly Gly Thr Thr Asp Phe Asn Ala Ala Phe Lys Ser
1               5                   10                  15

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Lys Ile Gly Phe His Ser Ala Val Asp Tyr
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ser Ser Gln Asn Ile Val His Ser Asn Gly Asn Thr Tyr Leu Glu
1               5                   10                  15

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Phe Gln Gly Ser His Ile Pro Phe Thr
1               5

<210> SEQ ID NO 98

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Thr Gly Gly Ser Thr Ala Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Val Gly Phe His Ser Ala Met Asp Tyr Trp Asp Gln Gly Thr Ser
            100                 105                 110

Val Thr Val Ser Ser
        115

<210> SEQ ID NO 99
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Phe Ser Leu Thr Thr Tyr Gly Val His
1               5                   10
```

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Ile Trp Thr Gly Gly Ser Thr Ala Tyr Asn Ala Ala Phe Met Ser
1               5                   10                  15

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Lys Val Gly Phe His Ser Ala Met Asp Tyr
1               5                   10

<210> SEQ ID NO 103
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Ser Ile Glu Asp Phe
                20                  25                  30

Tyr Ile His Trp Val Lys Gln Arg Pro Glu Gln Gly Leu Glu Trp Ile
            35                  40                  45

Gly Trp Ile Asp Pro Glu Asn Gly Asp Ser Lys Tyr Ala Pro Lys Phe
        50                  55                  60

Gln Gly Lys Ala Thr Met Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

His Ala Asp His Gly Asn Tyr Gly Ser Thr Met Asp Tyr Trp Gly Gln
            100                 105                 110

Gly Thr Ser Val Thr Val Ser Ser
        115                 120

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Asn Gln Ser Pro Ser Ser Leu Ser Ala Ser Leu Gly
1               5                   10                  15

Asp Thr Val Thr Ile Thr Cys His Ala Ser Gln His Ile Asn Val Trp
                20                  25                  30

```
Leu Ser Trp Tyr Gln Gln Lys Pro Gly Asp His Pro Lys Leu Leu Ile
         35                  40                  45

Tyr Lys Ala Ser Asn Leu His Thr Gly Val Pro Ser Arg Phe Ser Gly
     50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Thr Tyr Pro Arg
                 85                  90                  95

Thr Phe Gly Gly Gly Thr Lys Leu Glu Ile Lys
             100                 105
```

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Gly Phe Ser Ile Glu Asp Phe Tyr Ile His
 1               5                  10
```

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Trp Ile Asp Pro Glu Asn Gly Asp Ser Lys Tyr Ala Pro Lys Phe Gln
 1               5                  10                  15

Gly
```

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
His Ala Asp His Gly Asn Tyr Gly Ser Thr Met Asp Tyr
 1               5                  10
```

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
His Ala Ser Gln His Ile Asn Val Trp Leu Ser
 1               5                  10
```

<210> SEQ ID NO 109
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 109

Lys Ala Ser Asn Leu His Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Gly Gln Thr Tyr Pro Arg Thr
1               5

<210> SEQ ID NO 111
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Ile Glu Asp Phe
                20                  25                  30

Tyr Ile His Trp Val Arg Gln Ala Pro Gly Gln Gly Leu Glu Trp Met
            35                  40                  45

Gly Trp Ile Asp Pro Glu Asn Gly Asp Ser Lys Tyr Ala Pro Lys Phe
        50                  55                  60

Gln Gly Arg Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

His Ala Asp His Gly Asn Tyr Gly Ser Thr Met Asp Tyr Trp Gly Gln
            100                 105                 110

Gly Thr Leu Val Thr Val Ser Ser
        115                 120

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys His Ala Ser Gln His Ile Asn Val Trp
                20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Arg
                 85                  90                  95

Thr Phe Gly Gln Gly Thr Lys Val Glu Ile Lys
            100                 105

<210> SEQ ID NO 113
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Ser Ile Glu Asp Phe
                20                  25                  30

Tyr Ile His Trp Val Arg Gln Ala Pro Gly Gln Gly Leu Glu Trp Met
             35                  40                  45

Gly Trp Ile Asp Pro Glu Asn Gly Asp Ser Lys Tyr Ala Pro Lys Phe
         50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

His Ala Asp His Gly Asn Tyr Gly Ser Thr Met Asp Tyr Trp Gly Gln
            100                 105                 110

Gly Thr Leu Val Thr Val Ser Ser
        115                 120

<210> SEQ ID NO 114
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Ser Ile Glu Asp Phe
                20                  25                  30

Tyr Ile His Trp Val Arg Gln Ala Pro Gly Gln Gly Leu Glu Trp Met
             35                  40                  45

Gly Trp Ile Asp Pro Glu Gln Gly Asp Ser Lys Tyr Ala Pro Lys Phe
         50                  55                  60

Gln Gly Arg Ala Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

His Ala Asp His Gly Asn Tyr Gly Ser Thr Met Asp Tyr Trp Gly Gln
            100                 105                 110

Gly Thr Leu Val Thr Val Ser Ser
```

115                 120

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Trp Ile Asp Pro Glu Gln Gly Asp Ser Lys Tyr Ala Pro Lys Phe Gln
1               5                   10                  15

Gly

<210> SEQ ID NO 116
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Ile Glu Asp Phe
                20                  25                  30

Tyr Ile His Trp Val Arg Gln Ala Pro Gly Gln Gly Leu Glu Trp Met
            35                  40                  45

Gly Trp Ile Asp Pro Glu Asn Gly Glu Ser Lys Tyr Ala Pro Lys Phe
        50                  55                  60

Gln Gly Arg Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

His Ala Asp His Gly Asn Tyr Gly Ser Thr Met Asp Tyr Trp Gly Gln
            100                 105                 110

Gly Thr Leu Val Thr Val Ser Ser
        115                 120

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Ile Asp Pro Glu Asn Gly Glu Ser Lys Tyr Ala Pro Lys Phe Gln
1               5                   10                  15

Gly

<210> SEQ ID NO 118
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Ile Glu Asp Phe
                20                  25                  30

Tyr Ile His Trp Val Arg Gln Ala Pro Gly Gln Gly Leu Glu Trp Met
            35                  40                  45

Gly Trp Ile Asp Pro Glu Gln Gly Glu Ser Lys Tyr Ala Pro Lys Phe
    50                  55                  60

Gln Gly Arg Ala Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

His Ala Asp His Gly Asn Tyr Gly Ser Thr Met Asp Tyr Trp Gly Gln
                100                 105                 110

Gly Thr Leu Val Thr Val Ser Ser
            115                 120

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Ile Asp Pro Glu Gln Gly Glu Ser Lys Tyr Ala Pro Lys Phe Gln
1               5                   10                  15

Gly

<210> SEQ ID NO 120
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Ile Glu Asp Phe
                20                  25                  30

Tyr Ile His Trp Val Arg Gln Ala Pro Gly Gln Gly Leu Glu Trp Met
            35                  40                  45

Gly Trp Ile Asp Pro Glu Gln Gly Asp Ser Lys Tyr Ala Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

His Ala Asp His Gly Asn Tyr Gly Ser Thr Met Asp Tyr Trp Gly Gln
                100                 105                 110

Gly Thr Leu Val Thr Val Ser Ser
            115                 120

<210> SEQ ID NO 121
<211> LENGTH: 120

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Ile Glu Asp Phe
            20                  25                  30

Tyr Ile His Trp Val Arg Gln Ala Pro Gly Gln Gly Leu Glu Trp Met
        35                  40                  45

Gly Trp Ile Asp Pro Glu Asn Gly Glu Ser Lys Tyr Ala Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

His Ala Asp His Gly Asn Tyr Gly Ser Thr Met Asp Tyr Trp Gly Gln
            100                 105                 110

Gly Thr Leu Val Thr Val Ser Ser
        115                 120

<210> SEQ ID NO 122
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Ile Glu Asp Phe
            20                  25                  30

Tyr Ile His Trp Val Arg Gln Ala Pro Gly Gln Gly Leu Glu Trp Met
        35                  40                  45

Gly Trp Ile Asp Pro Glu Gln Gly Glu Ser Lys Tyr Ala Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

His Ala Asp His Gly Asn Tyr Gly Ser Thr Met Asp Tyr Trp Gly Gln
            100                 105                 110

Gly Thr Leu Val Thr Val Ser Ser
        115                 120

<210> SEQ ID NO 123
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Lys Leu Val Glu Ser Gly Gly Gly Leu Val Gln Pro Gly Gly
```

```
                1               5                  10                 15
Ser Leu Arg Leu Ser Cys Ala Thr Ser Gly Phe Thr Phe Thr Asp Tyr
                20                 25                 30

Tyr Met Ser Trp Val Arg Gln Pro Pro Gly Lys Ala Leu Glu Trp Leu
            35                 40                 45

Gly Phe Ile Arg Asn Lys Ala Asn Gly Tyr Thr Thr Glu Tyr Ser Ala
        50                 55                 60

Ser Val Lys Gly Arg Phe Thr Ile Ser Arg Asp Ile Ser Gln Ser Ile
65                 70                 75                  80

Leu Tyr Leu Gln Met Asn Thr Leu Arg Ala Glu Asp Ser Ala Thr Tyr
                85                 90                 95

Tyr Cys Ala Arg Val Leu Arg Ala Gln Gly Phe Ala Tyr Trp Gly Gln
                100                105                110

Gly Thr Leu Val Thr Val Ser Ala
            115                120

<210> SEQ ID NO 124
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Val Met Ser Gln Ser Pro Ser Ser Leu Ala Val Ser Val Gly
1               5                  10                 15

Glu Lys Val Thr Met Ser Cys Lys Ser Ser Gln Ser Leu Leu Tyr Ser
                20                 25                 30

Ser Asn Gln Lys Asn Tyr Leu Ala Trp Tyr Gln Gln Lys Pro Gly Gln
            35                 40                 45

Ser Pro Lys Leu Leu Ile Tyr Trp Ala Ser Thr Arg Glu Ser Gly Val
        50                 55                 60

Pro Asp Arg Phe Thr Gly Ser Gly Ser Gly Thr Asp Phe Thr Leu Thr
65                 70                 75                  80

Ile Ser Ser Val Lys Ala Glu Asp Leu Ala Val Tyr Tyr Cys Gln Gln
                85                 90                 95

Tyr Tyr Gly Tyr Pro Phe Thr Phe Gly Ser Gly Thr Lys Leu Glu Ile
                100                105                110

Lys

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Phe Thr Phe Thr Asp Tyr Tyr Met Ser
1               5                  10

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 126

Phe Ile Arg Asn Lys Ala Asn Gly Tyr Thr Thr Glu Tyr Ser Ala Ser
1               5                   10                  15

Val Lys Gly

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Arg Val Leu Arg Ala Gln Gly Phe Ala Tyr
1               5                   10

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Ser Ser Gln Ser Leu Leu Tyr Ser Ser Asn Gln Lys Asn Tyr Leu
1               5                   10                  15

Ala

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Tyr Tyr Gly Tyr Pro Phe Thr
1               5

<210> SEQ ID NO 130
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Lys Leu Val Glu Ser Gly Gly Gly Leu Val Gln Pro Gly Gly
1               5                   10                  15

Ser Leu Arg Leu Ser Cys Ser Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Asp Ser Ala Thr Tyr
```

```
                85                  90                  95

Tyr Cys Ala Arg Val Leu Arg Ala Gln Gly Phe Ala Tyr Trp Gly Gln
                100                 105                 110

Gly Thr Leu Val Ala Val Ser Ala
        115                 120

<210> SEQ ID NO 131
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Val Met Ser Gln Ser Pro Ser Ser Leu Ala Val Pro Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Ile Tyr Tyr Cys Gln Gln
                85                  90                  95

Tyr Tyr Gly Asn Pro Phe Thr Phe Gly Ser Gly Thr Lys Leu Asp Ile
                100                 105                 110

Lys

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Phe Ile Arg Asn Lys Ala Asn Gly Tyr Thr Thr Asp Tyr Ser Ala Ser
1               5                   10                  15

Val Lys Gly

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Gln Tyr Tyr Gly Asn Pro Phe Thr
1               5

<210> SEQ ID NO 134
<211> LENGTH: 120
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 134

Glu Val Thr Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asp Lys Ala Asn Gly Tyr Thr Thr Asp Tyr Ser Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Asp Ser Ala Thr Tyr
                85                  90                  95

Tyr Cys Ser Arg Leu Leu Arg Ala Gly Phe Ala Tyr Trp Gly Gln
            100                 105                 110

Gly Thr Leu Val Thr Val Ser Ala
            115                 120

<210> SEQ ID NO 135
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Val Met Ser Gln Ser Pro Ser Ser Leu Gly Val Ser Ile Gly
1               5                   10                  15

Glu Lys Val Ile Met Ser Cys Thr Ser Gly Gln Ser Leu Leu Tyr Ser
            20                  25                  30

Asn Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Lys Ala Glu Asp Leu Ala Val Tyr Tyr Cys Gln Gln
                85                  90                  95

Tyr Tyr Arg Asn Pro Phe Thr Phe Gly Ser Gly Thr Lys Leu Glu Ile
            100                 105                 110

Lys

<210> SEQ ID NO 136
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Phe Ile Arg Asp Lys Ala Asn Gly Tyr Thr Thr Asp Tyr Ser Ala Ser
1               5                   10                  15

Val Lys Gly

```
<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Arg Leu Leu Arg Ala Gln Gly Phe Ala Tyr
1               5                   10

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Ser Gly Gln Ser Leu Leu Tyr Ser Asn Asn Gln Lys Asn Tyr Leu
1               5                   10                  15

Ala

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Gln Tyr Tyr Arg Asn Pro Phe Thr
1               5

<210> SEQ ID NO 140
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Glu Ser His Gly Lys Ser Leu Glu Trp Ile
            35                  40                  45

Gly Gly Ile Asn Pro Asn Lys Gly Gly Ser Tyr Asn Gln Lys Phe
        50                  55                  60

Lys Gly Lys Ala Thr Leu Thr Val Asp Lys Ser Ser Thr Ala Tyr
65                  70                  75                  80

Met Asp Leu Arg Arg Leu Thr Ser Glu Asp Ser Ala Val Tyr Tyr Cys
                85                  90                  95

Ala Arg Gly Gly Tyr Glu Tyr Tyr Ala Leu Asp Tyr Trp Gly Gln Gly
                100                 105                 110

Thr Ser Val Thr Val Ser Ser
            115
```

```
<210> SEQ ID NO 141
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Val Met Ser Gln Ser Pro Ser Ser Leu Thr Val Ser Val Gly
1               5                   10                  15

Glu Arg Val Thr Met Ser Cys Lys Ser Ser Gln Ser Leu Leu Tyr Ser
                20                  25                  30

Arg Asn Gln Lys Asn Tyr Leu Ala Trp Tyr Gln Leu Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Ser Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Pro Thr Phe Gly Gly Gly Thr Lys Leu Glu Ile
            100                 105                 110

Lys

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Tyr Thr Phe Thr Glu Tyr Thr Met His
1               5                   10

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Ile Asn Pro Asn Lys Gly Gly Ser Ser Tyr Asn Gln Lys Phe Lys
1               5                   10                  15

Gly

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Arg Gly Gly Tyr Glu Tyr Tyr Ala Leu Asp Tyr
1               5                   10

<210> SEQ ID NO 145
```

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Lys Ser Ser Gln Ser Leu Leu Tyr Ser Arg Asn Gln Lys Asn Tyr Leu
1               5                   10                  15

Ala

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Gln Tyr Tyr Ser Tyr Pro Pro Thr
1               5

<210> SEQ ID NO 147
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Gln Gln Ser Gly Pro Val Leu Val Lys Pro Gly Ala
1               5                   10                  15

Ser Val Arg Met Ser Cys Lys Pro Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Ser Ile Asn Pro Tyr Thr Gly Gly Ser Ser Tyr Asn Gln Asn Phe
        50                  55                  60

Arg Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Gly Ser Tyr Tyr Ser Asn Leu Gly Phe Ala Tyr Trp Gly Gln
            100                 105                 110

Gly Thr Leu Val Thr Val Ser Ala
        115                 120

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Val Gln Leu Thr Gln Ser Pro Ser Phe Leu Thr Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
        35                  40                  45

Ser Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln Tyr Ser Glu Tyr Pro Phe
                 85                  90                  95

Thr Phe Gly Ser Gly Thr Lys Leu Glu Ile Lys
                100                 105

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Tyr Thr Phe Thr Asp Tyr Tyr Met Asn
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Ile Asn Pro Tyr Thr Gly Gly Ser Ser Tyr Asn Gln Asn Phe Arg
1               5                   10                  15

Gly

<210> SEQ ID NO 151
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Arg Gly Ser Tyr Tyr Ser Asn Leu Gly Phe Ala Tyr
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Ala Ser Lys Ser Ile Ser Lys Tyr Leu Ala
1               5                   10

<210> SEQ ID NO 153
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 153

Ser Gly Ser Thr Leu Gln Ser
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Gln Tyr Ser Glu Tyr Pro Phe Thr
1               5

<210> SEQ ID NO 155
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Gln Gln Ser Gly Pro Glu Leu Val Arg Thr Gly Ala
1               5                   10                  15

Ser Val Lys Ile Ser Cys Arg Ala Ser Ser Tyr Ser Phe Thr Asp Asn
            20                  25                  30

Tyr Ile His Trp Val Lys Gln Thr His Gly Arg Ser Leu Glu Trp Ile
        35                  40                  45

Gly Tyr Ile Ser Gly Tyr Thr Gly Ala Thr Ser Tyr Asn Gln Lys Phe
    50                  55                  60

Lys Gly Lys Ala Thr Phe Thr Val Asp Thr Ser Ser Ser Thr Ala Tyr
65                  70                  75                  80

Met Gln Phe Asn Ser Leu Thr Ser Glu Asp Ser Ala Val Tyr Tyr Cys
                85                  90                  95

Ala Arg Ser Thr Met Ile Ala Pro Tyr Gly Met Asp Tyr Trp Gly Gln
            100                 105                 110

Gly Thr Ser Val Thr Val Ser Ser
        115                 120

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
```

```
                50                  55                  60
Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Arg Tyr Pro Leu
                 85                  90                  95

Thr Phe Gly Ala Gly Thr Lys Leu Glu Leu Lys
            100                 105

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Tyr Ser Phe Thr Asp Asn Tyr Ile His
 1               5                  10

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Ile Ser Gly Tyr Thr Gly Ala Thr Ser Tyr Asn Gln Lys Phe Lys
 1               5                  10                  15

Gly

<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Arg Ser Thr Met Ile Ala Pro Tyr Gly Met Asp Tyr
 1               5                  10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Ala Ser Gln Asp Val Val Thr Ala Val Ala
 1               5                  10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161
```

```
Trp Ala Ser Thr Arg His Thr
1               5
```

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

```
Gln Gln Tyr Ser Arg Tyr Pro Leu Thr
1               5
```

<210> SEQ ID NO 163
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Lys Phe Thr Asp Tyr
            20                  25                  30

Tyr Met Asn Trp Val Lys Gln Ser His Gly Lys Ser Leu Glu Trp Ile
        35                  40                  45

Gly Thr Ile Asn Pro Tyr Ser Gly Ile Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Ala Ser Ala Val Tyr Tyr Cys
                85                  90                  95

Thr Arg Arg Asn Trp Asp Gly Arg Tyr Ala Met Asp Tyr Trp Gly Gln
            100                 105                 110

Gly Thr Ser Val Thr Val Ser Ser
        115                 120
```

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80
```

Glu Asp Leu Ala Glu Tyr Phe Cys Gln Gln Tyr Ser Ser Tyr Pro Phe
            85                  90                  95

Thr Phe Gly Gly Gly Thr Lys Leu Glu Ile Lys
            100                 105

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Tyr Lys Phe Thr Asp Tyr Tyr Met Asn
1               5                   10

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Ile Asn Pro Tyr Ser Gly Gly Ile Ser Tyr Asn Gln Lys Phe Lys
1               5                   10                  15

Gly

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Thr Arg Arg Asn Trp Asp Gly Arg Tyr Ala Met Asp Tyr
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Ala Ser Gln Asp Val Ser Thr Ala Val Ala
1               5                   10

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Tyr Ser Ser Tyr Pro Phe Thr
1               5

```
<210> SEQ ID NO 170
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Glu Val Gln Leu Gln Gln Ser Gly Pro Val Leu Val Lys Pro Gly Ala
1               5                   10                  15

Ser Leu Lys Met Ser Cys Arg Ala Ser Gly Tyr Thr Phe Thr Asp Tyr
                20                  25                  30

Tyr Val His Trp Val Lys Gln Ser His Gly Lys Ser Leu Glu Trp Ile
            35                  40                  45

Gly Leu Ile Asn Pro Tyr Thr Gly Thr Thr Ser Tyr Asn Gln Arg Phe
        50                  55                  60

Lys Gly Lys Ala Thr Leu Thr Val Asp Lys Ser Ser Ser Thr Ala Tyr
65                  70                  75                  80

Met Glu Val Asn Ser Leu Thr Ser Glu Asp Ser Ala Val Tyr Tyr Cys
                85                  90                  95

Ala Arg Ser Arg Val Tyr Gly Ser Ser Leu Phe Ala Phe Trp Gly
            100                 105                 110

Gln Gly Thr Leu Val Thr Val Ser Ala
        115                 120

<210> SEQ ID NO 171
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Tyr Thr Phe Gly Gly Gly Thr Lys Leu Glu Ile
            100                 105                 110

Lys

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172
```

Gly Tyr Thr Phe Thr Asp Tyr Tyr Val His
1               5                   10

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Ile Asn Pro Tyr Thr Gly Thr Thr Ser Tyr Asn Gln Arg Phe Lys
1               5                   10                  15

Gly

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Arg Ser Arg Val Tyr Tyr Gly Ser Ser Leu Phe Ala Phe
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Ser Ser Gln Ser Leu Leu Asn Ser Gly Asn Gln Lys Asn Tyr Leu
1               5                   10                  15

Ala

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ala Ser Thr Arg Glu Ser
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Asn Asp His Ser Tyr Pro Tyr Thr
1               5

<210> SEQ ID NO 178

```
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Arg Leu Gln Gln Ser Gly Ala Glu Leu Val Arg Pro Gly Ser
1               5                   10                  15

Ser Val Lys Leu Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Asn Phe
    50                  55                  60

Lys Gly Lys Ala Thr Leu Thr Ala Asp Asn Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Arg Asn Gly Asp Phe Gly Asp Tyr Ala Met Asp Tyr Trp
            100                 105                 110

Gly Gln Gly Thr Ser Val Thr Val Ser Ser
        115                 120

<210> SEQ ID NO 179
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Cys Trp Tyr Gln Gln Lys Pro Gly Ser Ser Pro Lys Pro Trp Ile Tyr
        35                  40                  45

Arg Thr Ser Thr Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Ala
65                  70                  75                  80

Asp Ala Ala Thr Tyr Tyr Cys Gln His Tyr His Ser Tyr Pro Phe Thr
                85                  90                  95

Phe Gly Ala Gly Thr Lys Leu Glu Leu Lys
            100                 105

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Tyr Ala Phe Ser Ser Tyr Trp Met Asn
1               5                   10
```

```
<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gln Ile Tyr Pro Gly Asp Gly Asp Thr Asn Tyr Asn Gly Asn Phe Lys
1               5                   10                  15

Gly

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Arg Arg Arg Asn Gly Asp Phe Gly Asp Tyr Ala Met Asp Tyr
1               5                   10                  15

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ala Ser Ser Ser Val Ser Tyr Met Cys
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Trp Ile Tyr Arg Thr Ser Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Tyr Tyr Cys Gln His Tyr His Ser Tyr
1               5

<210> SEQ ID NO 186
<211> LENGTH: 123
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 186

Gln Ile Gln Leu Val Gln Ser Gly Pro Glu Leu Arg Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Leu Pro Arg His Ser Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Val Tyr Tyr Gly Ser Arg Lys Thr Ala Trp Phe Ala Tyr
            100                 105                 110

Trp Gly Gln Gly Thr Leu Val Thr Val Ser Ala
        115                 120

<210> SEQ ID NO 187
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Leu Val Met Ser Gln Ser Pro Ser Ser Leu Ala Val Ser Val Gly
1               5                   10                  15

Glu Arg Val Thr Met Ser Cys Lys Ser Ser Gln Ser Leu Leu Tyr Ser
            20                  25                  30

Asn Asp Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Phe Cys Gln Gln
                85                  90                  95

Tyr Tyr Ser Tyr Pro Pro Thr Phe Gly Ala Gly Thr Lys Leu Glu Leu
            100                 105                 110

Lys

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Tyr Thr Phe Thr Thr Tyr Gly Met Ser
1               5                   10

<210> SEQ ID NO 189
<211> LENGTH: 17

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Trp Ile Asn Thr Tyr Ser Gly Leu Pro Arg His Ser Asp Asp Phe Lys
1               5                   10                  15
Gly

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Arg Glu Val Tyr Tyr Gly Ser Arg Lys Thr Ala Trp Phe Ala Tyr
1               5                   10                  15

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Lys Ser Ser Gln Ser Leu Leu Tyr Ser Asn Asp Gln Lys Asn Tyr Leu
1               5                   10                  15
Ala

<210> SEQ ID NO 192
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Leu Val Met Ser Gln Ser Pro Ser Ser Leu Ala Val Ser Val Gly
1               5                   10                  15

Glu Arg Ile Thr Met Thr Cys Lys Ser Ser Gln Ser Leu Leu Tyr Ser
            20                  25                  30

Asn Asp Gln Lys Asn Tyr Leu Ala Trp Tyr Gln Gln Ile Pro Gly Gln
        35                  40                  45

Ser Pro Lys Leu Leu Leu Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Phe Cys Gln Gln
                85                  90                  95

Tyr Tyr Asn Tyr Pro Pro Thr Phe Gly Ala Gly Thr Lys Leu Glu Leu
            100                 105                 110

Lys

<210> SEQ ID NO 193

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Gln Tyr Tyr Asn Tyr Pro Pro Thr
1               5

<210> SEQ ID NO 194
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Lys Gln Ser Gly Pro Gly Leu Leu Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ile Thr Leu Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Val Gly Tyr Gly Ser Ser Asp Tyr Trp Gly Gln Gly Thr Thr
            100                 105                 110

Leu Thr Val Ser Ser
        115

<210> SEQ ID NO 195
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Val Leu Met Thr Gln Ser Pro Leu Ser Leu Pro Val Ser Leu Gly
1               5                   10                  15

Asp Gln Ala Ser Phe Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Phe Ser Leu Thr Ser Tyr Gly Val His
1               5                   10

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Val Ile Trp Ser Gly Gly Ile Thr Leu Tyr Asn Ala Ala Phe Met Ser
1               5                   10                  15

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Lys Val Gly Tyr Gly Ser Ser Ser Asp Tyr
1               5                   10

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ser Ser Gln Ser Ile Val His Ser Asn Gly Asn Thr Tyr Leu Glu
1               5                   10                  15

<210> SEQ ID NO 200
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Thr Asn Gly Gly Arg Thr Tyr Tyr Pro Asp Thr Val
    50                  55                  60

-continued

```
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Leu Tyr Tyr Cys
                 85                  90                  95

Ala Arg Glu Ser Asp Gly Gly Ala Phe Ala Tyr Trp Gly Gln Gly Thr
            100                 105                 110

Leu Val Thr Val Ser Ala
            115
```

<210> SEQ ID NO 201
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Asn
                 85                  90                  95

Thr His Val Pro Leu Thr Phe Gly Ala Gly Thr Lys Leu Glu Leu Lys
            100                 105                 110
```

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

```
Gly Phe Thr Phe Ser Ser Tyr Tyr Met Ser
 1               5                  10
```

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

```
Ala Ile Asn Thr Asn Gly Gly Arg Thr Tyr Tyr Pro Asp Thr Val Lys
 1               5                  10                  15

Gly
```

<210> SEQ ID NO 204
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 204

Ala Arg Glu Ser Asp Gly Gly Ala Phe Ala Tyr
1               5                   10

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ser Ser Gln Ser Leu Val His Ser Asn Gly Asn Thr Tyr Leu His
1               5                   10                  15

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Gln Asn Thr His Val Pro Leu Thr
1               5

<210> SEQ ID NO 207
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Ile His Trp Val Lys Gln Ser His Gly Lys Ser Leu Glu Trp Ile
            35                  40                  45

Gly Tyr Ile Tyr Pro Tyr Asn Gly Val Thr Gly Tyr Asn Gln Lys Phe
        50                  55                  60

Lys Ser Lys Ala Thr Leu Thr Val Asp Asn Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Arg Val Asp Gly Asp Tyr Trp Gly Gln Gly Thr Thr Leu
                100                 105                 110

Thr Val Ser Ser
        115

<210> SEQ ID NO 208
<211> LENGTH: 112
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 208

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Tyr Ile Tyr Pro Tyr Asn Gly Val Thr Gly Tyr Asn Gln Lys Phe Lys
1               5                   10                  15

Ser

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Arg Ser Arg Val Asp Gly Asp Tyr
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Lys Ile Ser Asn Arg Phe Ser
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

```
Ser Gln Ser Thr His Val Pro Leu Thr
1               5
```

<210> SEQ ID NO 213
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Val His Trp Val Lys Gln Ser His Gly Lys Ser Leu Glu Trp Ile
        35                  40                  45

Gly Leu Ile Asn Pro Tyr Thr Gly Thr Thr Ser Tyr Asn Gln Arg Phe
    50                  55                  60

Arg Val Lys Ala Thr Leu Thr Val Asp Lys Ser Ser Ser Thr Ala Tyr
65                  70                  75                  80

Met Glu Val Asn Ser Leu Thr Ser Glu Asp Ser Ala Val Tyr Tyr Cys
                85                  90                  95

Ala Arg Ser Arg Val Tyr Tyr Gly Ser Ser Leu Phe Ala Phe Trp Gly
            100                 105                 110

Gln Gly Thr Leu Val Thr Val Ser Ala
        115                 120
```

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Gly Leu Ile Asn Pro Tyr Thr Gly Thr Thr Ser Tyr Asn Gln Arg Phe
1               5                   10                  15

Arg Val
```

<210> SEQ ID NO 215
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Ile Ile Asn Pro Tyr Ser Gly Gly Ile Ser Tyr Asn Gln Lys Phe
    50                  55                  60

Lys Gly Lys Ala Ile Leu Thr Val Asp Lys Ser Ser Ser Thr Ala Tyr
```

```
                65                  70                  75                  80
Met Glu Leu Asn Ser Leu Thr Ser Glu Ala Ser Ala Val Tyr Tyr Cys
                        85                  90                  95

Thr Arg Arg Asn Trp Asp Gly Arg Tyr Ala Met Asp Tyr Trp Gly Gln
                    100                 105                 110

Gly Thr Ser Val Thr Val Ser Ser
            115                 120
```

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Asp Ile Val Met Thr Gln Ser His Lys Phe Met Ser Thr Ser Val Gly
1               5                   10                  15

Asp Arg Val Ser Ile Thr Tyr Lys Ala Ser Gln Asp Val Gly Ser Ala
                20                  25                  30

Val Ala Trp Tyr Gln Gln Lys Pro Gly Gln Ser Pro Lys Leu Leu Ile
            35                  40                  45

Tyr Trp Thr Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Phe
                85                  90                  95

Thr Phe Gly Gly Gly Thr Lys Leu Glu Ile Lys
            100                 105
```

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Ile Ile Asn Pro Tyr Ser Gly Gly Ile Ser Tyr Asn Gln Lys Phe Lys
1               5                   10                  15

Gly
```

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Lys Ala Ser Gln Asp Val Gly Ser Ala Val Ala
1               5                   10
```

<210> SEQ ID NO 219
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 219

Trp Thr Ser Thr Arg His Thr
1               5

<210> SEQ ID NO 220
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Gln Gln Pro Gly Ala Asp Leu Val Lys Pro Gly Ala
1               5                   10                  15

Ser Val Lys Met Ser Cys Lys Ala Ser Gly Tyr Thr Phe Thr Asn Tyr
                20                  25                  30

Trp Ile Thr Trp Val Gln Arg Pro Gly Gln Gly Leu Glu Trp Ile
            35                  40                  45

Gly Asp Ile Tyr Pro Gly Ser Gly Asn Thr Asn Tyr Asn Glu Lys Phe
50                  55                  60

Arg Ser Lys Ala Thr Leu Thr Val Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ser Arg Glu Gly Tyr Gly Ile Ser Ala Trp Gly Gln Gly Thr Thr Leu
            100                 105                 110

Thr Val Ser Ser
            115

<210> SEQ ID NO 221
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Ile Val Leu Thr Gln Ser Pro Ala Phe Met Ser Ala Ser Pro Gly
1               5                   10                  15

Glu Lys Val Thr Ile Thr Cys Arg Ala Ser Ser Ser Val Ser Tyr Met
                20                  25                  30

His Trp Phe Gln Gln Lys Pro Gly Thr Ser Pro Lys Leu Trp Ile Phe
            35                  40                  45

Ser Thr Ser Asn Leu Ala Ser Gly Val Pro Ala Arg Phe Ser Gly Ser
50                  55                  60

Gly Ser Gly Thr Ser His Ser Leu Thr Ile Ser Arg Met Glu Ala Glu
65                  70                  75                  80

Asp Ala Ala Thr Tyr Tyr Cys Gln Gln Arg Ser Gly Tyr Pro Leu Thr
                85                  90                  95

Phe Gly Ala Gly Thr Lys Leu Glu Leu Lys
            100                 105

<210> SEQ ID NO 222
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 222

Gly Tyr Thr Phe Thr Asn Tyr Trp Ile Thr
1               5                   10

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asp Ile Tyr Pro Gly Ser Gly Asn Thr Asn Tyr Asn Glu Lys Phe Arg
1               5                   10                  15

Ser

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Arg Ala Ser Ser Ser Val Ser Tyr Met His
1               5                   10

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Gln Arg Ser Gly Tyr Pro Leu Thr
1               5

<210> SEQ ID NO 226
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Val Gln Leu Val Glu Ser Gly Gly Gly Leu Val Gln Pro Gly Lys
1               5                   10                  15

Ser Leu Lys Leu Ser Cys Ala Ala Ser Gly Phe Thr Phe Ser Tyr Tyr
            20                  25                  30

Gly Met Ala Trp Val Arg Gln Ala Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Gly Asn Ala Lys Asn Thr Leu Tyr
65                  70                  75                  80
```

```
Leu Gln Met Asp Ser Leu Arg Ser Glu Asp Thr Ala Thr Tyr Tyr Cys
                85                  90                  95

Ala Arg Gly Asp Ile Gly Thr Ser Tyr Trp Phe Thr Tyr Trp Gly Gln
            100                 105                 110

Gly Thr Leu Val Thr Val Ser Ser
        115                 120

<210> SEQ ID NO 227
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Asp Ile Gln Leu Thr Gln Ser Pro Ser Leu Ser Ala Ser Val Gly
1               5                   10                  15

Asp Arg Val Thr Leu Ser Cys Lys Gly Ser Gln Thr Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Trp Thr
                85                  90                  95

Phe Gly Gly Gly Thr Lys Leu Glu Leu Lys
            100                 105

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Phe Thr Phe Ser Tyr Tyr Gly Met Ala
1               5                   10

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Ile Ser Thr Gly Gly Gly Asn Thr Tyr Tyr Arg Asp Ser Val Lys
1               5                   10                  15

Gly

<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 230

Ala Arg Gly Asp Ile Gly Thr Ser Tyr Trp Phe Thr Tyr
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Lys Gly Ser Gln Thr Ile Asn Asn Tyr Leu Ala
1               5                   10

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Lys Thr Asn Ser Leu Gln Thr
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Tyr Gln Tyr Asn Asn Gly Trp Thr
1               5

<210> SEQ ID NO 234
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Glu Val Gln Leu Gln Gln Ser Gly Pro Val Leu Val Lys Pro Gly Ala
1               5                   10                  15

Ser Val Lys Met Ser Cys Lys Pro Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Ser Ile Asn Pro Tyr Thr Gly Gly Ser Tyr Asn Gln Lys Phe
        50                  55                  60

Arg Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Gly Ser Tyr Tyr Ser Asn Leu Gly Phe Ala Tyr Trp Gly Gln

```
                    100                 105                 110

Gly Thr Leu Val Thr Val Ser Ala
            115                 120

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Asp Val Gln Leu Thr Gln Ser Pro Ser Tyr Leu Thr Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Ser Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln Tyr Ser Glu Tyr Pro Phe
                85                  90                  95

Thr Phe Gly Ser Gly Thr Lys Leu Glu Ile Lys
            100                 105

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Ile Asn Pro Tyr Thr Gly Gly Ser Ser Tyr Asn Gln Lys Phe Arg
1               5                   10                  15

Gly

<210> SEQ ID NO 237
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Ala Leu Ser Trp Val Lys Gln Arg Thr Gly Gln Gly Leu Glu Trp Ile
        35                  40                  45

Gly Glu Ile Tyr Pro Arg Ser Gly Asn Thr Tyr Ser Asn Glu Lys Phe
    50                  55                  60

Lys Gly Lys Ala Thr Leu Thr Ala Asp Lys Ser Ser Ser Thr Ala Tyr
65                  70                  75                  80
```

```
Met Glu Leu Arg Ser Leu Thr Ser Glu Asp Ser Ala Val Tyr Phe Cys
                85                  90                  95

Ala Lys Gly Gly Val Tyr Tyr Gly Ser Ser Tyr Trp Tyr Phe Asp Val
            100                 105                 110

Trp Gly Thr Gly Thr Thr Val Thr Val Ser Ser
        115                 120
```

<210> SEQ ID NO 238
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Asp Val Val Met Thr Gln Thr Pro Leu Ser Leu Pro Val Ser Leu Gly
1               5                   10                  15

Asp Gln Ala Ser Ile Ser Cys Ser Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Thr Glu Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110
```

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

```
Gly Tyr Thr Phe Thr Ser Tyr Ala Leu Ser
1               5                   10
```

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

```
Glu Ile Tyr Pro Arg Ser Gly Asn Thr Tyr Ser Asn Glu Lys Phe Lys
1               5                   10                  15

Gly
```

<210> SEQ ID NO 241
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Lys Gly Gly Val Tyr Tyr Gly Ser Ser Tyr Trp Tyr Phe Asp Val
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Ser Ser Gln Ser Leu Val His Ser Asn Gly Asn Thr Tyr Leu His
1               5                   10                  15

<210> SEQ ID NO 243
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Tyr Tyr
                20                  25                  30

Gly Met Ala Trp Val Arg Gln Ala Pro Thr Lys Gly Leu Glu Trp Val
            35                  40                  45

Ala Ser Ile Ser Thr Gly Gly Gly Asn Thr Tyr Tyr Arg Asp Ser Val
        50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg Gly Asp Ile Gly Thr Thr Tyr Trp Phe Thr Tyr Trp Gly Gln
                100                 105                 110

Gly Thr Leu Val Thr Val Ser Ser
            115                 120

<210> SEQ ID NO 244
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asn Ile Gln Leu Thr Gln Ser Pro Ser Leu Ser Ala Ser Val Gly
1               5                   10                  15

Asp Arg Val Thr Leu Ser Cys Lys Gly Ser Gln Asn Ile Asn Asn Tyr
                20                  25                  30

Leu Ala Trp Tyr Gln Gln Lys Leu Gly Glu Ala Pro Lys Leu Leu Ile
            35                  40                  45

Tyr Lys Thr Asn Ser Leu Gln Thr Gly Ile Pro Ser Arg Phe Ser Gly
        50                  55                  60

Ser Gly Ser Gly Thr Asp Tyr Thr Leu Thr Ile Ser Ser Leu His Ser

```
            65                  70                  75                  80
Glu Asp Leu Ala Thr Tyr Tyr Cys Tyr Gln Tyr Asn Asn Gly Trp Thr
                    85                  90                  95

Phe Gly Gly Gly Thr Lys Leu Glu Leu Lys
            100                 105
```

<210> SEQ ID NO 245
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Ala Arg Gly Asp Ile Gly Thr Thr Tyr Trp Phe Thr Tyr
1               5                   10
```

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

```
Lys Gly Ser Gln Asn Ile Asn Asn Tyr Leu Ala
1               5                   10
```

<210> SEQ ID NO 247
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Glu Val Gln Leu Val Glu Ser Gly Gly Leu Val Gln Pro Gly Arg
1               5                   10                  15

Ser Leu Lys Leu Ser Cys Pro Ala Ser Gly Phe Thr Phe Ser Tyr Tyr
                20                  25                  30

Gly Met Ala Trp Val Arg Gln Ala Pro Thr Lys Gly Leu Glu Trp Val
            35                  40                  45

Ala Ser Ile Ser Thr Gly Gly Gly Asn Thr Tyr Tyr Arg Asp Ser Val
        50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg Gly Asp Ile Gly Thr Ala Tyr Trp Phe Thr Tyr Trp Gly Gln
            100                 105                 110

Gly Thr Leu Val Thr Val Ser Ser
        115                 120
```

<210> SEQ ID NO 248
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asn Ile Gln Leu Thr Gln Ser Pro Ser Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Leu Thr Gly Ile Pro Ser Arg Phe Ser Gly
50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Trp Thr
                85                  90                  95

Phe Gly Gly Gly Thr Lys Leu Glu Leu Lys
            100                 105

<210> SEQ ID NO 249
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Arg Gly Asp Ile Gly Thr Ala Tyr Trp Phe Thr Tyr
1               5                   10

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Lys Thr Asn Ser Leu Leu Thr
1               5

<210> SEQ ID NO 251
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Ile Gln Leu Val Gln Ser Gly Pro Glu Leu Lys Lys Pro Gly Glu
1               5                   10                  15

Ser Leu Lys Ile Ser Cys Lys Ala Ser Gly Tyr Thr Phe Thr Asp Tyr
            20                  25                  30

Ala Met Gln Trp Val Lys Gln Ala Pro Gly Lys Gly Leu Gln Tyr Met
        35                  40                  45

Gly Trp Ile Asn Thr Gln Thr Gly Lys Pro Thr Tyr Ala Asp Asp Phe
    50                  55                  60

Lys Glu Arg Phe Val Phe Ser Leu Glu Thr Ser Ala Ser Thr Ala Tyr
65                  70                  75                  80

Leu Lys Ile Asn Asn Leu Lys Asn Asp Asp Met Ala Thr Tyr Leu Cys

```
                    85                  90                  95
Ala Arg Ser Tyr Gly Gly Glu Tyr Asn Trp Ile Ala Tyr Trp Gly Gln
                100                 105                 110

Gly Thr Leu Val Thr Val Ser Ser
        115                 120

<210> SEQ ID NO 252
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ile Val Met Thr Gln Thr Pro Ser Ser Gln Ala Val Ser Ala Gly
1               5                   10                  15

Glu Lys Val Thr Met Asn Cys Lys Ser Ser Gln Ser Leu Leu Tyr Asn
                20                  25                  30

Glu Asn Lys Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Phe Pro Pro Thr Phe Gly Gly Gly Thr Lys Leu Glu Leu
                100                 105                 110

Lys

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Tyr Thr Phe Thr Asp Tyr Ala Met Gln
1               5                   10

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Ile Asn Thr Gln Thr Gly Lys Pro Thr Tyr Ala Asp Asp Phe Lys
1               5                   10                  15

Glu

<210> SEQ ID NO 255
<211> LENGTH: 13
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 255

Ala Arg Ser Tyr Gly Gly Glu Tyr Asn Trp Ile Ala Tyr
1               5                   10

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Lys Ser Ser Gln Ser Leu Leu Tyr Asn Glu Asn Lys Asn Tyr Leu
1               5                   10                  15

Ala

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gln Gln Ser Tyr Asn Phe Pro Pro Thr
1               5

<210> SEQ ID NO 258
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gln Ile Gln Leu Val Gln Ser Gly Pro Glu Leu Lys Lys Pro Gly Glu
1               5                   10                  15

Ser Leu Lys Ile Ser Cys Lys Ala Ser Gly Tyr Thr Phe Thr Asp Tyr
                20                  25                  30

Ala Met Gln Trp Val Lys Gln Ala Pro Glu Lys Gly Leu Gln Tyr Met
            35                  40                  45

Gly Trp Ile Asn Thr Gln Thr Gly Lys Pro Thr Tyr Ala Asp Asp Phe
        50                  55                  60

Lys Glu Arg Phe Val Phe Ser Leu Glu Thr Ser Ala Thr Thr Ala Tyr
65                  70                  75                  80

Leu Gln Ile Asn Asn Leu Lys Asn Glu Asp Met Ala Thr Tyr Phe Cys
                85                  90                  95

Val Arg Ser Tyr Asn Asn Tyr Glu Asn Trp Phe Ala Tyr Trp Gly Gln
                100                 105                 110

Gly Thr Leu Val Thr Val Ser Ser
            115                 120

<210> SEQ ID NO 259
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 259

Asp Ile Val Met Thr Gln Ser Pro Ser Ser Leu Ala Val Ser Ala Gly
1               5                   10                  15

Glu Thr Val Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Val Leu Ile Tyr Trp Ala Ser Thr Arg Gln Phe Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asn Ser Pro Ile Thr Phe Gly Ser Gly Thr Lys Leu Glu Ile
            100                 105                 110

Lys

<210> SEQ ID NO 260
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Arg Ser Tyr Asn Asn Tyr Glu Asn Trp Phe Ala Tyr
1               5                   10

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Lys Ser Ser Gln Ser Leu Leu Tyr Ser Gly Asn Gln Lys Asn Tyr Leu
1               5                   10                  15

Ala

<210> SEQ ID NO 262
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Trp Ala Ser Thr Arg Gln Phe
1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 263

Gln Gln Tyr Tyr Asn Ser Pro Ile Thr
1               5

<210> SEQ ID NO 264
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Glu Val Gln Leu Val Glu Ser Gly Gly Gly Leu Val Gln Pro Gly Arg
1               5                   10                  15

Ser Met Met Leu Ser Cys Ser Ala Ser Gly Phe Thr Phe Ser Asn Tyr
            20                  25                  30

His Met Ala Trp Val Arg Gln Ala Pro Thr Thr Gly Leu Glu Trp Val
        35                  40                  45

Ala Ser Ile Thr Thr Gly Ser Gly Asn Thr Tyr Tyr Arg His Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Ser Tyr Tyr Cys
                85                  90                  95

Ala Arg Arg Trp Tyr Gly Gly Tyr Glu Gly Tyr Tyr Phe Asp Tyr Trp
            100                 105                 110

Gly Gln Gly Val Met Val Thr Val Ser Ser
        115                 120

<210> SEQ ID NO 265
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Asp Ile Gln Met Thr Gln Ser Pro Ser Leu Leu Ser Ala Ser Val Gly
1               5                   10                  15

Asp Arg Val Thr Leu Ser Cys Lys Ala Gly Gln Asn Val Asn Asn Tyr
            20                  25                  30

Leu Ala Trp Tyr Gln Gln Lys Leu Gly Glu Ala Pro Lys Leu Leu Ile
        35                  40                  45

Tyr Asn Ala Asn Ile Leu Gln Thr Gly Phe Pro Ser Arg Phe Ser Gly
    50                  55                  60

Thr Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Gly Gly Thr Lys Leu Glu Leu Lys
            100                 105

<210> SEQ ID NO 266
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 266

Gly Phe Thr Phe Ser Asn Tyr His Met Ala
1               5                   10

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Ile Thr Thr Gly Ser Gly Asn Thr Tyr Tyr Arg His Ser Val Lys
1               5                   10                  15

Gly

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Arg Arg Trp Tyr Gly Gly Tyr Glu Gly Tyr Tyr Phe Asp Tyr
1               5                   10                  15

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Lys Ala Gly Gln Asn Val Asn Asn Tyr Leu Ala
1               5                   10

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asn Ala Asn Ile Leu Gln Thr
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gln Gln Tyr Asn Ser Trp Thr Thr
1               5
```

<210> SEQ ID NO 272
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Glu Val Gln Leu Val Glu Ser Gly Gly Gly Leu Val Gln Pro Gly Arg
1               5                   10                  15

Ser Met Lys Leu Ser Cys Ala Ala Leu Gly Phe Thr Phe Ser Asn Tyr
            20                  25                  30

Tyr Met Ala Trp Val Arg Gln Ala Pro Arg Lys Gly Leu Glu Trp Val
        35                  40                  45

Ala Ser Ile Ser Thr Gly Gly Asp Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Met Gln Met Asp Ser Leu Arg Ser Glu Asp Thr Ala Thr Tyr Tyr Cys
                85                  90                  95

Val Arg Ser Phe Ile Val Gly Thr Thr Gly Tyr Tyr Phe Asp Tyr Trp
            100                 105                 110

Gly Gln Gly Val Met Val Thr Val Ser Ser
        115                 120

<210> SEQ ID NO 273
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asp Ile Val Leu Thr Gln Ser Pro Ala Leu Ala Val Ser Leu Gly Gln
1               5                   10                  15

Arg Ala Thr Ile Ser Cys Lys Thr Asn Gln Asn Val Asp Tyr Tyr Gly
            20                  25                  30

Asn Asn Tyr Met His Trp Tyr Gln Gln Thr Pro Gly Gln Gln Pro Lys
        35                  40                  45

Leu Leu Ile Tyr Phe Ala Ser Asn Leu Ala Ser Gly Ile Pro Ala Arg
    50                  55                  60

Phe Ser Gly Arg Gly Ser Gly Thr Asp Phe Thr Leu Thr Ile Asp Pro
65                  70                  75                  80

Val Glu Ala Asp Asp Thr Ala Thr Tyr Tyr Cys Gln Gln Ser Arg Asn
                85                  90                  95

Leu Pro Thr Phe Gly Gly Gly Thr Lys Leu Glu Leu Lys
            100                 105

<210> SEQ ID NO 274
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

```
Gly Phe Thr Phe Ser Asn Tyr Tyr Met Ala
1               5                   10
```

<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

```
Ser Ile Ser Thr Gly Gly Asp Asn Thr Tyr Tyr Arg Asp Ser Val Lys
1               5                   10                  15

Gly
```

<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

```
Val Arg Ser Phe Ile Val Gly Thr Thr Gly Tyr Tyr Phe Asp Tyr
1               5                   10                  15
```

<210> SEQ ID NO 277
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

```
Lys Thr Asn Gln Asn Val Asp Tyr Tyr Gly Asn Asn Tyr Met His
1               5                   10                  15
```

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

```
Phe Ala Ser Asn Leu Ala Ser
1               5
```

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

```
Gln Gln Ser Arg Asn Leu Pro Thr
1               5
```

<210> SEQ ID NO 280
<211> LENGTH: 125
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 280

Glu Val Lys Leu Leu Glu Ser Gly Gly Gly Leu Val Gln Pro Gly Ser
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Arg Ala Pro Glu Trp Leu
        35                  40                  45

Gly Phe Phe Arg Asn Ile Val Asp Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Ser Gly Tyr Ser Ser Tyr Ile Tyr Gly Gly Thr Phe
            100                 105                 110

Ala Tyr Trp Gly Gln Gly Thr Leu Val Thr Val Ser Ser
        115                 120                 125

<210> SEQ ID NO 281
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Glu Thr Val Met Thr Gln Ser Pro Thr Ser Met Ser Thr Ser Ile Gly
1               5                   10                  15

Glu Arg Val Thr Leu Asn Cys Lys Ala Ser Gln Ser Val Gly Ile His
            20                  25                  30

Val Asp Trp Tyr Gln Gln Thr Pro Gly Gln Ser Pro Lys Leu Leu Ile
        35                  40                  45

Tyr Gly Ala Ser Asn Arg His Thr Gly Val Pro Asp Arg Phe Thr Gly
    50                  55                  60

Ser Gly Phe Gly Arg Asp Phe Thr Leu Thr Ile Ser Asn Val Glu Ala
65                  70                  75                  80

Glu Asp Leu Ala Val Tyr Tyr Cys Leu Gln Tyr Gly Ser Ile Pro Trp
                85                  90                  95

Thr Phe Gly Gly Gly Thr Lys Leu Glu Leu Lys
            100                 105

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Phe Thr Phe Thr Asp Phe Tyr Met Asn
1               5                   10

<210> SEQ ID NO 283

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Phe Phe Arg Asn Ile Val Asp Gly Tyr Thr Thr Glu Tyr Asn Pro Ser
1               5                   10                  15

Val Lys Gly

<210> SEQ ID NO 284
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Arg Ser Gly Tyr Ser Ser Tyr Ile Tyr Gly Gly Thr Phe Ala Tyr
1               5                   10                  15

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Lys Ala Ser Gln Ser Val Gly Ile His Val Asp
1               5                   10

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Ala Ser Asn Arg His Thr
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Leu Gln Tyr Gly Ser Ile Pro Trp Thr
1               5

<210> SEQ ID NO 288
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 288

Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Ile Arg Gln Pro Pro Gly Lys Ala Pro Glu Trp Leu
        35                  40                  45

Gly Val Ile Arg Asn Lys Ala Asn Gly Phe Thr Thr Glu Tyr Asn Thr
50                  55                  60

Ser Val Lys Gly Arg Phe Thr Ile Ser Arg Asp Tyr Thr Gln Asn Ile
65                  70                  75                  80

Leu His Leu Gln Thr Asn Thr Leu Arg Ala Glu Asp Thr Ala Ile Tyr
                85                  90                  95

Tyr Cys Ala Arg Leu Thr Tyr Gly Phe Asp Tyr Trp Gly Gln Gly Val
            100                 105                 110

Met Val Thr Val Ser Ser
        115

<210> SEQ ID NO 289
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Val Ile Arg Asn Lys Ala Asn Gly Phe Thr Thr Glu Tyr Asn Thr Ser
1               5                   10                  15

Val Lys Gly

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Gln Phe Leu Glu Leu Pro Phe Thr
1               5

<210> SEQ ID NO 291
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
        35                  40                  45

Pro Gln Phe Leu Ile Tyr Trp Met Ser Thr Arg Ala Ser Gly Val Ser
50                  55                  60
```

-continued

```
Asp Arg Phe Ser Gly Ser Gly Ser Gly Thr Asp Phe Thr Leu Lys Ile
 65                  70                  75                  80

Ser Ser Val Glu Ala Glu Asp Val Gly Val Tyr Tyr Cys Gln Gln Phe
                 85                  90                  95

Leu Glu Leu Pro Phe Thr Phe Gly Ser Gly Thr Lys Leu Glu Ile Lys
            100                 105                 110

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gln Gln Ser Trp Ser Ile Pro Trp Thr
 1               5

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N, S, or D
<220> FEATURE:
<221> NAME/KEY: MOD_RES
<222> LOCATION: (8)..(8)
<223> OTHER INFORMATION: W or N
<220> FEATURE:
<221> NAME/KEY: MOD_RES
<222> LOCATION: (9)..(9)
<223> OTHER INFORMATION: I or M
<220> FEATURE:
<221> NAME/KEY: MOD_RES
<222> LOCATION: (10)..(10)
<223> OTHER INFORMATION: S, T, M, or H

<400> SEQUENCE: 293

Gly Tyr Thr Phe Thr Xaa Tyr Xaa Xaa Xaa
 1               5                  10

<210> SEQ ID NO 294
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D or Y
<220> FEATURE:
<221> NAME/KEY: MOD_RES
<222> LOCATION: (3)..(3)
<223> OTHER INFORMATION: Y or F
<220> FEATURE:
<221> NAME/KEY: MOD_RES
<222> LOCATION: (5)..(5)
<223> OTHER INFORMATION: H, G, S, N, or Y
<220> FEATURE:
<221> NAME/KEY: MOD_RES
<222> LOCATION: (6)..(6)
<223> OTHER INFORMATION: S or N
<220> FEATURE:
<221> NAME/KEY: MOD_RES
```

```
<222> LOCATION: (7)..(7)
<223> OTHER INFORMATION: T or G
<220> FEATURE:
<221> NAME/KEY: MOD_RES
<222> LOCATION: (8)..(8)
<223> OTHER INFORMATION: S, N, or G
<220> FEATURE:
<221> NAME/KEY: MOD_RES
<222> LOCATION: (9)..(9)
<223> OTHER INFORMATION: T or N
<220> FEATURE:
<221> NAME/KEY: MOD_RES
<222> LOCATION: (10)..(10)
<223> OTHER INFORMATION: N or G
<220> FEATURE:
<221> NAME/KEY: MOD_RES
<222> LOCATION: (13)..(13)
<223> OTHER INFORMATION: E or Q
<220> FEATURE:
<221> NAME/KEY: MOD_RES
<222> LOCATION: (14)..(14)
<223> OTHER INFORMATION: R or K
<220> FEATURE:
<221> NAME/KEY: MOD_RES
<222> LOCATION: (16)..(16)
<223> OTHER INFORMATION: R or K
<220> FEATURE:
<221> NAME/KEY: MOD_RES
<222> LOCATION: (17)..(17)
<223> OTHER INFORMATION: S, G, or N

<400> SEQUENCE: 294

Xaa Ile Xaa Pro Xaa Xaa Xaa Xaa Xaa Xaa Tyr Asn Xaa Xaa Phe Xaa
1               5                   10                  15

Xaa

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or S
<220> FEATURE:
<221> NAME/KEY: MOD_RES
<222> LOCATION: (3)..(3)
<223> OTHER INFORMATION: E or S
<220> FEATURE:
<221> NAME/KEY: MOD_RES
<222> LOCATION: (5)..(5)
<223> OTHER INFORMATION: F, Y, R, or T
<220> FEATURE:
<221> NAME/KEY: MOD_RES
<222> LOCATION: (7)..(7)
<223> OTHER INFORMATION: I or F
<220> FEATURE:
<221> NAME/KEY: MOD_RES
<222> LOCATION: (8)..(8)
<223> OTHER INFORMATION: S or A
<220> FEATURE:
<221> NAME/KEY: MOD_RES
<222> LOCATION: (9)..(9)
<223> OTHER INFORMATION: A or Y

<400> SEQUENCE: 295

Xaa Arg Xaa Gly Xaa Gly Xaa Xaa Xaa
1               5

<210> SEQ ID NO 296
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S or K
<220> FEATURE:
<221> NAME/KEY: MOD_RES
<222> LOCATION: (3)..(3)
<223> OTHER INFORMATION: T or S
<220> FEATURE:
<221> NAME/KEY: MOD_RES
<222> LOCATION: (4)..(4)
<223> OTHER INFORMATION: S or E
<220> FEATURE:
<221> NAME/KEY: MOD_RES
<222> LOCATION: (5)..(5)
<223> OTHER INFORMATION: S or N
<220> FEATURE:
<221> NAME/KEY: MOD_RES
<222> LOCATION: (7)..(7)
<223> OTHER INFORMATION: absent or G
<220> FEATURE:
<221> NAME/KEY: MOD_RES
<222> LOCATION: (8)..(8)
<223> OTHER INFORMATION: S or T
<220> FEATURE:
<221> NAME/KEY: MOD_RES
<222> LOCATION: (10)..(10)
<223> OTHER INFORMATION: M or V
<220> FEATURE:
<221> NAME/KEY: MOD_RES
<222> LOCATION: (11)..(11)
<223> OTHER INFORMATION: H or S

<400> SEQUENCE: 296

Xaa Ala Xaa Xaa Xaa Val Xaa Xaa Tyr Xaa Xaa
1               5                   10

<210> SEQ ID NO 297
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: K or R
<220> FEATURE:
<221> NAME/KEY: MOD_RES
<222> LOCATION: (4)..(4)
<223> OTHER INFORMATION: Q or K
<220> FEATURE:
<221> NAME/KEY: MOD_RES
<222> LOCATION: (8)..(8)
<223> OTHER INFORMATION: N or H
<220> FEATURE:
<221> NAME/KEY: MOD_RES
<222> LOCATION: (10)..(10)
<223> OTHER INFORMATION: G or absent
<220> FEATURE:
<221> NAME/KEY: MOD_RES
<222> LOCATION: (12)..(12)
<223> OTHER INFORMATION: Q or G
<220> FEATURE:
<221> NAME/KEY: MOD_RES
<222> LOCATION: (13)..(13)
<223> OTHER INFORMATION: K or N
<220> FEATURE:
<221> NAME/KEY: MOD_RES
<222> LOCATION: (14)..(14)
<223> OTHER INFORMATION: N or T
```

```
<220> FEATURE:
<221> NAME/KEY: MOD_RES
<222> LOCATION: (17)..(17)
<223> OTHER INFORMATION: T or Y

<400> SEQUENCE: 297

Xaa Ser Ser Xaa Ser Leu Leu Xaa Ser Xaa Asn Xaa Xaa Xaa Tyr Leu
1               5                   10                  15

Xaa

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, G, W or Q
<220> FEATURE:
<221> NAME/KEY: MOD_RES
<222> LOCATION: (2)..(2)
<223> OTHER INFORMATION: T, A, or M
<220> FEATURE:
<221> NAME/KEY: MOD_RES
<222> LOCATION: (4)..(4)
<223> OTHER INFORMATION: N or T
<220> FEATURE:
<221> NAME/KEY: MOD_RES
<222> LOCATION: (5)..(5)
<223> OTHER INFORMATION: L or R
<220> FEATURE:
<221> NAME/KEY: MOD_RES
<222> LOCATION: (6)..(6)
<223> OTHER INFORMATION: A, Y, or E
<220> FEATURE:
<221> NAME/KEY: MOD_RES
<222> LOCATION: (7)..(7)
<223> OTHER INFORMATION: S or T

<400> SEQUENCE: 298

Xaa Xaa Ser Xaa Xaa Xaa Xaa
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q, G, or M
<220> FEATURE:
<221> NAME/KEY: MOD_RES
<222> LOCATION: (2)..(2)
<223> OTHER INFORMATION: Q or N
<220> FEATURE:
<221> NAME/KEY: MOD_RES
<222> LOCATION: (3)..(3)
<223> OTHER INFORMATION: R, S, D, or H
<220> FEATURE:
<221> NAME/KEY: MOD_RES
<222> LOCATION: (4)..(4)
<223> OTHER INFORMATION: S, Y, or L
<220> FEATURE:
<221> NAME/KEY: MOD_RES
<222> LOCATION: (5)..(5)
<223> OTHER INFORMATION: S or Q
<220> FEATURE:
```

```
<221> NAME/KEY: MOD_RES
<222> LOCATION: (6)..(6)
<223> OTHER INFORMATION: Y or F
<220> FEATURE:
<221> NAME/KEY: MOD_RES
<222> LOCATION: (8)..(8)
<223> OTHER INFORMATION: L, F, or Y

<400> SEQUENCE: 299

Xaa Xaa Xaa Xaa Xaa Xaa Pro Xaa Thr
1               5

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N or S
<220> FEATURE:
<221> NAME/KEY: MOD_RES
<222> LOCATION: (10)..(10)
<223> OTHER INFORMATION: S, T or M

<400> SEQUENCE: 300

Gly Tyr Thr Phe Thr Xaa Tyr Trp Ile Xaa
1               5                   10

<210> SEQ ID NO 301
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: H, G, or S
<220> FEATURE:
<221> NAME/KEY: MOD_RES
<222> LOCATION: (7)..(7)
<223> OTHER INFORMATION: T or G
<220> FEATURE:
<221> NAME/KEY: MOD_RES
<222> LOCATION: (8)..(8)
<223> OTHER INFORMATION: S or N
<220> FEATURE:
<221> NAME/KEY: MOD_RES
<222> LOCATION: (14)..(14)
<223> OTHER INFORMATION: R or K
<220> FEATURE:
<221> NAME/KEY: MOD_RES
<222> LOCATION: (16)..(16)
<223> OTHER INFORMATION: R or K
<220> FEATURE:
<221> NAME/KEY: MOD_RES
<222> LOCATION: (17)..(17)
<223> OTHER INFORMATION: S or N

<400> SEQUENCE: 301

Asp Ile Tyr Pro Xaa Ser Xaa Xaa Thr Asn Tyr Asn Glu Xaa Phe Xaa
1               5                   10                  15

Xaa

<210> SEQ ID NO 302
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or S
<220> FEATURE:
<221> NAME/KEY: MOD_RES
<222> LOCATION: (5)..(5)
<223> OTHER INFORMATION: F or Y

<400> SEQUENCE: 302

Xaa Arg Glu Gly Xaa Gly Ile Ser Ala
1               5

<210> SEQ ID NO 303
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S or K
<220> FEATURE:
<221> NAME/KEY: MOD_RES
<222> LOCATION: (3)..(3)
<223> OTHER INFORMATION: T or S
<220> FEATURE:
<221> NAME/KEY: MOD_RES
<222> LOCATION: (4)..(4)
<223> OTHER INFORMATION: S or E
<220> FEATURE:
<221> NAME/KEY: MOD_RES
<222> LOCATION: (5)..(5)
<223> OTHER INFORMATION: S or N
<220> FEATURE:
<221> NAME/KEY: MOD_RES
<222> LOCATION: (7)..(7)
<223> OTHER INFORMATION: absent or G
<220> FEATURE:
<221> NAME/KEY: MOD_RES
<222> LOCATION: (8)..(8)
<223> OTHER INFORMATION: absent or T
<220> FEATURE:
<221> NAME/KEY: MOD_RES
<222> LOCATION: (10)..(10)
<223> OTHER INFORMATION: M or V
<220> FEATURE:
<221> NAME/KEY: MOD_RES
<222> LOCATION: (11)..(11)
<223> OTHER INFORMATION: H or S

<400> SEQUENCE: 303

Xaa Ala Xaa Xaa Xaa Val Xaa Xaa Tyr Xaa Xaa
1               5                   10

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S or G
<220> FEATURE:
<221> NAME/KEY: MOD_RES
<222> LOCATION: (2)..(2)
```

```
<223> OTHER INFORMATION: T or A
<220> FEATURE:
<221> NAME/KEY: MOD_RES
<222> LOCATION: (5)..(5)
<223> OTHER INFORMATION: L or R
<220> FEATURE:
<221> NAME/KEY: MOD_RES
<222> LOCATION: (6)..(6)
<223> OTHER INFORMATION: A or Y
<220> FEATURE:
<221> NAME/KEY: MOD_RES
<222> LOCATION: (7)..(7)
<223> OTHER INFORMATION: S or T

<400> SEQUENCE: 304

Xaa Xaa Ser Asn Xaa Xaa Xaa
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q or G
<220> FEATURE:
<221> NAME/KEY: MOD_RES
<222> LOCATION: (3)..(3)
<223> OTHER INFORMATION: R or S
<220> FEATURE:
<221> NAME/KEY: MOD_RES
<222> LOCATION: (4)..(4)
<223> OTHER INFORMATION: S or Y
<220> FEATURE:
<221> NAME/KEY: MOD_RES
<222> LOCATION: (6)..(6)
<223> OTHER INFORMATION: Y or F
<220> FEATURE:
<221> NAME/KEY: MOD_RES
<222> LOCATION: (8)..(8)
<223> OTHER INFORMATION: L or F

<400> SEQUENCE: 305

Xaa Gln Xaa Xaa Ser Xaa Pro Xaa Thr
1               5

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or K
<220> FEATURE:
<221> NAME/KEY: MOD_RES
<222> LOCATION: (5)..(5)
<223> OTHER INFORMATION: T or P
<220> FEATURE:
<221> NAME/KEY: MOD_RES
<222> LOCATION: (7)..(7)
<223> OTHER INFORMATION: Y or F
<220> FEATURE:
<221> NAME/KEY: MOD_RES
<222> LOCATION: (8)..(8)
<223> OTHER INFORMATION: L or I
<220> FEATURE:
<221> NAME/KEY: MOD_RES
```

```
<222> LOCATION: (9)..(9)
<223> OTHER INFORMATION: M or I
<220> FEATURE:
<221> NAME/KEY: MOD_RES
<222> LOCATION: (10)..(10)
<223> OTHER INFORMATION: N or H

<400> SEQUENCE: 306

Gly Tyr Xaa Phe Xaa Ser Xaa Xaa Xaa Xaa
1               5                   10

<210> SEQ ID NO 307
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A or D
<220> FEATURE:
<221> NAME/KEY: MOD_RES
<222> LOCATION: (9)..(9)
<223> OTHER INFORMATION: S or T
<220> FEATURE:
<221> NAME/KEY: MOD_RES
<222> LOCATION: (17)..(17)
<223> OTHER INFORMATION: D or G

<400> SEQUENCE: 307

Tyr Ile Asn Pro Tyr Ser Xaa Gly Xaa Asn Tyr Asn Glu Lys Phe Lys
1               5                   10                  15

Xaa

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Y or S
<220> FEATURE:
<221> NAME/KEY: MOD_RES
<222> LOCATION: (6)..(6)
<223> OTHER INFORMATION: T or I

<400> SEQUENCE: 308

Gln Gln Xaa Trp Ser Xaa Pro Trp Thr
1               5

<210> SEQ ID NO 309
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N or Q
<220> FEATURE:
<221> NAME/KEY: MOD_RES
<222> LOCATION: (8)..(8)
<223> OTHER INFORMATION: D or E
```

-continued

<400> SEQUENCE: 309

Trp Ile Asp Pro Glu Xaa Gly Xaa Ser Lys Tyr Ala Pro Lys Phe Gln
1               5                   10                  15

Gly

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: T or S
<220> FEATURE:
<221> NAME/KEY: MOD_RES
<222> LOCATION: (9)..(9)
<223> OTHER INFORMATION: I or V
<220> FEATURE:
<221> NAME/KEY: MOD_RES
<222> LOCATION: (10)..(10)
<223> OTHER INFORMATION: H or Q

<400> SEQUENCE: 310

Gly Phe Ser Leu Thr Xaa Tyr Gly Xaa Xaa
1               5                   10

<210> SEQ ID NO 311
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: S or T
<220> FEATURE:
<221> NAME/KEY: MOD_RES
<222> LOCATION: (9)..(9)
<223> OTHER INFORMATION: A or D
<220> FEATURE:
<221> NAME/KEY: MOD_RES
<222> LOCATION: (10)..(10)
<223> OTHER INFORMATION: F or Y

<400> SEQUENCE: 311

Val Ile Trp Thr Gly Gly Xaa Thr Xaa Xaa Asn Ala Ala Phe Met Ser
1               5                   10                  15

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: V or I
<220> FEATURE:
<221> NAME/KEY: MOD_RES
<222> LOCATION: (9)..(9)
<223> OTHER INFORMATION: T, M, or V

<400> SEQUENCE: 312

Ala Lys Xaa Gly Phe His Ser Ala Xaa Asp Tyr

```
1               5                   10
```

```
<210> SEQ ID NO 313
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: L or I

<400> SEQUENCE: 313

Arg Ser Ser Gln Asn Xaa Val His Ser Asn Gly Asn Thr Tyr Leu Glu
1               5                   10                  15

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: V or I

<400> SEQUENCE: 314

Phe Gln Gly Ser His Xaa Pro Phe Thr
1               5

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D or N

<400> SEQUENCE: 315

Gly Phe Thr Phe Thr Xaa Phe Tyr Met Ser
1               5                   10

<210> SEQ ID NO 316
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: K or R
<220> FEATURE:
<221> NAME/KEY: MOD_RES
<222> LOCATION: (6)..(6)
<223> OTHER INFORMATION: A or P
<220> FEATURE:
<221> NAME/KEY: MOD_RES
<222> LOCATION: (8)..(8)
<223> OTHER INFORMATION: G or A
<220> FEATURE:
<221> NAME/KEY: MOD_RES
<222> LOCATION: (11)..(11)
```

```
<223> OTHER INFORMATION: A or T
<220> FEATURE:
<221> NAME/KEY: MOD_RES
<222> LOCATION: (12)..(12)
<223> OTHER INFORMATION: G or D

<400> SEQUENCE: 316

Val Ile Arg Asn Xaa Xaa Asn Xaa Tyr Thr Xaa Xaa Tyr Asn Pro Ser
1               5                   10                  15
Val Lys Gly

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or T
<220> FEATURE:
<221> NAME/KEY: MOD_RES
<222> LOCATION: (4)..(4)
<223> OTHER INFORMATION: T or S

<400> SEQUENCE: 317

Xaa Arg Leu Xaa Tyr Gly Phe Asp Tyr
1               5

<210> SEQ ID NO 318
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: N or T

<400> SEQUENCE: 318

Gln Ser Ser Lys Ser Leu Leu His Ser Xaa Gly Lys Thr Tyr Leu Asn
1               5                   10                  15

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Y or F

<400> SEQUENCE: 319

Gln Gln Phe Leu Glu Xaa Pro Phe Thr
1               5

<210> SEQ ID NO 320
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: N or D
<220> FEATURE:
<221> NAME/KEY: MOD_RES
<222> LOCATION: (12)..(12)
<223> OTHER INFORMATION: E or D

<400> SEQUENCE: 320

Phe Ile Arg Xaa Lys Ala Asn Gly Tyr Thr Thr Xaa Tyr Ser Ala Ser
1               5                   10                  15

Val Lys Gly

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or S
<220> FEATURE:
<221> NAME/KEY: MOD_RES
<222> LOCATION: (3)..(3)
<223> OTHER INFORMATION: V or L

<400> SEQUENCE: 321

Xaa Arg Xaa Leu Arg Ala Gln Gly Phe Ala Tyr
1               5                   10

<210> SEQ ID NO 322
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T or K
<220> FEATURE:
<221> NAME/KEY: MOD_RES
<222> LOCATION: (3)..(3)
<223> OTHER INFORMATION: G or S
<220> FEATURE:
<221> NAME/KEY: MOD_RES
<222> LOCATION: (10)..(10)
<223> OTHER INFORMATION: N or S

<400> SEQUENCE: 322

Xaa Ser Xaa Gln Ser Leu Leu Tyr Ser Xaa Asn Gln Lys Asn Tyr Leu
1               5                   10                  15

Ala

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: R or G
```

<400> SEQUENCE: 323

Gln Gln Tyr Tyr Xaa Asn Pro Phe Thr
1               5

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
aggaatgtgg ggagcacgga g                                      21

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
tgcatcgcat tgtctgagta ggtg                                   24

<210> SEQ ID NO 326
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
accctagtcc tgactgttgc tc                                     22

<210> SEQ ID NO 327
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
tataggaact tcgcgacacg gacac                                  25

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
acaggaggga cctaccttca g                                      21

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 329
gcctgccttt cagagacctc agtc                                              24

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
cctctccggc tgctcatctt actc                                              24

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
gtctctcagc cctggcagag tttg                                              24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
cgcctaccct agtcctgact gttg                                              24

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
aaagcctaca gcatcctcac ctc                                               23

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
gcatcatggg gttgtagatt ccg                                               23

<210> SEQ ID NO 335
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335
```

```
Gly Gly Gly Gly Ser
1               5

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 336

His His His His His His
1               5

<210> SEQ ID NO 337
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Ser Pro Gly Arg Gly Leu Glu Trp Ile
        35                  40                  45

Gly Arg Ser Asp Pro Thr Thr Gly Gly Thr Asn Tyr Asn Glu Lys Phe
    50                  55                  60

Lys Thr Lys Ala Thr Leu Thr Val Asp Lys Pro Ser Ser Thr Ala Tyr
65                  70                  75                  80

Met Gln Leu Ser Ser Leu Thr Ser Asp Asp Ser Ala Val Tyr Tyr Cys
                85                  90                  95

Val Arg Thr Ser Gly Thr Gly Asp Tyr Trp Gly Gln Gly Thr Ser Leu
            100                 105                 110

Thr Val Ser Ser Ala Lys Thr Thr Ala Pro Ser Val Tyr Pro Leu Ala
        115                 120                 125

Pro Val Cys Gly Gly Thr Thr Gly Ser Ser Val Thr
    130                 135                 140

<210> SEQ ID NO 338
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Phe Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Pro Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe
        130                 135                 140

<210> SEQ ID NO 339
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Asp Ile Val Met Thr Gln Ser Pro Asp Ser Leu Ala Val Ser Leu Gly
1               5                   10                  15

Glu Arg Ala Thr Ile Asn Cys Gln Ser Ser Lys Ser Leu Leu His Ser
                20                  25                  30

Asn Gly Lys Thr Tyr Leu Asn Trp Tyr Gln Gln Lys Pro Gly Gln Pro
            35                  40                  45

Pro Lys Leu Leu Ile Tyr Trp Met Ser Thr Arg Ala Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Phe
                85                  90                  95

Leu Glu Phe Pro Phe Thr Phe Gly Gln Gly Thr Lys Val Glu Ile Lys
            100                 105                 110

<210> SEQ ID NO 340
<211> LENGTH: 7
<212> TYPE: PRT
<213> ORGANISM: Homo sapiens

<400> SEQUENCE: 340

Phe Pro Gly Glu Ser Glu Ser
1               5

<210> SEQ ID NO 341
<211> LENGTH: 9
<212> TYPE: PRT
<213> ORGANISM: Homo sapiens

<400> SEQUENCE: 341

Gly Glu Lys Gly Pro Cys Gln Arg Val
1               5

<210> SEQ ID NO 342
<211> LENGTH: 12
<212> TYPE: PRT
<213> ORGANISM: Homo sapiens

<400> SEQUENCE: 342

Thr Leu Arg Asn Leu Gln Pro His Asp Ala Gly Leu
1               5                   10
```

```
<210> SEQ ID NO 343
<211> LENGTH: 4
<212> TYPE: PRT
<213> ORGANISM: Homo sapiens

<400> SEQUENCE: 343

Val Glu Val Leu
1

<210> SEQ ID NO 344
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Val Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Arg
                85                  90                  95

Asn Phe Gly Gln Gly Thr Lys Leu Glu Ile Lys
            100                 105

<210> SEQ ID NO 345
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Glu Val Gln Leu Val Gln Ser Gly Ala Glu Val Lys Lys Pro Gly Glu
1               5                   10                  15

Ser Leu Lys Ile Ser Cys Lys Gly Ser Gly His Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Phe Cys
                85                  90                  95

Ala Arg Gln Arg Thr Phe Tyr Tyr Asp Ser Ser Gly Tyr Phe Asp Tyr
            100                 105                 110

Trp Gly Gln Gly Thr Leu Val Thr Val Ser Ser
        115                 120
```

<210> SEQ ID NO 346
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
                85                  90                  95

Thr Phe Gly Gln Gly Thr Lys Leu Glu Ile Lys
            100                 105

<210> SEQ ID NO 347
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Phe Asp Tyr
            100                 105                 110

Trp Gly Gln Gly Thr Leu Val Thr Val Ser Ser
        115                 120

<210> SEQ ID NO 348
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Asp Val Val Met Thr Gln Ser Pro Asp Ser Leu Ala Val Ser Leu Gly

```
                1               5                   10                  15
            Glu Arg Ala Thr Ile Asn Cys Arg Ser Ser Gln Ser Leu Val His Ser
                            20                  25                  30

Asn Arg Tyr Thr Tyr Leu His Trp Tyr Gln Gln Lys Pro Gly Gln Ser
                        35                  40                  45

Pro Lys Leu Leu Ile Tyr Lys Val Ser Asn Arg Phe Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Ser Gln Ser
                            85                  90                  95

Thr Arg Val Pro Tyr Thr Phe Gly Gln Gly Thr Lys Leu Glu Ile Lys
                        100                 105                 110
```

<210> SEQ ID NO 349
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

```
            Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Ala Phe Ser Ser Gln
                            20                  25                  30

Trp Met Asn Trp Val Arg Gln Ala Pro Gly Gln Arg Leu Glu Trp Ile
                        35                  40                  45

Gly Arg Ile Tyr Pro Gly Gly Gly Asp Thr Asn Tyr Ala Gly Lys Phe
                    50                  55                  60

Gln Gly Arg Val Thr Ile Thr Ala Asp Thr Ser Ala Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Leu Leu Arg Asn Gln Pro Gly Glu Ser Tyr Ala Met Asp Tyr
                        100                 105                 110

Trp Gly Gln Gly Thr Leu Val Thr Val Ser Ser
                    115                 120
```

<210> SEQ ID NO 350
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

```
            Glu Val Gln Leu Val Glu Ser Gly Gly Gly Leu Val Gln Pro Gly Gly
            1               5                   10                  15

Ser Leu Arg Leu Ser Cys Ala Gly Ser Gly Phe Thr Phe Thr Asp Phe
                            20                  25                  30

Tyr Met Ser Trp Val Arg Gln Ala Pro Gly Lys Gly Pro Glu Trp Leu
                        35                  40                  45

Ser Val Ile Arg Asn Lys Ala Asn Gly Tyr Thr Ala Gly Tyr Asn Pro
                    50                  55                  60

Ser Val Lys Gly Arg Phe Thr Ile Ser Arg Asp Asn Ser Lys Asn Thr
```

Leu Tyr Leu Gln Met Asn Ser Leu Arg Ala Glu Asp Thr Ala Val Tyr
65                  70                  75                  80

Tyr Cys Ala Arg Leu Thr Tyr Gly Phe Asp Tyr Trp Gly Gln Gly Thr
            85                  90                  95

Leu Val Thr Val Ser Ser
        100                 105                 110

115

<210> SEQ ID NO 351
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asn Gly Asp Ser
1

<210> SEQ ID NO 352
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gln Gly Asp Ser
1

<210> SEQ ID NO 353
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asn Gly Glu Ser
1

<210> SEQ ID NO 354
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Gly Glu Ser
1